(12) United States Patent
Suzuki et al.

(10) Patent No.: US 10,233,199 B2
(45) Date of Patent: *Mar. 19, 2019

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hiroki Suzuki, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,210

(22) Filed: Oct. 20, 2017

(65) Prior Publication Data

US 2018/0099983 A1    Apr. 12, 2018

Related U.S. Application Data

(63) Continuation of application No. 14/947,827, filed on Nov. 20, 2015, now Pat. No. 9,796,736, which is a (Continued)

(30) Foreign Application Priority Data

Nov. 13, 2009    (JP) .................................. 2009-260240

(51) Int. Cl.
*H01L 51/50*    (2006.01)
*C07F 5/02*    (2006.01)
(Continued)

(52) U.S. Cl.
CPC ............ *C07F 5/025* (2013.01); *C07D 307/91* (2013.01); *C07D 333/76* (2013.01); *C09K 11/06* (2013.01);
(Continued)

(58) Field of Classification Search
None
See application file for complete search history.

(56) References Cited

U.S. PATENT DOCUMENTS 7,498,356 B2    3/2009    Whitehouse et al.
7,732,065 B2    6/2010    Lyu et al.
(Continued)

FOREIGN PATENT DOCUMENTS

CN    001984897 A    6/2007
CN    101473012 A    7/2009
(Continued)

OTHER PUBLICATIONS

European Search Report re Application No. EP 10190684.0, dated Mar. 24, 2011.
(Continued)

*Primary Examiner* — Gregory D Clark
(74) *Attorney, Agent, or Firm* — Husch Blackwell LLP

(57) ABSTRACT

Provided are a heterocyclic compound which emits blue light and is represented by General Formula (G1) below, and a light-emitting element, a light-emitting device, an electronic device and a lighting device which are formed using the heterocyclic compound represented by General Formula (G1) below. The use of the heterocyclic compound represented by General Formula (G1) makes it possible to provide a light-emitting element which has high emission efficiency, and also a light-emitting device, an electronic device and a lighting device which have reduced power consumption (Continued)

(G1)

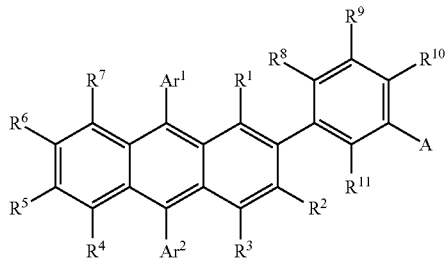

(S1)

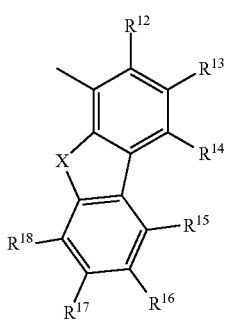

(S2)

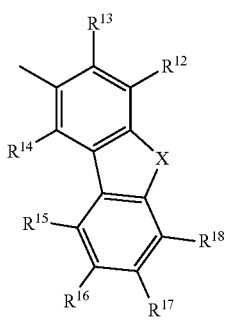

8 Claims, 47 Drawing Sheets

Related U.S. Application Data continuation of application No. 14/301,957, filed on Jun. 11, 2014, now Pat. No. 9,196,836, which is a continuation of application No. 12/942,214, filed on Nov. 9, 2010, now Pat. No. 8,771,840.

(51) Int. Cl.
*H01L 51/00* (2006.01)
*H05B 33/10* (2006.01)
*C09K 11/06* (2006.01)
*C07D 333/76* (2006.01)
*C07D 307/91* (2006.01)

(52) U.S. Cl.
CPC ...... *H01L 51/0052* (2013.01); *H01L 51/0058* (2013.01); *H01L 51/0073* (2013.01); *H01L 51/0074* (2013.01); *H05B 33/10* (2013.01); *C09K 2211/1007* (2013.01); *C09K 2211/1011* (2013.01); *C09K 2211/1088* (2013.01); *C09K 2211/1092* (2013.01); *H01L 51/006* (2013.01); *H01L 51/0059* (2013.01); *H01L 51/0081* (2013.01); *H01L 51/5012* (2013.01); *H01L 51/5016* (2013.01)

(56) References Cited

U.S. PATENT DOCUMENTS

| | | | |
|---|---|---|---|
| 8,084,146 B2 | 12/2011 | Murase et al. | |
| 8,293,381 B2 | 10/2012 | Je et al. | |
| 8,512,875 B2 | 8/2013 | Kawamura et al. | |
| 8,729,530 B2 | 5/2014 | Nagao et al. | |
| 2003/0127967 A1 | 7/2003 | Tsutsui et al. | |
| 2006/0122222 A1 | 6/2006 | Whitehouse et al. | |
| 2007/0247063 A1 | 10/2007 | Murase et al. | |
| 2008/0152950 A1 | 6/2008 | Je et al. | |
| 2008/0315754 A1 | 12/2008 | Kawamura et al. | |
| 2012/0138907 A1 | 6/2012 | Murase et al. | |
| 2013/0313538 A1 | 11/2013 | Kawamura et al. | |

FOREIGN PATENT DOCUMENTS

| | | |
|---|---|---|
| EP | 1 748 045 A1 | 1/2007 |
| EP | 2 028 249 A1 | 2/2009 |
| EP | 2 163 550 A1 | 3/2010 |
| EP | 2 450 356 A1 | 5/2012 |
| JP | 2009-158848 A | 7/2009 |
| KR | 2008-0042589 A | 5/2008 |
| KR | 2008-0061800 A | 7/2008 |
| TW | 200833813 | 8/2008 |
| TW | 200914575 | 4/2009 |
| WO | WO 2005/113531 A1 | 12/2005 |
| WO | WO 2006/055725 A2 | 5/2006 |
| WO | WO 2008/143229 A1 | 11/2008 |

OTHER PUBLICATIONS

Chinese Office Action re Application No. CN 201010553975.9, dated Dec. 6, 2013.
Chinese Office Action re Application No. CN 201510203547.6, dated May 4, 2016.
Kauffman, J. et al., "Syntheses and Photophysical Properties of Fluorescent Dibenzofurans, A Dibenzothiophene, and Carbazoles Substituted with Benzoxazole and Hydroxyl Groups to Produce Excited State Intramolecular Proton-Transfer," Journal of Heterocyclic Chemistry, Sep. 1, 1995, vol. 32. No. 5, pp. 1541-1555.

HETEROCYCLIC COMPOUND, LIGHT-EMITTING ELEMENT, LIGHT-EMITTING DEVICE, ELECTRONIC DEVICE, AND LIGHTING DEVICE

This application is a continuation of copending U.S. application Ser. No. 14/947,827, filed on Nov. 20, 2015 which is a continuation of U.S. application Ser. No. 14/301,957, filed on Jun. 11, 2014 (now U.S. Pat. No. 9,196,836 issued Nov. 24, 2015) which is a continuation of U.S. application Ser. No. 12/942,214, filed on Nov. 9, 2010 (now U.S. Pat. No. 8,771,840 issued Jul. 8, 2014), which are all incorporated herein by reference.

BACKGROUND OF THE INVENTION

1. Field of the Invention

The present invention relates to a heterocyclic compound. Also, the present invention relates to a light-emitting element, a light-emitting device, an electronic device, and a lighting device using the heterocyclic compound.

2. Description of the Related Art

In recent years, research and development have been extensively conducted on light-emitting elements using electroluminescence (EL). In the basic structure of such a light-emitting element, a layer which contains a light-emitting substance is interposed between a pair of electrodes. By voltage application to this element, light emission from the light-emitting substance can be obtained.

Since such light-emitting elements are self-luminous elements, they have advantages over liquid crystal displays in having high pixel visibility and eliminating the need for a backlight, for example, thereby being considered as suitable for flat panel display elements. Light-emitting elements are also highly advantageous in that they can be thin and lightweight. Furthermore, very high speed response is one of the features of such elements.

Furthermore, since such light-emitting elements can be formed in a film form, they make it easy to provide planar light emission, thereby achieving large-area elements utilizing planar light emission. This is difficult to obtain with point light sources typified by incandescent lamps and LEDs or linear light sources typified by fluorescent lamps. Thus, light-emitting elements have great potential as surface light sources applicable to lightings and the like.

A light-emitting element utilizing EL is driven by injection of electrons from a cathode and holes from an anode into a layer containing a light-emitting substance which is interposed between a pair of electrodes. The electrons injected from the cathode and the holes injected from the anode recombine in the layer containing the light-emitting substance to form molecular excitons. The molecular excitons release energy in returning to a ground state. In the case where the energy is released as light having a wavelength corresponding to that of visible light, light emission can be seen. Excited states of organic compounds can be a singlet state and a triplet state, and light emission can occur either of the excited state.

The emission wavelength of a light-emitting element is determined by the difference of energy between the ground state and the excited state, that is, an energy gap. Therefore, by appropriate selection or modification of a structure of the molecule that contributes to light emission, any color of light can be obtained. When a light-emitting device is fabricated using light-emitting elements capable of emitting light of red, blue, and green, which are the three primary colors of light, the light-emitting device can perform full color display.

Manufacture of high performance full-color light-emitting devices needs red, blue, and green light-emitting elements which are excellent in lifetime, emission efficiency, and the like. The recent development of materials has achieved good characteristics of red and green light-emitting elements. However, as for blue light-emitting elements, sufficient characteristics have not been obtained. For example, Patent Documents 1 and 2 reported a light-emitting element having relatively high emission efficiency. However, in order to realize high performance full-color displays, further higher emission efficiency have been required.

REFERENCES

Patent Documents

[Patent Document 1] International Publication WO 2008/143229 Pamphlet

[Patent Document 2] International Publication WO 2005/113531 Pamphlet

SUMMARY OF THE INVENTION

An object of one embodiment of the present invention is to provide a novel heterocyclic compound that exhibits blue light emission. Another object of one embodiment of the present invention is to provide a light-emitting element having high emission efficiency. Still another object of an embodiment of the present invention is to provide a light-emitting device, an electronic device, and a lighting device in each of which power consumption is reduced by use of the above light-emitting element.

An embodiment of the present invention is a heterocyclic compound having a structure represented by General Formula (G1) below.

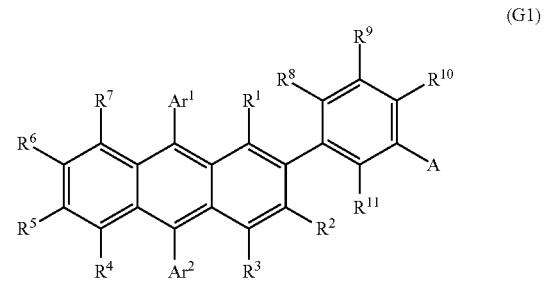

(G1)

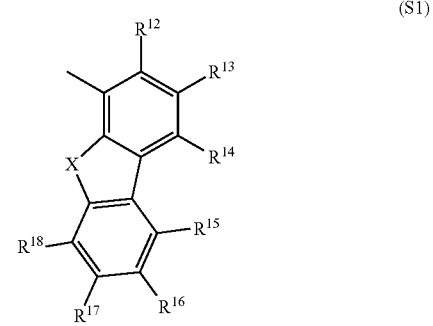

(S1)

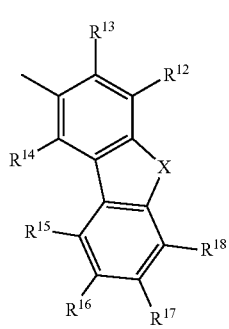

In General Formula (G1), $Ar^1$ and $Ar^2$ independently represent a substituted or unsubstituted aryl group having 6 to 13 carbon atoms, $R^1$ to $R^{11}$ independently represent any of hydrogen, an alkyl group having 1 to 4 carbon atoms, and a substituted or unsubstituted aryl group having 6 to 13 carbon atoms, and A represents a substituent represented by General Formula (S1) or (S2). In General Formulae (S1) and (S2), X represents oxygen or sulfur, and $R^{12}$ to $R^{18}$ independently represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G2-1) below.

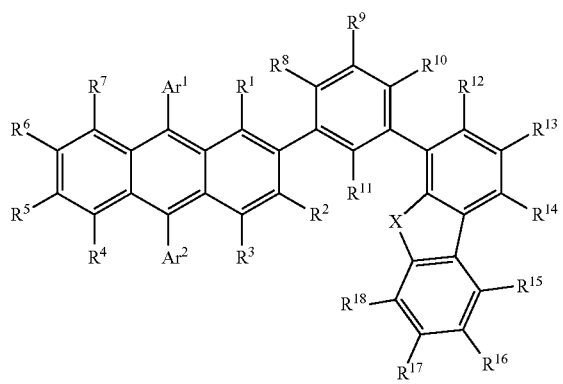

In General Formula (G2-1), $Ar^1$ and $Ar^2$ independently represent a substituted or unsubstituted aryl group having 6 to 13 carbon atoms, X represents oxygen or sulfur, and $R^1$ to $R^{18}$ independently represent any of hydrogen, an alkyl group having 1 to 4 carbon atoms, and a substituted or unsubstituted aryl group having 6 to 13 carbon atoms.

Yet another embodiment of the present invention is a heterocyclic compound having a structure represented by General Formula (G3) below.

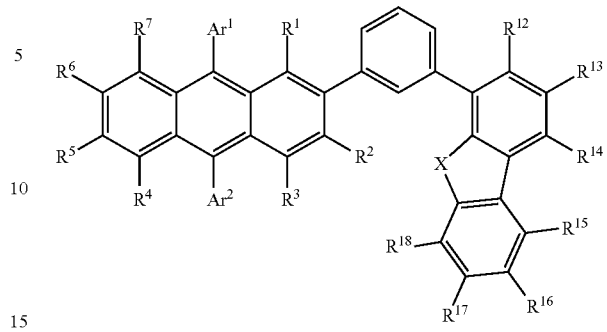

In General Formula (G3), $Ar^1$ and $Ar^2$ independently represent a substituted or unsubstituted aryl group having 6 to 13 carbon atoms, X represents oxygen or sulfur, and $R^1$ to $R^7$ and $R^{12}$ to $R^{18}$ independently represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G4) below.

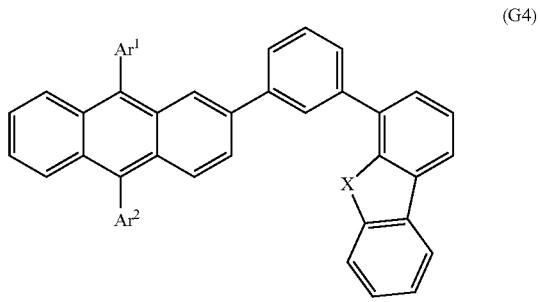

In General Formula (G4), $Ar^1$ and $Ar^2$ independently represent a substituted or unsubstituted aryl group having 6 to 13 carbon atoms, and X represents oxygen or sulfur.

As the heterocyclic compound of one embodiment of the present invention, there are a dibenzofuran derivative and a dibenzothiophene derivative each having the structure represented by the above General Formula (G1). Therefore, another embodiment of the present invention is a dibenzofuran derivative having a structure represented by Structural Formula (100) below.

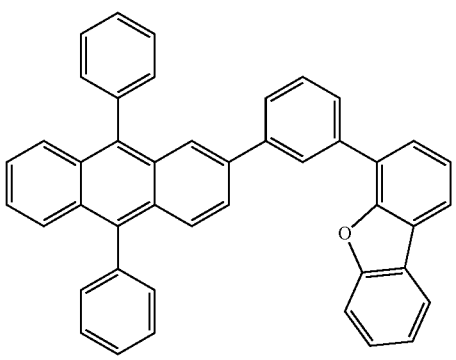

Still another embodiment of the present invention is a dibenzothiophene derivative having a structure represented by Structural Formula (300) below.

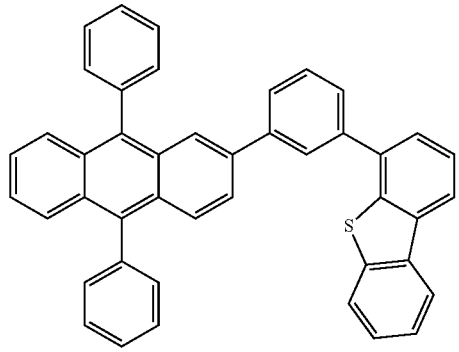

(300)

The above heterocyclic compounds which are embodiments of the present invention represented by any of General Formulae (G1), (G2-1), (G3), and (G4) and Structural Formulae (100) and (300) can be preferably used as a material for a light-emitting element or an organic device such as an organic transistor. Therefore, a light-emitting element including the above heterocyclic compound is one embodiment of the present invention.

Another embodiment of the present invention is a light-emitting element including a light-emitting layer that includes the above heterocyclic compound. The heterocyclic compound which is one embodiment of the present invention exhibits blue light emission and high emission efficiency, and therefore can be preferably used as a material for a light-emitting layer of a light-emitting element.

Still another embodiment of the present invention is a light-emitting element including a light-emitting layer that includes the above heterocyclic compound and a light-emitting substance. The heterocyclic compound which is one embodiment of the present invention has a wide energy gap. Therefore, in a light-emitting element, such a heterocyclic compound achieves high emission efficiency, when used as a host material in which the light-emitting substance of the light-emitting layer is dispersed. In particular, when the heterocyclic compound is used as a host material for a blue light-emitting substance, a blue light-emitting element having high emission efficiency can be provided.

Yet another embodiment of the present invention is a light-emitting element having at least a light-emitting layer and a hole-transport layer between a pair of electrodes, in which the hole-transport layer includes the above heterocyclic compound. Since the heterocyclic compound of one embodiment of the present invention has a high hole-transport property, the heterocyclic compound can be preferably used as a material for the hole-transport layer.

Since the light-emitting element of one embodiment of the present invention which is obtained as above can realize high emission efficiency, a light-emitting device (such as an image display device) using this light-emitting element can realize low power consumption. Therefore, a light-emitting device using the above light-emitting element is one embodiment of the present invention. In addition, an electronic device and a lighting device using the light-emitting device are also embodiments of the present invention.

The light-emitting device in this specification cover an image display device using a light-emitting element and also the following devices: a module including a light-emitting element to which a connector such as an anisotropic conductive film, a tape automated bonding (TAB) tape, or a tape carrier package (TCP) is added; a module in which the top of the TAB tape or the TCP is provided with a printed wiring board; a module in which an integrated circuit (IC) is directly mounted on a light-emitting element by a chip on glass (COG) technique; and the like. Furthermore, a light-emitting device used in a lighting device and the like is also included.

One embodiment of the present invention can provide a novel heterocyclic compound that exhibits blue light emission. Further, the heterocyclic compound which is one embodiment of the present invention has high emission efficiency. Therefore, by using the heterocyclic compound of one embodiment of the present invention for a light-emitting element, the light-emitting element can have high emission efficiency. Further, the use of the heterocyclic compound of one embodiment of the present invention enables the production of a light-emitting device, an electronic device, and a lighting device in each of which power consumption is reduced.

DETAILED DESCRIPTION OF THE INVENTION

Figure 1A:
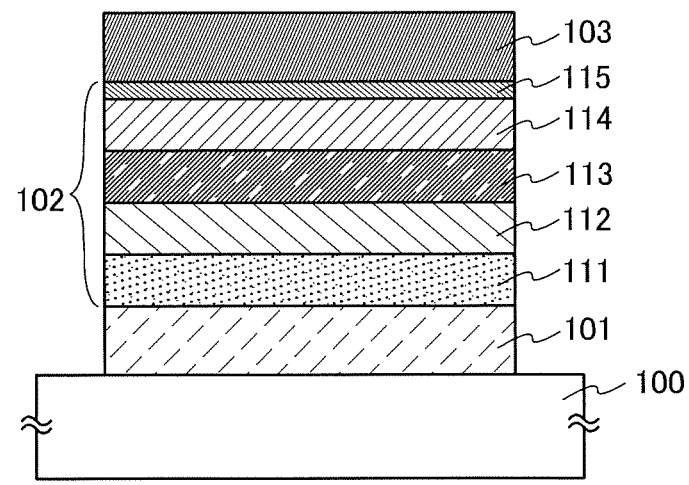
FIGS. 1A and 1B each illustrate a light-emitting element of one embodiment of the present invention.

Embodiments of the present invention will now be described with reference to the accompanying drawings. Note that the invention is not limited to the description below, and it will be easily understood by those skilled in the art that various changes and modifications can be made without departing from the spirit and scope of the invention. Therefore, the invention should not be construed as being limited to the description in the following embodiments.

Embodiment 1

In Embodiment 1, a heterocyclic compound of one embodiment of the present invention is described.

One embodiment of the present invention is the heterocyclic compound represented by General Formula (G1).

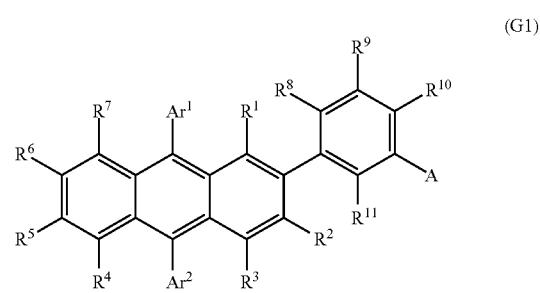

(G1)

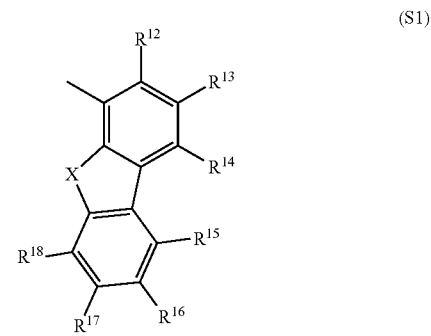

(S1)

-continued

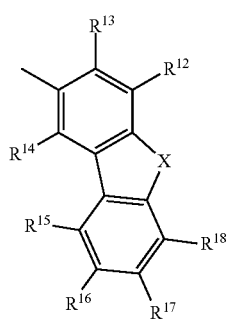
(S2)

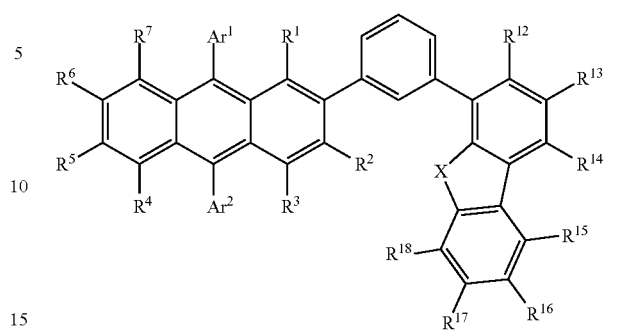
(G3)

In General Formula (G1), $Ar^1$ and $Ar^2$ independently represent a substituted or unsubstituted aryl group having 6 to 13 carbon atoms, $R^1$ to $R^{11}$ independently represent any of hydrogen, an alkyl group having 1 to 4 carbon atoms, and a substituted or unsubstituted aryl group having 6 to 13 carbon atoms, and A represents a substituent represented by General Formula (S1) or (S2). In General Formulae (S1) and (S2), X represents oxygen or sulfur, and $R^{12}$ to $R^{18}$ independently represent any of hydrogen, an alkyl group having 1 to 4 carbon atoms, and a substituted or unsubstituted aryl group having 6 to 13 carbon atoms. Note that the carbon atoms in an aryl group in this specification mean carbon atoms which form a ring of the main skeleton, not including carbon atoms in a substituent bonded to the main skeleton.

Another embodiment of the present invention is a heterocyclic compound (G2-1) in which, in General Formula (G1), A is the substituent represented by General Formula (S1).

Because of its easy synthesis, further preferred is a heterocyclic compound (G4) of one embodiment of the present invention in which, in General Formula (G2-1), $R^1$ to $R^{18}$ are each substituted with hydrogen.

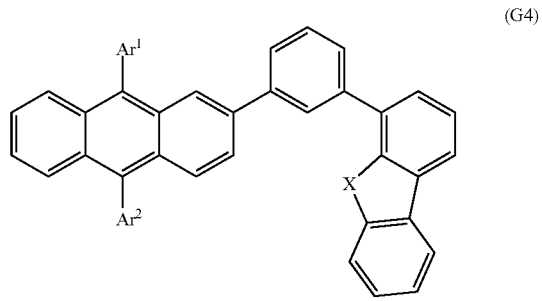
(G4)

Still another embodiment of the present invention is a heterocyclic compound (G2-2) in which, in General Formula (G1), A is the substituent represented by General Formula (S2).

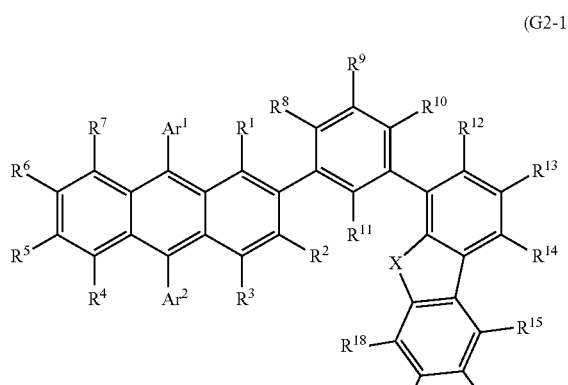
(G2-1)

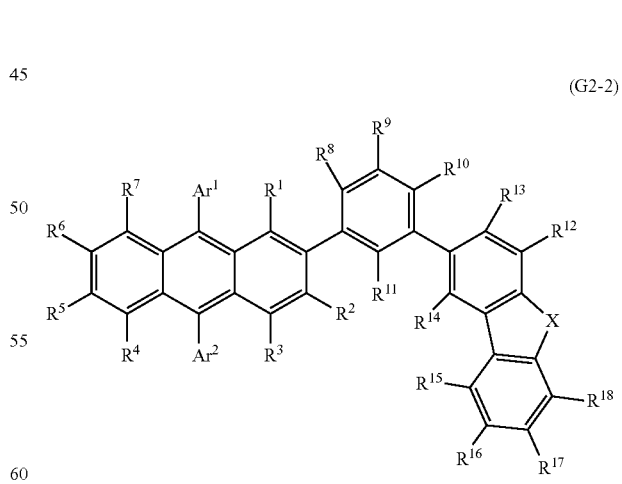
(G2-2)

Because of its easy synthesis, preferred is a heterocyclic compound (G3) of one embodiment of the present invention in which, in General Formula (G2-1), $R^8$ to $R^{11}$ are each substituted with hydrogen.

As specific structures of $Ar^1$ and $Ar^2$ in General Formula (G1), there are substituents represented by Structural Formulae (1-1) to (1-16).

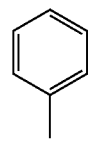 (1-1)
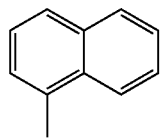 (1-2)
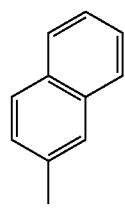 (1-3)
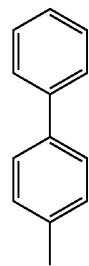 (1-4)
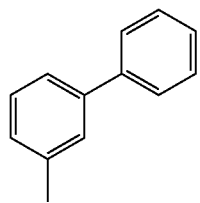 (1-5)
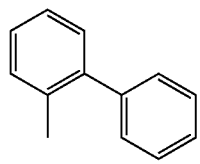 (1-6)
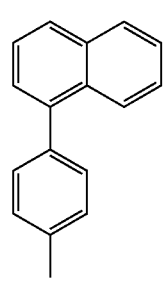 (1-7)
-continued
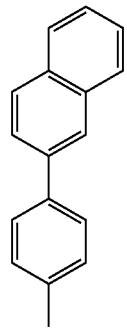 (1-8)
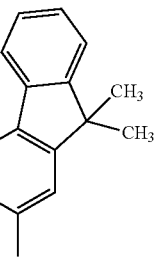 (1-9)
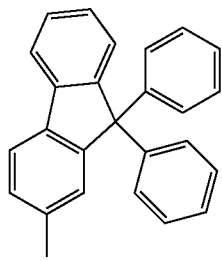 (1-10)
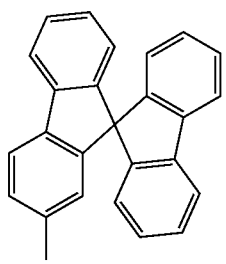 (1-11)
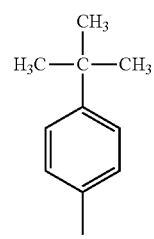 (1-12)
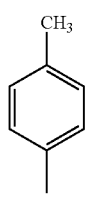 (1-13)

-continued (1-14)
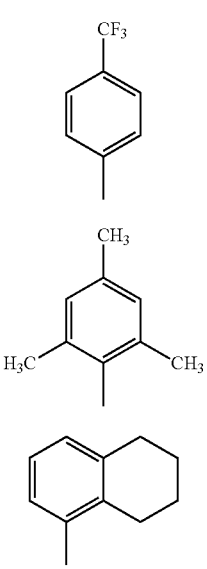
(1-15)
(1-16)

As specific structures of $R^1$ to $R^{11}$ in General Formula (G1), there are substituents represented by Structural Formulae (2-1) to (2-9) in addition to Structural Formulae (1-1) to (1-16) above.

(2-1)
(2-2)
(2-3)
(2-4)
(2-5)
(2-6)
(2-7)
(2-8)
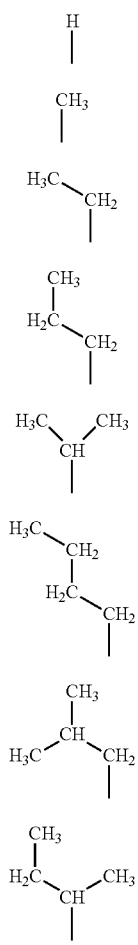

-continued (2-9)
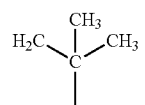

As specific structures of $R^{12}$ to $R^{18}$ in General Formulae (S1) and (S2), there are substituents represented by the above-described Structural Formulae (1-1) to (1-16) and (2-1) to (2-9).

Specific examples of the heterocyclic compound represented by General Formula (G1) include, but not limited to, dibenzofuran derivatives represented by Structural Formulae (100) to (203) and dibenzothiophene derivatives represented by Structural Formulae (300) to (400).

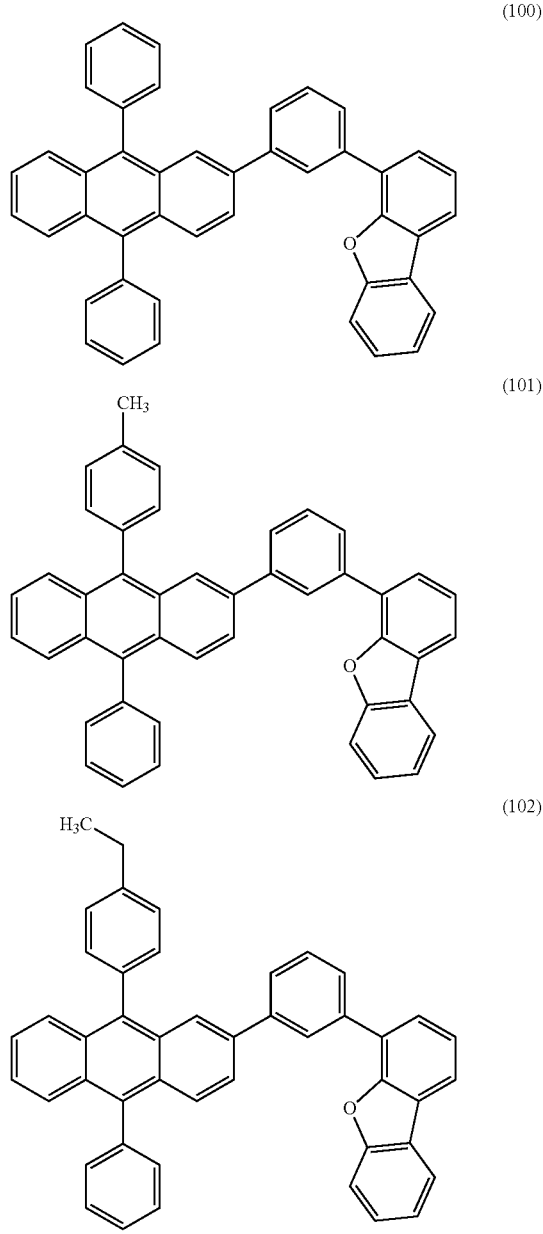

(100)

(101)

(102)

(103)
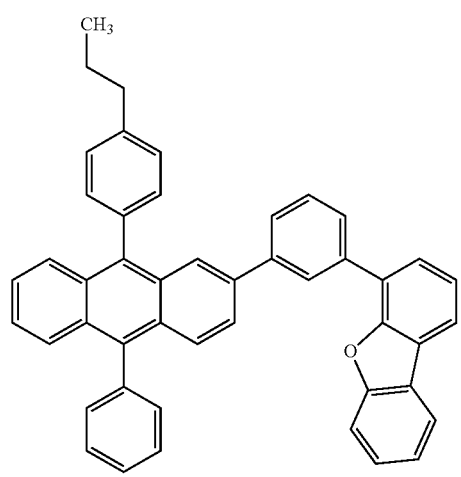
(106)
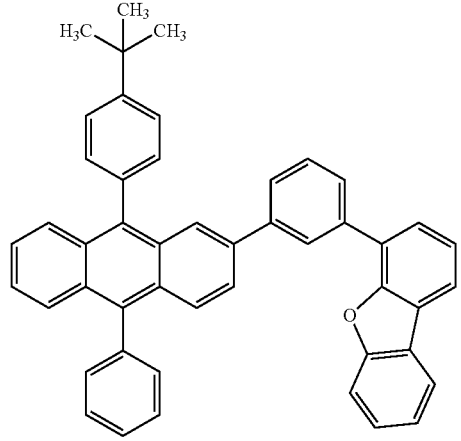
(104)
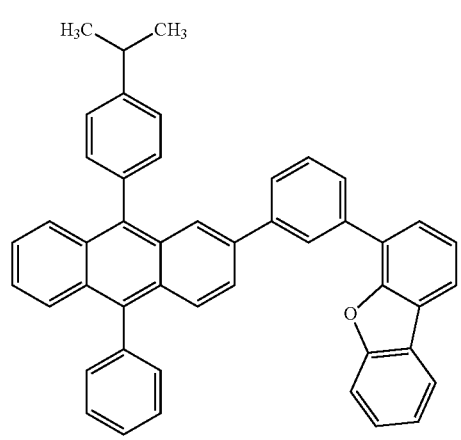
(107)
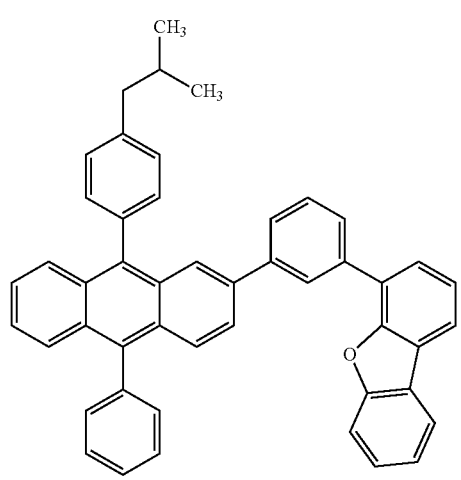
(105)
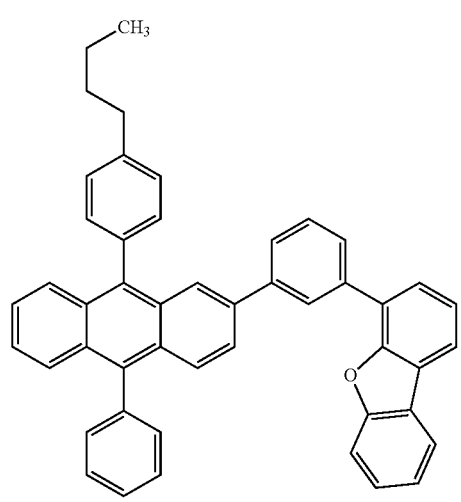
(108)
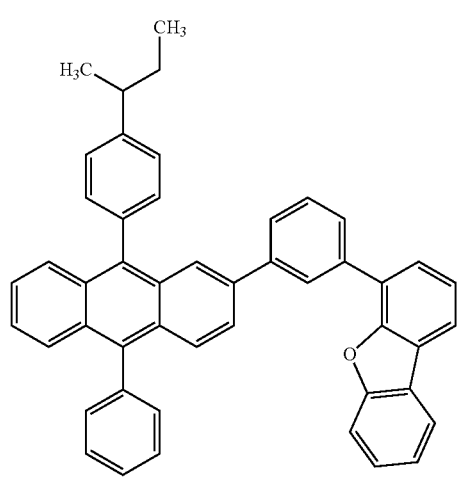

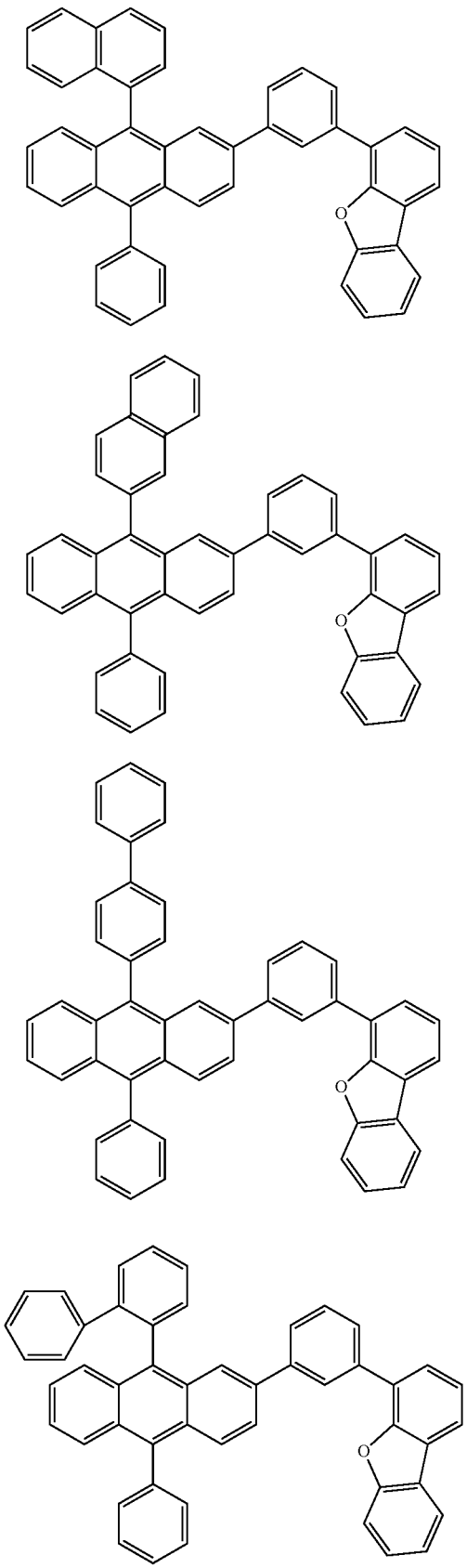
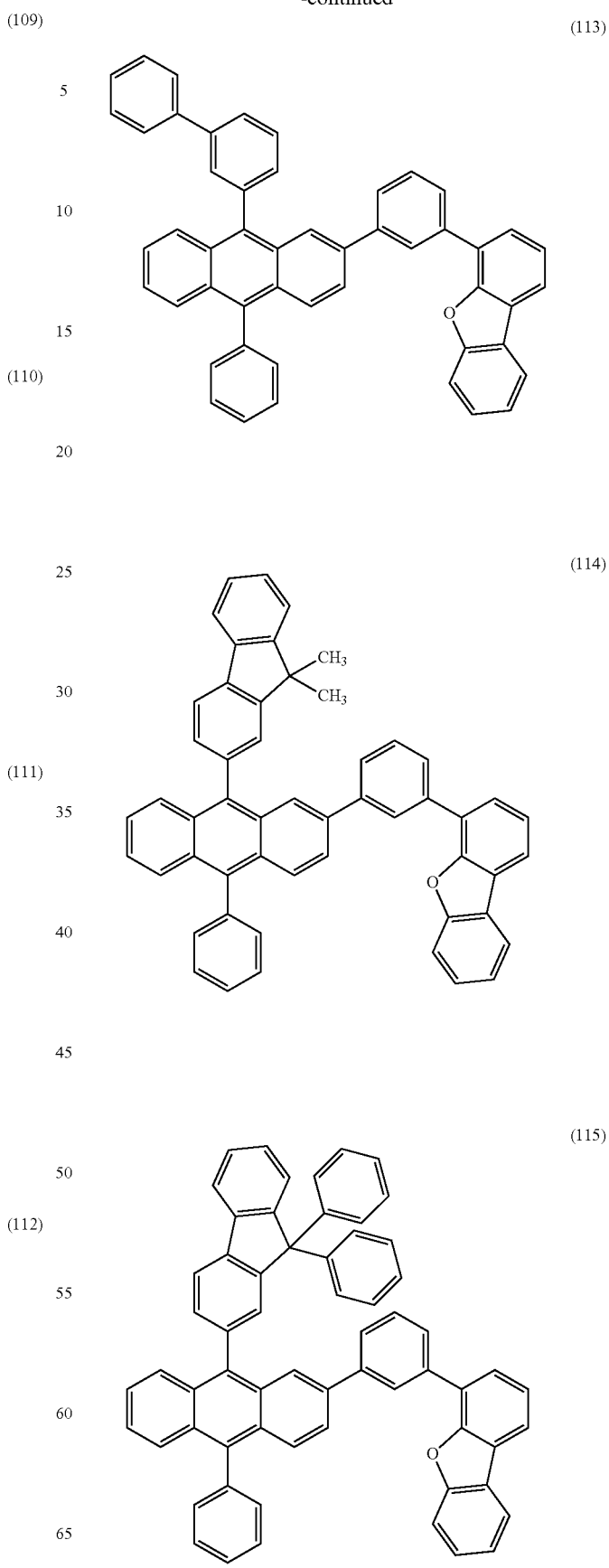

-continued
(116)
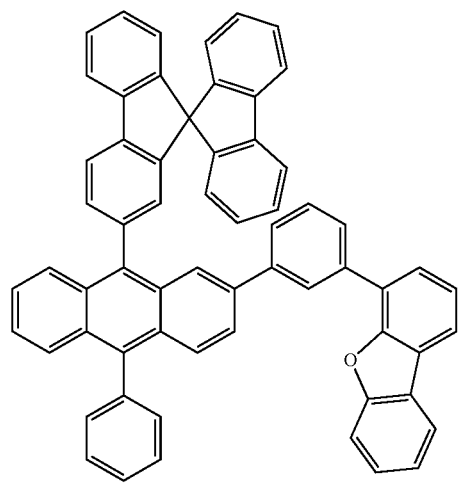
(117)
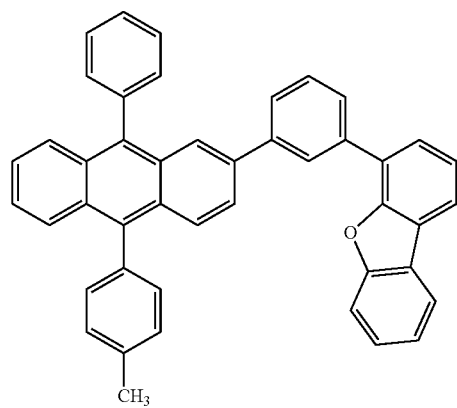
(118)
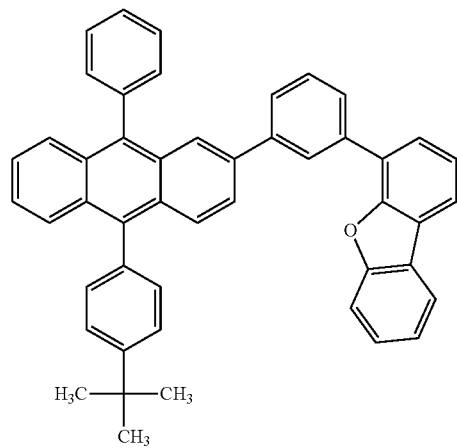
-continued
(119)
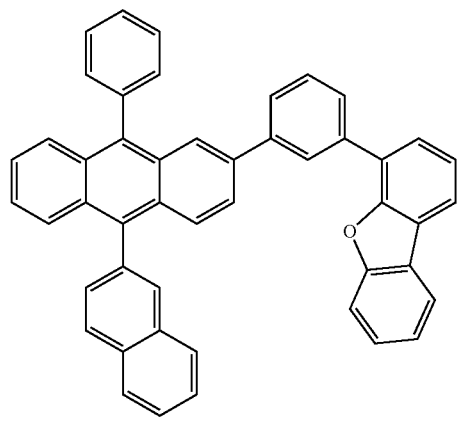
(120)
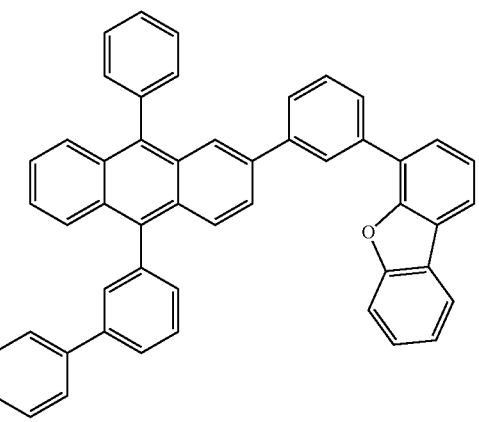
(121)
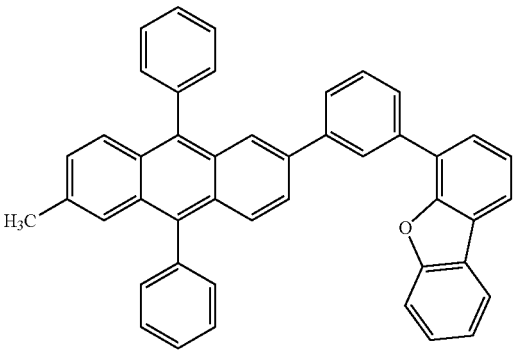
(122)
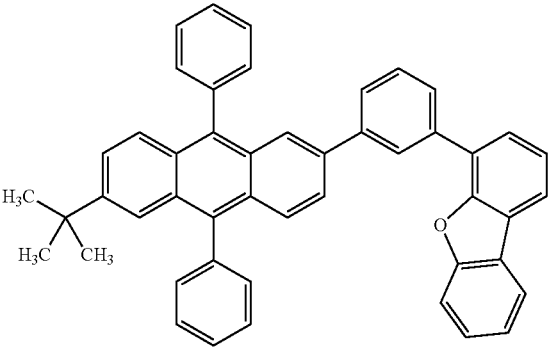

-continued
(123)
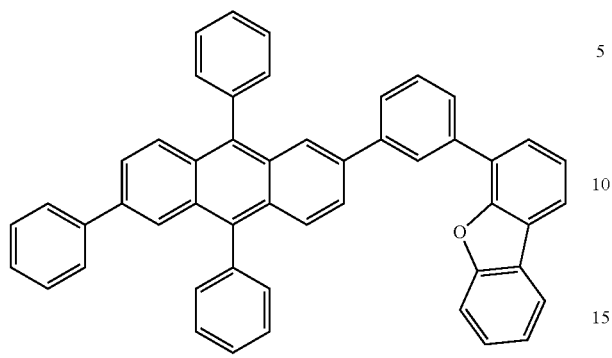
(124)
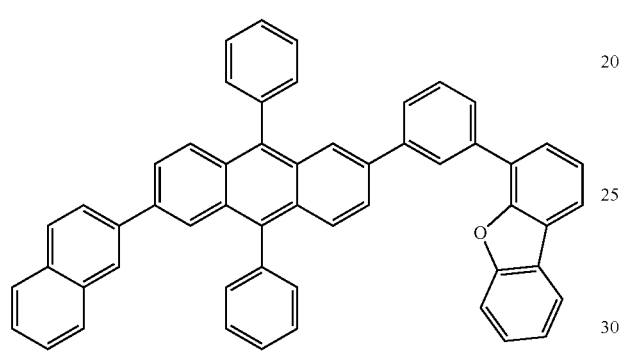
(125)
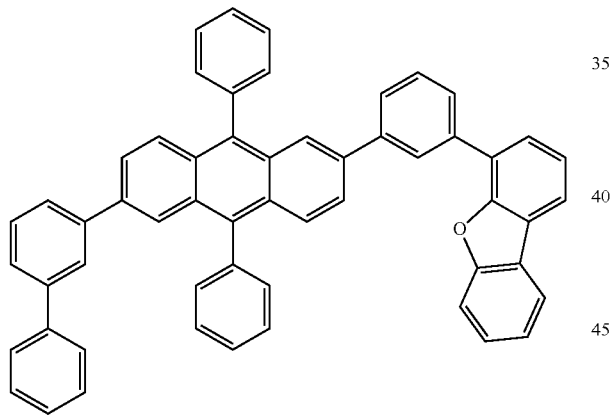
(126)
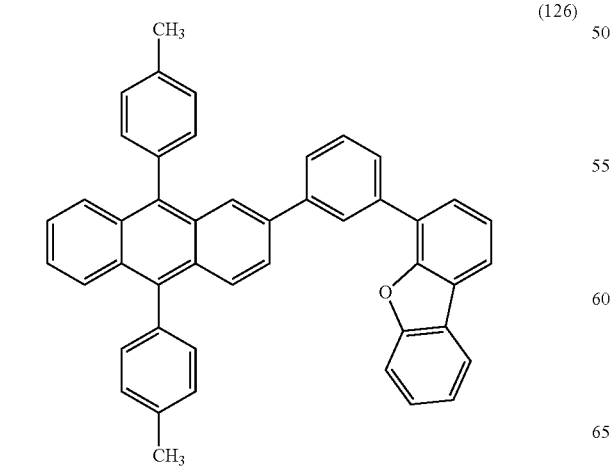
(127)
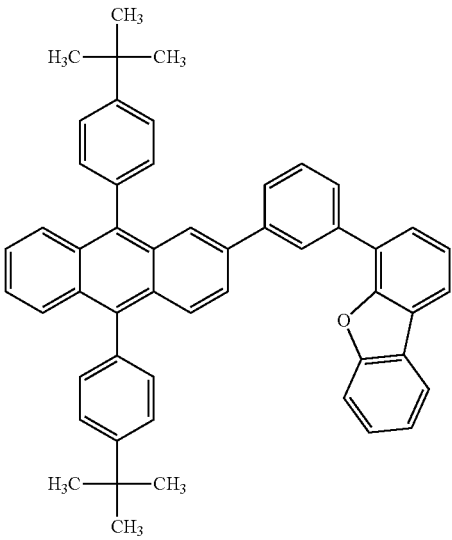
(128)
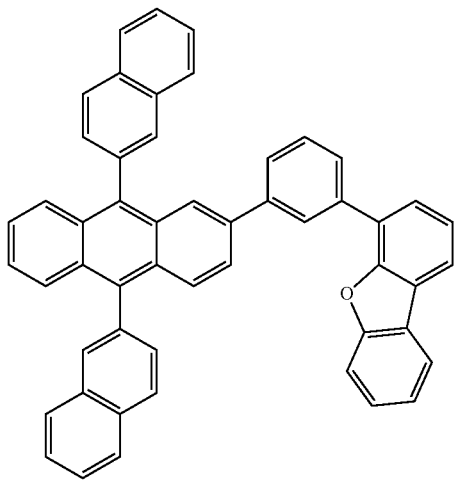
(129)
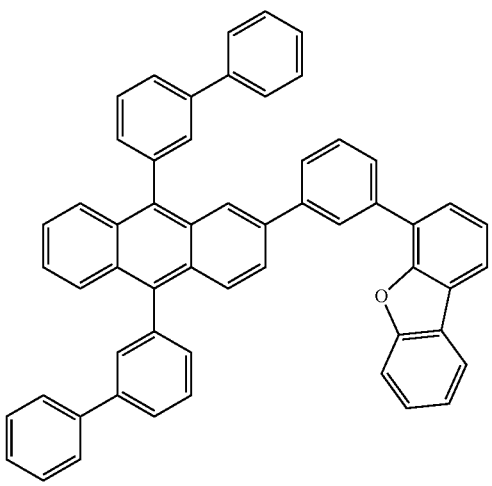

(130)
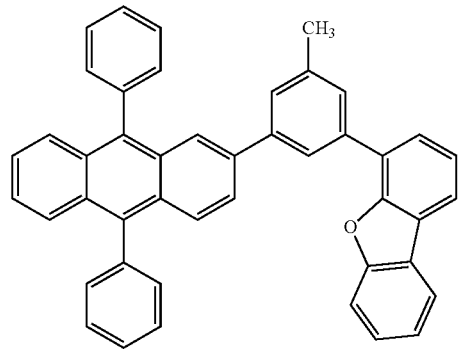
(131)
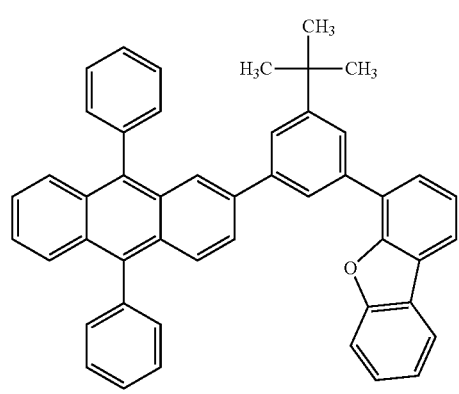
(132)
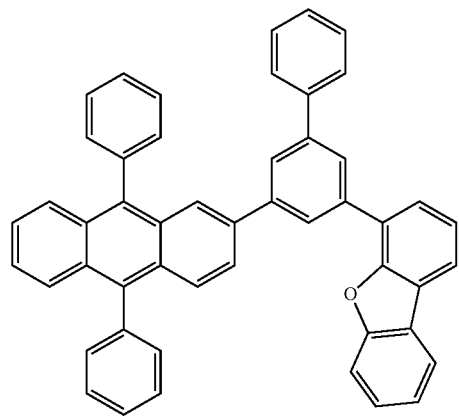
(133)
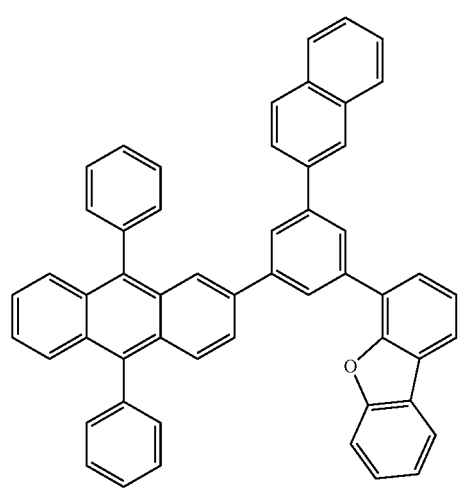
(134)
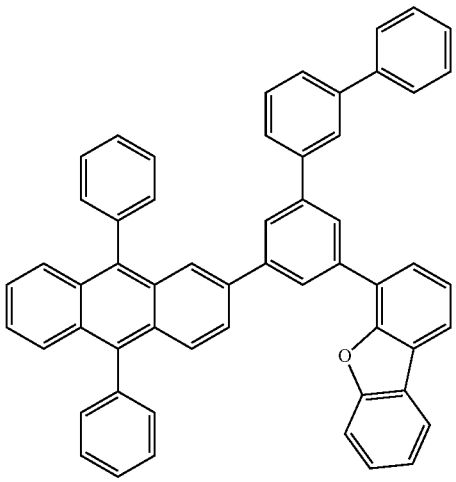
(135)
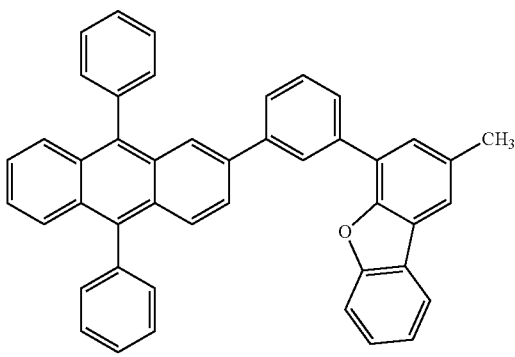
(136)
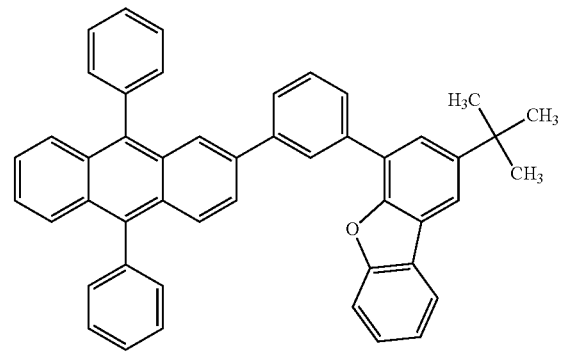
(137)
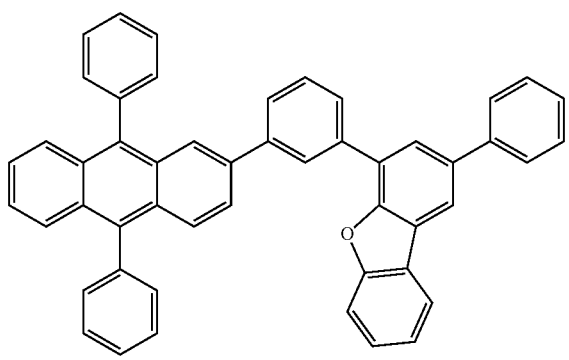

(138)
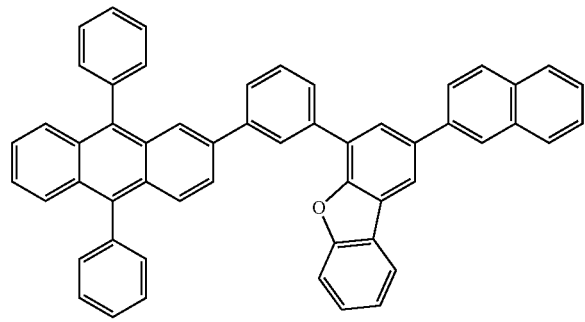
(139)
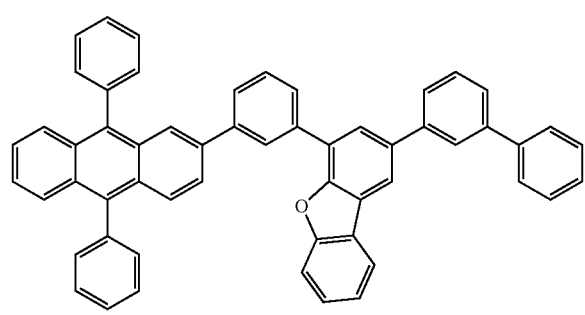
(140)
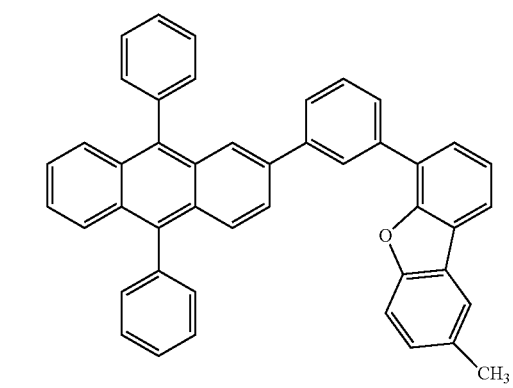
(141)
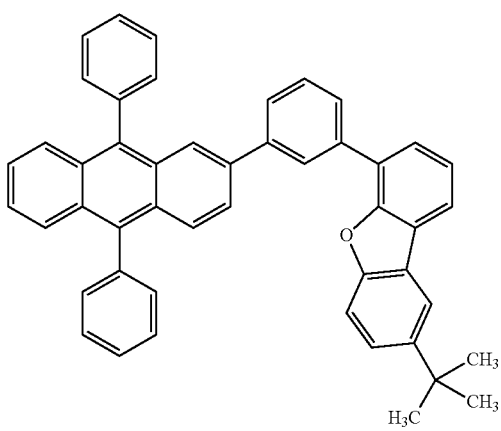
(142)
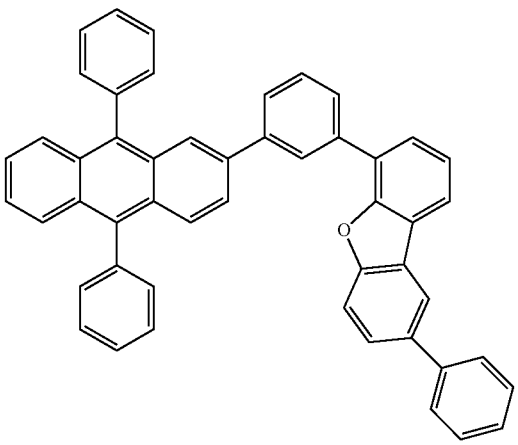
(143)
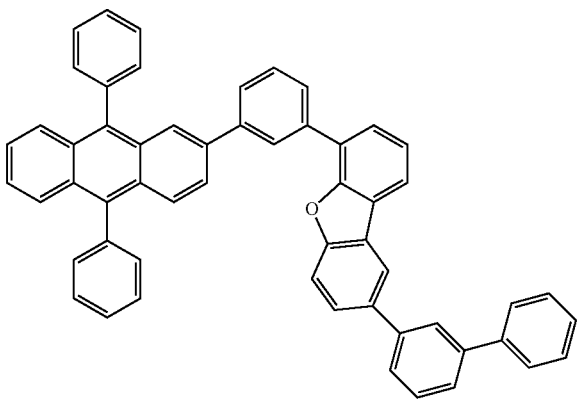
(144)

(145)
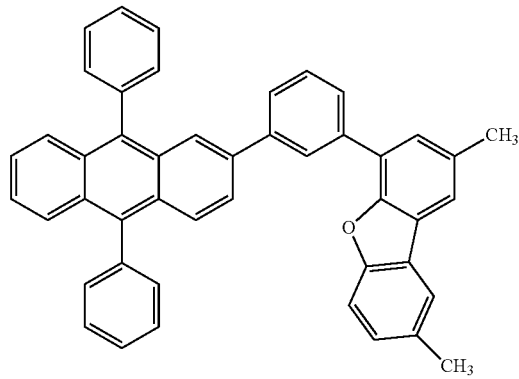
(146)
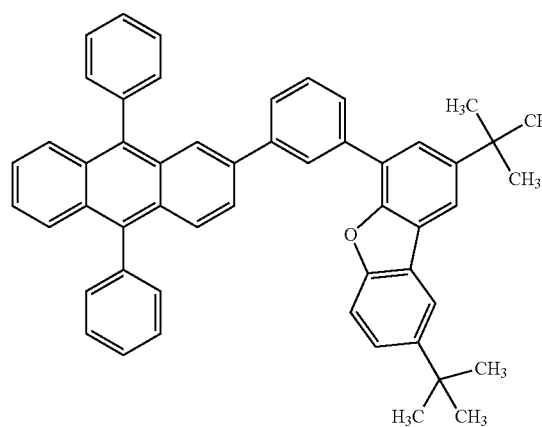
(147)
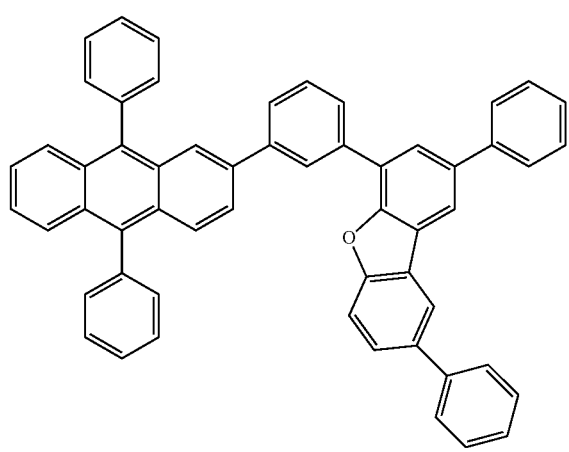
(148)
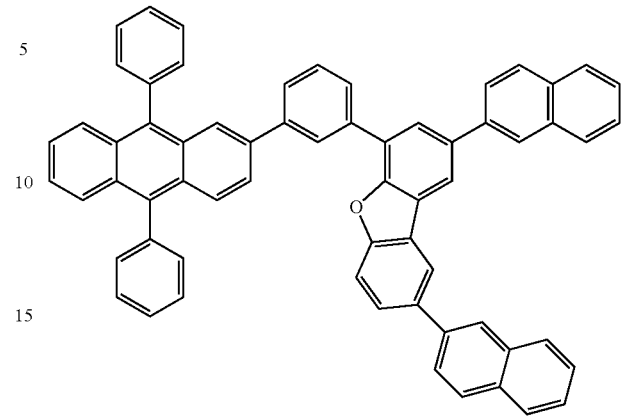
(149)
(150)
(151)
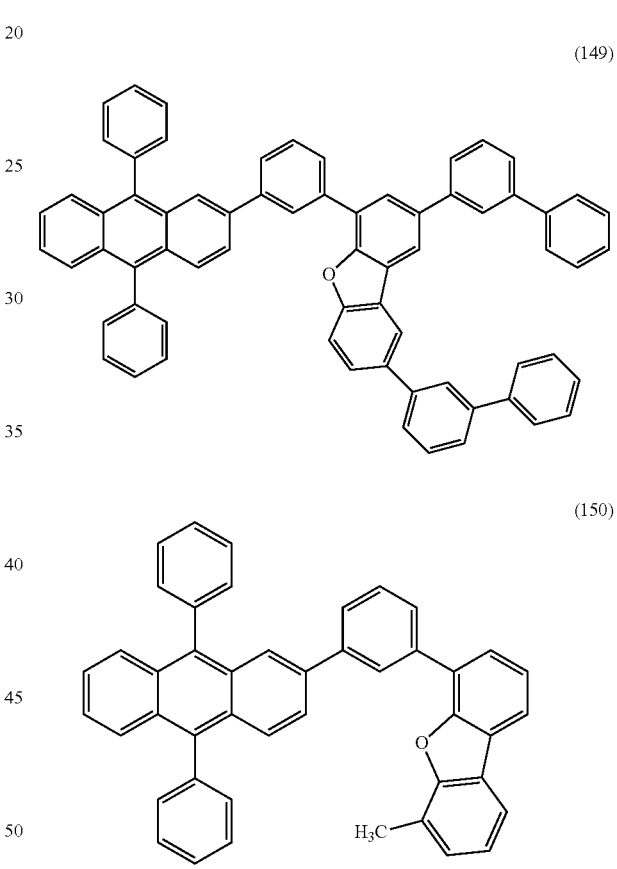
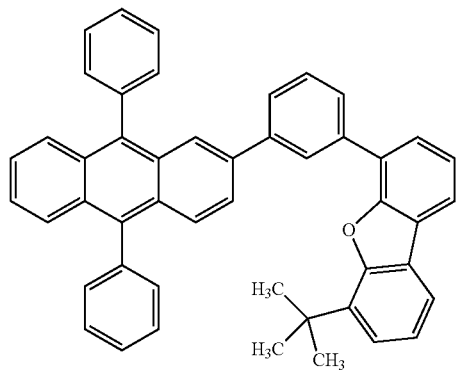

(152)
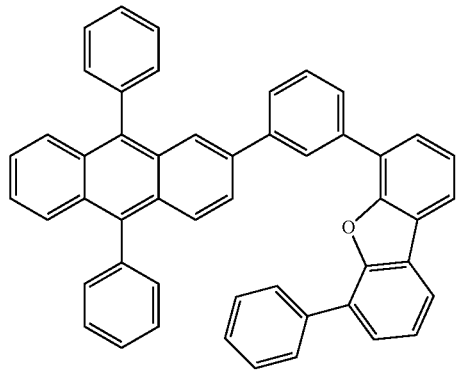
(153)
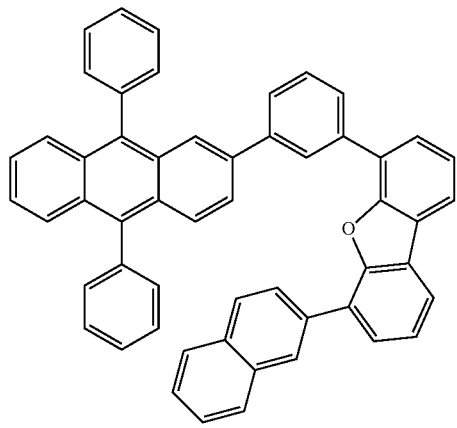
(154)
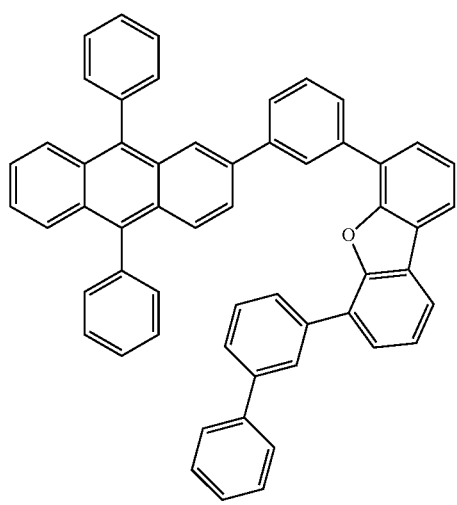
(155)
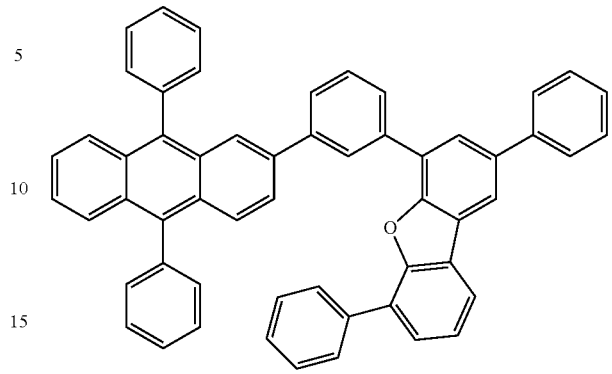
(156)
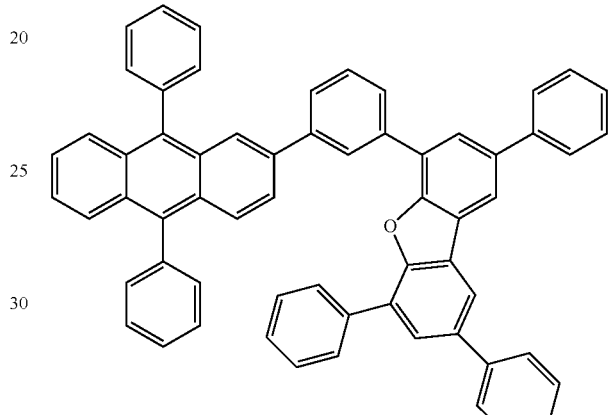
(157)
(158)
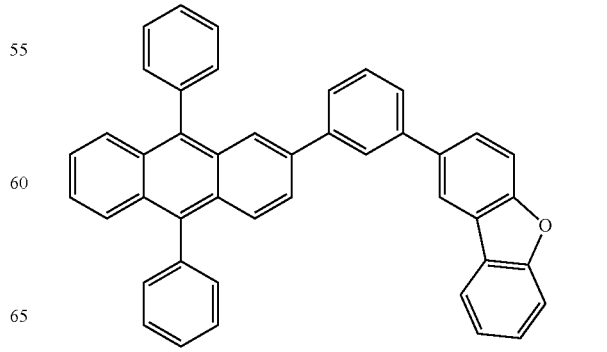

-continued
(159)
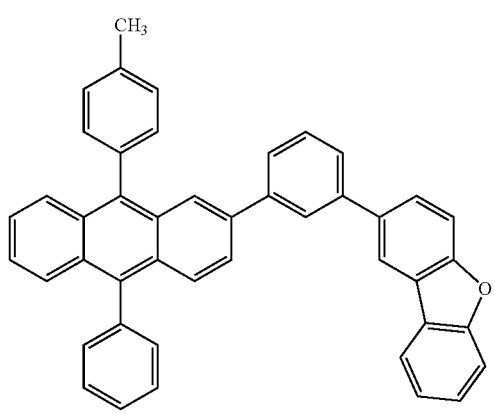
(160)
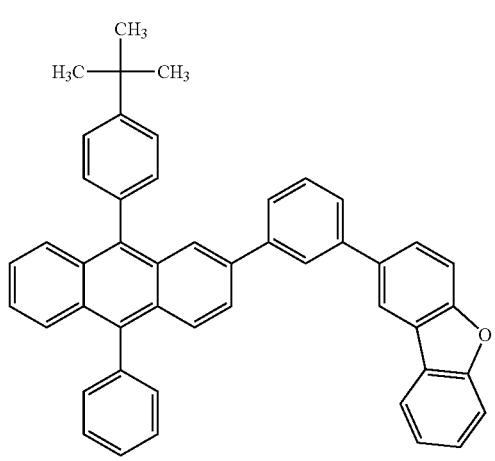
(161)
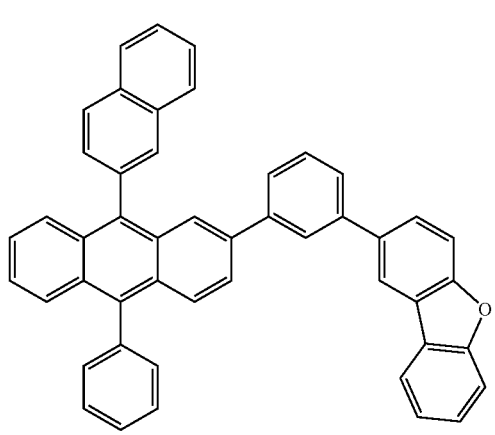
-continued
(162)
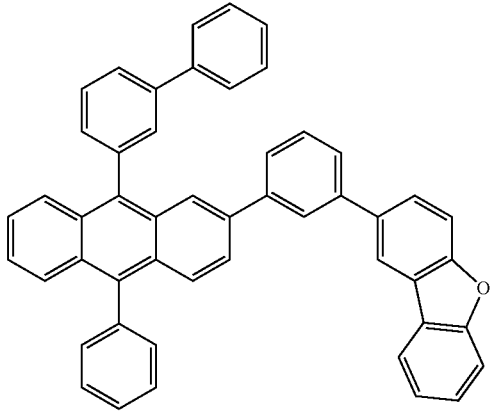
(163)
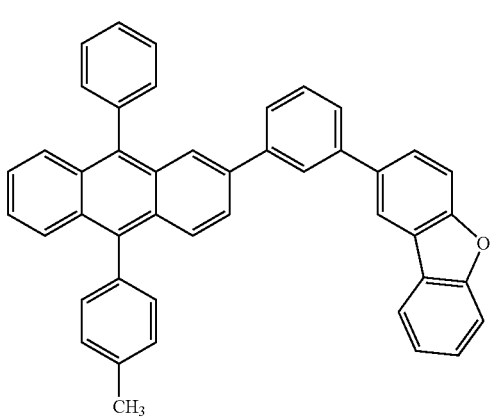
(164)
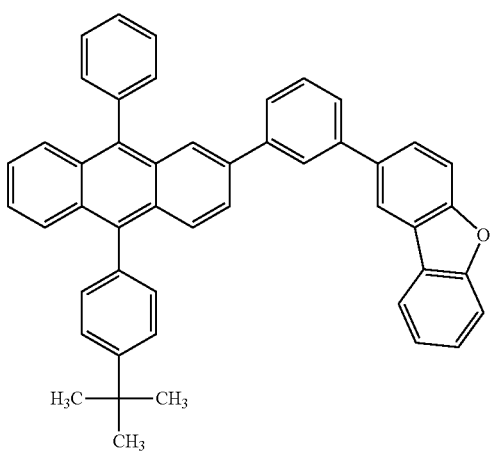

(165)
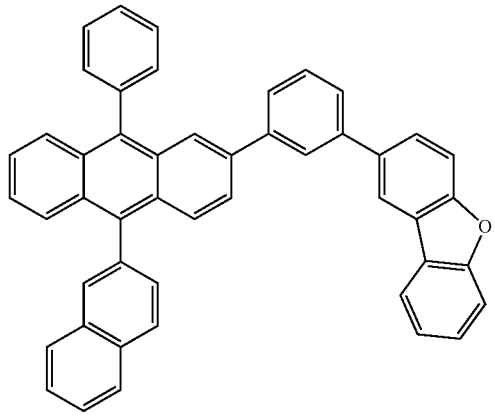
(166)
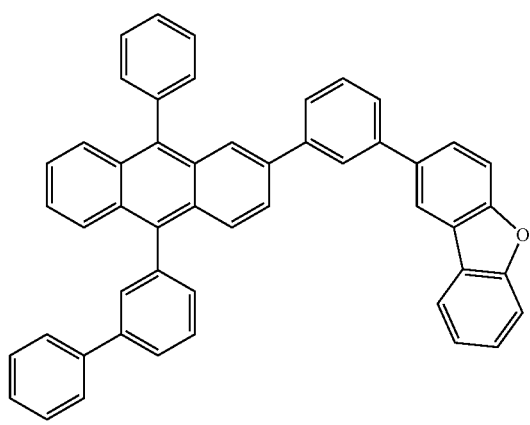
(167)
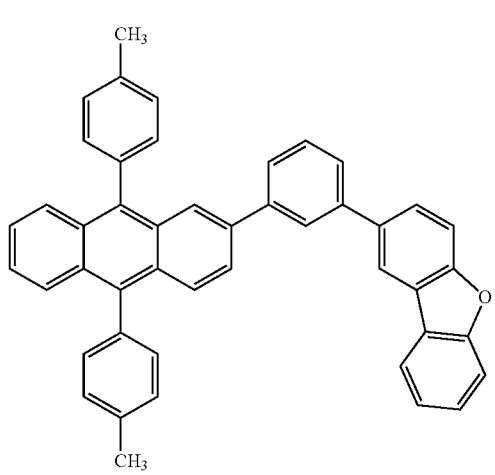
(168)
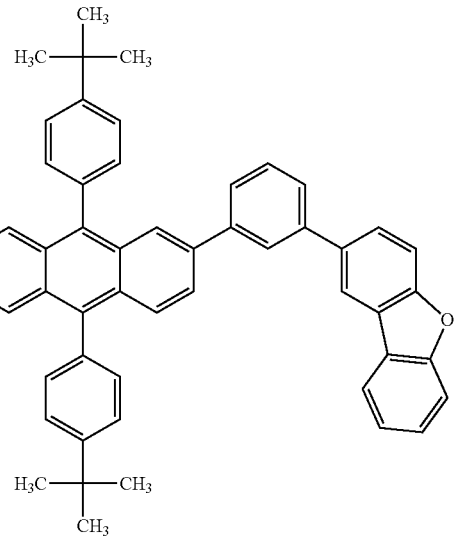
(169)
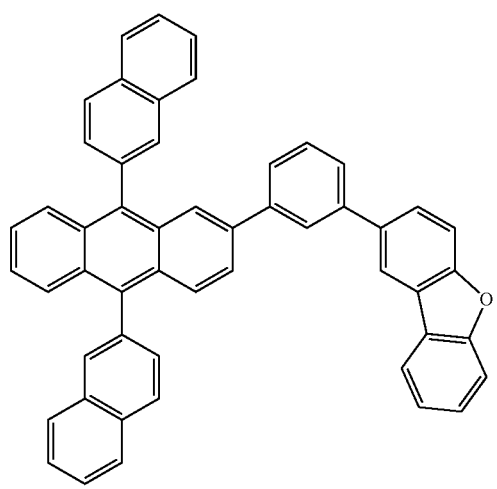
(170)
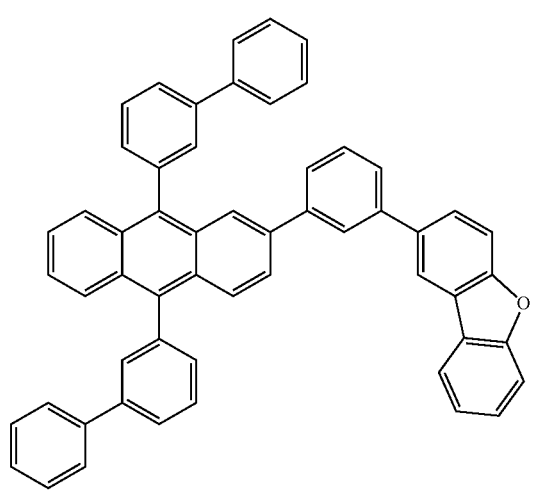

(171) 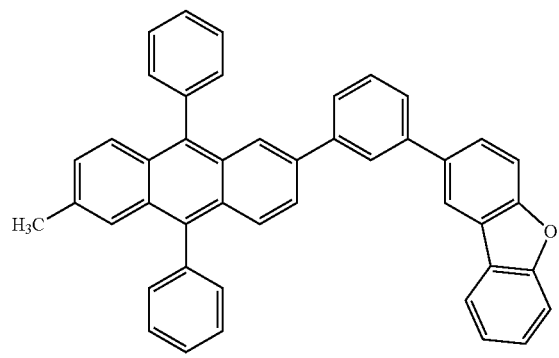
(172) 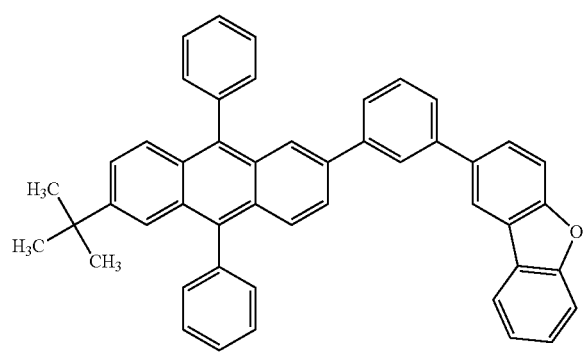
(173) 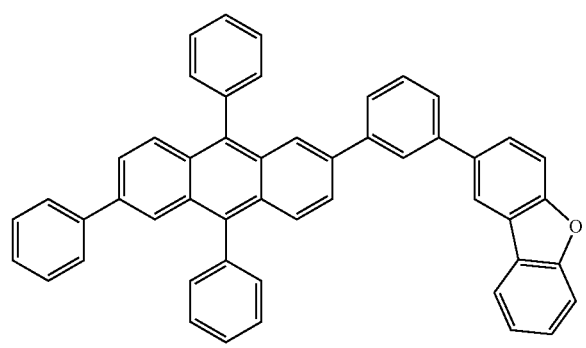
(174) 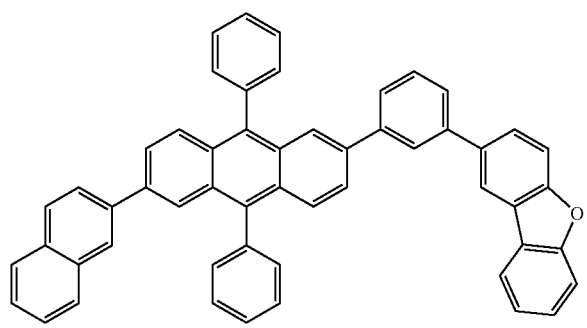
(175) 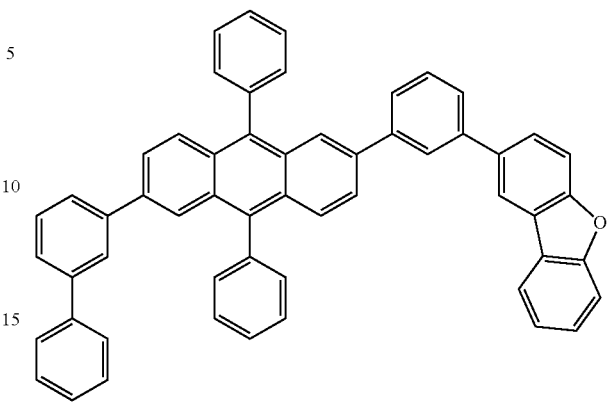
(176) 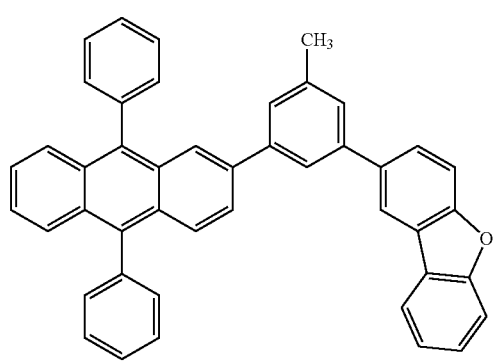
(177) 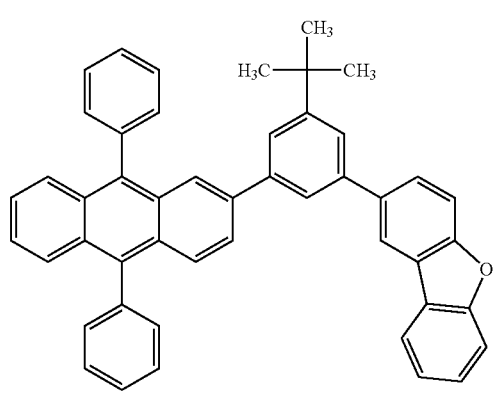
(178) 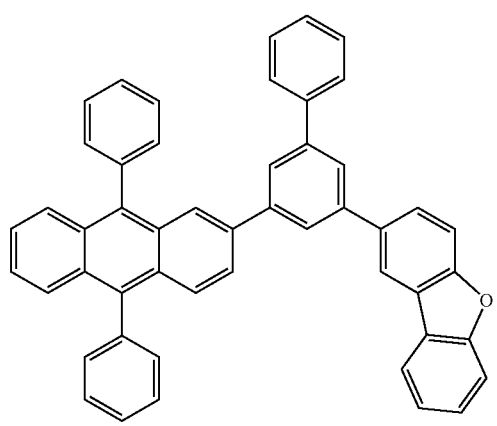

(179)
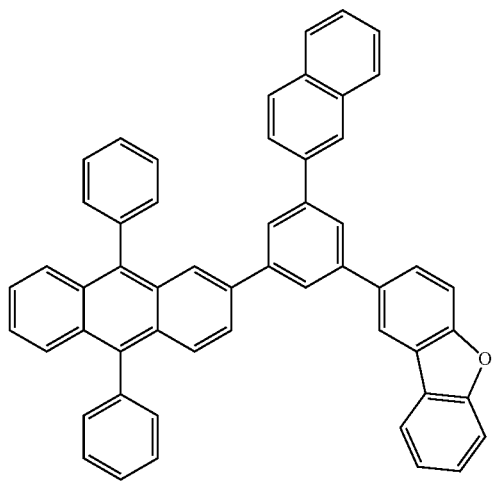
(180)
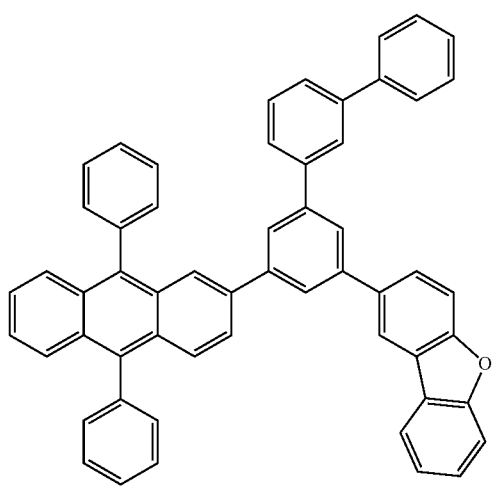
(181)
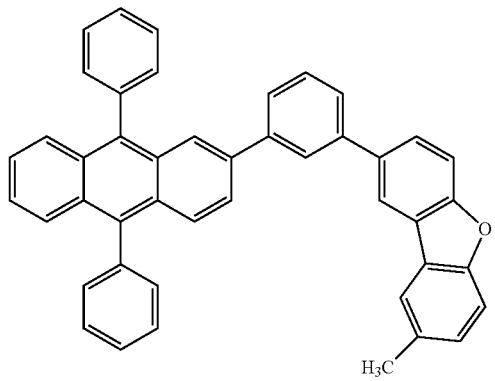
(182)
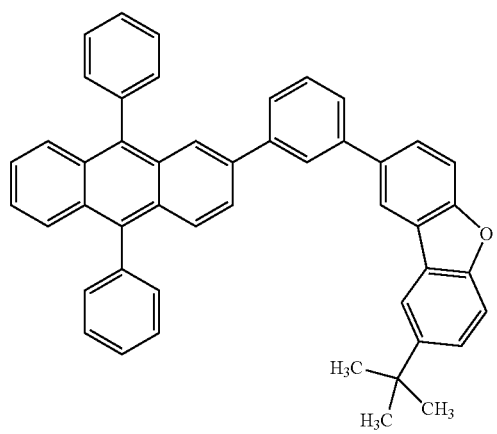
(183)
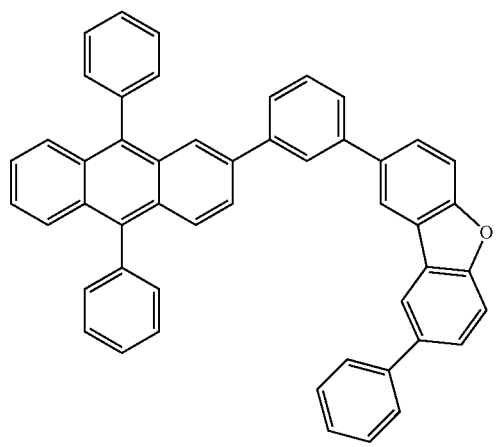
(184)
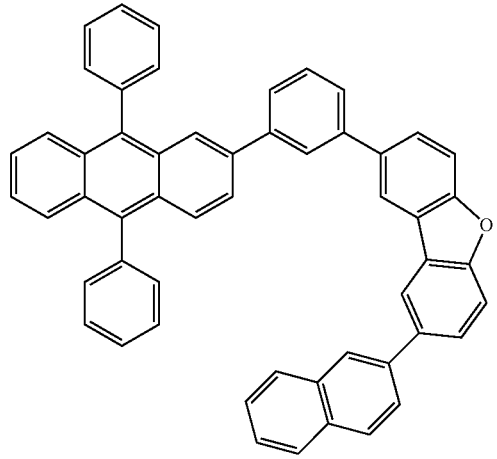

(185)
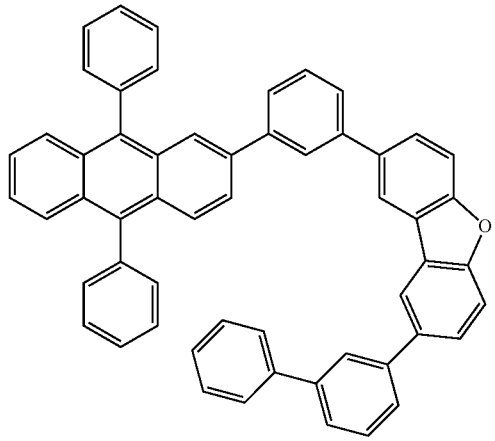
(186)
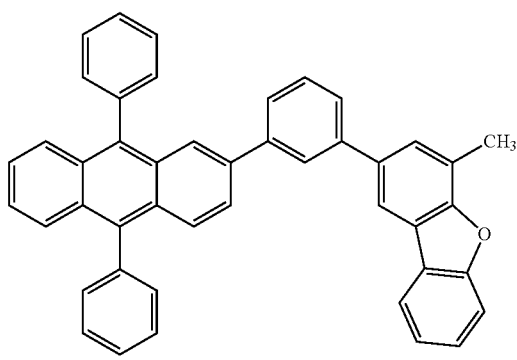
(187)
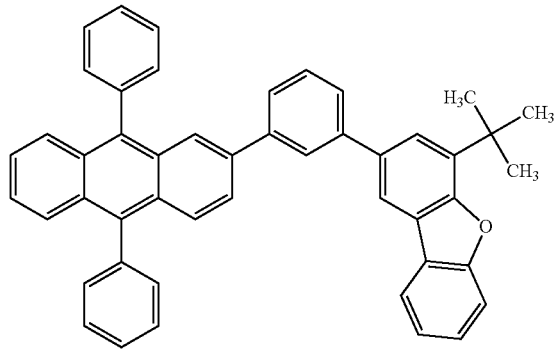
(188)
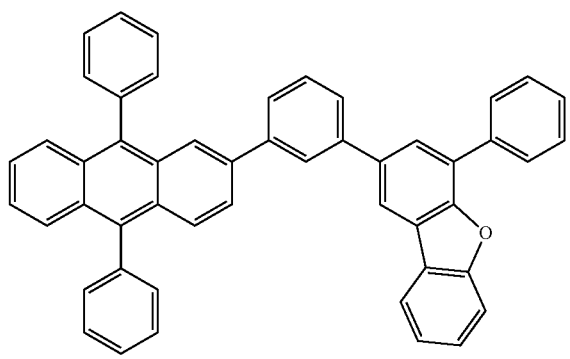
(189)
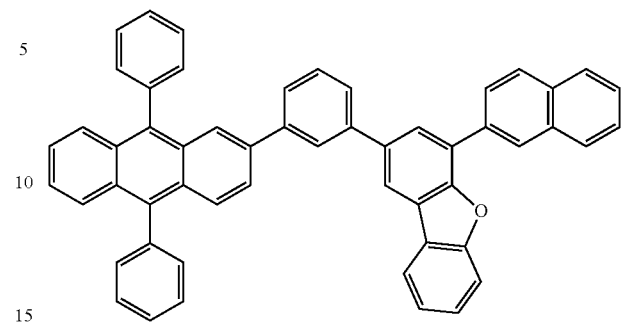
(190)
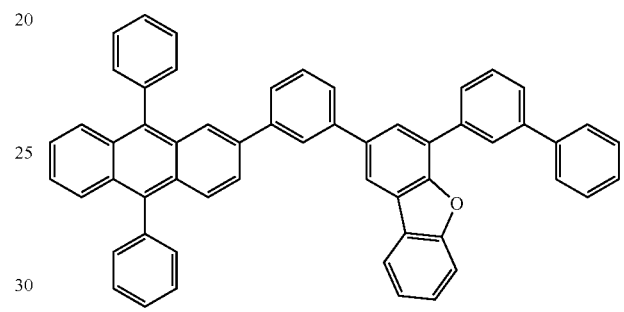
(191)
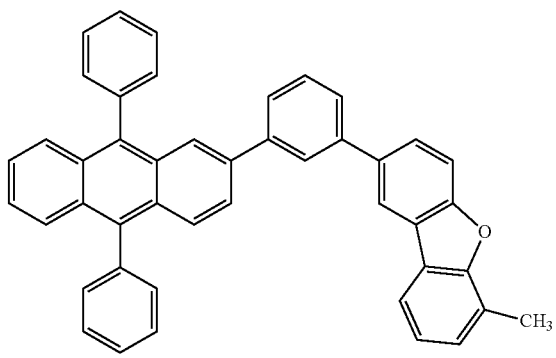
(192)
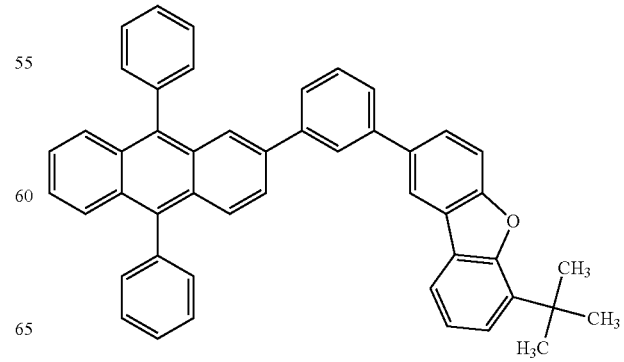

(193)
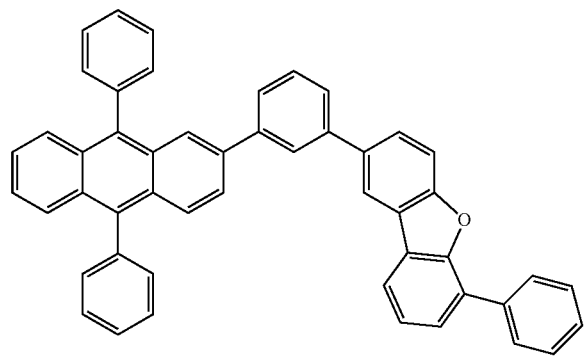
(194)
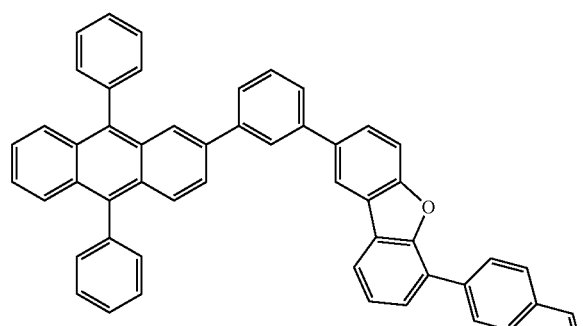
(195)
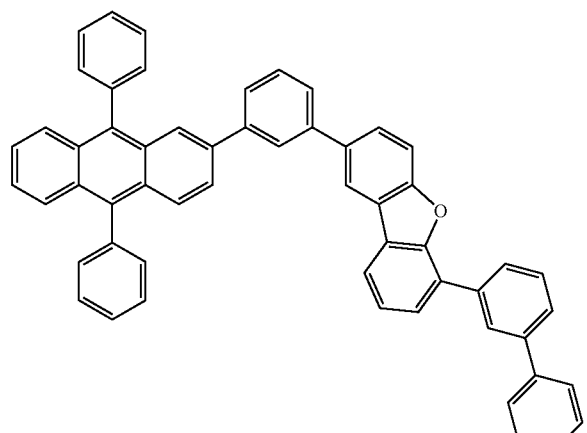
(196)
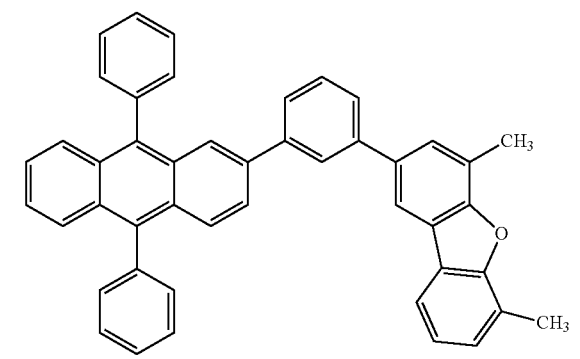
(197)
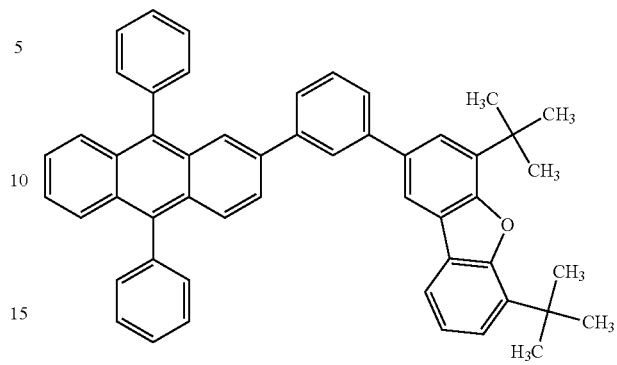
(198)
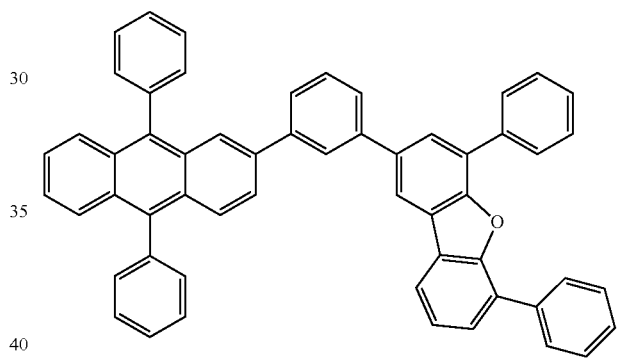
(199)
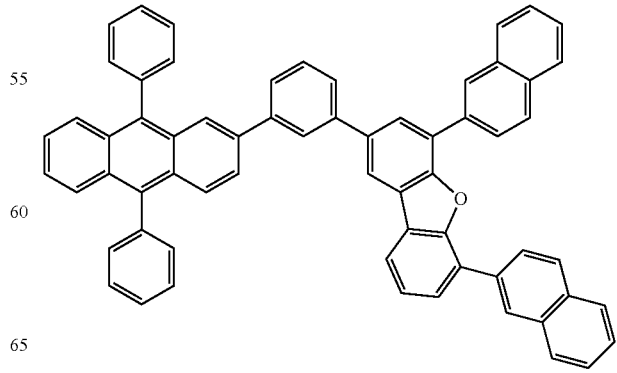

(200)
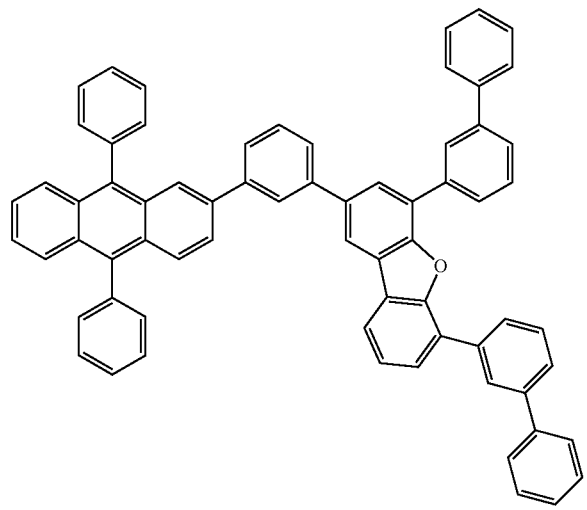
(201)
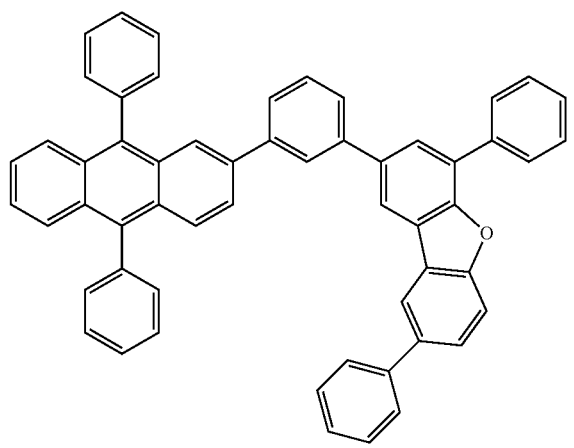
(202)
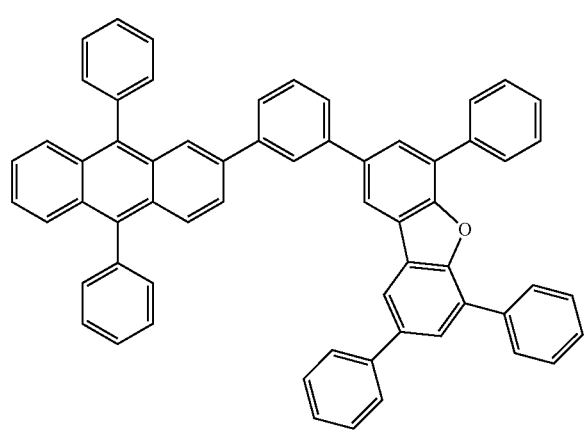
(203)
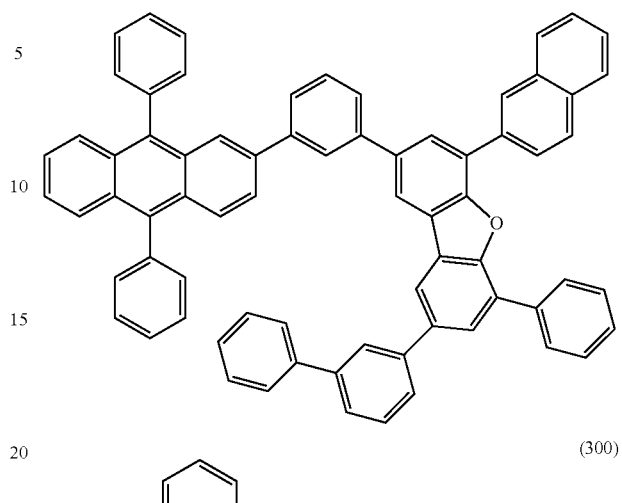
(300)
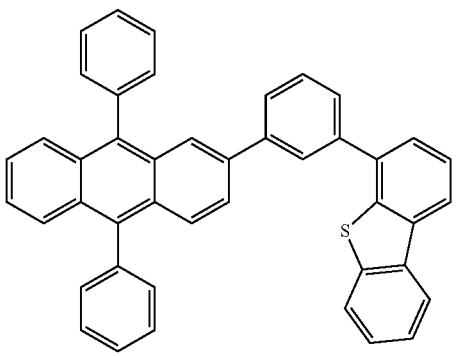
(301)
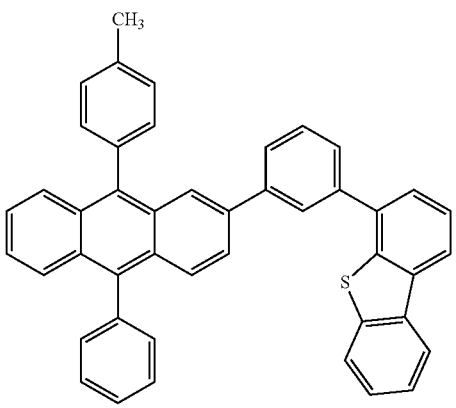
(302)
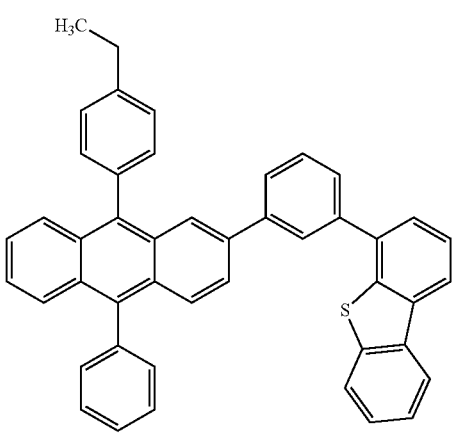

(303)
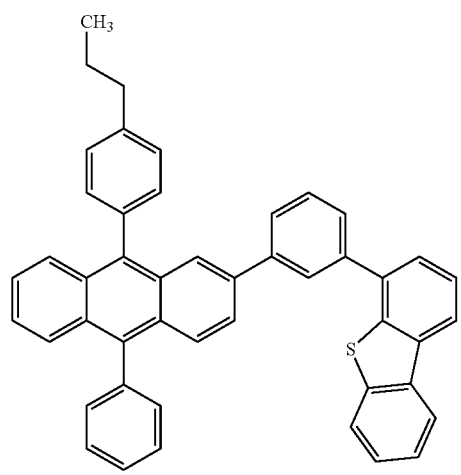
(304)
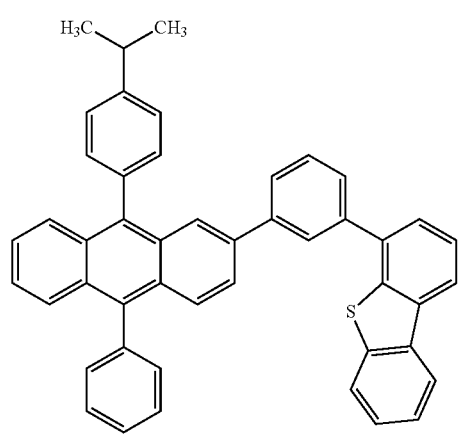
(305)
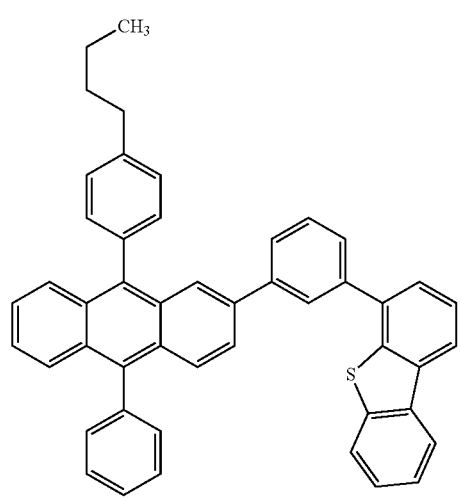
(306)
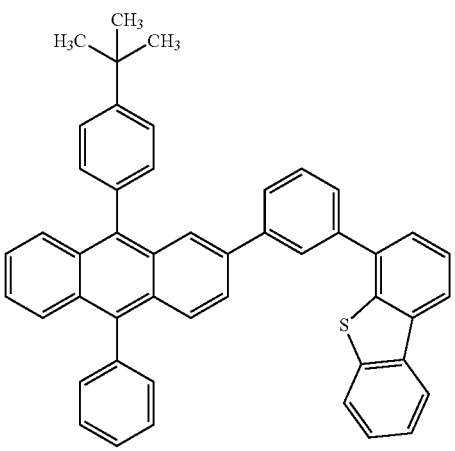
(307)
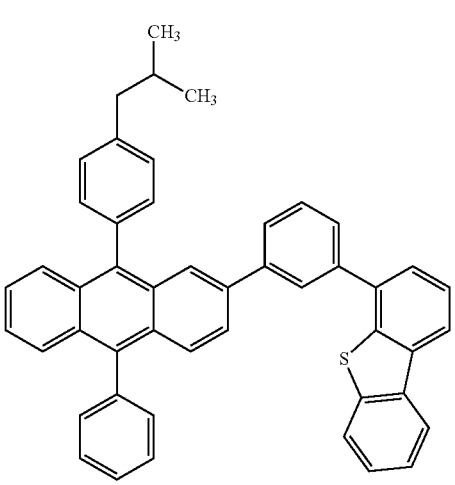
(308)
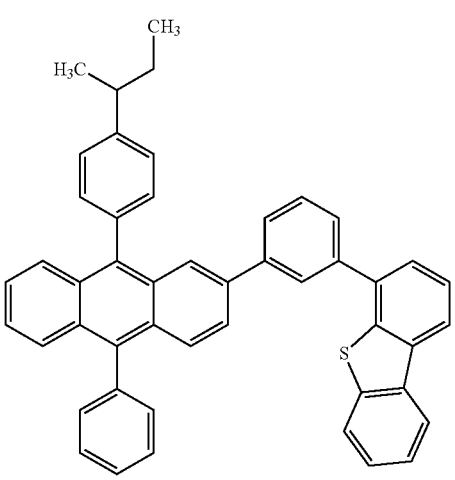

(309)
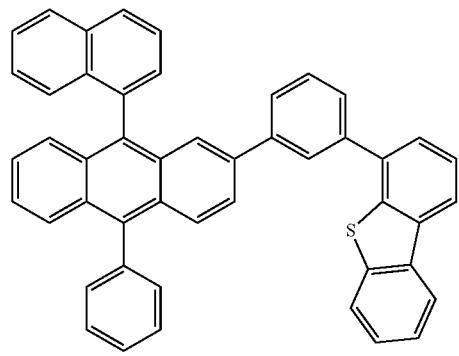
(310)
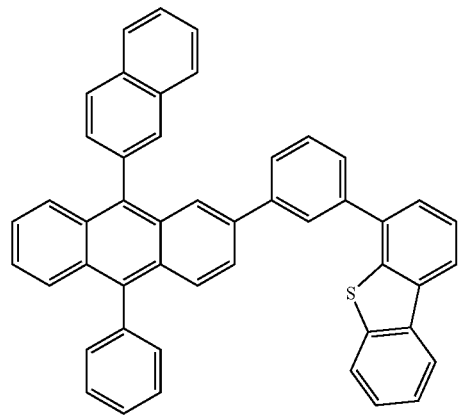
(311)
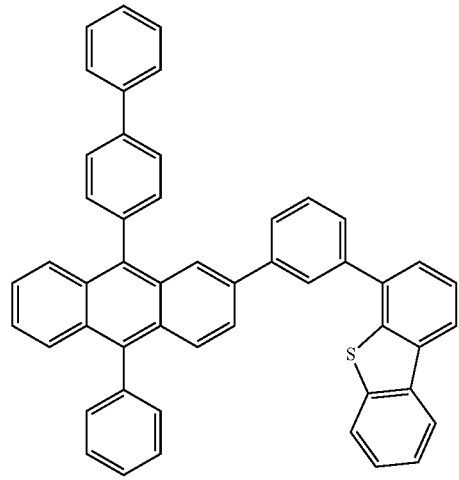
(312)
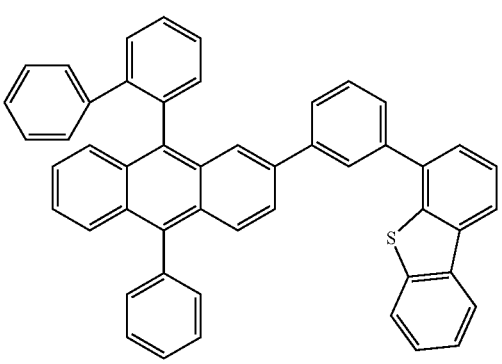
(313)
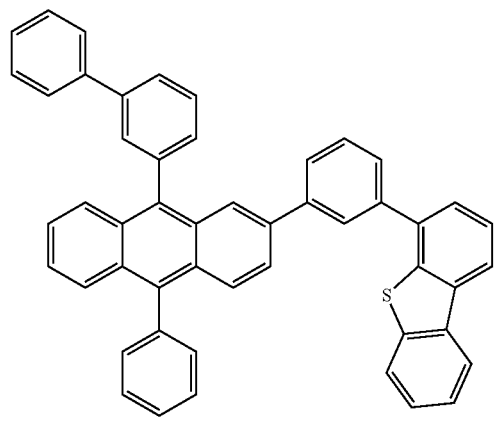
(314)
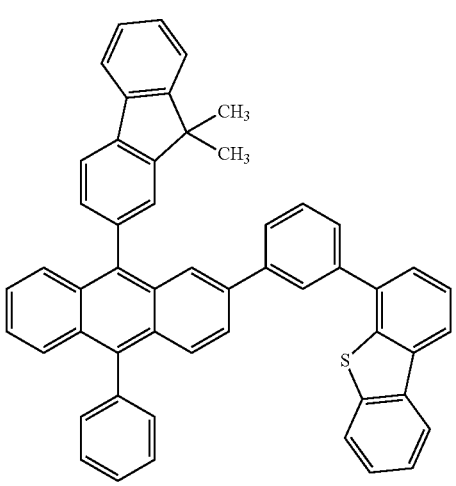
(315)

(316)
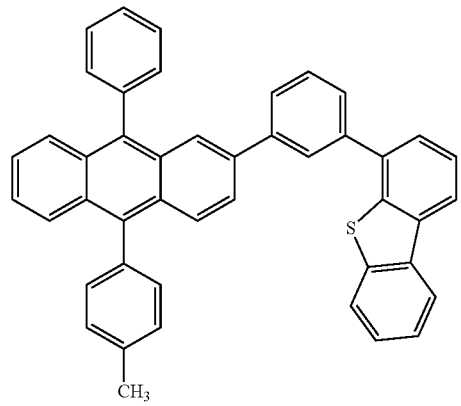
(317)
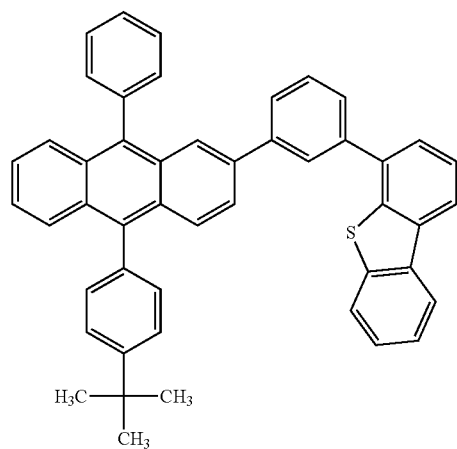
(318)
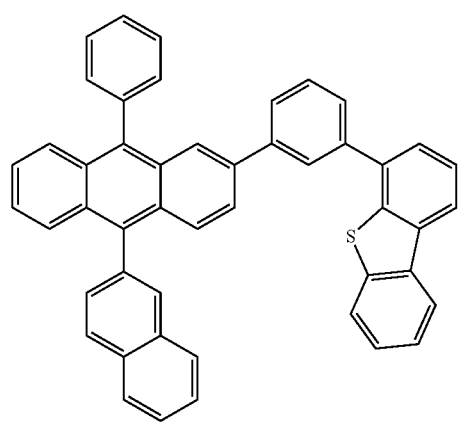
(319)
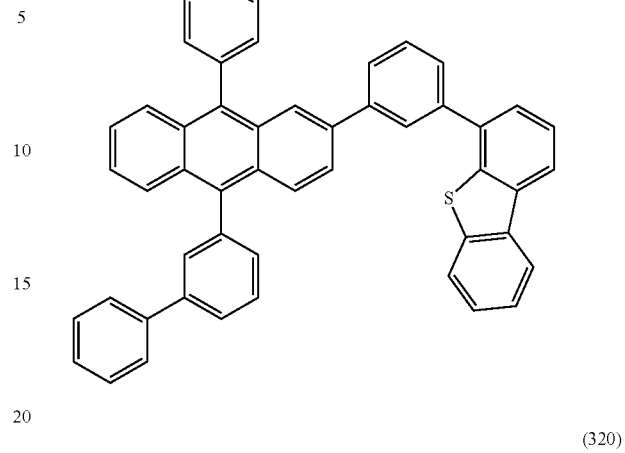
(320)
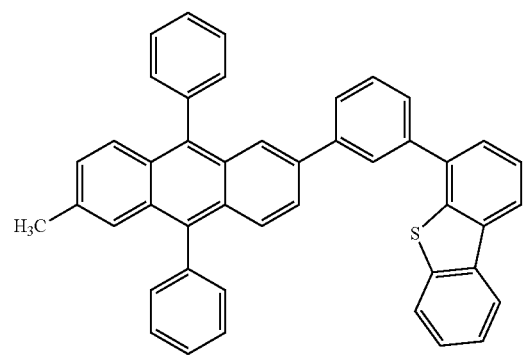
(321)
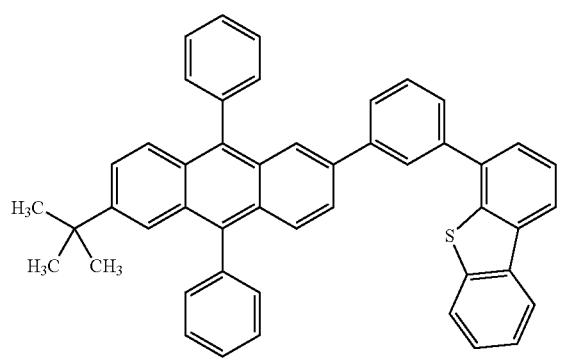
(322)
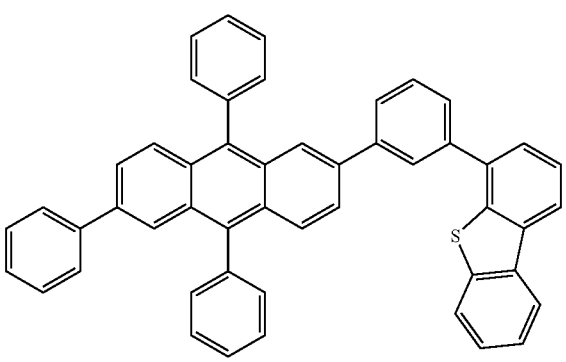

(323)
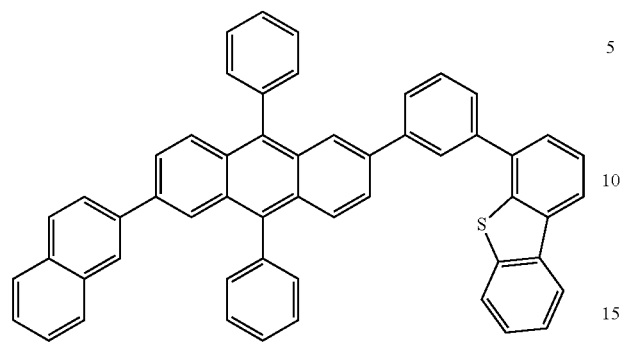
(324)
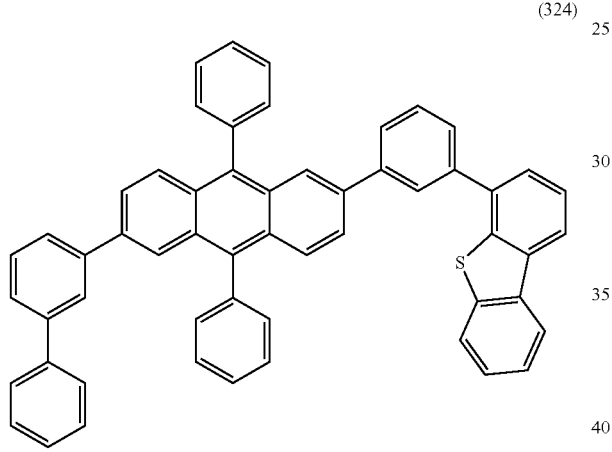
(325)
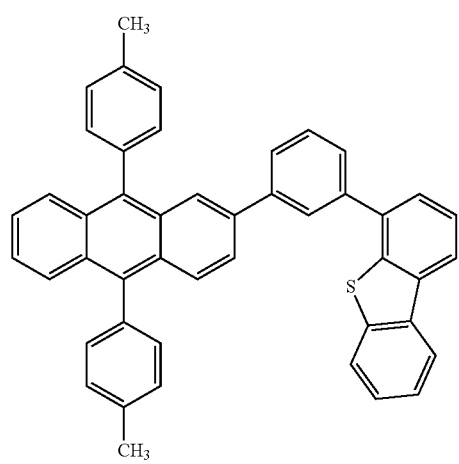
(326)
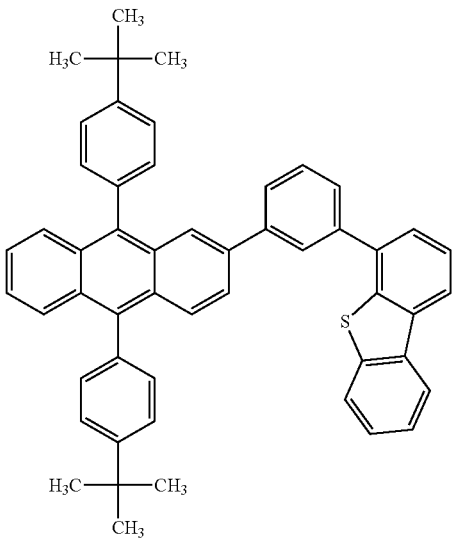
(327)
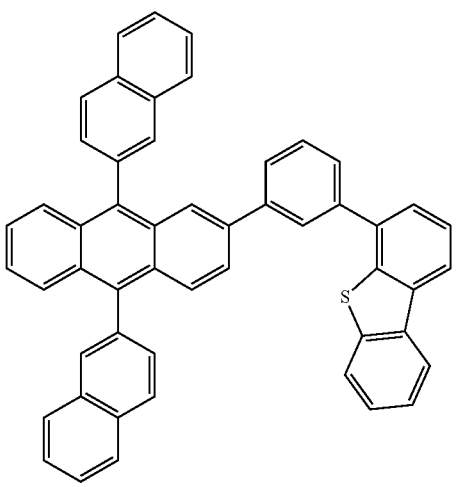
(328)
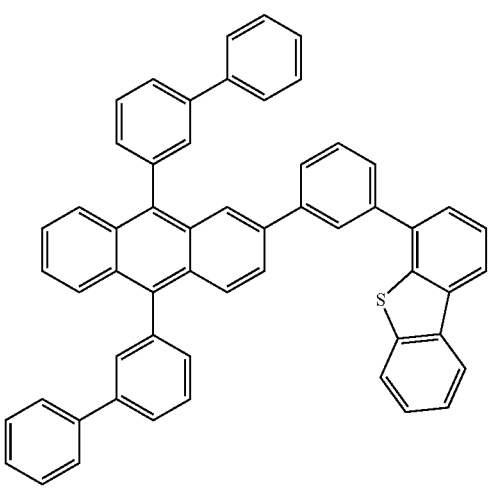

(329)
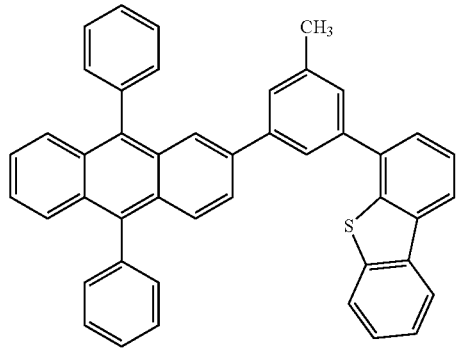
(330)
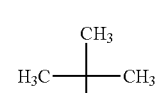
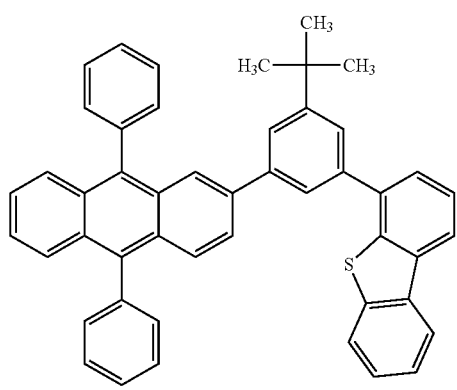
(331)
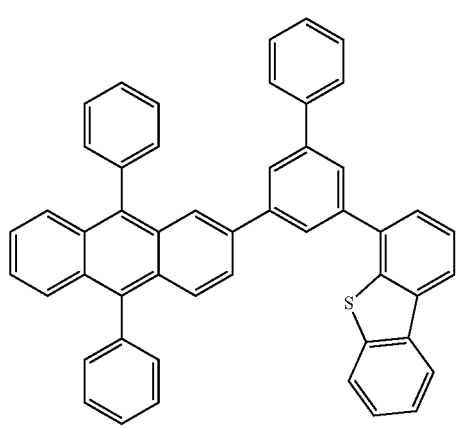
(332)
(333)
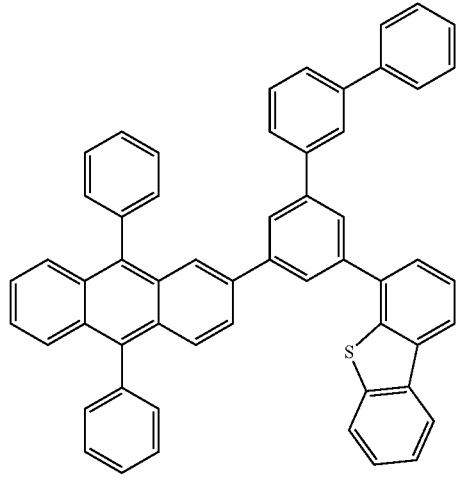
(334)
(335)
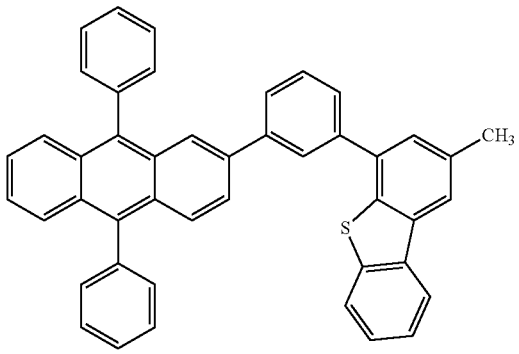
(336)
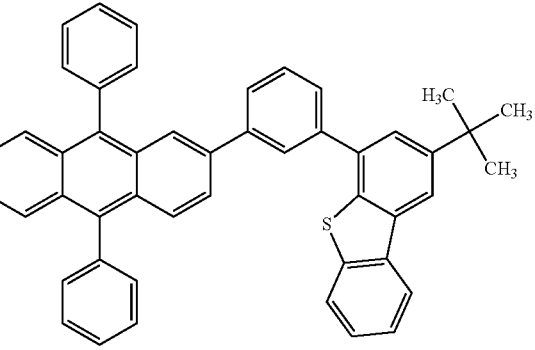
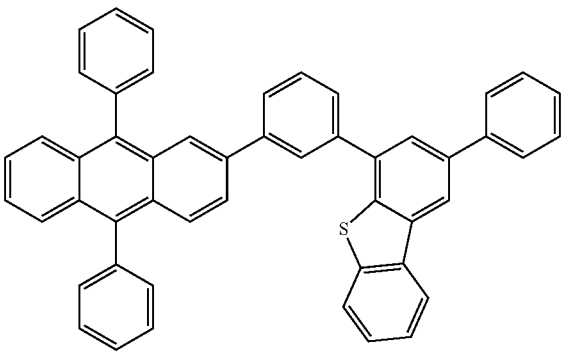

(337)
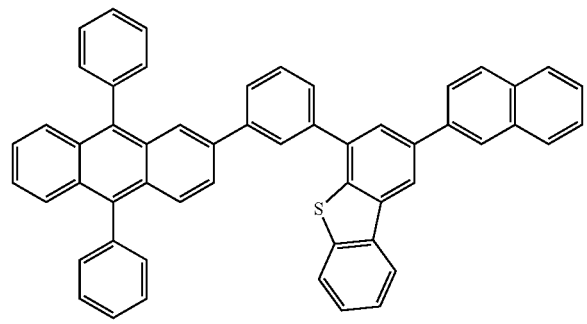
(338)
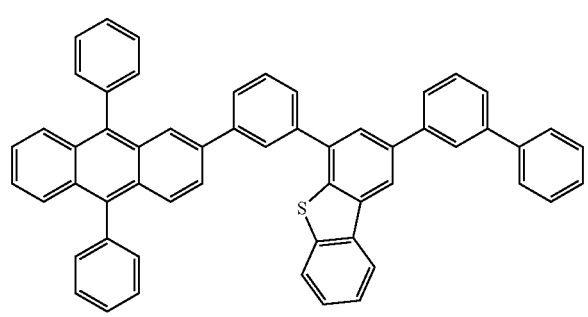
(339)
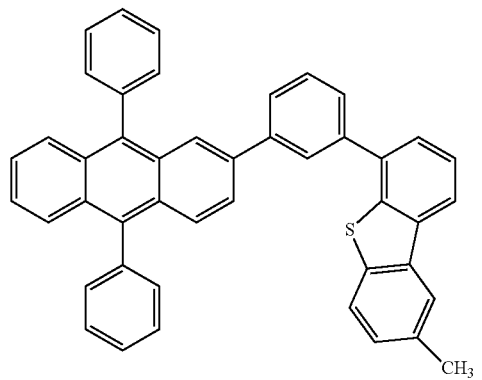
(340)
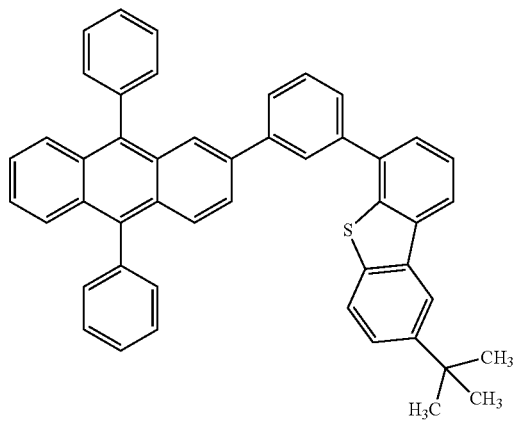
(341)
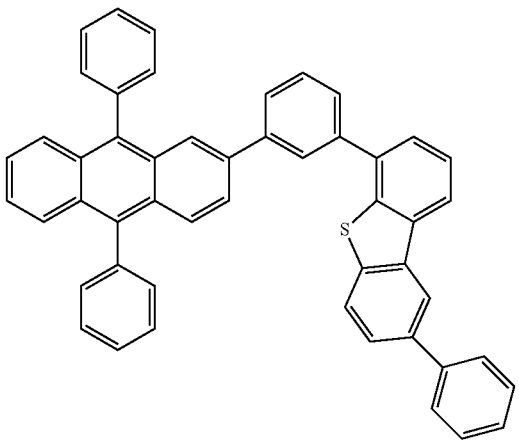
(342)
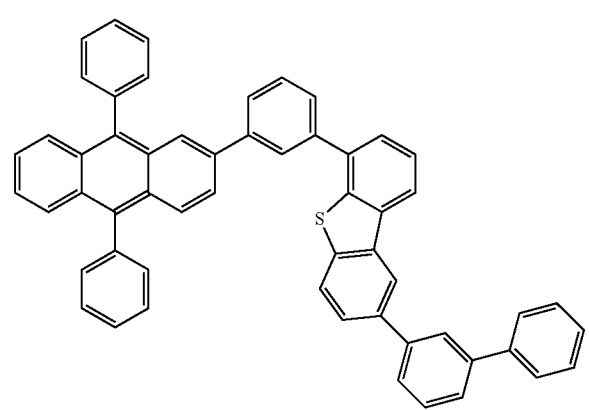
(343)

(344)
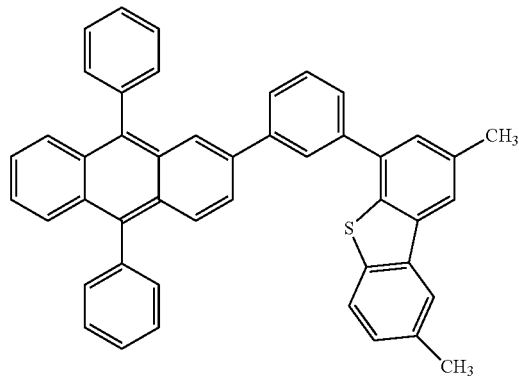
(345)
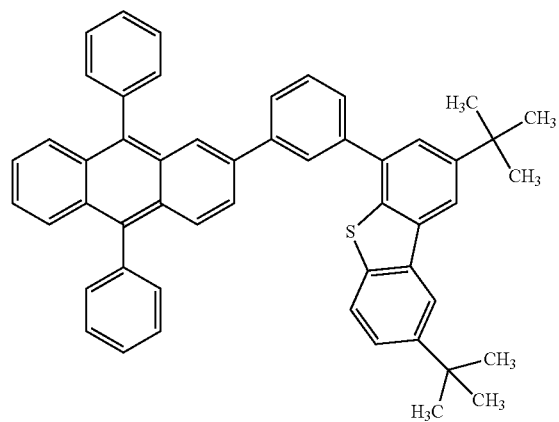
(346)
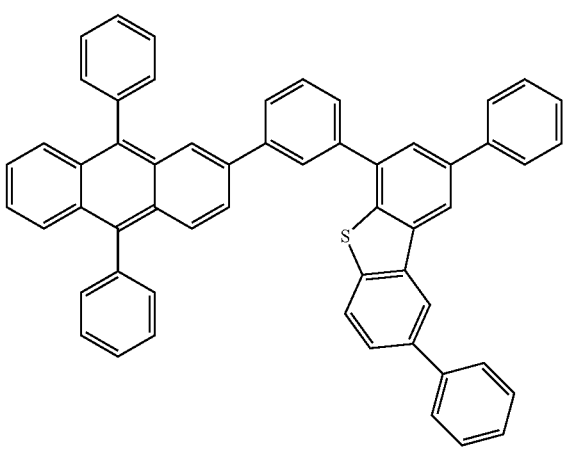
(347)
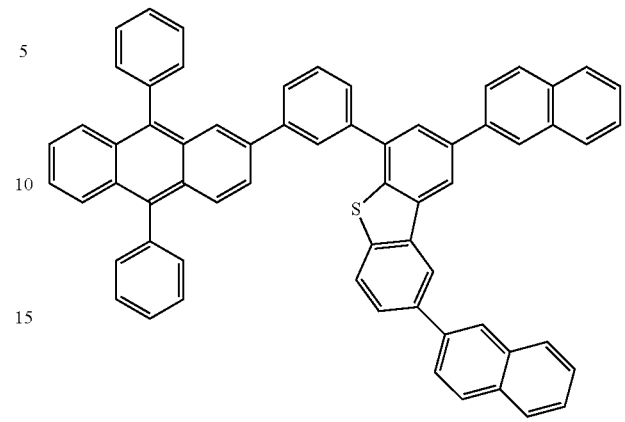
(348)
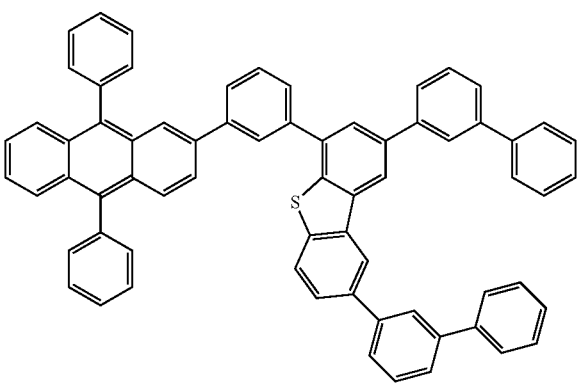
(349)
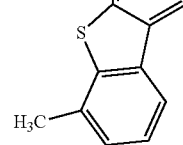
(350)
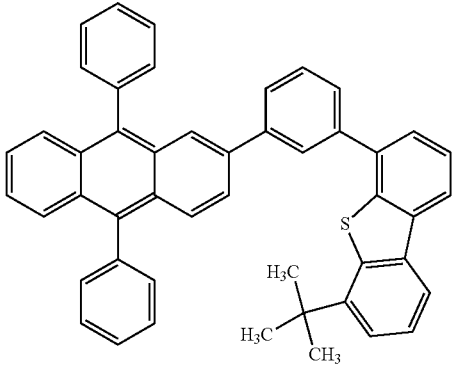

(351)
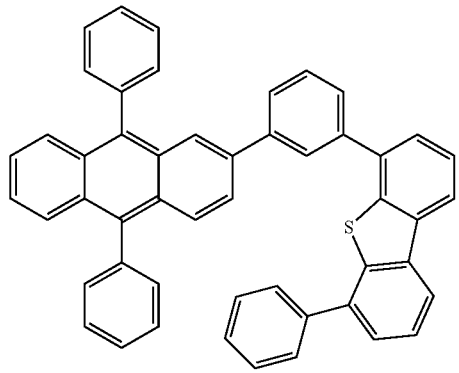
(352)
(353)
(354)
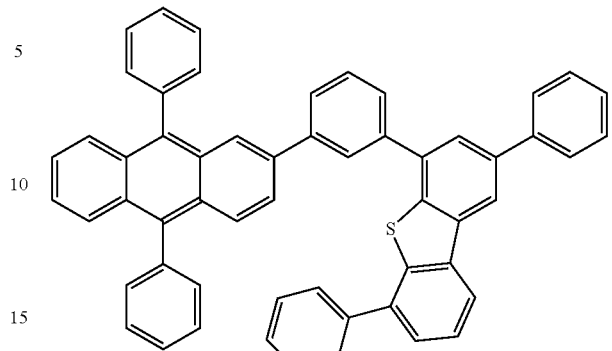
(355)
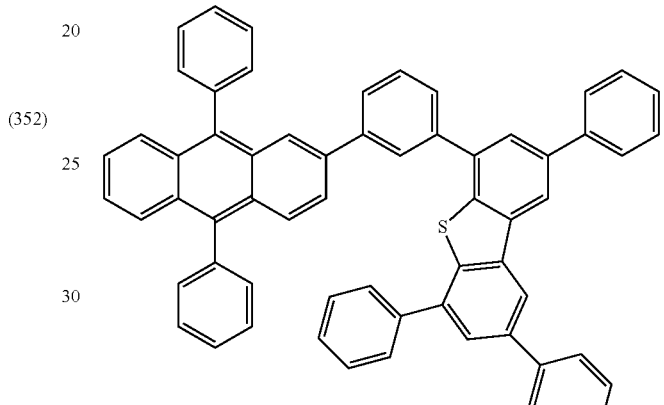
(356)
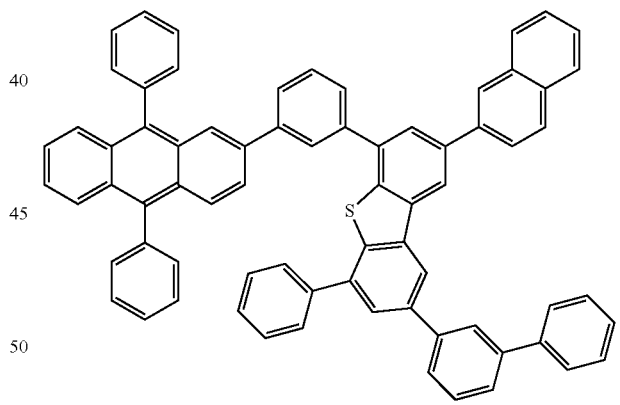
(357)
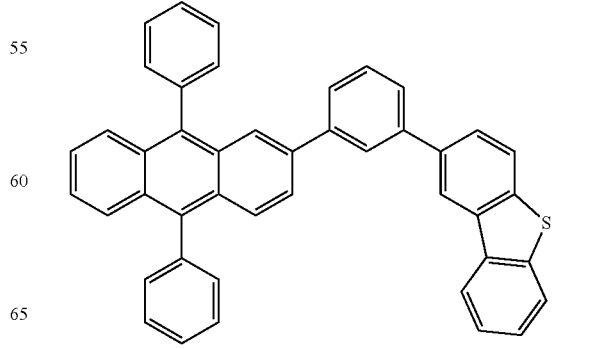

(358)
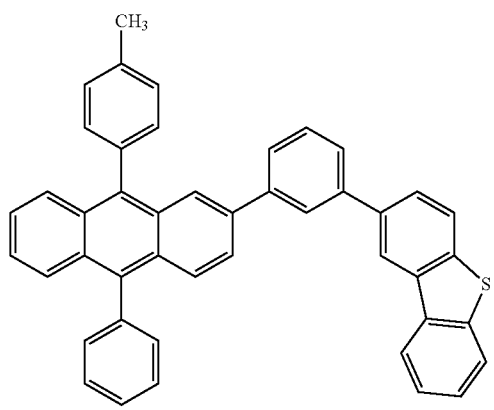
(361)
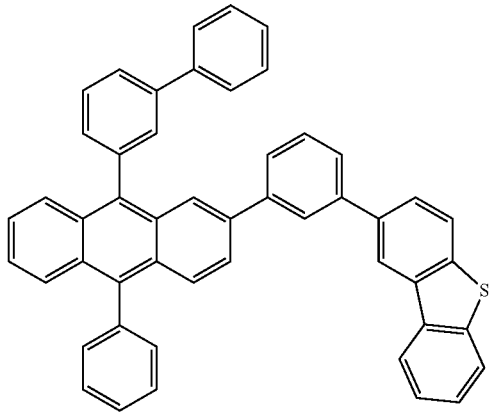
(359)
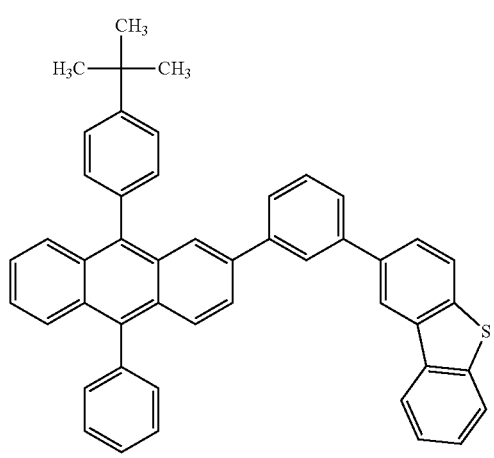
(362)
(360)
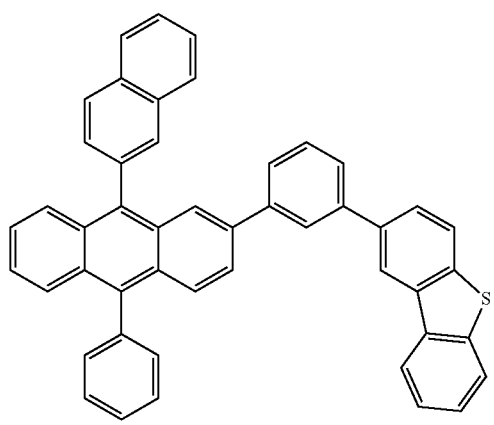
(363)
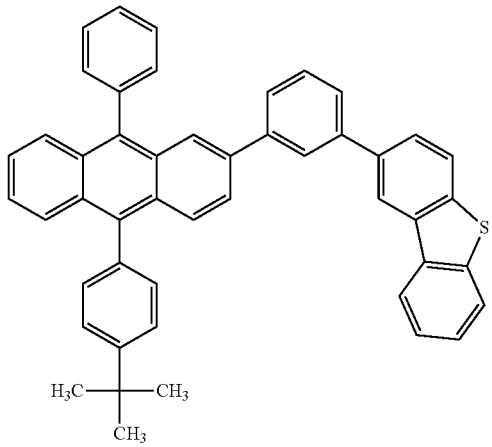

-continued
(364)
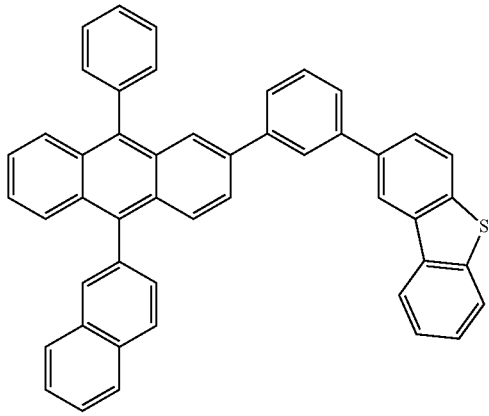
(365)
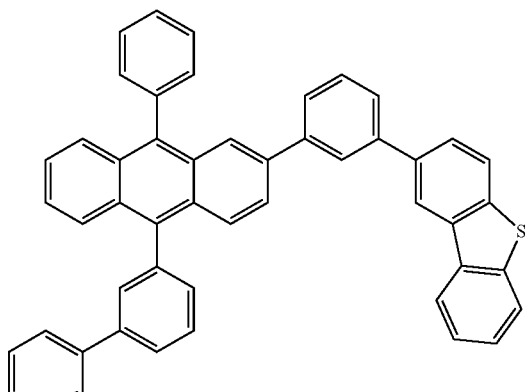
(366)
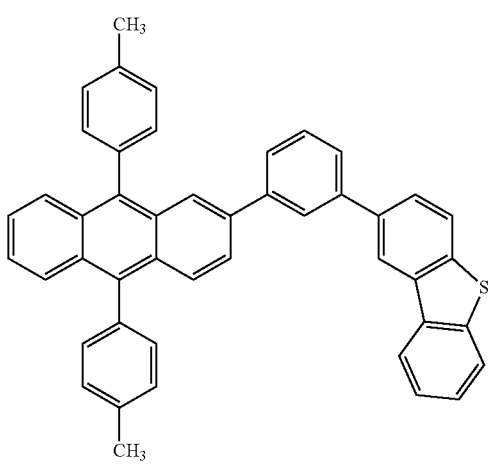
-continued
(367)
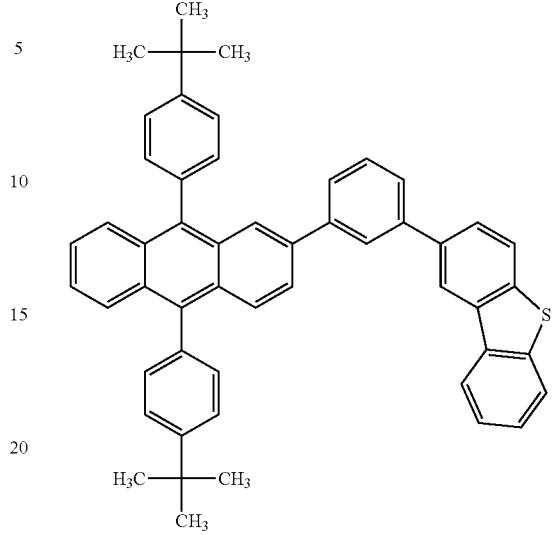
(368)
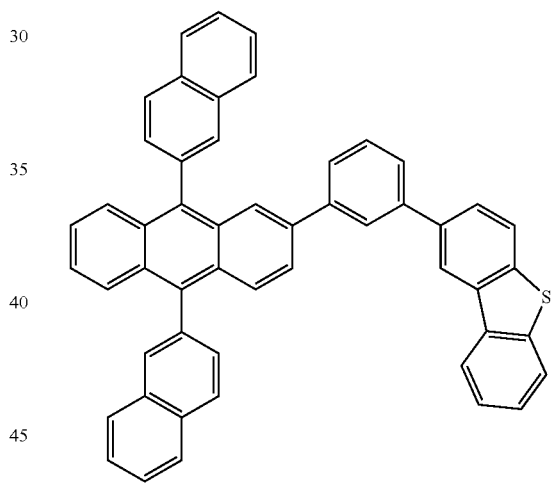
(369)
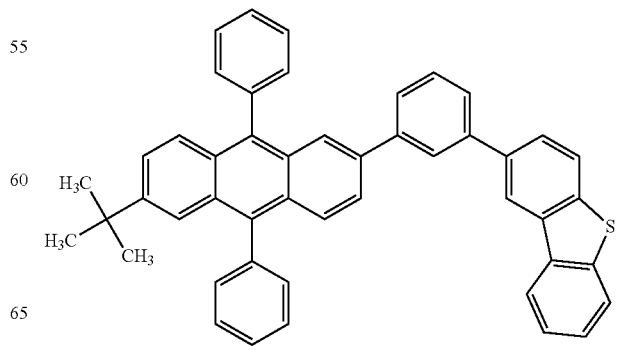

-continued
(370)
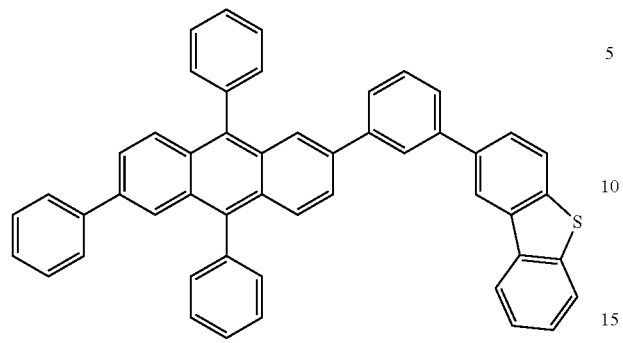
(371)
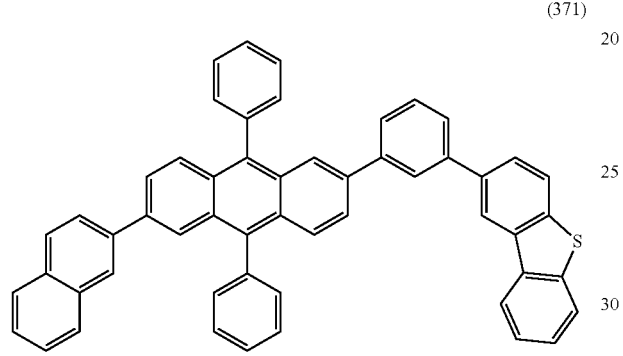
(372)
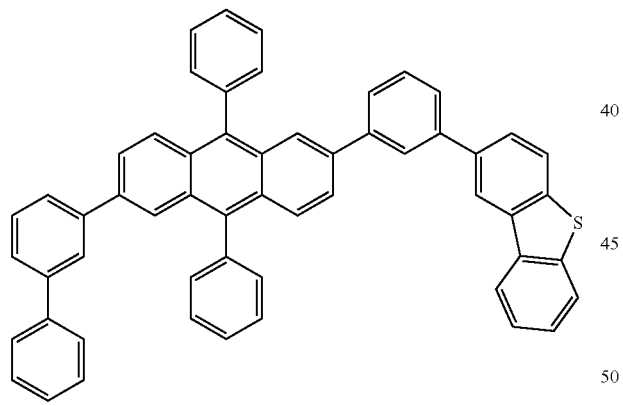
(373)
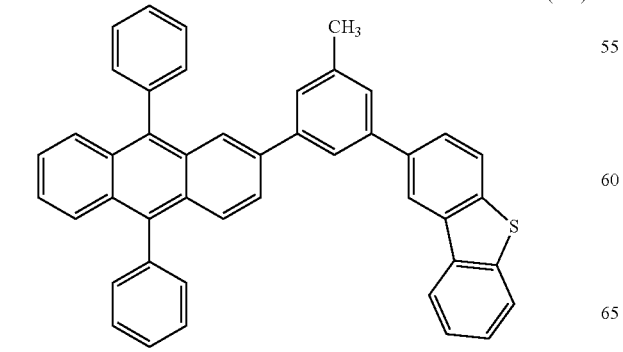
-continued
(374)
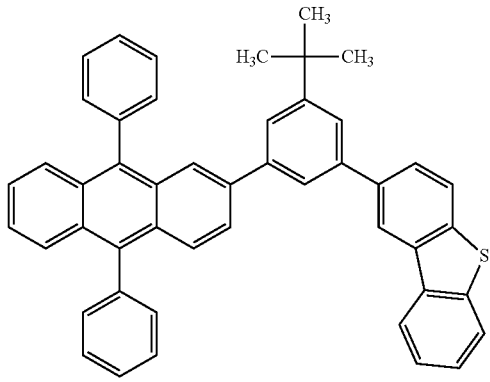
(375)
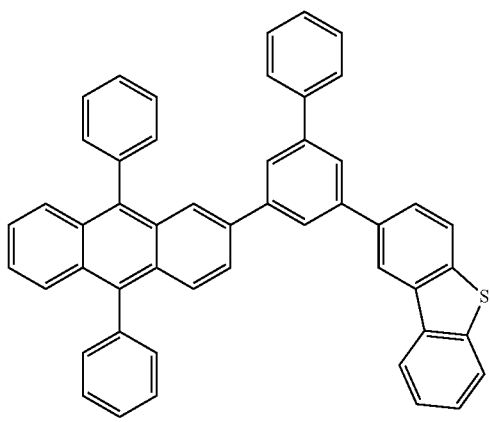
(376)
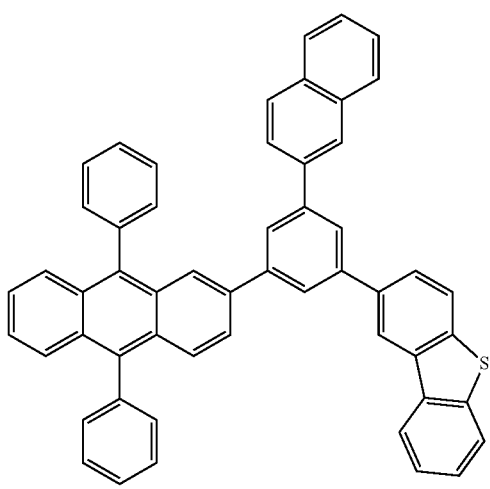

(377)
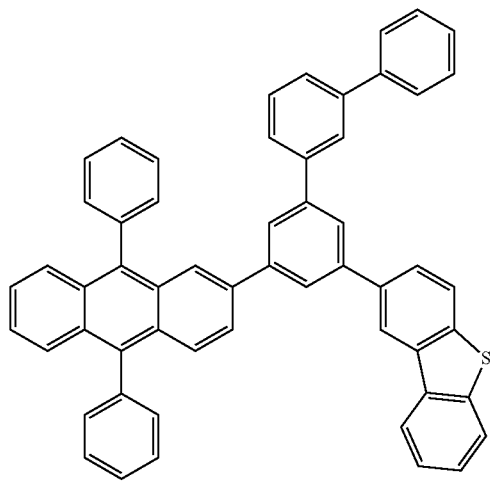
(380)
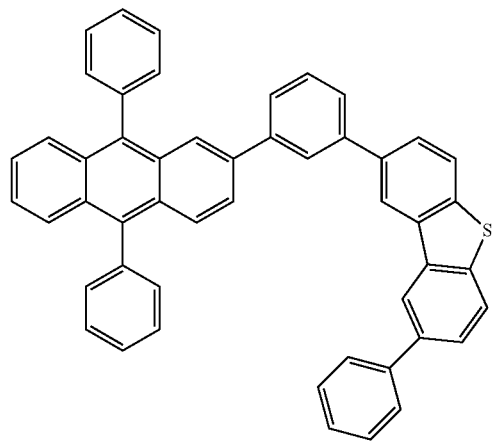
(378)
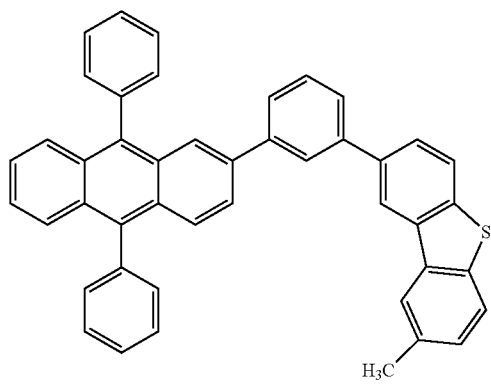
(381)
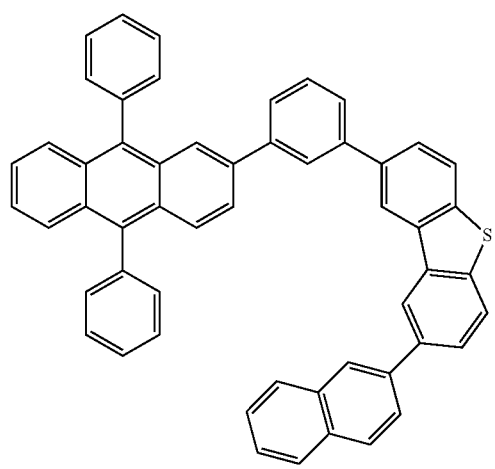
(379)
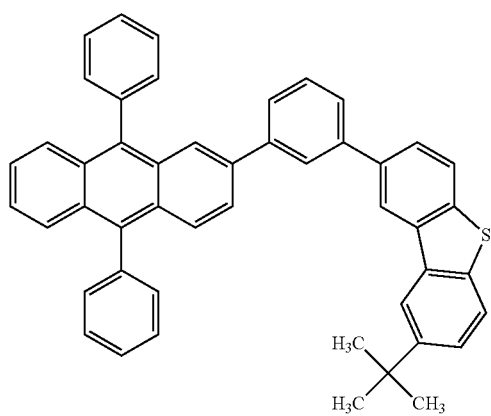
(382)
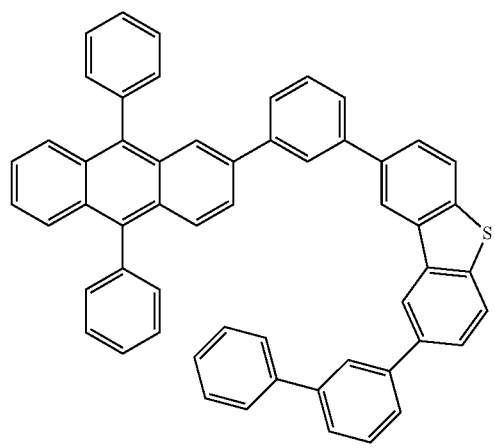

(383)
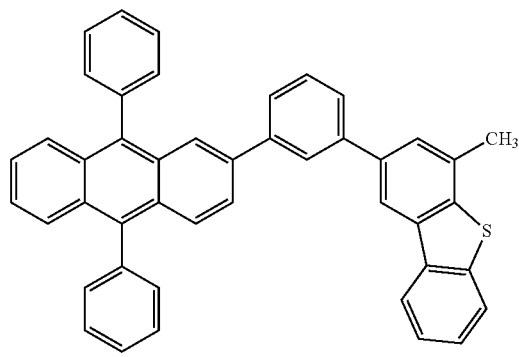
(384)
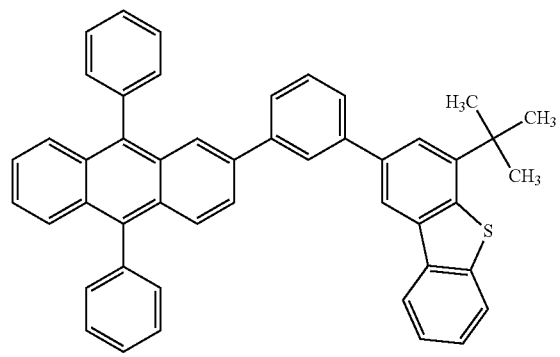
(385)
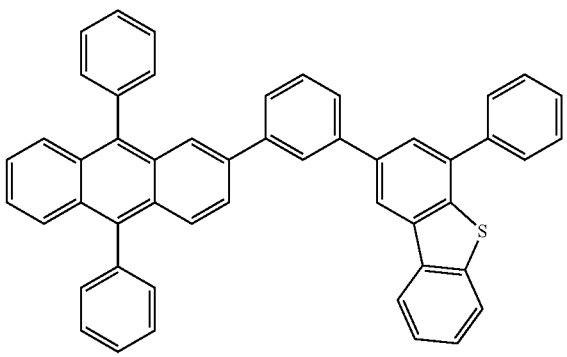
(386)
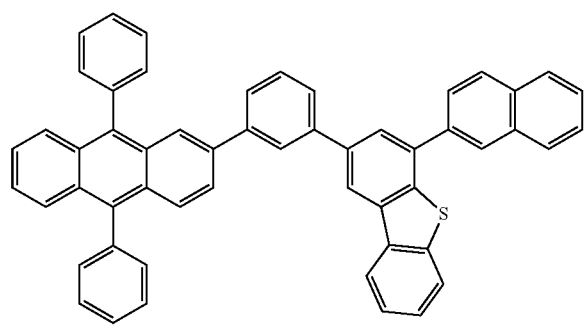
(387)
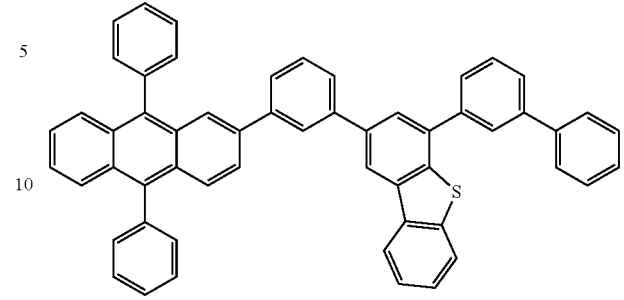
(388)
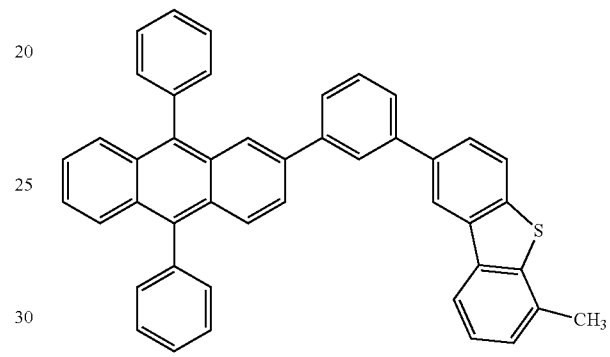
(389)
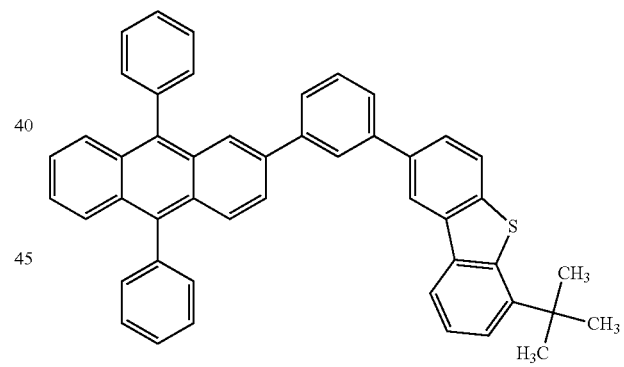
(390)
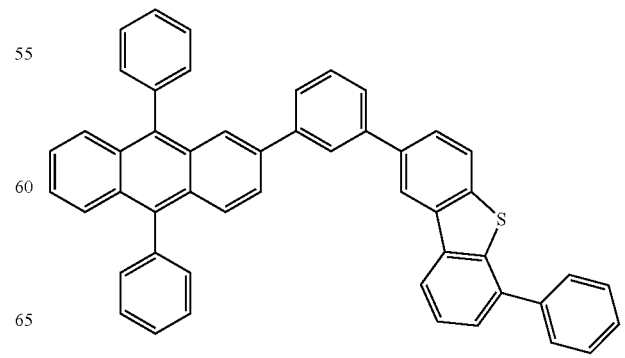

(391)
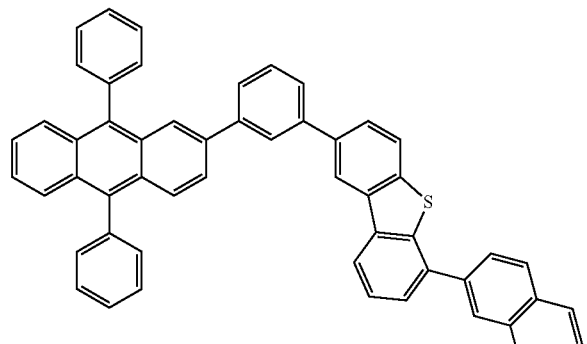
(392)
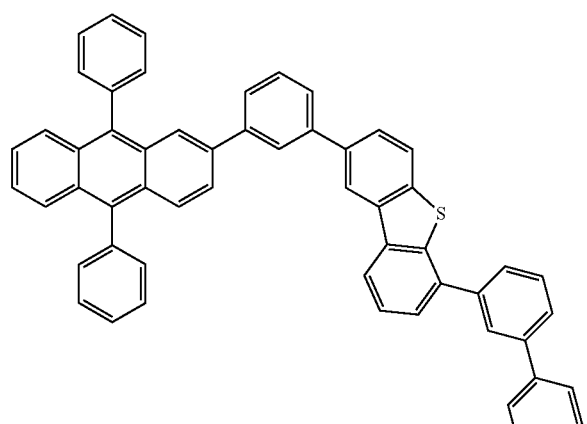
(393)
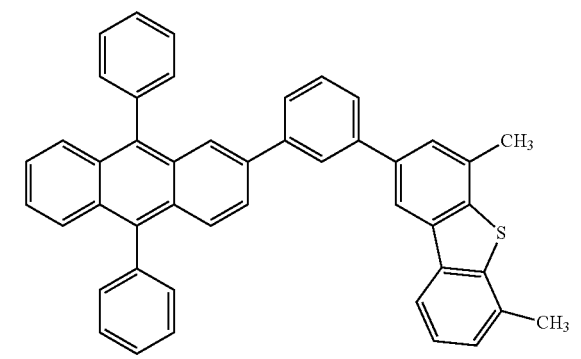
(394)
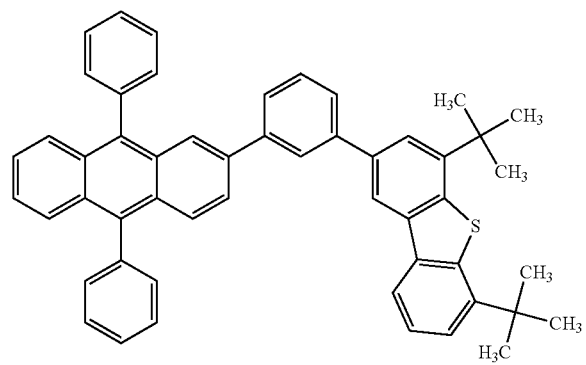
(395)
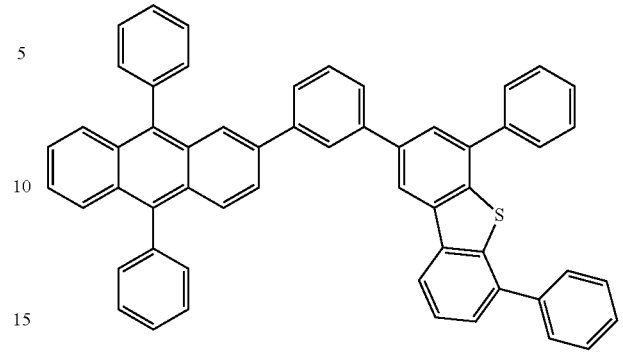
(396)
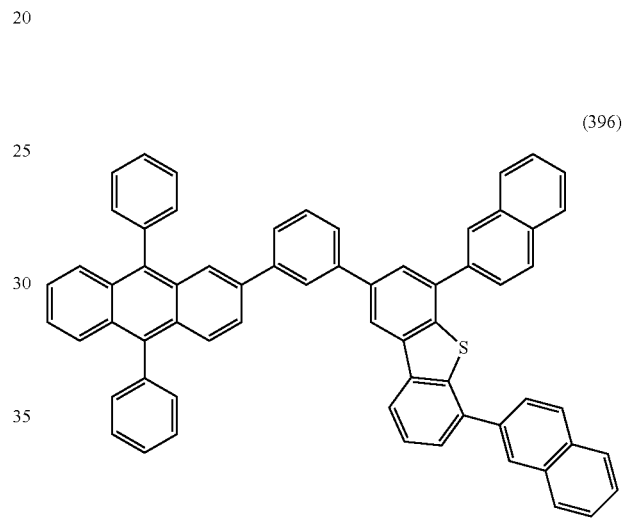
(397)
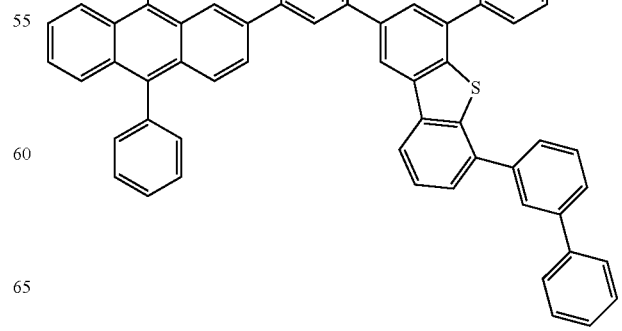

(398)

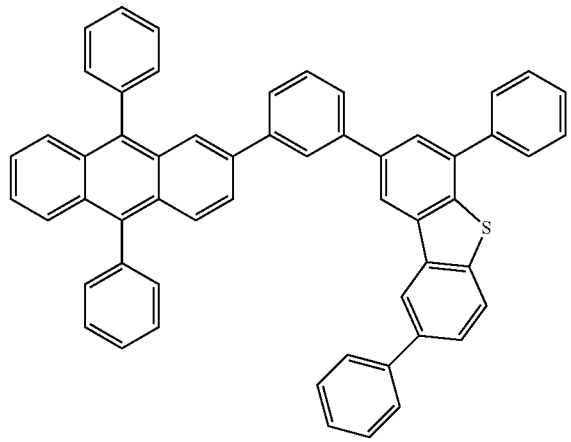

(399)

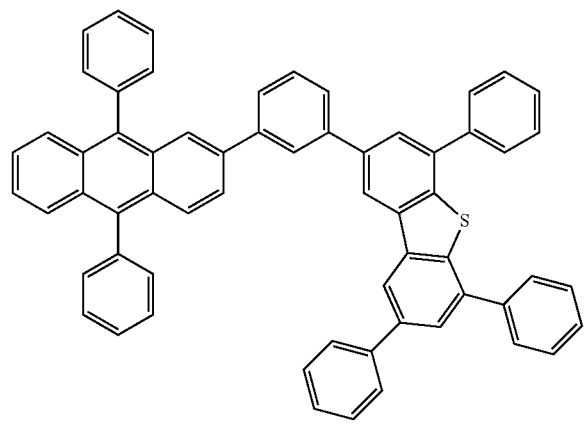

(400)

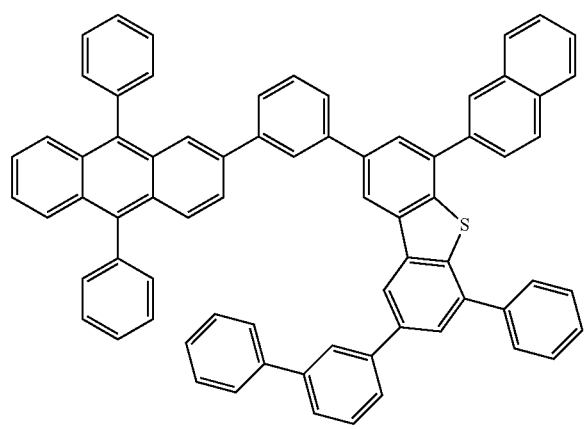

A variety of reactions can be applied to a synthesis method of the heterocyclic compound which is one embodiment of the present invention. For example, synthesis reactions described below enable the synthesis of the heterocyclic compound of one embodiment of the present invention represented by General Formula (G1). Synthesis Method 1 is a method of synthesizing the heterocyclic compound (G2-1) of one embodiment of the present invention in which, in General Formula (G1), A is the substituent represented by General Formula (S1). Further, Synthesis Method 2 is a method of synthesizing the heterocyclic compound (G2-2) of one embodiment of the present invention in which, in General Formula (G1), A is the substituent represented by General Formula (S2). Note that the synthesis methods of the heterocyclic compound which is one embodiment of the present invention are not limited to the synthesis methods below.

<Synthesis Method 1 of heterocyclic compound represented by General Formula (G1)>

First, Synthesis Scheme (A-1) will be shown.

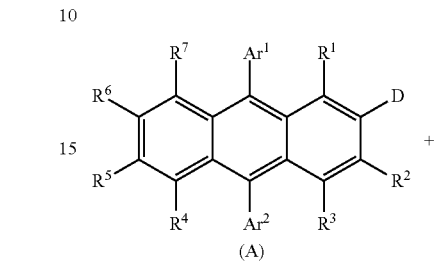

(A)

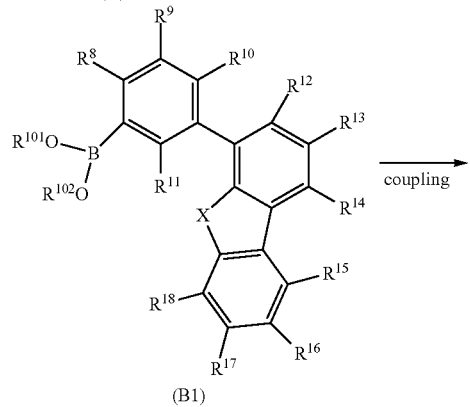

(B1)

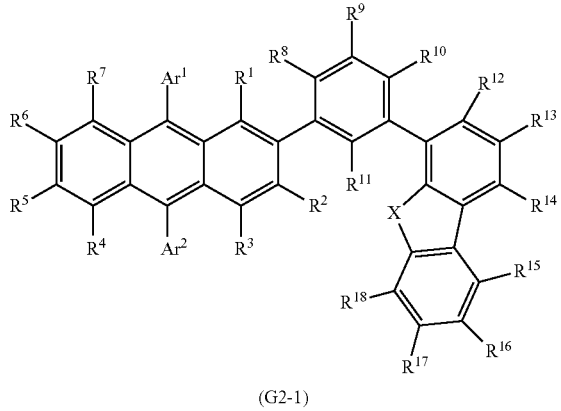

(G2-1)

The heterocyclic compound (G2-1) of one embodiment of the present invention can be synthesized according to Synthesis Scheme (A-1). Specifically, a halogen compound of an anthracene derivative (Compound A) is coupled with an organoboron compound of a dibenzofuran derivative or a dibenzothiophene derivative (Compound B1) according to a Suzuki-Miyaura reaction using a palladium catalyst, whereby the heterocyclic compound (Compound G2-1) described in this embodiment can be provided.

In Synthesis Scheme (A-1), X represents oxygen or sulfur. In Synthesis Scheme (A-1), D represents a halogen. As the halogen, iodine or bromine is preferable.

In Synthesis Scheme (A-1), $R^{101}$ and $R^{102}$ independently represent hydrogen or an alkyl group having 1 to 6 carbon atoms, may be the same or different from each other, and may be combined with each other to form a ring.

Examples of the palladium catalyst that can be used in Synthesis Scheme (A-1) include palladium(II) acetate, tetrakis(triphenylphosphine)palladium(0), and the like. Examples of a ligand of the palladium catalyst which can be used in Synthesis Scheme (A-1) include tri(ortho-tolyl)phosphine, triphenylphosphine, tricyclohexylphosphine, and the like.

Examples of a base that can be used in Synthesis Scheme (A-1) include an organic base such as sodium tert-butoxide, an inorganic base such as potassium carbonate, and the like.

Examples of solvents that can be used in Synthesis Scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. Use of a mixed solvent of toluene and water or a mixed solvent of toluene, ethanol, and water is more preferable.

Thus, the heterocyclic compound of this embodiment can be synthesized.

<Synthesis Method 2 of heterocyclic compound represented by General Formula (G1)>

First, Synthesis Scheme (B-1) will be shown.

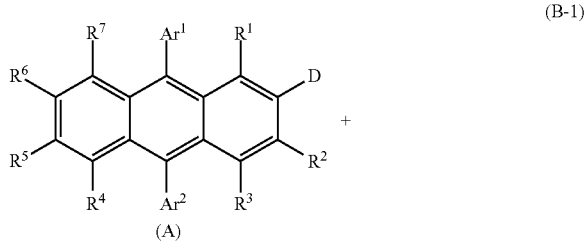

(A)

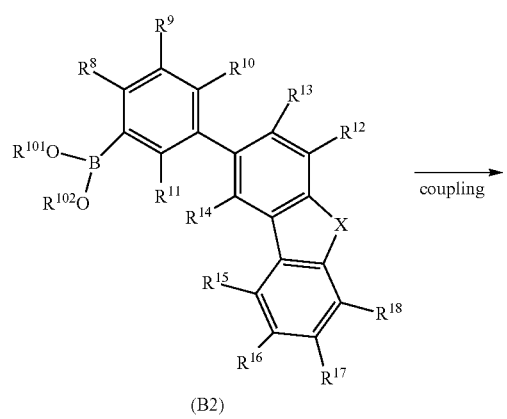

(B2)

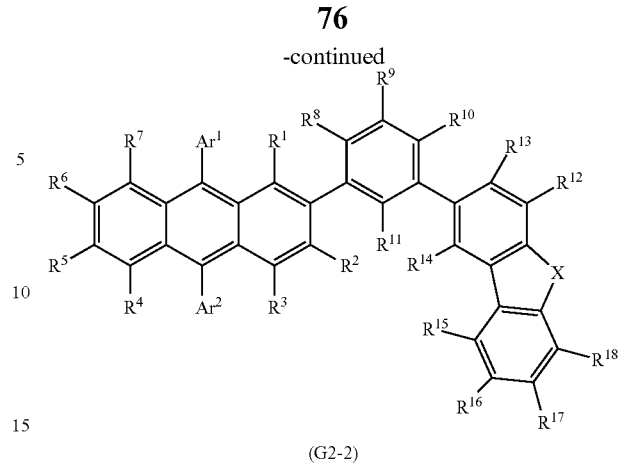

(G2-2)

The heterocyclic compound (G2-2) of one embodiment of the present invention can be synthesized according to Synthesis Scheme (B-1). Specifically, a halogen compound of an anthracene derivative (Compound A) is coupled with an organoboron compound of a dibenzofuran derivative or a dibenzothiophene derivative (Compound B2) according to a Suzuki-Miyaura reaction using a palladium catalyst, whereby the heterocyclic compound (Compound G2-2) described in this embodiment can be provided.

In Synthesis Scheme (B-1), X represents oxygen or sulfur. In Synthesis Scheme (B-1), D represents a halogen. As the halogen, iodine or bromine is preferable.

In Synthesis Scheme (B-1), $R^{101}$ and $R^{102}$ independently represent hydrogen or an alkyl group having 1 to 6 carbon atoms, may be the same or different from each other, and may be combined with each other to foul a ring.

Examples of the palladium catalyst that can be used in Synthesis Scheme (B-1) include palladium(II) acetate, tetrakis(triphenylphosphine)palladium(0), and the like. Examples of a ligand of the palladium catalyst which can be used in Synthesis Scheme (B-1) include tri(ortho-tolyl)phosphine, triphenylphosphine, tricyclohexylphosphine, and the like.

Examples of a base that can be used in Synthesis Scheme (B-1) include an organic base such as sodium tert-butoxide, an inorganic base such as potassium carbonate, and the like.

Examples of solvents that can be used in Synthesis Scheme (B-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent having an ether such as 1,2-dimethoxyethane and water; and the like. Use of a mixed solvent of toluene and water or a mixed solvent of toluene, ethanol, and water is more preferable.

Thus, the heterocyclic compound of this embodiment can be synthesized.

The heterocyclic compound of this embodiment emits blue light and has a hole-transport property. Also, the heterocyclic compound of this embodiment exhibits high emission efficiency. Accordingly, with the use of the heterocyclic compound of this embodiment for a light-emitting element, the light-emitting element can exhibit high emission efficiency. Further, the use of the heterocyclic compound of this embodiment can provide a light-emitting device, an electronic device, and a lighting device each having reduced power consumption.

Embodiment 2

In Embodiment 2, a light-emitting element in which the heterocyclic compound of one embodiment of the present invention is used for an EL layer will be described with reference to FIGS. 1A and 1B.

In the light-emitting element of this embodiment, the EL layer having at least a light-emitting layer is interposed between a pair of electrodes. The EL layer may also have a plurality of layers in addition to the light-emitting layer. The plurality of layers is a combination of layers that include a substance having a high carrier-injection property and a substance having a high carrier-transport property. Those layers are stacked so that a light-emitting region is formed in a region away from the electrodes, that is, carriers recombine in a region away from the electrodes. In this specification, the layer that includes a substance having a high carrier-injection property or a substance having a high carrier-transport property is also called a functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes: the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. Alternatively, a flexible substrate may be used. The flexible substrate is a substrate that can be bent, such as a plastic substrate made of polycarbonate, polyarylate, or polyether sulfone, for example. Alternatively, a film (made of polypropylene, polyester, vinyl, polyvinyl fluoride, vinyl chloride, or the like), an inorganic film formed by evaporation, or the like can be used. Note that materials other than glass and plastic can be used as long as they can function as a support of the light-emitting element.

For the first electrode 101, a metal, an alloy, an electrically conductive compound, a mixture thereof, or the like which has a high work function (specifically, a work function of 4.0 eV or more) is preferably used. Specific examples include indium tin oxide (ITO), indium tin oxide containing silicon or silicon oxide, indium zinc oxide (IZO), indium oxide containing tungsten oxide and zinc oxide (IWZO), and the like. Films of these conductive metal oxides are usually formed by sputtering; however, a sol-gel method or the like may also be used. For example, indium oxide-zinc oxide (IZO) can be formed by a sputtering method using a target in which 1 wt % to 20 wt % of zinc oxide is added to indium oxide. IWZO can be formed by a sputtering method using a target in which 0.5 wt % to 5 wt % of tungsten oxide and 0.1 wt % to 1 wt % of zinc oxide are added to indium oxide. Further, gold (Au), platinum (Pt), nickel (Ni), tungsten (W), chromium (Cr), molybdenum(Mo), iron (Fe), cobalt (Co), copper (Cu), palladium (Pd), nitrides of metal materials (e.g., titanium nitride), and the like can be given.

Note that, in the EL layer 102, when a layer in contact with the first electrode 101 is formed using a composite material in which an organic compound and an electron acceptor (acceptor) described later are mixed, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., Al—Si), or the like can be used.

The EL layer 102 formed over the first electrode 101 includes at least the light-emitting layer 113, and part of the EL layer 102 is formed using the heterocyclic compound which is one embodiment of the present invention. For the part of the EL layer 102, a known substance can be used, and either a low molecular compound or a high molecular compound can be used. Note that the substance used for forming the EL layer 102 may have not only a structure formed of only an organic compound but also a structure in which an inorganic compound is partially contained.

Figure 1B:
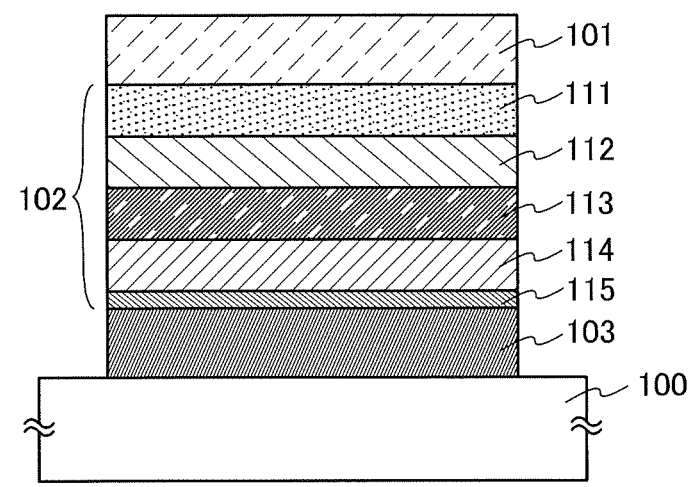

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination as well as the light-emitting layer 113.

The hole-injection layer 111 includes a substance having a high hole-injection property. As the substance having a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. Alternatively, a phthalocyanine-based compound such as phthalocyanine (abbreviation: H$_2$Pc), copper(II) phthalocyanine (abbreviation: CuPc), or vanadyl phthalocyanine (abbreviation: VOPc) can be used.

Further, as examples of low molecular organic compounds, there are aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. Examples of the high molecular compounds include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacryla mide] (abbreviation: PTPDMA), poly[N,N'-bis(4-butylphenyl)-N,N'-bis(phenyl)benzidine] (abbreviation: Poly-TPD), and the like. Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

For the hole-injection layer 111, a composite material in which an organic compound and an electron acceptor (acceptor) are mixed may be used. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound for the composite material, a variety of compounds such as an aromatic amine compound, a carbazole derivative, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ cm$^2$/Vs or more is preferably used. Note that a substance other than the above may be used as long as it has a hole-transport property higher than its electron-transport property. The organic compounds which can be used for the composite material are specifically shown below.

For example, as the organic compounds that can be used for the composite material, there are aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl-2,3,5,6-tetraphenylbenzene.

Alternatively, any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, and the like.

Still alternatively, any of the following aromatic hydrocarbon compounds can be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As electron acceptors, organic compounds such as 7,7,8,8-tetracyano-2,3,5,6-tetrafluoroquinodimethane (abbreviation: F$_4$-TCNQ) and chloranil, and a transition metal oxide can be given. In addition, oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

Note that the hole-injection layer 111 may be formed using a composite material of the above-described high molecular compound, such as PVK, PVTPA, PTPDMA, or Poly-TPD, and the above-described electron acceptor.

The hole-transport layer 112 includes a substance having a high hole-transport property. The heterocyclic compound of one embodiment of the present invention described in Embodiment 1 has an excellent hole-transport property and therefore can be preferably used for the hole-transport layer 112.

As the substance having a high hole-transport property, it is possible to use an aromatic amine compound such as NPB, TPD, 4,4'-bis[N-(9,9-dimethylfluoren-2-yl)-N-phenylamino]biphenyl (abbreviation: DFLDPBi), or 4,4'-bis[N-(Spiro-9,9'-bifluoren-2-yl)-N-phenylamino]biphenyl (abbreviation: BSPB), for example. The materials described here are mainly materials having a hole mobility of $10^{-6}$ cm$^2$/Vs or more. Note that a substance other than the above may be used as long as it has a hole-transport property higher than its electron-transport property. The layer containing a substance having a high hole-transport property is not limited to a single layer, and a stacked layer in which two or more layers containing the above-described substance are stacked may be used.

Alternatively, for the hole-transport layer 112, a high molecular compound such as PVK, PVTPA, PTPDMA, or Poly-TPD can be used.

The light-emitting layer 113 includes a light-emitting substance. As the light-emitting substance, for example, a fluorescent compound which exhibits fluorescence or a phosphorescent compound which exhibits phosphorescence can be used, other than the heterocyclic compound of one embodiment of the present invention described in Embodiment 1.

The phosphorescent compounds that can be used for the light-emitting layer 113 will be given. Examples of the materials for blue light emission include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. In addition, examples of the materials for green light emission include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of the materials for yellow light emission include rubrene, 5,12-bis(1,1'-biphenyl-4-yl)-6,11-diphenyltetracene (abbreviation: BPT), and the like. Furthemiore, examples of the materials for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-α] fluoranthene-3,10-diamine (abbreviation: p-mPhAFD), and the like.

In addition, the phosphorescent compounds that can be used for the light-emitting layer 113 will be given. Examples of the materials for blue light emission include bis[2-(4',6'-difluorophenyl)pyridinato-N,$C^2$] iridium(III)tetrakis(1-pyrazolyl)borate (abbreviation: FIr6), bis[2-(4',6'-difluorophenyl)pyridinato-N,$C^{2'}$]iridium(III)picolinate (abbreviation: FIrpic), bis {2-[3',5'-bis(trifluoromethyl)phenyl]pyridinato-N,$C^{2'}$}firidium(III)picolinate (abbreviation: Ir($CF_3$ppy)$_2$(pic)), bis[2-(4',6'-difluorophenyl)pyridinato-N,$C^{2'}$]iridium(III)acetylacetonate (abbreviation: FIr(acac)), and the like. Examples of the materials for green light emission include tris(2-phenylpyridinato-N,$C^{2'}$)iridium(III) (abbreviation: Ir(ppy)$_3$), bis(2-phenylpyridinato-N,$C^{2'}$)iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), and the like. Examples of the materials for yellow light emission include bis(2,4-diphenyl-1,3-oxazolato-N,$C^{2'}$)iridium(III)acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), and the like. Examples of the materials for orange light emission include tris(2-phenylquinolinato-N,$C^{2'}$)iridium(III) (abbreviation: Ir(pq)$_3$), bis(2-phenylquinolinato-N,$C^{2'}$)iridium(III)acetylacetonate (abbreviation: Ir(pq)$_2$(acac)), and the like. Examples of the materials for red light emission include organometallic complexes such as bis[2-(2'-benzo[4,5-α]thienyl)pyridinato-N,$C^{3'}$)iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphine platinum(II) (abbreviation: PtOEP). Furthermore, since light emission from a rare earth metal ion (electron transition between different multiplicities) can be obtained by rare earth metal complexes such as tris(acetylacetonato)(monophenanthroline)terbium(III) (abbreviation: Tb(acac)$_3$(Phen)), tris(1,3-diphenyl-1,3-propanedionato)(monophenanthroline)europium (III) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)), such rare earth metal complexes can be used as a phosphorescent compound.

Note that the light-emitting layer 113 may have a structure in which any of the above light-emitting substances (a guest material) is dispersed in another substance (a host material). By using the heterocyclic compound of one embodiment of the present invention for the light-emitting layer 113, the light-emitting layer 113 can be a light-emitting layer having a high hole-transport property. In the light-emitting layer 113, the heterocyclic compound of one embodiment of the present invention described in Embodiment 1 can be used as a host material, and a guest material which is a light-emitting substance is dispersed in the heterocyclic compound of Embodiment 1; in this manner, it is possible to obtain light emission from the guest material.

When the heterocyclic compound of one embodiment of the present invention is used as a host material (a substance in which a light-emitting substance different from the host material is dispersed), the emission color of the light-emitting substance can be obtained. It is also possible to obtain the mixed color of the emission color of the heterocyclic compound of one embodiment of the present invention and the emission color of the light-emitting substance dispersed in this heterocyclic compound.

As the substance in which a light-emitting substance is dispersed, a variety of substances can be used other than the heterocyclic compound of one embodiment of the present invention described in Embodiment 1. It is preferable to use a substance whose lowest unoccupied molecular orbital (LUMO) level is higher than that of the light-emitting substance and whose highest occupied molecular orbital (HOMO) level is lower than that of the light-emitting substance.

As the substance in which the light-emitting substance is dispersed, specifically, any of the following materials can be used as an alternative to the heterocyclic compound of one embodiment of the present invention: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds such as N,N-dipheyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; or the like.

As the substance (host material) in which the light-emitting substance (guest material) is dispersed, plural kinds of substances can be used.

As the light-emitting substance, a high molecular compound can also be used. Specifically, examples of the materials for blue light emission include poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. Further, examples of the materials for green light emission include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyloxy)-1,4-phenylene)], and the like. Furthermore, examples of the materials for orange to red light emission include poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The electron-transport layer 114 includes a substance having a high electron-transport property. The electron-transport layer 114 is formed using, for example, a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq). Alternatively, a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Other than the metal complexes, 2-(4-biphenylyl)-5-(4-tent-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly materials having an electron mobility of $10^{-6}$ cm$^2$/Vs or more. Further, the electron-transport layer is not limited to a single layer, and a stacked layer in which two or more layers containing any of the above-described substances are stacked may be used.

The electron-injection layer 115 includes a substance having a high electron-injection property. For the electron-injection layer 115, an alkali metal, an alkaline earth metal, or a compound thereof, such as lithium (Li), cesium (Cs), calcium (Ca), lithium fluoride (LiF), cesium fluoride (CsF), calcium fluoride (CaF$_2$), or lithium oxide (LiO$_x$), can be used. Alternatively, a rare earth metal compound like erbium fluoride (ErF$_3$) can be used. Alternatively, the above-mentioned substances for forming the electron-transport layer 114 can also be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and Li, Cs, magnesium (Mg), Ca, erbium (Er), ytterbium (Yb), and the like are given. In addition, alkali metal oxide or alkaline earth metal oxide such as lithium oxide, calcium oxide, barium oxide, and the like can be given. Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, and electron-injection layer 115 can be formed by a method such as an evaporation method (which includes a vacuum evaporation method), an inkjet method, or a coating method.

When the second electrode 103 functions as a cathode, it can be formed using a metal, an alloy, an electrically-conductive compound, a mixture thereof, or the like having a low work function (preferably, a work function of 3.8 eV or less). Specifically, Al, Ag, or the like can be used besides an element belonging to Group 1 or Group 2 of the periodic table, that is, an alkali metal such Li or Cs and an alkaline earth metal such as magnesium (Mg), calcium (Ca), or strontium (Sr); an alloy of the above metals (e.g., Mg-Ag or Al-Li); a rare earth metal such as europium (Eu) or ytterbium (Yb); an alloy of the above metals, or the like.

Note that, in the case where in the EL layer 102, a layer formed in contact with the second electrode 103 is formed using a composite material in which the organic compound and the electron donor (donor), which are described above, are mixed, a variety of conductive materials such as Al, Ag, ITO, and indium tin oxide containing silicon or silicon oxide can be used regardless of the work function.

Note that the second electrode 103 can be formed by a vacuum evaporation method or a sputtering method. Alternatively, in the case of using a silver paste or the like, a coating method, an inkjet method, or the like can be used.

In the above-described light-emitting element of this embodiment, a current flows due to a potential difference generated between the first electrode 101 and the second electrode 103, and holes and electrons recombine in the EL layer 102, so that light is emitted. Then, this emitted light is extracted out through one or both of the first electrode 101 and the second electrode 103. Therefore, one of or both the first electrode 101 and the second electrode 103 is/are an electrode having the property of transmitting visible light.

Further, a structure of a layer provided between the first electrode 101 and the second electrode 103 is not limited to the above described structure. A structure other than the above may alternatively be employed as long as a light-emitting region in which holes and electrons recombine is provided in a portion away from the first electrode 101 and the second electrode 103 in order to prevent quenching due to proximity of the light-emitting region to a metal.

In other words, a layered structure of the layer is not particularly limited, and a layer formed using a substance having a high electron-transport property, a substance having a high hole-transport property, a substance having a high electron-injection property, a substance having a high hole-injection property, a bipolar substance (a substance having a high electron-transport property and a high hole-transport property), a hole blocking material, or the like may freely be combined with a light-emitting layer including the heterocyclic compound described in Embodiment 1.

In a light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes: the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

A method of forming a light-emitting element will now be specifically described.

The light-emitting element of this embodiment has a structure in which an EL layer is interposed between a pair of electrodes. The EL layer at least has a light-emitting layer and is formed using the heterocyclic compound described in Embodiment 1. Further, the EL layer may include a functional layer (e.g., a hole-injection layer, a hole-transport layer, an electron-transport layer, or an electron-injection layer) in addition to the light-emitting layer. Each electrode (the first electrode or the second electrode), the light-emitting layer, and each functional layer may be formed by any of the wet processes such as a droplet discharging method (an inkjet method), a spin coating method, or a printing method, or by a dry process such as a vacuum evaporation method, a CVD method, or a sputtering method. A wet process allows formation at atmospheric pressure with a simple device and process, thereby having the effects of simplifying the process and improving the productivity. In contrast, a dry process does not need dissolution of a material to enable use of a material that has low solubility in a solution, thereby expanding the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the first electrode, and the like which are stacked over the light-emitting layer may be formed by a dry process. Further alternatively, the second electrode and the functional layer may be formed by a dry process before the formation of the light-emitting layer whereas the light-emitting layer, the functional layer stacked thereover, and the first electrode may be formed by a wet process. Needless to say, this embodiment is not limited to this, and the light-emitting element can be formed by appropriate selection from a wet method and a dry method depending on a material to be used, necessary film thickness, and the interface state.

In this embodiment, the light-emitting element is fabricated over a substrate made of glass, plastic or the like. By forming a plurality of such light-emitting elements over one substrate, a passive matrix light-emitting device can be manufactured. Alternatively, a thin film transistor (TFT), for instance, may be formed over a substrate formed of glass, plastic, or the like, and a light-emitting element may be fabricated over an electrode electrically connected to the TFT; thus, an active matrix light-emitting device in which the TFT controls the drive of the light-emitting element can be manufactured. Note that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be constructed from both n-channel and p-channel TFTs or from one of n-channel and p-channel TFTs.

The heterocyclic compound of one embodiment of the present invention described in Embodiment 1 has a high hole-transport property and high emission efficiency. Accordingly, by using the heterocyclic compound described in Embodiment 1 for a light-emitting element, the light-emitting element can exhibit high emission efficiency.

Since the light-emitting element of an embodiment of the present invention thus obtained has high emission efficiency, a light-emitting device (such as an image display device) that uses this light-emitting element can realize low power consumption.

Note that by use of the light-emitting element described in this embodiment, a passive matrix light-emitting device or an active matrix light-emitting device in which the driving of the light-emitting element is controlled by a TFT can be manufactured.

In this embodiment, the structures can be combined with those of the other embodiments, as appropriate.

Embodiment 3

In Embodiment 3, a mode of a light-emitting element having a structure in which a plurality of light-emitting units is stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
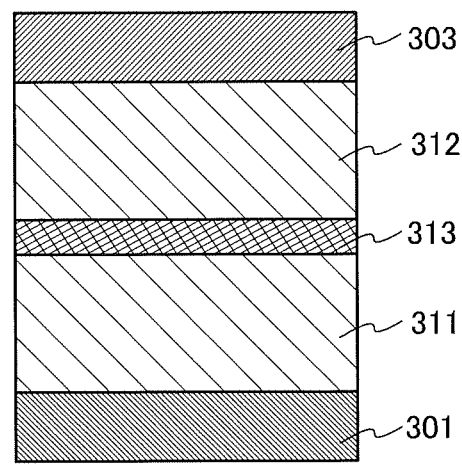
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. The structures of the first light-emitting unit 311 and the second light-emitting unit 312 may be the same or different from each other, and can be the same as those described in Embodiment 2.

Further, a charge generating layer 313 is provided between the first light-emitting unit 311 and the second light-emitting unit 312. The charge generation layer 313 functions so that electrons are injected into one light-emitting unit and holes are injected into the other light-emitting unit by application of a voltage between the first electrode 301 and the second electrode 303. In this embodiment, when a voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has the property of transmitting visible light in terms of light extraction efficiency. Further, the charge generation layer 313 functions even when it has lower conductivity than the first electrode 301 or the second electrode 303.

The charge generation layer 313 may have either a structure including an organic compound having a high hole-transport property and an electron acceptor or a structure including an organic compound having a high electron-transport property and an electron donor. Alternatively, both of these structures may be stacked.

In the case where the charge generation layer 313 contains an electron acceptor and an organic compound having a high hole-transport property, as the organic compound having a high hole-transport property, for example, the heterocyclic compound of one embodiment of the present invention, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The materials described here are mainly materials having a hole mobility of $10^{-6}$ cm$^2$/Vs or more. Note that a substance other than the above may be used as long as it is an organic compound having a hole-transport property higher than its electron-transport property.

Further, as the electron acceptor, 7,7,8,8-tetracyano-2,3,5,6-tetrafluoroquinodimethane (abbreviation: $F_4$-TCNQ), chloranil, and the like can be given. In addition, transition metal oxides can be given. Moreover, oxides of metals belonging to Groups 4 to 8 of the periodic table can be used. Specifically, vanadium oxide, niobium oxide, tantalum oxide, chromium oxide, molybdenum oxide, tungsten oxide, manganese oxide, and rhenium oxide are preferable because they have a high electron-accepting property. Among these metal oxides, molybdenum oxide, which is easy to handle, is preferred because of its stability in air and low hygroscopic property.

On the other hand, in the case where the charge generation layer 313 includes an electron donor and an organic compound having a high hole-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The materials described here are mainly materials having an electron mobility of $10^{-6}$ cm$^2$/Vs or more. Note that a substance other than the above may be used as long as it is an organic compound having an electron-transport property higher than its hole-transport property.

Further, as the electron donor, an alkali metal, an alkaline earth metal, a rare earth metal, a metal belonging to Group 13 of the periodic table, or an oxide or carbonate thereof can be used. Specifically, Li, Cs, Mg, Ca, Yb, indium (In), lithium oxide, cesium carbonate, or the like is preferably used. Alternatively, an organic compound such as tetrathianaphthacene may be used as the electron donor.

Note that by formation of the charge generation layer 313 using any of the above materials, it is possible to suppress an increase in drive voltage caused by stacking the EL layers.

Figure 2B:
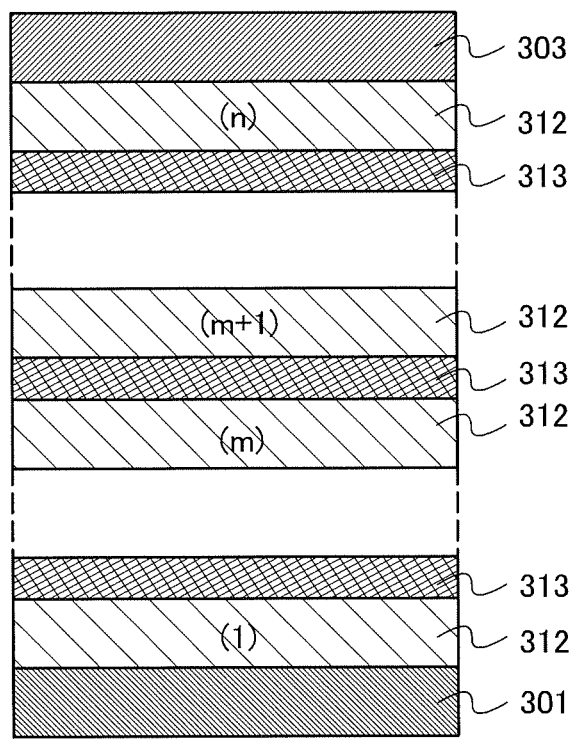

In this embodiment, the light-emitting element having two light-emitting units is described; however, one embodiment of the present invention can be similarly applied to a light-emitting element in which three or more light-emitting units are stacked as illustrated in FIG. 2B. By arrangement of a plurality of light-emitting units, which are partitioned by the charge-generation layer between a pair of electrodes, as in the light-emitting element of this embodiment, light emission in a high luminance region can be achieved with current density kept low. Thus, its current density can be kept low, so that a light-emitting element having a long lifetime can be realized.

With light-emitting units having emission colors different from each other, the light-emitting element can be made to exhibit light emission of a desired color as a whole. For example, in a light-emitting element having two light-emitting units, the emission colors of the first light-emitting unit and the second light-emitting unit are made complementary; thus, the light-emitting element which emits white light as a whole can be obtained. Note that the word "complementary" means color relationship in which an achromatic color is obtained when colors are mixed. That is, white light emission can be obtained by mixture of light obtained from substances emitting the lights of complementary colors. The same can be applied to a light-emitting element which has three light-emitting units. For example, the light-emitting element as a whole can provide white light emission when the emission color of the first light-emitting unit is red, the emission color of the second light-emitting unit is green, and the emission color of the third light-emitting unit is blue.

Note that this embodiment can be combined with any other embodiment as appropriate.

Embodiment 4

Figure 3A:
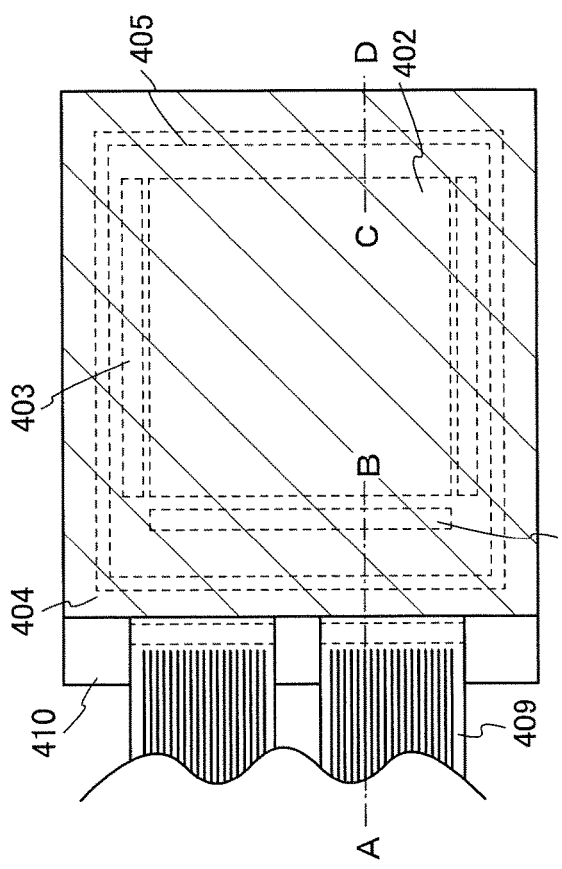
FIGS. 3A and 3B illustrate a light-emitting device of one embodiment of the present invention.
Figure 3B:
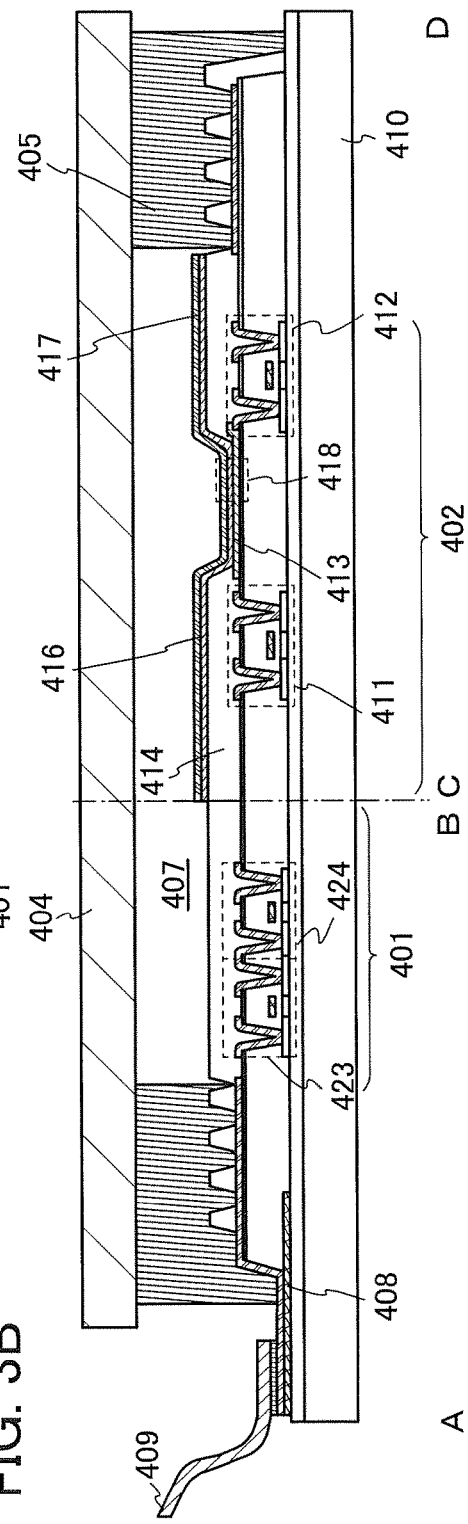

In Embodiment 4, a light-emitting device having a light-emitting element of one embodiment of the present invention will be described with reference to FIGS. 3A and 3B. FIG. 3A is a top view illustrating a light-emitting device while FIG. 3B is a cross-sectional view taken along lines A-B and C-D of FIG. 3A.

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. In this case, one pixel in the pixel portion 402 and the source side driver circuit 401 which is the driver circuit portion are illustrated.

A CMOS circuit, which is a combination of an n-channel TFT 423 with a p-channel TFT 424, is formed as the source side driver circuit 401. Such a driver circuit may be any of a variety of circuits formed using TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed using a positive type photosensitive acrylic resin film.

In order to improve the coverage, the insulator 414 is provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 μm to 3 μm). Alternatively, the insulator 414 can be formed using either a negative type that becomes insoluble in an etchant by light irradiation or a positive type that becomes soluble in an etchant by light irradiation.

A light-emitting layer 416 and a second electrode 417 are formed over the first electrode 413. Here, as a material for forming the first electrode 413 functioning as the anode, it is preferable to use a material having a high work function. For example, a single layer of an ITO film, an indium tin oxide film that includes silicon, an indium oxide film that includes 2 wt % to 20 wt % of zinc oxide (ZnO), a titanium nitride film, a Cr film, a W film, a (zinc) Zn film, a Pt film, or the like, a stacked layer of a titanium nitride film and a film that mainly includes aluminum, a three-layer structure of a titanium nitride film, a film that mainly includes aluminum and a titanium nitride film, or the like can be used. Note that, when a stacked structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes the heterocyclic compound described in Embodiment 1. Further, the light-emitting layer 416 may include another material such as a low molecular material, an oligomer, a dendrimer, or a high molecular material.

As a material used for the second electrode 417 which is formed over the light-emitting layer 416 and serves as a cathode, it is preferable to use a material having a low work function (e.g., Al, Mg, Li, Ca, or an alloy or compound thereof such as MgAg, Mg—In, Al—Li, LiF, or $CaF_2$). In the case where light generated in the light-emitting layer 416 is transmitted through the second electrode 417, the second electrode 417 may be formed of a stack of a metal thin film having a reduced thickness and a transparent conductive film (e.g., ITO, indium oxide containing 2 wt % to 20 wt % of zinc oxide, indium tin oxide containing silicon or silicon oxide, or zinc oxide (ZnO)).

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as possible. As a material for the sealing substrate 404, a glass substrate, a quartz substrate, or a plastic substrate including fiberglass-reinforced plastics (FRP), polyvinyl fluoride (PVF), polyester, acrylic, or the like can be used.

As described above, the active matrix light-emitting device having the light-emitting element of one embodiment of the present invention can be obtained.

Figure 4A:
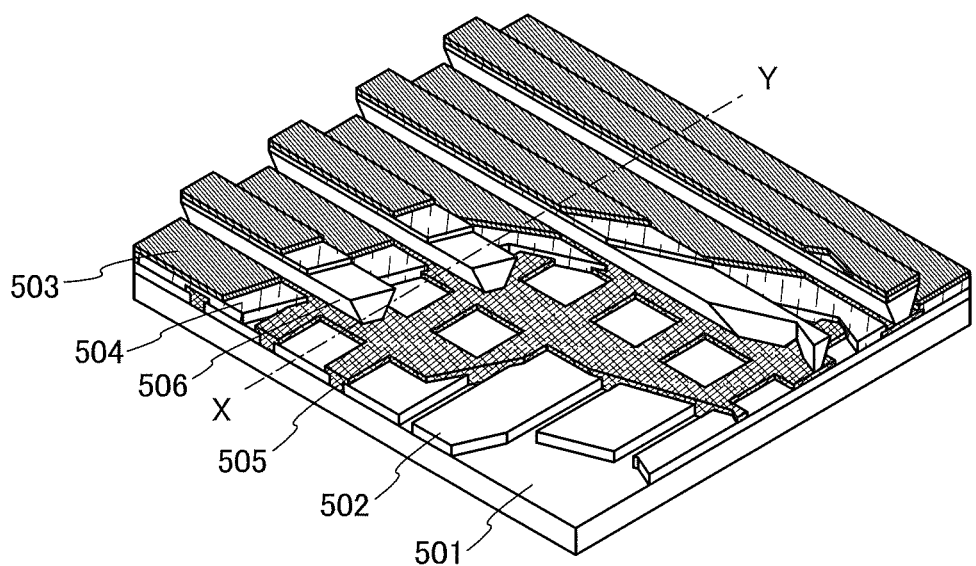
FIGS. 4A and 4B illustrate a light-emitting device of one embodiment of the present invention.
Figure 4B:
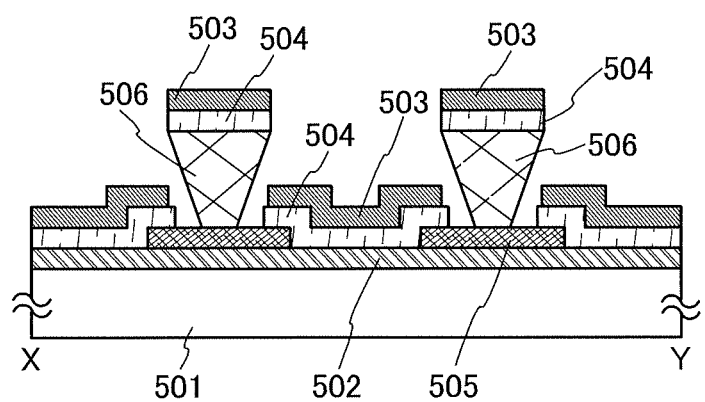

Further, the light-emitting element of the present invention can be used for a passive matrix light-emitting device as well as the above active matrix light-emitting device. FIGS. 4A and 4B illustrate a perspective view and a cross-sectional view of a passive matrix light-emitting device using the light-emitting element of the present invention. FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both sidewalls is gradually narrowed toward the surface of the substrate. In other words, a cross section taken along the direction of the short side of the partition layer 506 is trapezoidal, and the lower side (a side in contact with the insulating layer 505) is shorter than the upper side (a side not in contact with the insulating layer 505). By provision of the partition layer 506 in such a manner, a defect of the light-emitting element due to static electricity or the like can be prevented.

Thus, the passive matrix light-emitting device having the light-emitting element of one embodiment of the present invention can be obtained.

The light-emitting devices described in this embodiment (the active matrix light-emitting device and the passive matrix light-emitting device) are both formed using the light-emitting element of one embodiment of the present invention, thereby having high emission efficiency.

Note that in this embodiment, an appropriate combination of the structures described in any other embodiment can be used.

Embodiment 5

Embodiment 5 will show electronic devices and lighting devices including the light-emitting device of one embodiment of the present invention described in Embodiment 4 as a part. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like. Specific examples of these electronic devices are shown in FIGS. 5A to 5D.

Figure 5A:
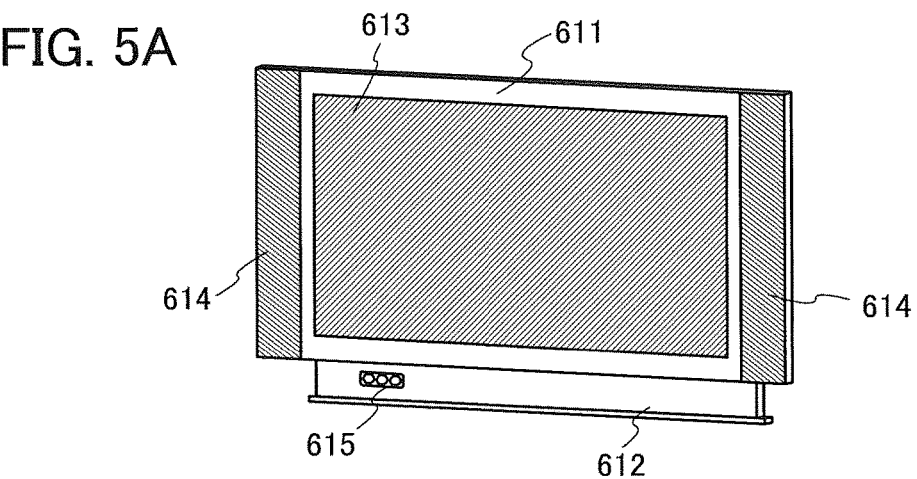
FIGS. 5A to 5D each illustrate an electronic device of one embodiment of the present invention.

FIG. 5A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention has high emission efficiency, a television set with low power consumption can be obtained by application of the light-emitting device of one embodiment of the present invention.

Figure 5B:
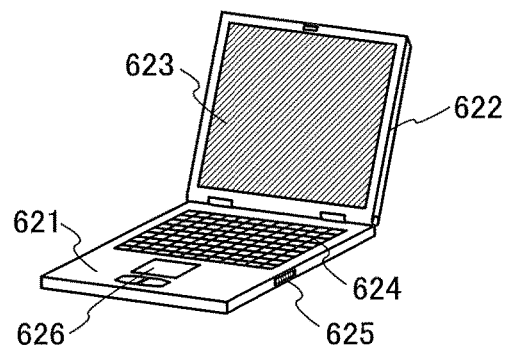

FIG. 5B illustrates a computer according to one embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of one embodiment of the present invention has high emission efficiency, a computer with low power consumption can be obtained by application of the light-emitting device of one embodiment of the present invention.

Figure 5C:
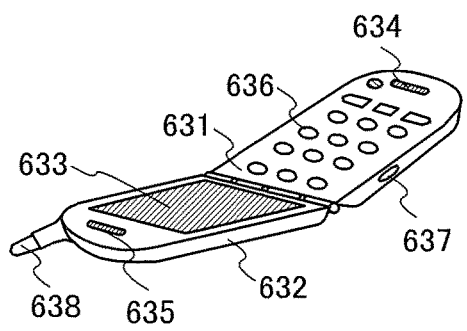

FIG. 5C shows a cellular phone of one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since the light-emitting device of one embodiment of the present invention has high emission efficiency, a cellular phone having reduced power consumption can be obtained by application of the light-emitting device of one embodiment of the present invention.

Figure 5D:
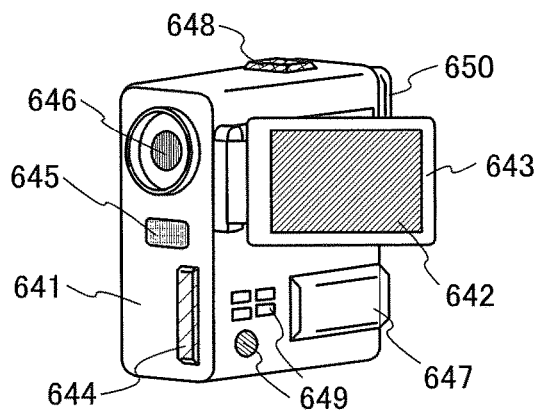

FIG. 5D shows a camera of one embodiment of the present invention, which includes a main body 641, a display portion 642, a housing 643, an external connection port 644, a portion 645 for receiving signals from a remote control, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention has high emission efficiency, a camera having reduced power consumption can be obtained by application of the light-emitting device of one embodiment of the present invention.

As thus described, application range of the light-emitting device of one embodiment of the present invention is quite wide, and this light-emitting device can be applied to electronic devices of a variety of fields. With use of the light-emitting device of one embodiment of the present invention, an electronic device having reduced power consumption can be obtained.

Figure 6:
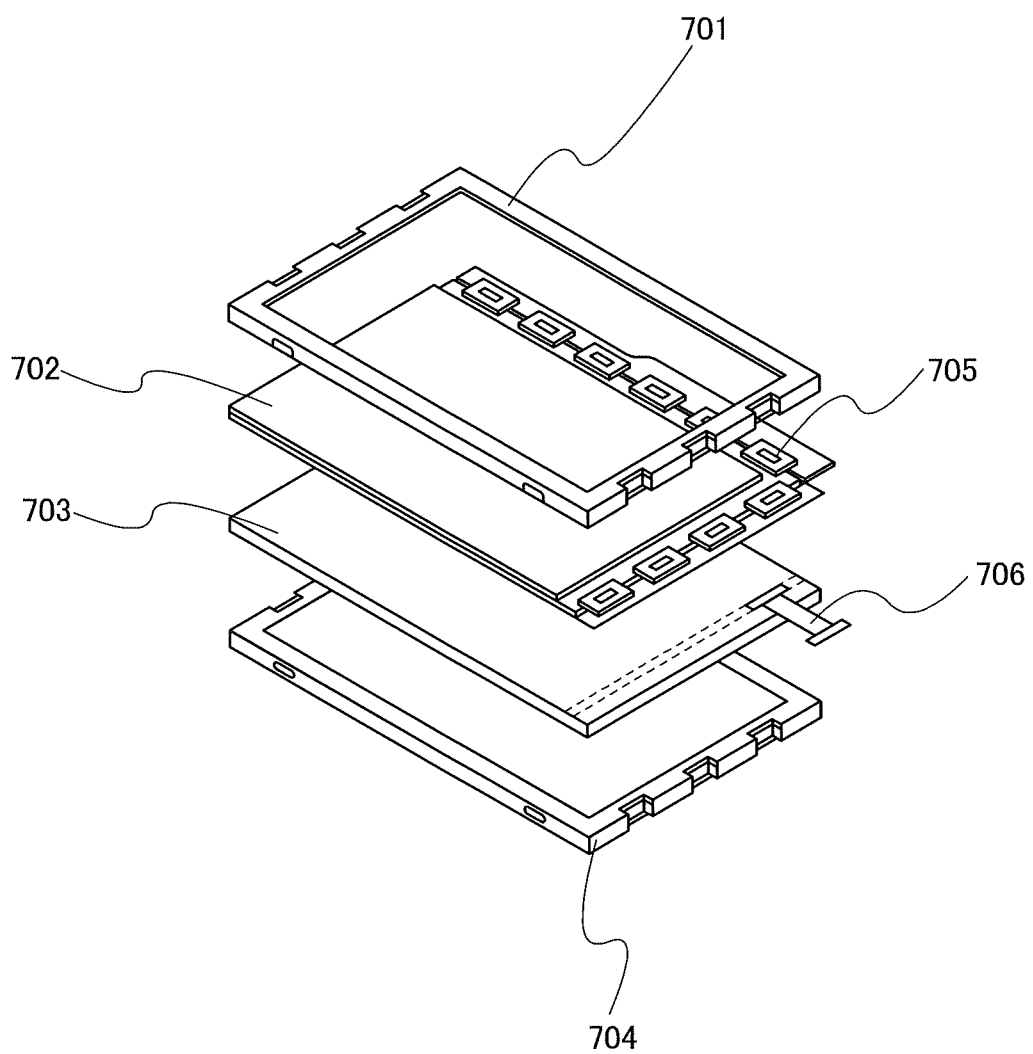
FIG. 6 illustrates a lighting device according to one embodiment of one embodiment of the present invention.

Moreover, the light-emitting device of one embodiment of the present invention can be used as a lighting device. FIG. 6 illustrates an example of a liquid crystal display device using the light-emitting device of one embodiment of the present invention as a backlight. The liquid crystal display device illustrated in FIG. 6 includes a housing 701, a liquid crystal layer 702, a backlight 703, and a housing 704. The liquid crystal layer 702 is connected to a driver IC 705. The light-emitting device of one embodiment of the present invention is used as the backlight 703, and a current is supplied through a terminal 706.

By using the light-emitting device of one embodiment of the present invention as a backlight of a liquid crystal display device as described above, a backlight having low power consumption can be obtained. Moreover, since the light-emitting device of one embodiment of the present invention is a lighting device for surface light emission and the enlargement of the light-emitting device is possible, the backlight can be made larger. Accordingly, a larger-area liquid crystal display device having low power consumption can be obtained.

Figure 7:
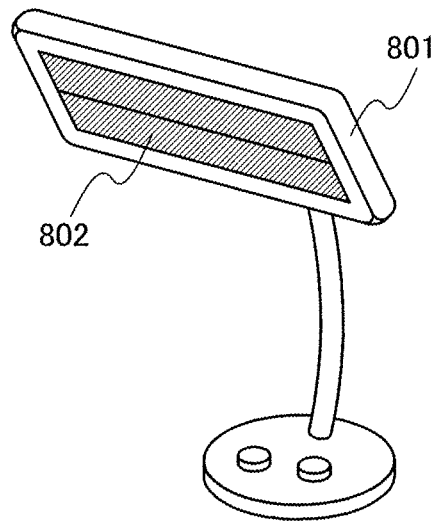
FIG. 7 illustrates a lighting device according to one embodiment of the present invention.

FIG. 7 illustrates an example in which the light-emitting device of one embodiment of the present invention is used for a desk lamp which is a lighting device. The desk lamp in FIG. 7 has a housing 801 and a light source 802, and the light-emitting device of one embodiment of the present invention is used as the light source 802. The light-emitting device of one embodiment of the present invention has the light-emitting element having high emission efficiency and therefore can be used for a desk lamp having low power consumption.

Figure 8:
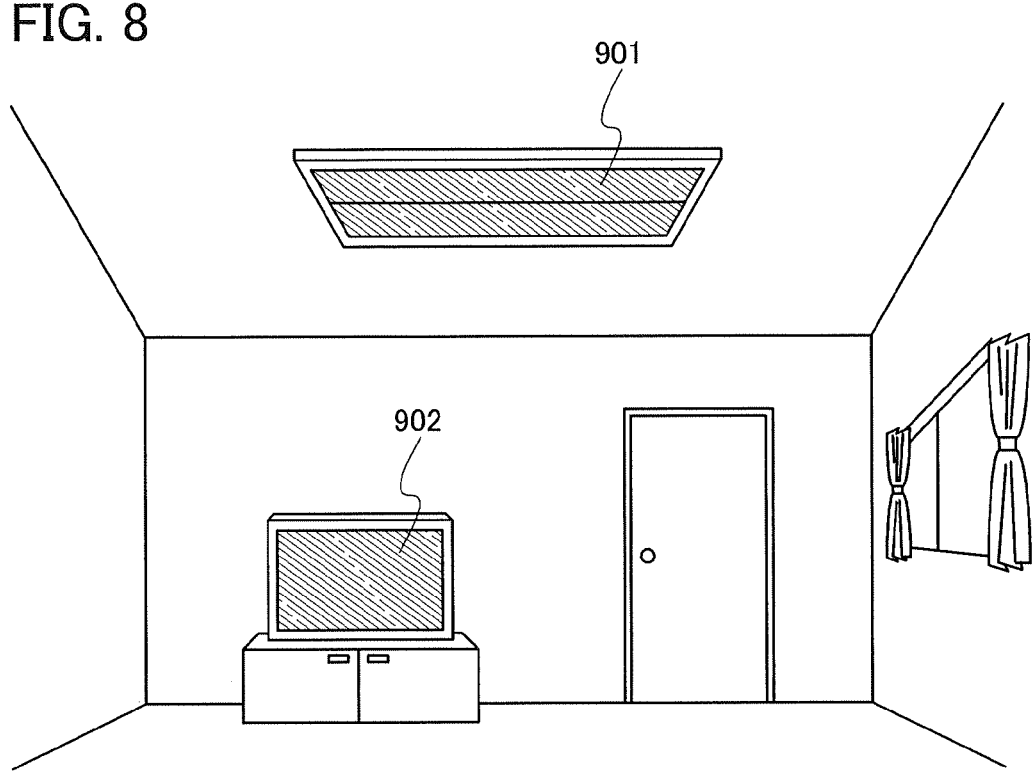
FIG. 8 illustrates a lighting device according to one embodiment of the present invention.

FIG. 8 illustrates an example in which the light-emitting device of one embodiment of the present invention is used for an indoor lighting device 901. Since the light-emitting device of an embodiment of the present invention can have a larger area, the light-emitting device of an embodiment of the present invention can be used as a lighting system having a large area. Further, the light-emitting device of one embodiment of the present invention has the light-emitting element having high emission efficiency and therefore can be used as a lighting device having low power consumption. In a room where the light-emitting device of one embodiment of the present invention is used as the indoor lighting device 901 as above, a television set 902 of one embodiment of the present invention as described referring to FIG. 5A can be installed so that pubic broadcasting and movies can be watched.

Note that the structure described of this embodiment can be implemented in combination with any of the structures described in other embodiments as appropriate.

EXAMPLE 1

Synthesis Example 1

This example will show a method of synthesizing 4-[3-(9,10-diphenyl-2-anthryl)phenyl]dibenzofuran (abbreviation: 2mDBFPPA-II) represented by the following Structural formula (100).

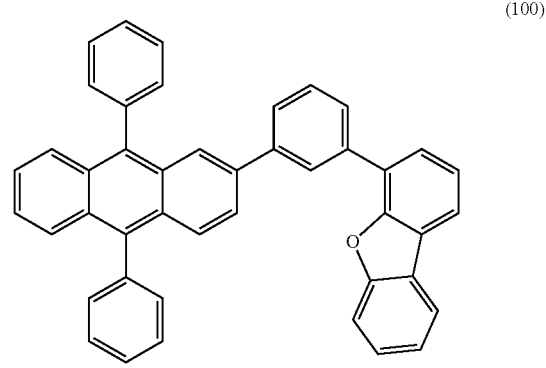 [SMILES: c1ccc(-c2c3ccccc3c(-c3ccccc3)c3cc(-c4cccc(-c5cccc6c5oc5ccccc56)c4)ccc23)cc1]

(100)

The method of synthesizing 2mDBFPPA-II is represented by Synthesis Scheme (C-1), and reaction in the synthesis will be detailed below.

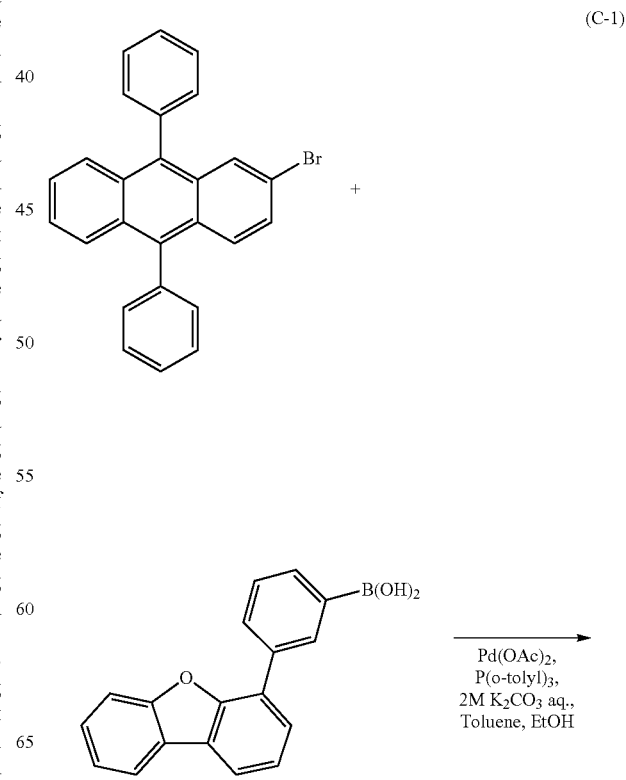

(C-1)

-continued

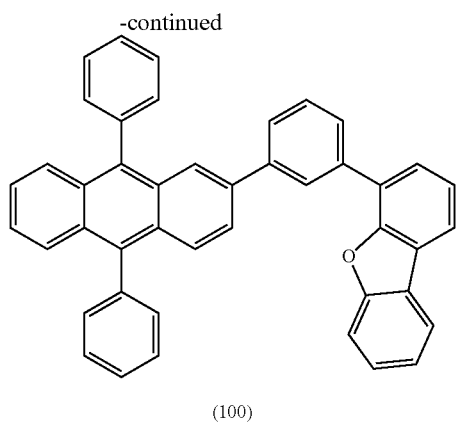

(100)

In a 100 mL three-neck flask were put 1.2 g (3.0 mmol) of 2-bromo-9,10-diphenylanthracene, 0.87 g (3.0 mmol) of 3-(dibenzofuran-4-yl)phenylboronic acid, and 0.23 g (0.75 mmol) of tri(ortho-tolyl)phosphine. The air in the flask was replaced with nitrogen. To this mixture were added 15 mL of toluene, 5.0 mL of ethanol, and 3.0 mL of a 2.0 mol/L aqueous solution of potassium carbonate. While the pressure was reduced, this mixture was stirred to be degassed.

Then, 34 mg (0.15 mmol) of palladium(II) acetate was added to this mixture, and the mixture was stirred under a nitrogen stream at 80° C. for 4 hours. Then, the aqueous layer of this mixture was extracted with ethyl acetate, and the extracted solution and the organic layer were combined and washed with saturated brine. The organic layer was dried with magnesium sulfate. Then, this mixture was gravity filtered. The resulting filtrate was concentrated to give a solid, and the solid was purified by silica gel column chromatography. The chromatography was carried out using a mixed solvent having a 5:1 ratio of hexane to toluene as a developing solvent, whereby a solid was obtained. Recrystallization of the solid from a mixed solvent of toluene and hexane gave 1.4 g of a yellow powder in 79% yield, which was the substance to be produced.

By a train sublimation method, 1.4 g of the obtained yellow powdered solid was purified. In the purification, the yellow powdered solid was heated at 270° C. under a pressure of 3.0 Pa with a flow rate of argon gas of 4.0 mL/min. After the purification, 1.1 g of a yellow solid was obtained in a yield of 81%, which was the substance to be produced.

A nuclear magnetic resonance (NMR) method identified this compound as 4-[3-(9,10-diphenyl-2-anthryl)phenyl] dibenzofuran (abbreviation: 2mDBFPPA-II), which was the substance to be produced.

$^1$H NMR data of the obtained compound are: $^1$H NMR (CDCl$_3$, 300 MHz): δ =7.31-7.67 (m, 19H), 7.69-7.73 (m, 3H), 7.80-7.86 (m, 2H), 7.95 (dd, J$_1$=0.90 Hz, J$_2$=1.8 Hz, 1H), 7.98-8.01 (m, 2H), 8.07 (s, 1H).

Figure 9A:
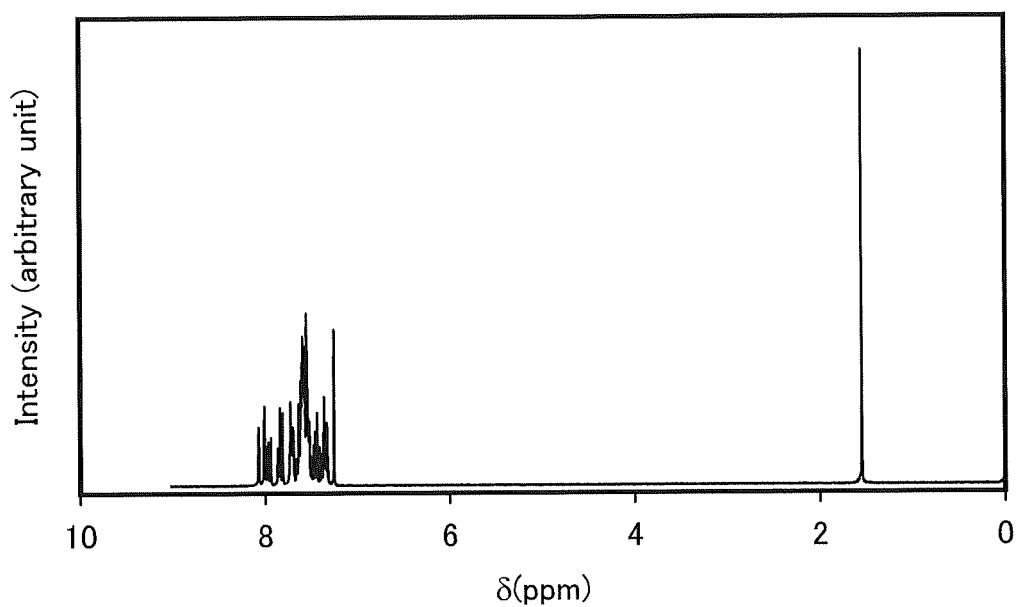
FIGS. 9A and 9B show $^1$H NMR charts of 4-[3-(9,10-diphenyl-2-anthryl)phenyl]dibenzofuran.
Figure 9B:
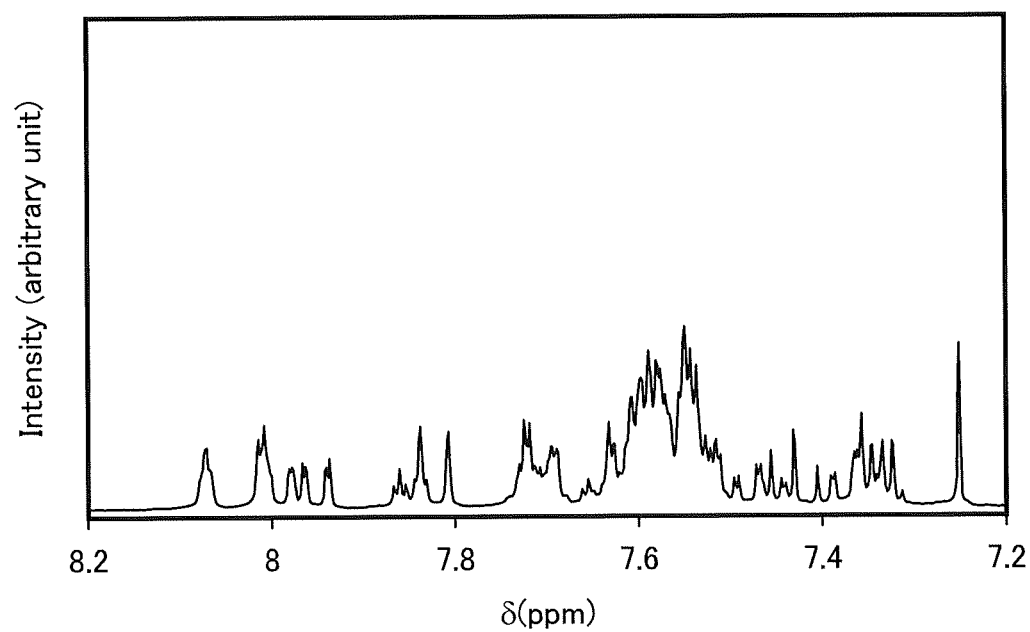

FIGS. 9A and 9B show the $^1$H NMR charts. Note that FIG. 9B is a chart showing an enlarged part of FIG. 9A in the range of 7.2 to 8.2 ppm.

Thermogravimetry-differential thermal analysis (TG-DTA) of 2mDBFPPA-II, which was obtained, was performed. A high vacuum differential type differential thermal balance (manufactured by Bruker AXS K. K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) demonstrates that the temperature at which the weight at the start of the measurement is reduced by 5% (5% weight loss temperature) is 418.0° C., which is indicative of high heat resistance.

Figure 10A:
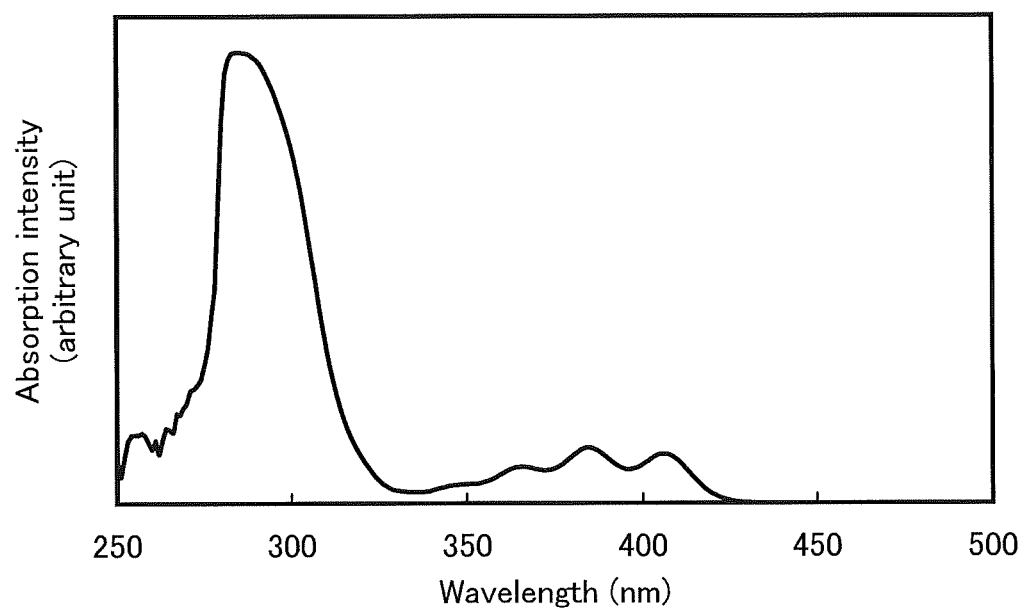
FIGS. 10A and 10B show an absorption spectrum and an emission spectrum of a toluene solution of 4-[3-(9,10-diphenyl-2-anthryl)phenyl]dibenzofuran.
Figure 10B:
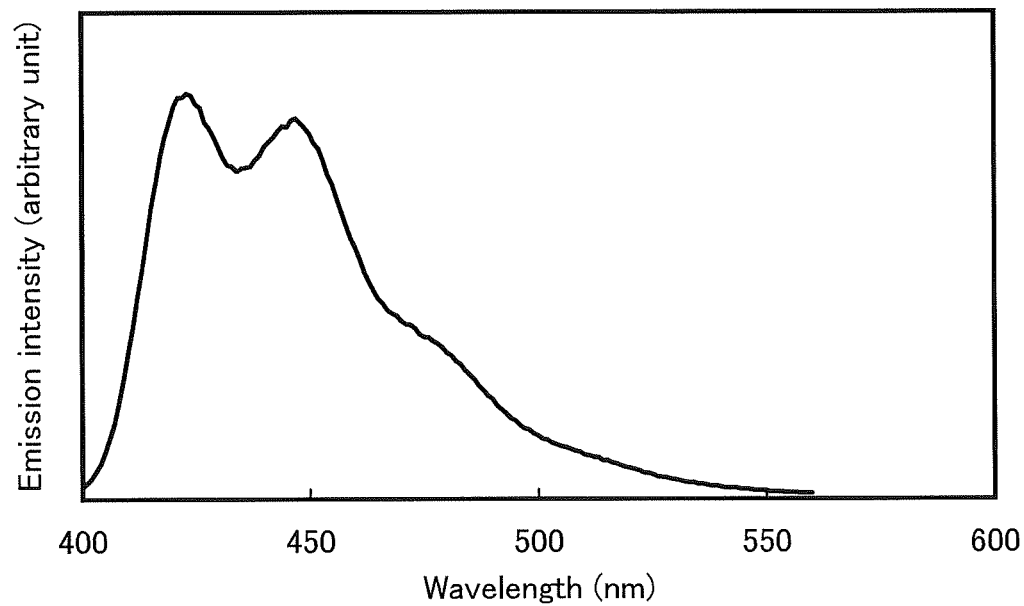
Figure 11A:
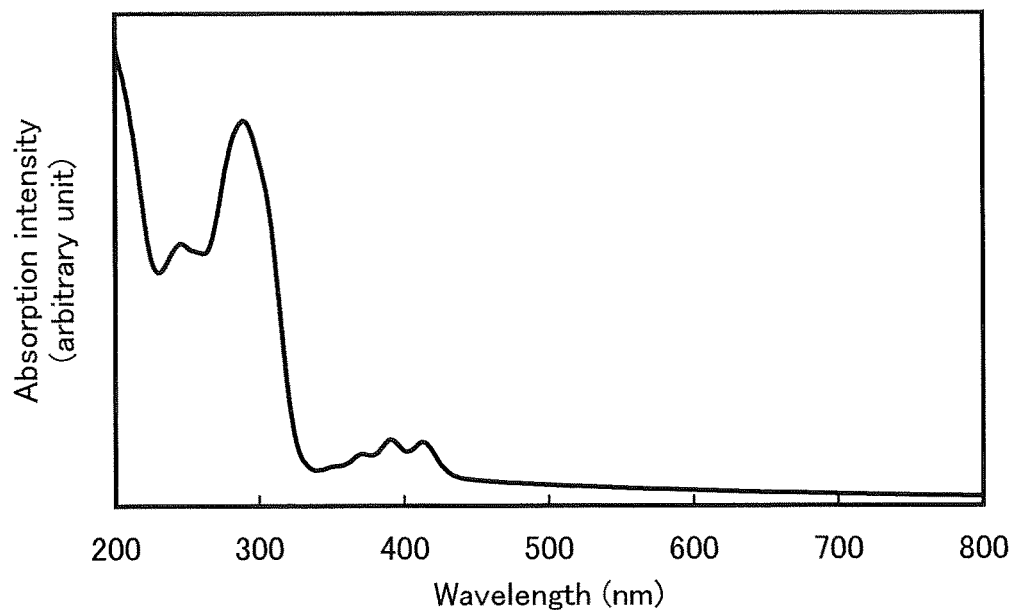
FIGS. 11A and 11B show an absorption spectrum and an emission spectrum of a thin film of 4-[3-(9,10-diphenyl-2-anthryl)phenyl]dibenzofuran.
Figure 11B:
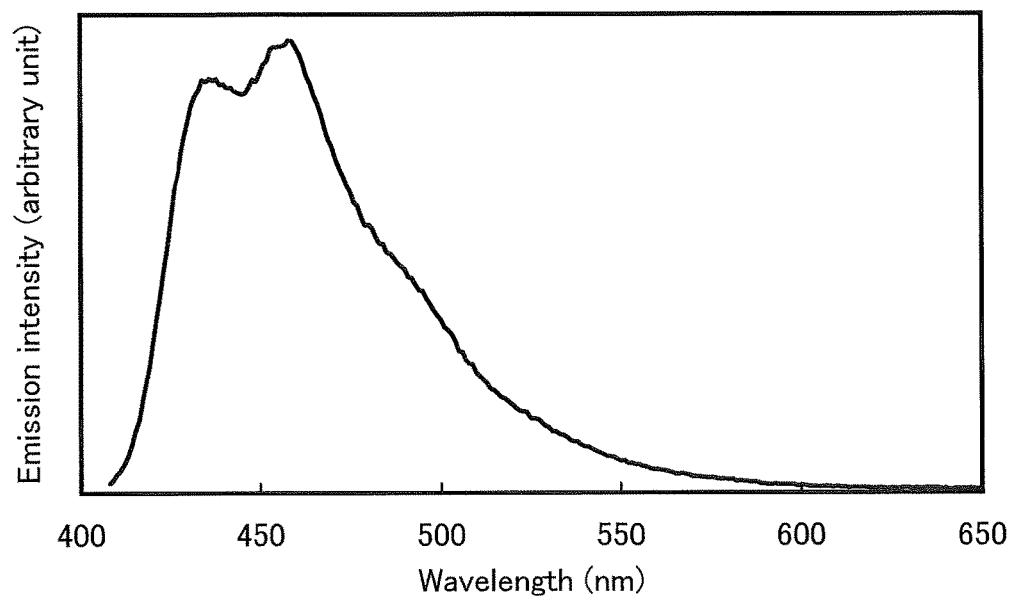

Further, FIG. 10A shows an absorption spectrum of a toluene solution of 2mDBFPPA-II, and FIG. 10B shows an emission spectrum thereof. FIG. 11A shows an absorption spectrum of a thin film of 2mDBFPPA-II, and FIG. 11B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 10A and 10B and FIGS. 11A and 11B, the horizontal axis represents wavelength (nm) and the vertical axis represents intensity (arbitrary unit). In the case of the toluene solution, absorption was observed at around 406 nm, and the emission wavelengths were 424 nm and 447 nm (excitation wavelength: 384 nm). In the case of the thin film, absorption was observed at around 246 nm, 289 nm, 371 nm, 391 nm and 413 nm, and the emission wavelengths were 437 nm and 458 nm (excitation wavelength: 392 nm).

The HOMO level and the LUMO level of the thin film of 2mDBFPPA-II were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, which was obtained from Tauc plot with an assumption of direct transition using data on the absorption spectrum of the thin film of 2mDBFPPA-II which is shown in FIG. 11A, was regarded as an optical energy gap and added to the value of the HOMO level. As a result, the HOMO level and LUMO level of 2mDBFPPA-II were found to be −5.66 eV and −2.79 eV, respectively.

The oxidation characteristic and reduction characteristic of 2mDBFPPA-II were measured. In the measurements of the oxidation and reduction characteristics, cyclic voltammetry (CV) measurement was employed, and an electrochemical analyzer (ALS model 600A, manufactured by BAS Inc.) was used.

As a solution used in the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 reference electrode for nonaqueous solvent) was used as a reference electrode. Note that the measurement was conducted at room temperature. In addition, the scan rate at the CV measurement was set to 0.1 V/s in all the measurement.

The reduction characteristic of 2mDBFPPA-II was examined by 100 measurement cycles in which the potential of the working electrode with respect to the reference electrode was scanned from −1.48 V to −2.27 V and then from −2.27 V to −1.48 V in each cycle. Similarly, the oxidation characteristic of 2mDBFPPA-II was evaluated by 100 measurement cycles in which the potential of the working electrode with respect to the reference electrode was scanned from 0.18 V to 1.02 V and then from 1.02 V to 0.18 V in each cycle.

Figure 12A:
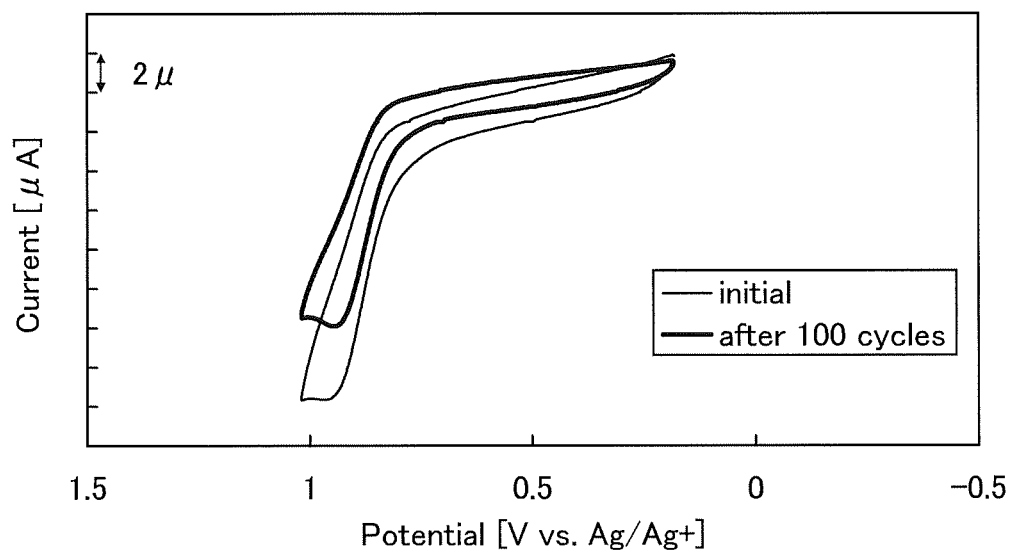
FIGS. 12A and 12B show CV measurement results of 4-[3-(9,10-diphenyl-2-anthryl)phenyl]dibenzofuran.
Figure 12B:
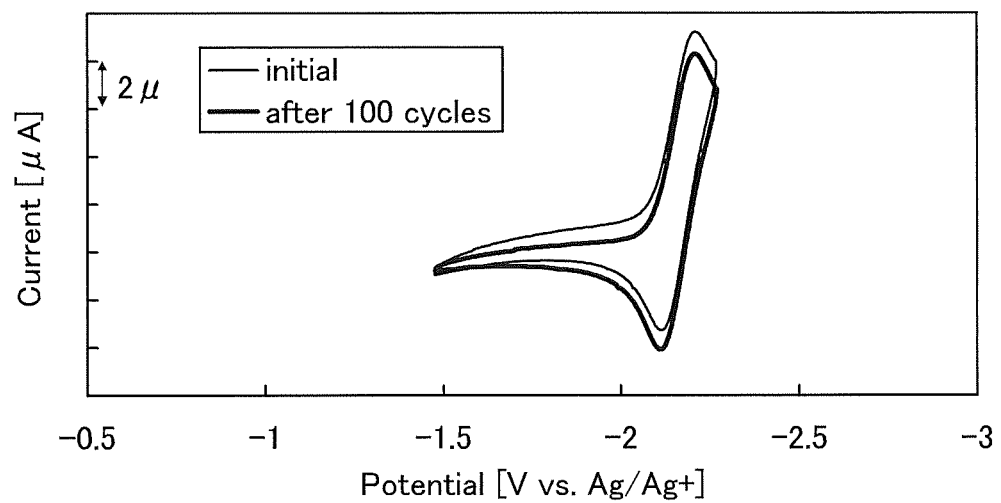

According to the measurement results, a peak current corresponding to oxidation at around 0.89 V (vs. Ag/Ag$^+$) and a peak current corresponding to reduction at around −2.16 V (vs. Ag/Ag$^+$) were observed. FIG. 12 shows a graph of the results.

Even after as many as 100 scan cycles, 2mDBFPPA-II showed no significant change in the peak position of the CV curves representing oxidation and reduction and kept the peak intensity at 76% of the initial intensity on the oxidation side and at 90% on the reduction side. Thus, it is understood that 2mDBFPPA-II is relatively stable, when subjected to repetitions of oxidation from a neutral state to an oxidized state and reduction from the oxidized state to the neutral state or repetitions of reduction from a neutral state to a reduced state and oxidation from the reduced state to the neutral state.

EXAMPLE 2

Synthesis Example 2

This example will show a method of synthesizing 4-[3-(9,10-diphenyl-2-anthryl)phenyl]dibenzothiophene (abbreviation: 2mDBTPPA-II) represented by the following Structural formula (300).

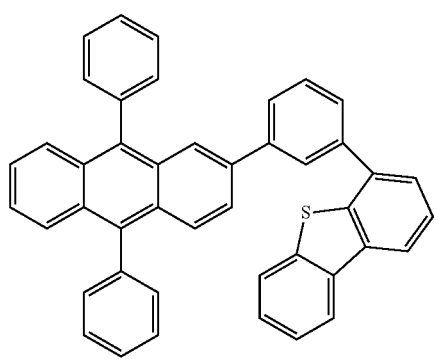

(300)

The method of synthesizing 2mDBTPPA-II is represented by Synthesis Scheme (D-1), and reaction in the synthesis will be detailed below.

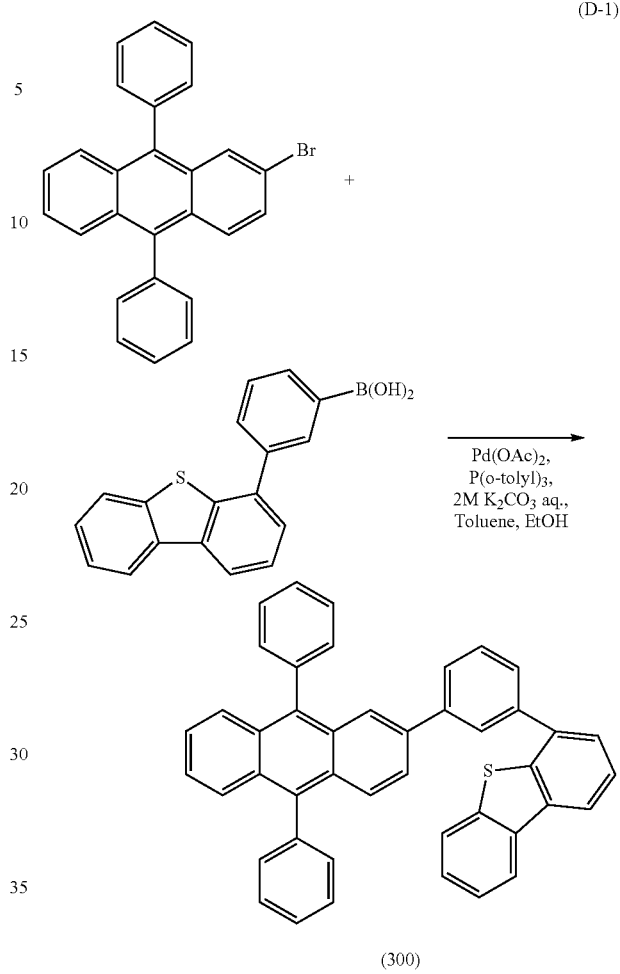

(D-1)

In a 100 mL three-neck flask were put 1.6 g (4.0 mmol) of 2-bromo-9,10-diphenylanthracene, 1.2 g (4.0 mmol) of 3-(dibenzothiophen-4-yl)phenylboronic acid, and 0.30 g (1.0 mmol) of tri(ortho-tolyl)phosphine. The air in the flask was replaced with nitrogen. To this mixture were added 25 mL of toluene, 5.0 mL of ethanol, and 5.0 mL of a 2.0 mol/L aqueous solution of potassium carbonate. While the pressure was reduced, this mixture was stirred to be degassed.

Then, 45 mg (0.20 mmol) of palladium(II) acetate was added to this mixture, and the mixture was stirred under a nitrogen stream at 80° C. for 5 hours. Then, the aqueous layer of this mixture was extracted with toluene, and the toluene solution and the organic layer were combined and washed with saturated brine. The organic layer was dried with magnesium sulfate. Then, this mixture was gravity filtered. The resulting filtrate was concentrated to give an oily substance. The obtained oily substance was purified by silica gel column chromatography. The chromatography was carried out using a mixed solvent having a 5:1 ratio of hexane to toluene as a developing solvent, whereby a solid was obtained. Recrystallization of the solid from a mixed solvent of toluene and hexane gave 1.6 g of a yellow powder in 70% yield, which was the substance to be produced.

By a train sublimation method, 1.6 g of the obtained yellow powdered solid was purified. In the purification, the yellow powdered solid was heated at 290° C. under a pressure of 3.0 Pa with a flow rate of argon gas of 4.0 mL/min. After the purification, 1.4 g of a yellow solid was obtained in a yield of 87%, which was the substance to be produced.

A nuclear magnetic resonance (NMR) method identified this compound as 4-[3-(9,10-diphenyl-2-anthryl)phenyl] dibenzothiophene (abbreviation: 2mDBTPPA-II), which was the substance to be produced.

$^1$H NMR data of the obtained compound are: $^1$H NMR (CDCl$_3$, 300 MHz): δ =7.33 (q, J$_1$=3.3 Hz, 2H), 7.46-7.73 (m, 20H), 7.80-7.87 (m, 2H), 7.99 (st, J$_1$=1.8 Hz, 1H), 8.03 (sd, J$_1$=1.5 Hz, 1H), 8.14-8.20 (m, 2H).

Figure 13A:
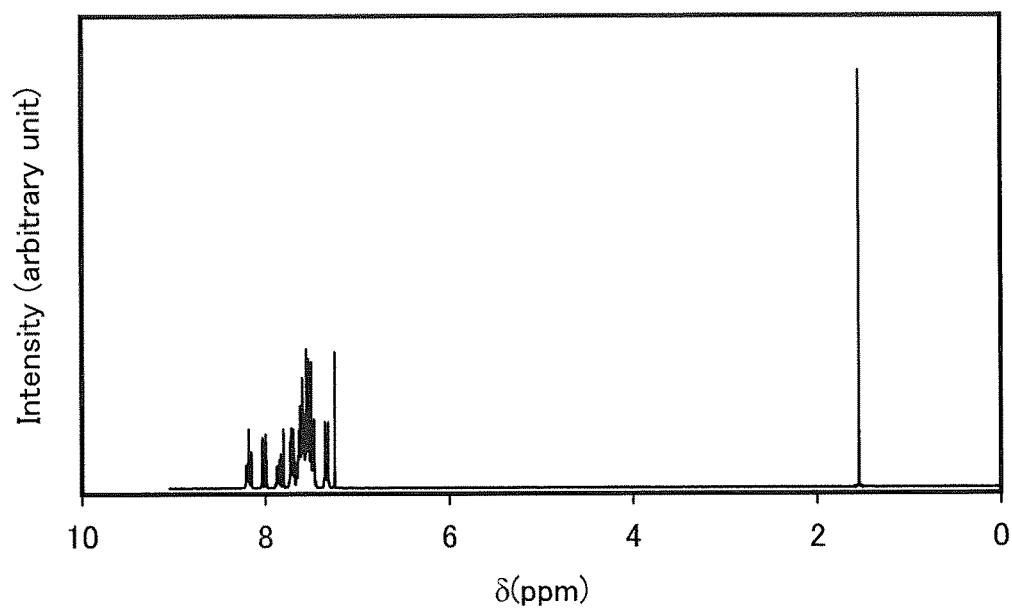
FIGS. 13A and 13B show $^1$H NMR charts of 4-[3-(9,10-diphenyl-2-anthryl)phenyl]dibenzothiophene.
Figure 13B:
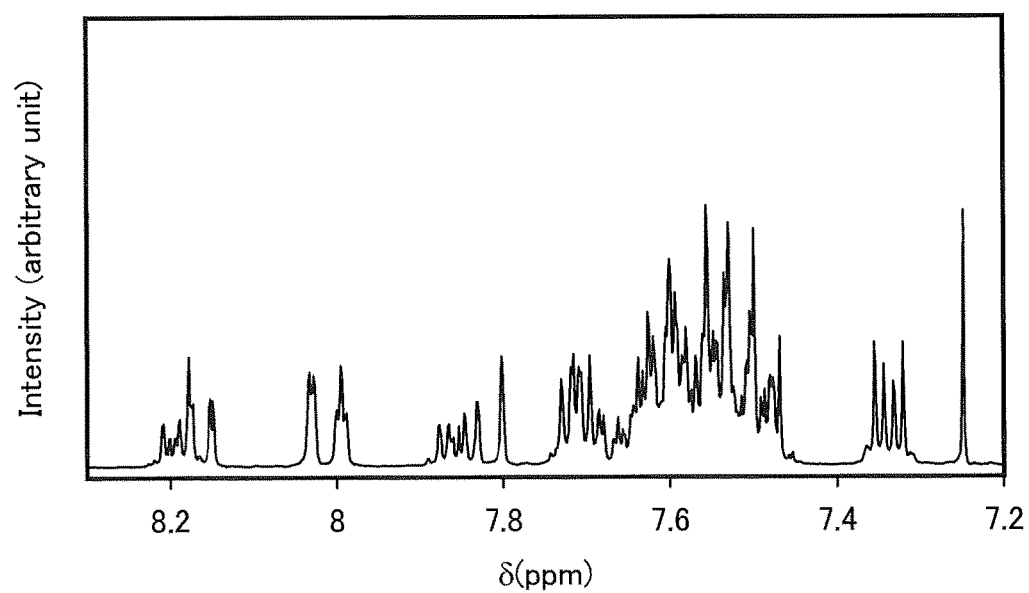

FIGS. 13A and 13B show the $^1$H NMR charts. Note that FIG. 13B is a chart showing an enlarged part of FIG. 13A in the range of 7.2 to 8.3 ppm.

Thermogravimetry-differential thermal analysis (TG-DTA) of 2mDBTPPA-II, which was obtained, was performed. A high vacuum differential type differential thermal balance (manufactured by Bruker AXS K. K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) demonstrates that the 5% weight loss temperature is 441.1° C., which is indicative of high heat resistance.

Figure 14A:
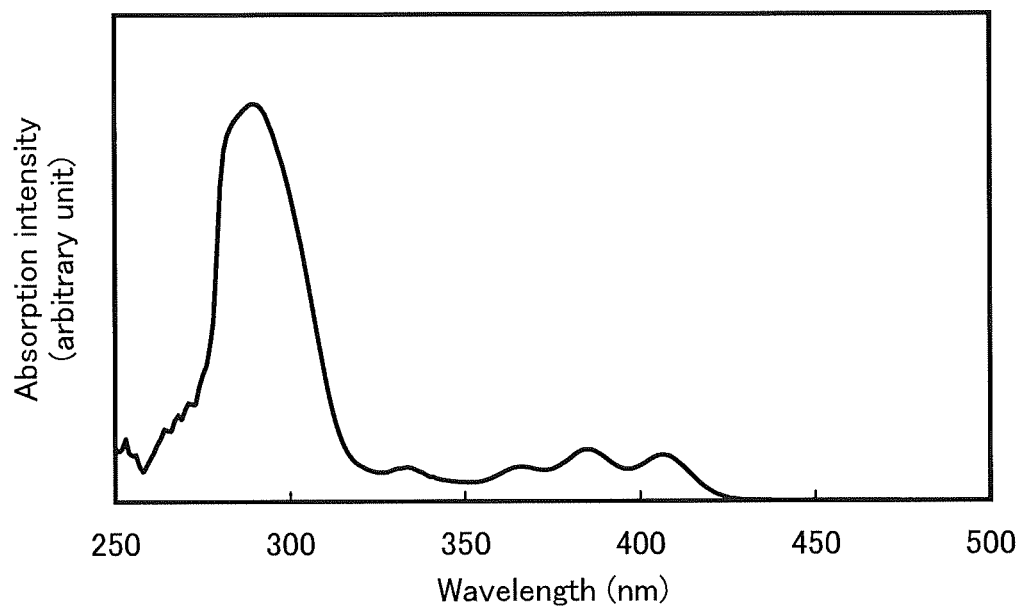
FIGS. 14A and 14B show an absorption spectrum and an emission spectrum of a toluene solution of 4-[3-(9,10-diphenyl-2-anthryl)phenyl]dibenzothiophene.
Figure 14B:
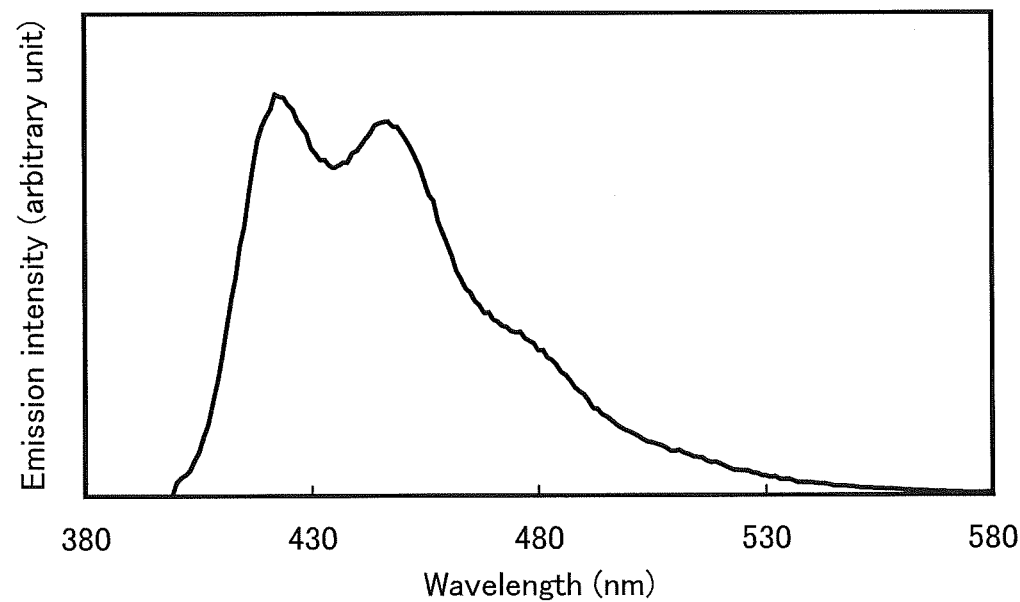
Figure 15A:
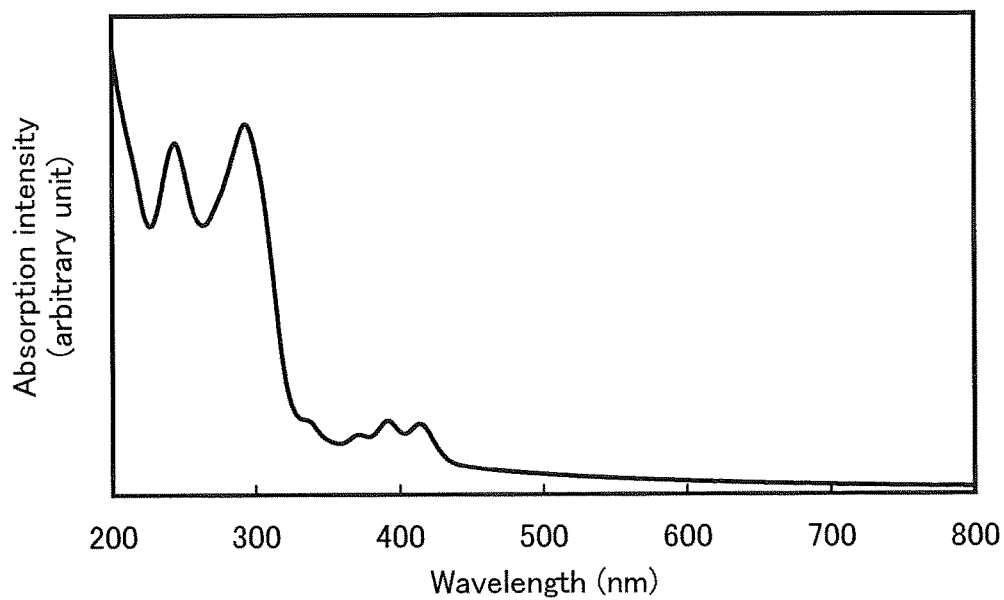
FIGS. 15A and 15B show an absorption spectrum and an emission spectrum of a thin film of 4-[3-(9,10-diphenyl-2-anthryl)phenyl]dibenzothiophene.
Figure 15B:
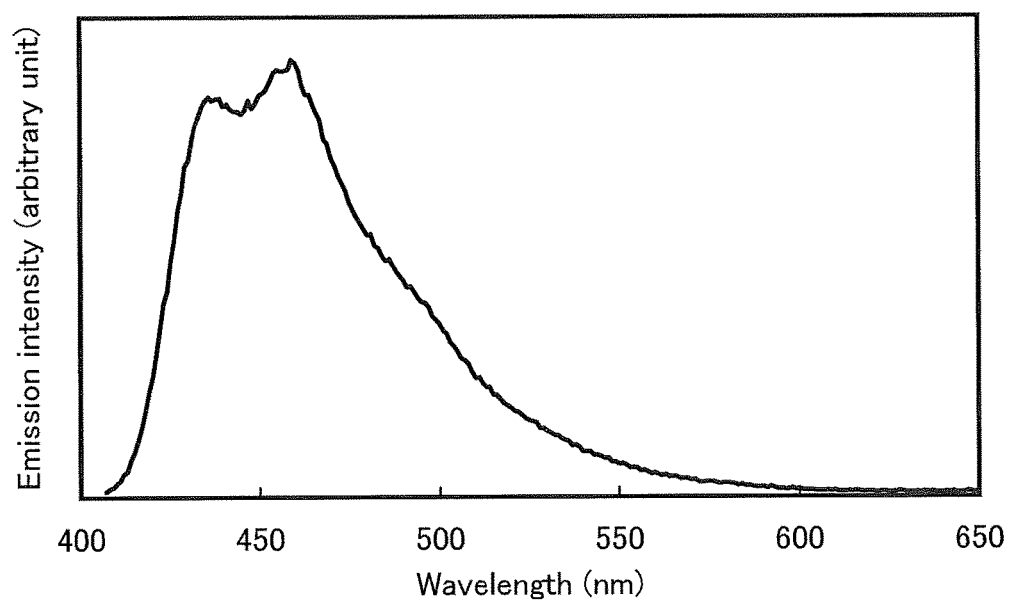

Further, FIG. 14A shows an absorption spectrum of a toluene solution of 2mDBTPPA-II, and FIG. 14B shows an emission spectrum thereof. FIG. 15A shows an absorption spectrum of a thin film of 2mDBTPPA-II, and FIG. 15B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 14A and 14B and FIGS. 15A and 15B, the horizontal axis represents wavelength (nm) and the vertical axis represents intensity (arbitrary unit). In the case of the toluene solution, absorption was observed at around 407 nm, and the emission wavelengths were 423 nm and 446 nm (excitation wavelength: 385 nm). In the case of the thin film, absorption was observed at around 244 nm, 293 nm, 371 nm, 392 nm and 414 nm, and the emission wavelengths were 437 nm and 459 run (excitation wavelength: 391 nm).

The HOMO level and the LUMO level of the thin film of 2mDBTPPA-II were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, which was obtained from Tauc plot with an assumption of direct transition using data on the absorption spectrum of the thin film of 2mDBTPPA-II which is shown in FIG. 15A, was regarded as an optical energy gap and added to the value of the HOMO level. As a result, the HOMO level and LUMO level of 2mDBTPPA-II were found to be −5.71 eV and −2.85 eV, respectively.

The oxidation characteristic and reduction characteristic of 2mDBTPPA-II were measured. In the measurements of the oxidation and reduction characteristics, cyclic voltammetry (CV) measurement was employed, and an electrochemical analyzer (ALS model 600A, manufactured by BAS Inc.) was used.

As a solution used in the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 reference electrode for nonaqueous solvent) was used as a reference electrode. Note that the measurement was conducted at room temperature. In addition, the scan rate at the CV measurement was set to 0.1 V/s in all the measurement.

The reduction characteristic of 2mDBTPPA-II was examined by 100 measurement cycles in which the potential of the working electrode with respect to the reference electrode was scanned from −1.46 V to −2.25 V and then from −2.25 V to −1.46 V in each cycle. Similarly, the oxidation characteristic of 2mDBTPPA-II was evaluated by 100 measurement cycles in which the potential of the working electrode with respect to the reference electrode was scanned from 0.32 V to 1.00 V and then from 1.00 V to 0.32 V in each cycle.

Figure 16A:
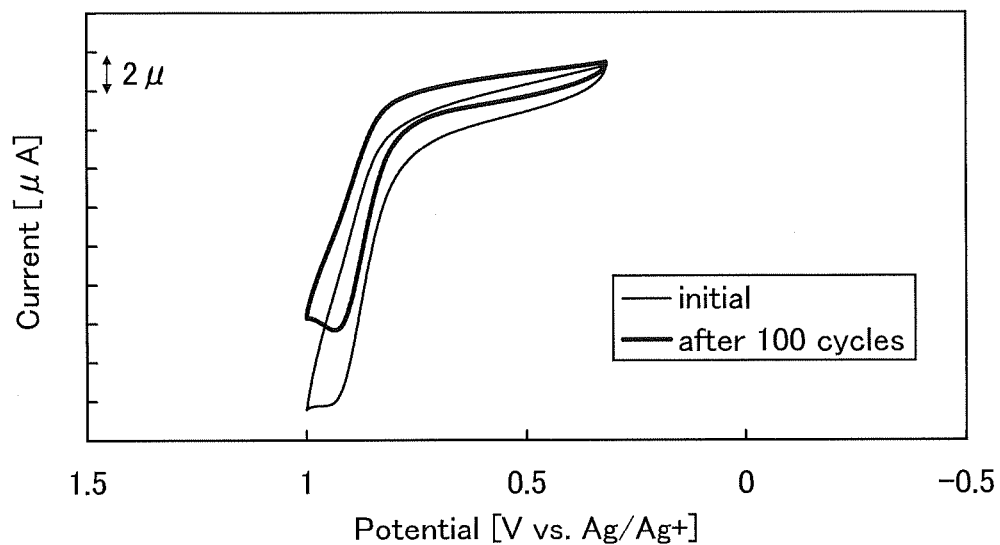
FIGS. 16A and 16B show CV measurement results of 4-[3-(9,10-diphenyl-2-anthryl)phenyl]dibenzothiophene.
Figure 16B:
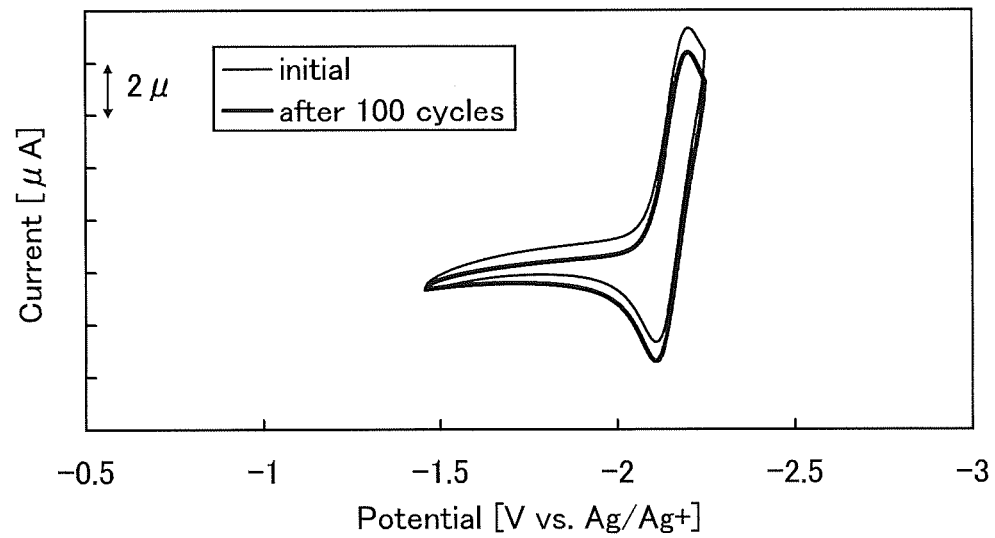

According to the measurement results, a peak current corresponding to oxidation at around 0.88 V (vs. Ag/Ag$^+$) and a peak current corresponding to reduction at around −2.16 V (vs. Ag/Ag$^+$) were observed. FIG. 16 shows a graph of the results.

Even after as many as 100 scan cycles, 2mDBIPPA-II showed no significant change in the peak position of the CV curves representing oxidation and reduction and kept the peak intensity at 76% of the initial intensity on the oxidation side and at 90% on the reduction side. Thus, it is understood that 2mDBTPPA-II is relatively stable, when subjected to repetitions of oxidation from a neutral state to an oxidized state and reduction from the oxidized state to the neutral state or repetitions of reduction from a neutral state to a reduced state and oxidation from the reduced state to the neutral state.

EXAMPLE 3

Figure 37A:
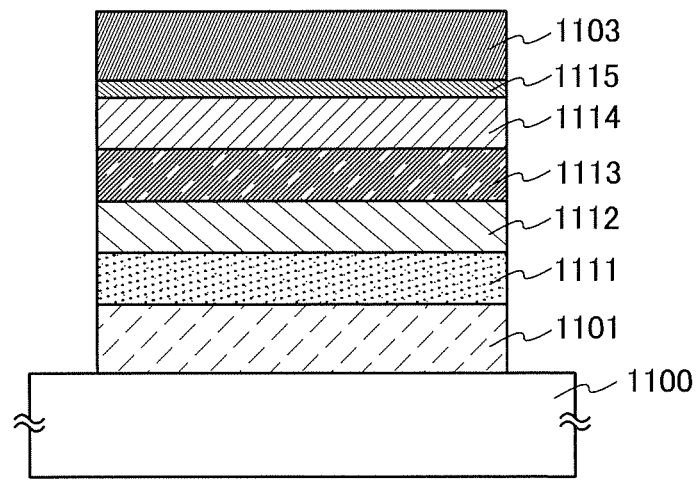
FIGS. 37A and 37B each illustrate a light-emitting element of Examples.

In this example, a light-emitting element of one embodiment of the present invention will be described referring to FIG. 37A. Chemical formulae of materials used in this example are shown below.

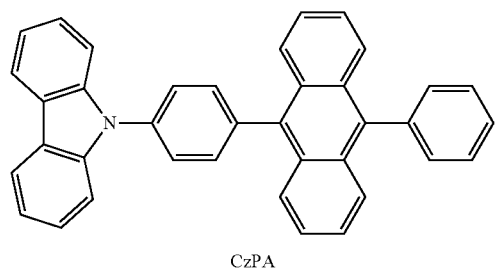

CzPA

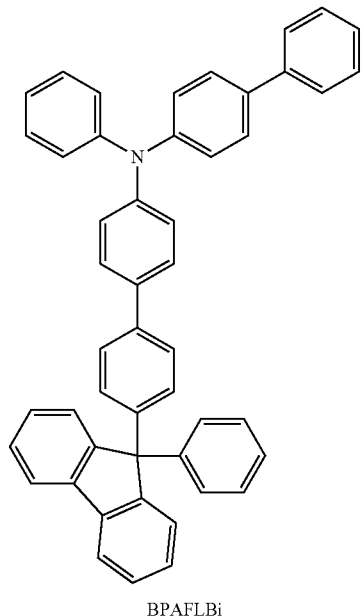

BPAFLBi

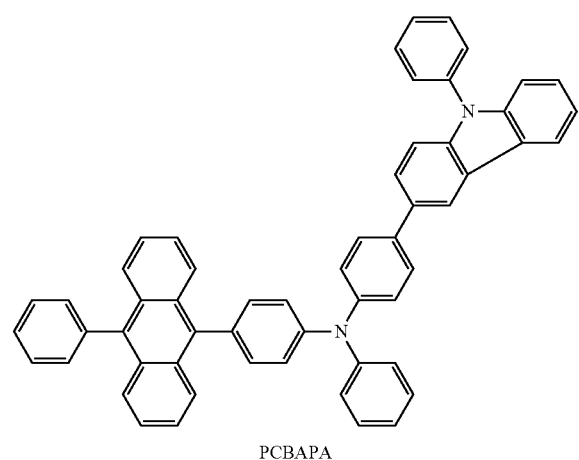

PCBAPA

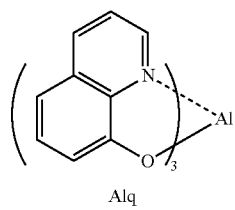

Alq

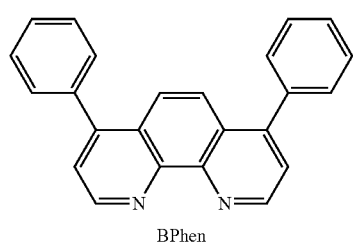

BPhen

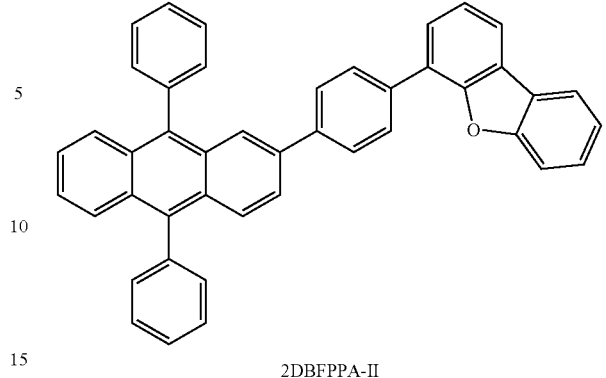

2DBFPPA-II

Methods of fabricating Light-emitting Element 1 of this example and Reference Light-emitting Element 1 will now be described.

(Light-emitting Element 1)

First, indium tin oxide containing silicon oxide (ITSO) was deposited by a sputtering method on a glass substrate 1100, whereby a first electrode 1101 was formed. Its thickness was 110 nm and the electrode area was 2 mm ×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, 9-[4-(10-phenyl-9-anthryl)phenyl]-9H-carbazole (abbreviation: CzPA) which is a substance having a high hole-transport property and molybdenum(VI) oxide which is an acceptor substance were co-evaporated to form a hole-injection layer 1111 over the first electrode 1101. The thickness of the hole-injection layer 1111 was 50 nm, and the weight ratio of CzPA to molybdenum(VI) oxide was controlled to be 4:2 (=CzPA: molybdenum(VI) oxide). Note that the co-evaporation method refers to an evaporation method in which evaporation is carried out from a plurality of evaporation sources at the same time in one treatment chamber.

Next, 4-phenyl-4'-[4-(9-phenylfluoren-9-yl)phenyl]triphenylamine (abbreviation: BPAFLBi) was deposited to a thickness of 10 nm over the hole-injection layer 1111, whereby a hole-transport layer 1112 was formed.

Furthermore, 2mDBFPPA-II synthesized in Example 1 and 4-(10-phenyl-9-anthryl)-4'-(9-phenyl-9H-carbazol-3-yl)triphenylamine (abbreviation: PCBAPA) were co-evaporated to form a light-emitting layer 1113 over the hole-transport layer. The weight ratio of 2mDBFPPA-II to PCBAPA was adjusted to 1:0.1 (=2mDBFPPA-II:PCBAPA). The thickness of the light-emitting layer 1113 was set to 30 nm.

Then, over the light-emitting layer 1113, a 10 nm thick layer of tris(8-quinolinolato)aluminum(III) (abbreviation: Alq) and, a 15 nm thick layer of bathophenanthroline (abbreviation: BPhen) were deposited on the Alq layer, whereby an electron-transport layer 1114 including Alq and BPhen was obtained.

Further, a 1 nm thick film of lithium fluoride (LiF) was formed over the electron-transport layer 1114 by evaporation, whereby an electron-injection layer 1115 was formed.

Lastly, a 200 nm thick film of aluminum was formed by evaporation to form a second electrode 1103 functioning as a cathode. Thus, Light-emitting Element 1 of this example was fabricated.

Note that, in the above evaporation process, evaporation was all performed by a resistance heating method.
(Reference Light-emitting Element 1)

The light-emitting layer 1113 of Reference Light-emitting Element 1 was formed by co-evaporation of 4-[4-(9,10-diphenyl-2-anthryl)phenyl]dibenzofuran (abbreviation: 2DBFPPA-II) and PCBAPA, instead of the material used for Light-emitting Element 1. The weight ratio of 2DBFPPA-II and PCBAPA was adjusted to 1:0.1 (=2DBFPPA-II:PCBAPA). The thickness of the light-emitting layer 1113 was set to 30 mn. The layers other than the light-emitting layer 1113 were formed in the same manner as Light-emitting Element 1.

Figure 19:
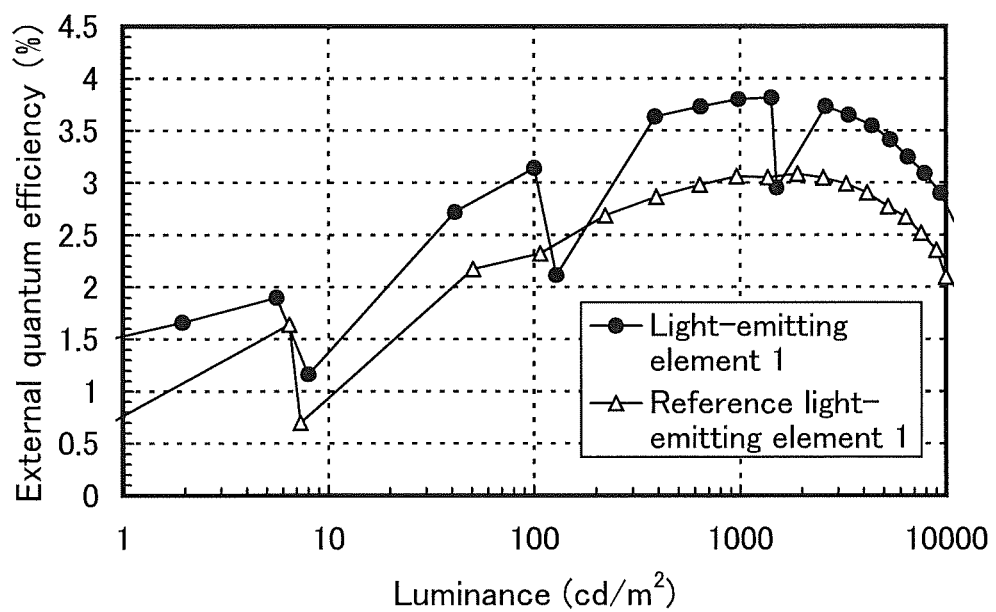
FIG. 19 shows luminance vs. external quantum efficiency characteristics of Light-emitting Element 1 and Reference Light-emitting Element 1.
Figure 20:
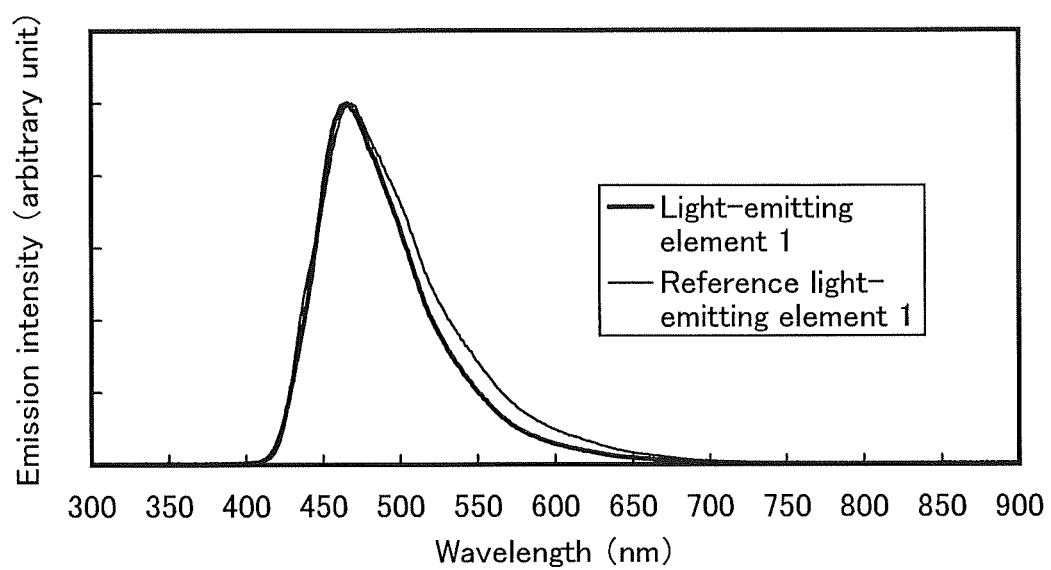
FIG. 20 shows emission spectra of Light-emitting Element 1 and Reference Light-emitting Element 1.

Table 1 shows element structures of Light-emitting Element 1 and Reference Light-emitting Element 1 formed as described above.

represents applied voltage (V) and the vertical axis represents luminance (cd/m²). FIG. 19 shows the luminance vs. external quantum efficiency characteristics. In FIG. 19, the horizontal axis represents luminance (cd/m²) and the vertical axis represents external quantum efficiency (%). FIG. 20 shows the emission spectra with a current supply of 1 mA. In FIG. 20, the horizontal axis represents wavelength (nm) and the vertical axis represents intensity (arbitrary unit). Further, Table 2 shows the voltage (V), current density (mAkm²), CIE chromaticity coordinates (x, y), current efficiency (cd/A), and external quantum efficiency (%) of each light-emitting element at a luminance of around 1000 cd/m².

TABLE 2

| | Voltage (V) | Current density (mA/cm²) | Chromaticity x | Chromaticity y | Luminance (cd/m²) | Current efficiency (cd/A) | External quantum efficiency (%) |
|---|---|---|---|---|---|---|---|
| Light-emitting Element 1 | 4.6 | 17 | 0.17 | 0.21 | 980 | 5.7 | 3.8 |
| Reference Light-emitting Element 1 | 4.6 | 19 | 0.18 | 0.24 | 960 | 5.2 | 3.1 |

Figure 17:
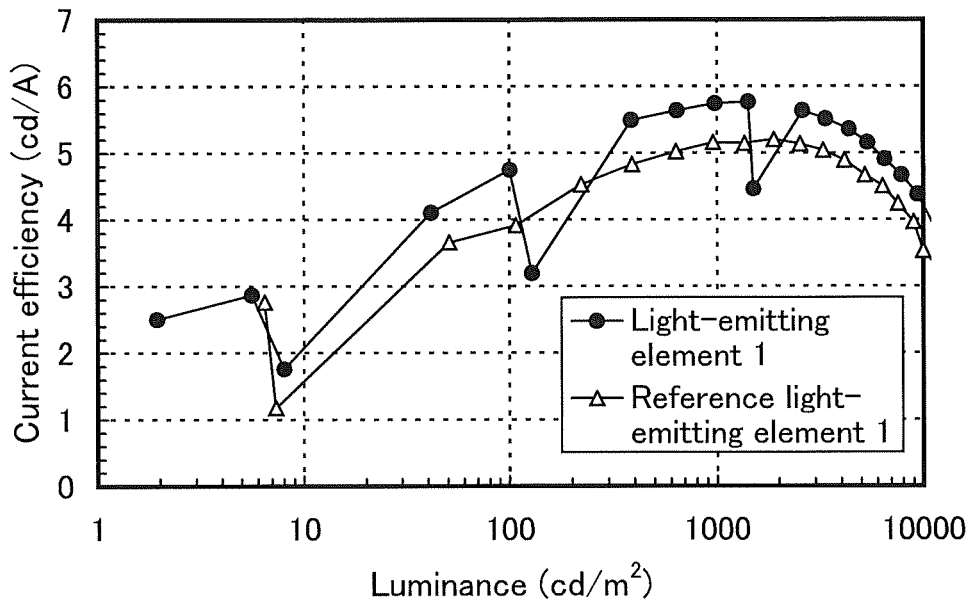
FIG. 17 shows luminance vs. current efficiency characteristics of Light-emitting Element 1 and Reference Light-emitting Element 1.
Figure 18:
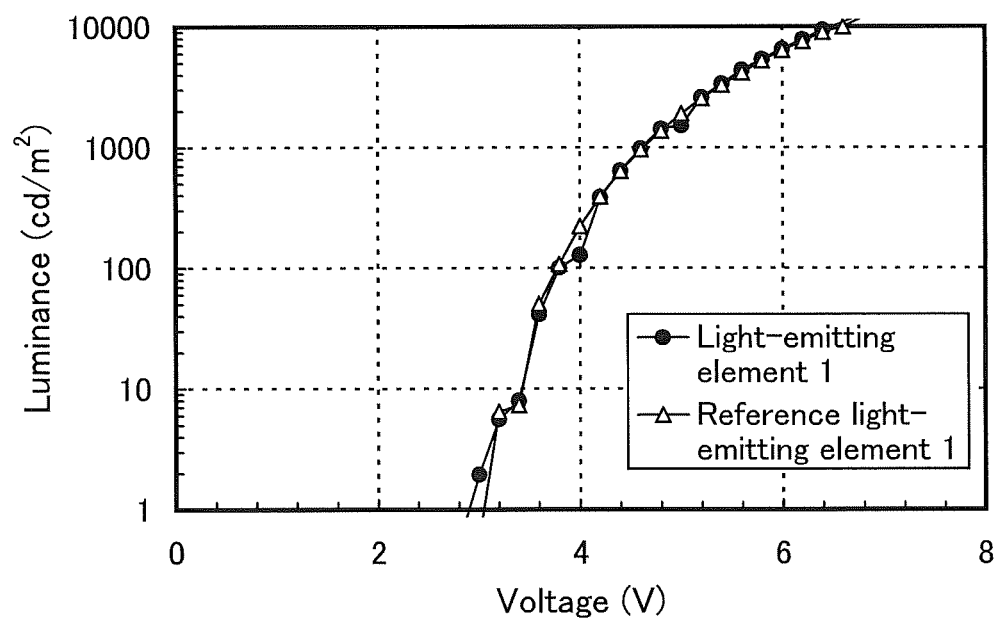
FIG. 18 shows voltage vs. luminance characteristics of Light-emitting Element 1 and Reference Light-emitting Element 1.

As seen from FIG. 20 and the CIE chromaticity coordinates in Table 2, blue light emission is shown by Light-emitting Element 1 and Reference Light-emitting Element 1, which were formed. FIG. 17, FIG. 18, FIG. 19, and Table 2 reveal that Light-emitting Element 1 exhibits better chromaticity and higher current efficiency and external quantum efficiency than those of Reference Light-emitting Element 1.

As described above, 2mDBFPPA-II produced in Example 1 was used as the host material of the light-emitting layer, whereby the light-emitting element achieved good chromaticity and high emission efficiency.

Figure 21:
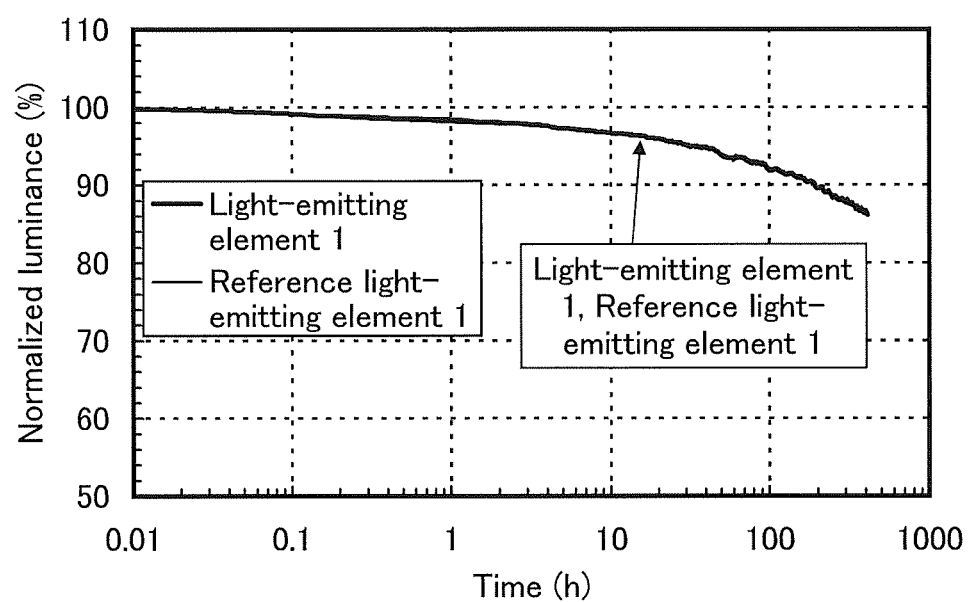
FIG. 21 shows results of reliability tests of Light-emitting Element 1 and Reference Light-emitting Element 1.

Next, Light-emitting Element 1 and Reference Light-emitting Element 1 were subjected to reliability tests. Results of the reliability tests are shown in FIG. 21. In FIG. 21, the vertical axis represents normalized luminance (%) with an initial luminance of 100%, and the horizontal axis represents driving time (h) of the elements. In the reliability

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting Element 1 | ITSO 110 nm | CzPA:MoOx (=4:2) 50 nm | BPAFLBi 10 nm | 2mDBFPPA-II:PCBAPA (=1:0.1) 30 nm | Alq 10 nm | BPhen 15 nm | LiF 1 nm | Al 200 nm |
| Reference Light-emitting Element 1 | ITSO 110 nm | CzPA:MoOx (=4:2) 50 nm | BPAFLBi 10 nm | 2DBFPPA-II:PCBAPA (=1:0.1) 30 nm | Alq 10 nm | BPhen 15 nm | LiF 1 nm | Al 200 nm |

Light-emitting Element 1 and Reference Light-emitting Element 1 were sealed in a glove box containing a nitrogen atmosphere so as not to be exposed to air. Then, operation characteristics of the elements were measured. Note that the measurement was carried out at room temperature (in the atmosphere kept at 25° C.).

FIG. 17 shows luminance vs. current density characteristics of Light-emitting Element 1 and Reference Light-emitting Element 1. In FIG. 17, the horizontal axis represents luminance (cd/m²) and the vertical axis represents current efficiency (cd/A). FIG. 18 shows the voltage vs. luminance characteristics. In FIG. 18, the horizontal axis tests, Light-emitting Element 1 of this example and Reference Light-emitting Element 1 were driven under the conditions where the current density was constant and the initial luminance was 1000 cd/m². FIG. 21 shows that Light-emitting Element 1 and Reference Light-emitting Element 1 kept 86% of the initial luminance after the driving for 410 hours. Thus, Light-emitting Element 1 is equal in reliability to Reference Light-emitting Element 1 as well as has better chromaticity and higher emission efficiency than those of Reference Light-emitting Element 1.

Light-emitting Element 1 exhibited better chromaticity and higher emission efficiency than those of Reference Light-emitting Element 1. The difference in host material structure between the light-emitting layers of Light-emitting Element 1 and Reference Light-emitting Element 1 is that the 2-position of an anthracene skeleton and the 4-position of a dibenzofuran skeleton in a dibenzofuran derivative which is the host material are bonded through a phenylene group at the para-position in Reference Light-emitting Element 1 while bonded through a phenylene group at the meta-position in Light-emitting Element 1. Whether what lies between the 2-position of the anthracene skeleton and the 4-position of the dibenzofuran skeleton is the phenylene group at the para-position or that at the meta-position makes a difference in emission efficiency between Light-emitting Element 1 and Reference Light-emitting Element 1. This reveals that the dibenzofuran derivative of one embodiment of the present invention is effective in realizing high emission efficiency, in respect of its structure where the 2-position of the anthracene skeleton and the 4-position of the dibenzofuran skeleton are bonded through the phenylene group at the meta-position. Further, it is understood that, by using the dibenzofuran derivative of one embodiment of the present invention in a light-emitting element, the light-emitting element can provide good chromaticity and high emission efficiency.

EXAMPLE 4

Figure 37B:
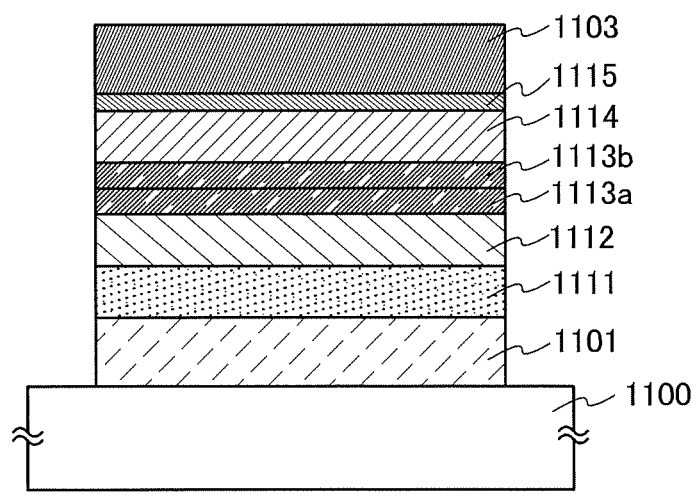

In this example, a light-emitting element of one embodiment of the present invention will be described referring to FIG. 37B.

Methods of fabricating Light-emitting Element 2 of this example and Reference Light-emitting Element 2 will now be described. Materials used in the present example are the same as those used in Example 3, and their chemical formulae are omitted here.

(Light-emitting Element 2)

First, ITSO was deposited over the glass substrate 1100 by a sputtering method, whereby the first electrode 1101 was formed. Its thickness was 110 nm and the electrode area was 2 mm ×2 mm. Here, the first electrode 1101 is an electrode that functions as an anode of the light-emitting element.

Next, as pretreatment for forming the light-emitting element over the substrate, a surface of the substrate was washed with water, baked at 200° C. for one hour, and subjected to UV ozone treatment for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate was cooled down for about 30 minutes.

Next, the substrate was fixed to a substrate holder in a vacuum evaporation apparatus so that a surface of the substrate on which the first electrode was formed faced downward. The pressure in the vacuum evaporation apparatus was reduced to about $10^{-4}$ Pa. Then, CzPA which is a substance having a high hole-transport property and molybdenum(VI) oxide which is an acceptor substance were co-evaporated to form the hole-injection layer 1111 over the first electrode. The thickness of the hole-injection layer 1111 was 50 nm, and the weight ratio of CzPA to molybdenum (VI) oxide was controlled to be 4:2 (=CzPA:molybdenum (VI) oxide).

Next, BPAFLBi was deposited to a thickness of 10 nm over the hole-injection layer 1111, whereby the hole-transport layer 1112 was formed.

Further, PCBAPA was deposited to a thickness of 25 mn over the hole-transport layer 1112, whereby a first light-emitting layer 1113a was formed. Then, 2mDBFPPA-II synthesized in Example 1 and PCBAPA were co-evaporated to form a second light-emitting layer 1113b over the first light-emitting layer 1113a. The weight ratio of 2mDBFPPA-II to PCBAPA was adjusted to 1:0.1 (=2mDBFPPA-II: PCBAPA). The thickness of the second light-emitting layer 1113b was set to 30 nm.

Then, on the second light-emitting layer 1113b, a 10 mn thick layer of Alq and, a 15 nm thick layer of BPhen were deposited on the Alq layer, whereby the electron-transport layer 1114 including Alq and BPhen was obtained.

Further, a 1 nm thick film of LiF was formed over the electron-transport layer 1114 by evaporation, whereby the electron-injection layer 1115 was formed.

Lastly, a 200 nm thick film of aluminum was formed by evaporation to form a second electrode 1103 functioning as a cathode. Thus, Light-emitting Element 2 of this example was fabricated.

Note that, in the above evaporation process, evaporation was all performed by a resistance heating method.

(Reference Light-3mitting Element 2)

The second light-emitting layer 1113b of Reference Light-emitting Element 2 was formed by co-evaporation of 2DBF-PPA-II and PCBAPA, instead of the material used for Light-emitting Element 2. The weight ratio of 2DBFPPA-II and PCBAPA was adjusted to 1:0.1 (=2DBFPPA-II: PCBAPA). The thickness of the second light-emitting layer 1113b was set to 30 nm. The layers other than the second light-emitting layer 1113b were formed in the same manner as Light-emitting Element 2.

Table 3 shows element structures of Light-emitting Element 2 and Reference Light-emitting Element 2 formed as described above.

TABLE 3

| | First electrode | Hole-injection layer | Hole-transport layer | First light-emitting layer | Second light-emitting layer | Electron-transport layer | Electron-injection layer | Second electrode |
|---|---|---|---|---|---|---|---|---|
| Light-emitting Element 2 | ITSO 110 nm | CzPA:MoOx (=4:2) 50 nm | BPAFLBi 10 nm | PCBAPA 25 nm | 2mDBFPPA-II:PCBAPA (=1:0.1) 30 nm | Alq 10 nm | BPhen 15 nm | LiF 1 nm | Al 200 nm |
| Reference Light-emitting Element 2 | ITSO 110 nm | CzPA:MoOx (=4:2) 50 nm | BPAFLBi 10 nm | PCBAPA 25 nm | 2DBFPPA-II:PCBAPA (=1:0.1) 30 nm | Alq 10 nm | BPhen 15 nm | LiF 1 nm | Al 200 nm |

Light-emitting Element 2 and Reference Light-emitting Element 2 were sealed in a glove box containing a nitrogen atmosphere so as not to be exposed to air. Then, operation characteristics of the elements were measured. Note that the measurement was carried out at room temperature (in the atmosphere kept at 25° C.).

Figure 22:
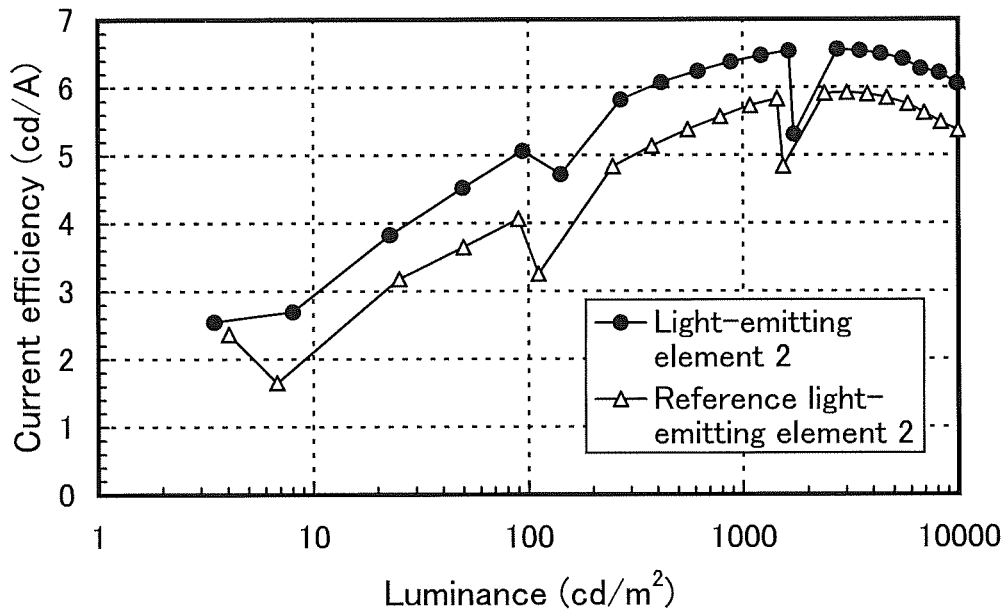
FIG. 22 shows luminance vs. current efficiency characteristics of Light-emitting Element 2 and Reference Light-emitting Element 2.
Figure 23:
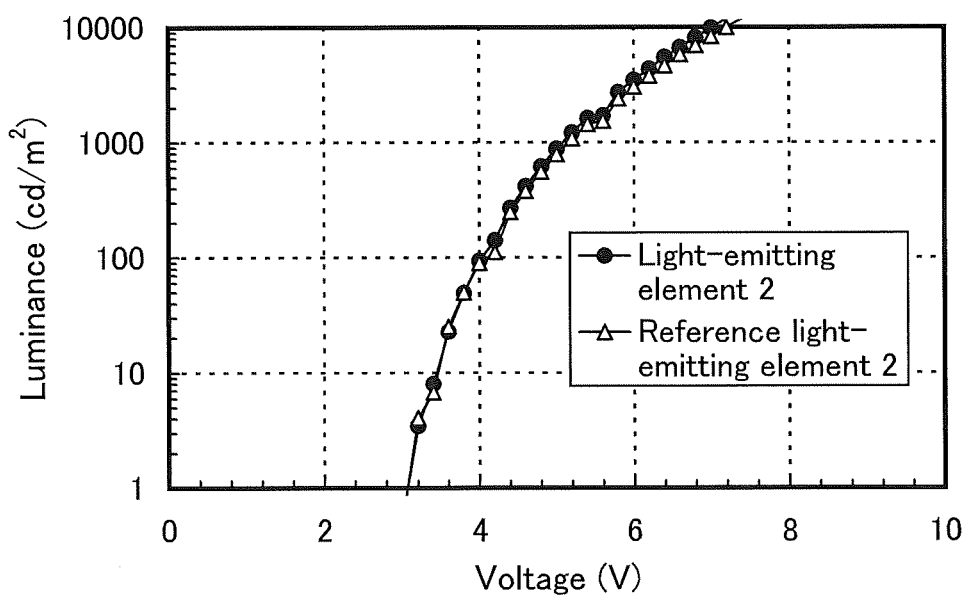
FIG. 23 shows voltage vs. luminance characteristics of Light-emitting Element 2 and Reference Light-emitting Element 2.
Figure 24:
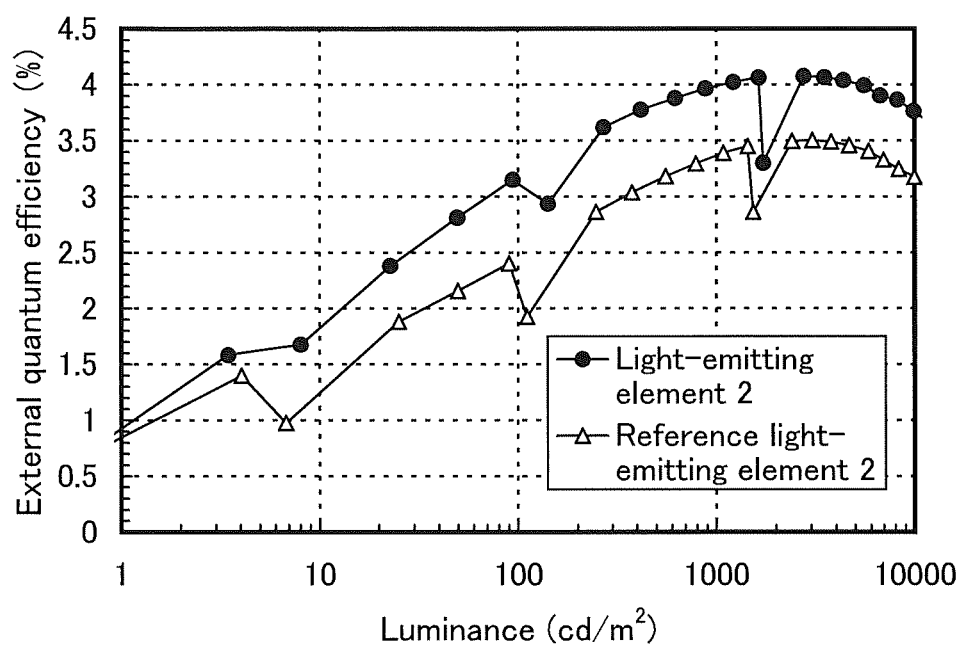
FIG. 24 shows luminance vs. external quantum efficiency characteristics of Light-emitting Element 2 and Reference Light-emitting Element 2.
Figure 25:
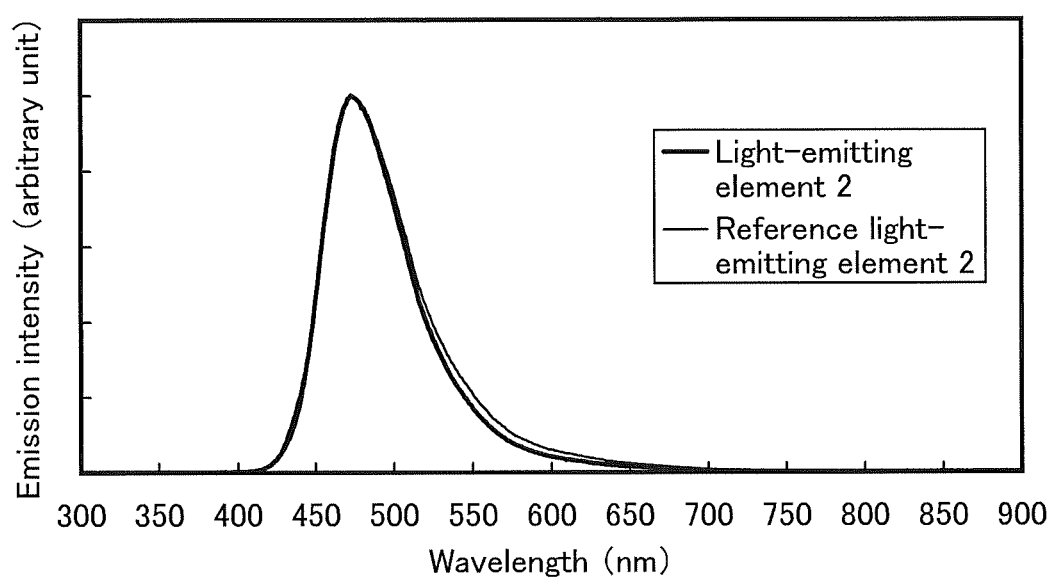
FIG. 25 shows emission spectra of Light-emitting Element 2 and Reference Light-emitting Element 2.

FIG. 22 shows luminance vs. current density characteristics of Light-emitting Element 2 and Reference Light-emitting Element 2. In FIG. 22, the horizontal axis represents luminance ($cd/m^2$) and the vertical axis represents current efficiency (cd/A). FIG. 23 shows the voltage vs. luminance characteristics. In FIG. 23, the horizontal axis represents applied voltage (V) and the vertical axis represents luminance ($cd/m^2$). FIG. 24 shows the luminance vs. external quantum efficiency characteristics. In FIG. 24, the horizontal axis represents luminance ($cd/m^2$) and the vertical axis represents external quantum efficiency (%). FIG. 25 shows the emission spectra with a current supply of 1 mA. In FIG. 25, the horizontal axis represents wavelength (nm) and the vertical axis represents intensity (arbitrary unit). Further, Table 4 shows the voltage (V), current density ($mA/cm^2$), CIE chromaticity coordinates (x, y), current efficiency (cd/A), and external quantum efficiency (%) of each light-emitting element at a luminance of around 1000 $cd/m^2$.

Figure 26:
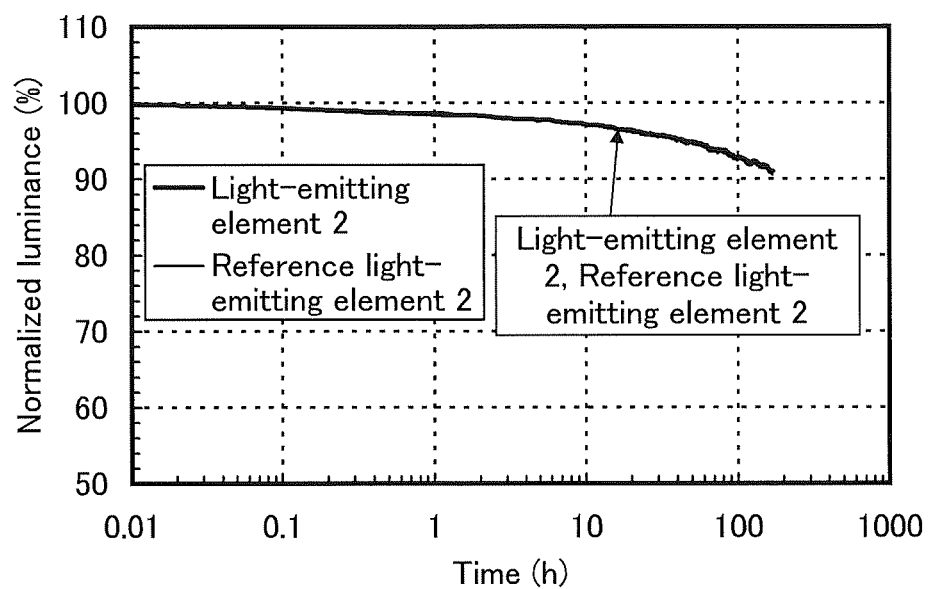
FIG. 26 shows results of reliability tests of Light-emitting Element 2 and Reference Light-emitting Element 2.

26, the vertical axis represents nothialized luminance (%) with an initial luminance of 100%, and the horizontal axis represents driving time (h) of the elements. In the reliability tests, Light-emitting Element 2 of this example and Reference Light-emitting Element 2 were driven under the conditions where the current density was constant and the initial luminance was 1000 $cd/m^2$. FIG. 26 shows that Light-emitting Element 2 and Reference Light-emitting Element 2 kept 91% of the initial luminance after the driving for 170 hours. Thus, Light-emitting Element 2 is equal in reliability to Reference Light-emitting Element 2 as well as higher emission efficiency than those of Reference Light-emitting Element 2. Furthermore, the results of the reliability tests demonstrate that the light-emitting element to which one embodiment of the present invention is applied is effective in realizing a light-emitting element having a long lifetime.

Light-emitting Element 2 exhibited better chromaticity and higher emission efficiency than those of Reference Light-emitting Element 2. The difference in host material structure between the light-emitting layers of Light-emitting Element 2 and Reference Light-emitting Element 2 is that the 2-position of an anthracene skeleton and the 4-position of a dibenzofuran skeleton in a dibenzofuran derivative which is the host material are bonded through a phenylene group at the para-position in Reference Light-emitting Element 2 while bonded through a phenylene group at the meta-position in Light-emitting Element 2. Whether what lies between the 2-position of the anthracene skeleton and the 4-position of the dibenzofuran skeleton is the phenylene group at the para-position or that at the meta-position makes a difference in emission efficiency between Light-emitting Element 2 and Reference Light-emitting Element 2. This reveals that the dibenzofuran derivative of one embodiment of the present invention is effective in realizing high emis-

TABLE 4

| | Voltage (V) | Current density ($mA/cm^2$) | Chromaticity x | Chromaticity y | Luminance ($cd/m^2$) | Current efficiency (cd/A) | External quantum efficiency (%) |
|---|---|---|---|---|---|---|---|
| Light-emitting Element 2 | 5.0 | 14 | 0.16 | 0.25 | 880 | 6.4 | 4.0 |
| Reference Light-emitting Element 2 | 5.2 | 19 | 0.17 | 0.26 | 1100 | 5.7 | 3.4 |

As seen from FIG. 25 and the CIE chromaticity coordinates in Table 4, blue light emission is shown by Light-emitting Element 2 and Reference Light-emitting Element 2, which were formed. FIG. 22, FIG. 23, FIG. 24, and Table 4 reveal that Light-emitting Element 2 exhibits higher current efficiency and external quantum efficiency than those of Reference Light-emitting Element 2.

As described above, 2mDBFPPA-II produced in Example 1 was used as the host material of the light-emitting layer, whereby the light-emitting element achieved high emission efficiency when the light-emitting layer had a two-layer structure as well.

Next, Light-emitting Element 2 and Reference Light-emitting Element 2 were subjected to reliability tests. Results of the reliability tests are shown in FIG. 26. In FIG.

sion efficiency, in respect of its structure where the 2-position of the anthracene skeleton and the 4-position of the dibenzofuran skeleton are bonded through the phenylene group at the meta-position. Further, it is understood that, by using the dibenzofuran derivative of one embodiment of the present invention in a light-emitting element, the light-emitting element can provide good chromaticity and high emission efficiency.

EXAMPLE 5

In this example, a light-emitting element of one embodiment of the present invention will be described referring to FIG. 37A. Chemical formulae of materials used in this example are shown below. Note that the materials the chemical formulae of which are described above will be omitted.

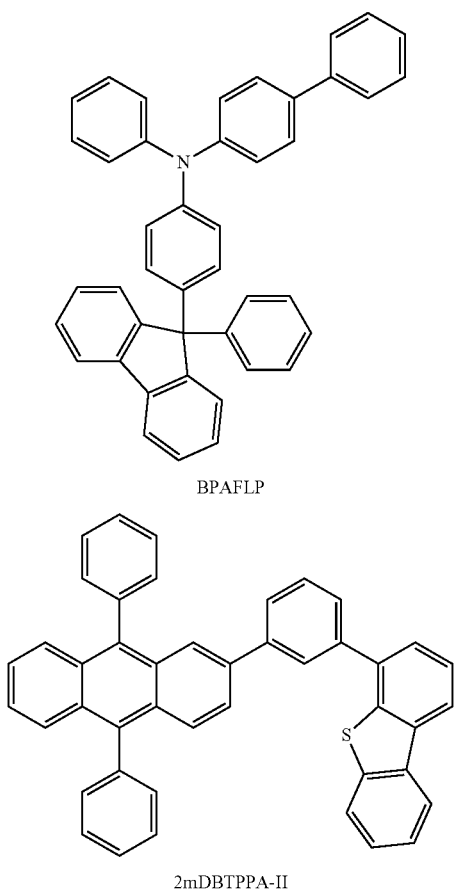

BPAFLP

2mDBTPPA-II

A method of fabricating Light-emitting Element 3 of this example will now be described.

substrate 1100 on which the first electrode 1101 was formed faced downward. The pressure in the vacuum evaporation apparatus was reduced to about $10^{-4}$ Pa. Then, by an evaporation method using resistance heating, CzPA which is a substance having a high hole-transport property and molybdenum(VI) oxide which is an acceptor substance were co-evaporated to form the hole-injection layer 1111 over the first electrode 1101. The thickness of the hole-injection layer 1111 was 50 nm, and the weight ratio of CzPA to molybdenum(VI) oxide was controlled to be 4:2 (=CzPA:molybdenum(VI) oxide). Note that the co-evaporation method refers to an evaporation method in which evaporation is carried out from a plurality of evaporation sources at the same time in one treatment chamber.

Next, 4-phenyl-4'-(9-phenylfluoren-9-yl)triphenylamine (abbreviation: BPAFLP) was deposited to a thickness of 10 nm over the hole-injection layer 1111, whereby the hole-transport layer 1112 was formed.

Further, 2mDBTPPA-II synthesized in Example 2 and PCBAPA were co-evaporated to form the light-emitting layer 1113 over the hole-transport layer 1112. The weight ratio of 2mDBTPPA-II to PCBAPA was adjusted to 1:0.1 (=2mDBTPPA-II:PCBAPA). The thickness of the light-emitting layer 1113 was set to 30 nm.

Then, over the light-emitting layer 1113, a 10 nm thick layer of Alq and, a 15 nm thick layer of BPhen were deposited on the Alq layer, whereby the electron-transport layer 1114 including Alq and BPhen was obtained.

Further, a 1 nm thick film of LiF was formed over the electron-transport layer 1114 by evaporation, whereby the electron-injection layer 1115 was formed.

Lastly, a 200 nm thick film of aluminum was formed by evaporation to form a second electrode 1103 functioning as a cathode. Thus, Light-emitting Element 3 of this example was fabricated.

Note that, in the above evaporation process, evaporation was all performed by a resistance heating method.

Table 5 shows element structures of Light-emitting Element 3 formed as described above.

TABLE 5

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Light-emitting Element 3 | ITSO 110 nm | CzPA:MoOx (=4:2) 50 nm | BPAFLP 10 nm | 2mDBTPPA-II:PCBAPA (=1:0.1) 30 nm | Alq 10 nm | BPhen 15 nm | LiF 1 nm | Al 200 nm |

(Light-Emitting Element 3)

First, ITSO was deposited over the glass substrate 1100 by a sputtering method, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the Light-emitting Element 3 was sealed in a glove box containing a nitrogen atmosphere so as not to be exposed to air. Then, operation characteristics of the element were measured. Note that the measurement was carried out at room temperature (in the atmosphere kept at 25° C.).

Figure 27:
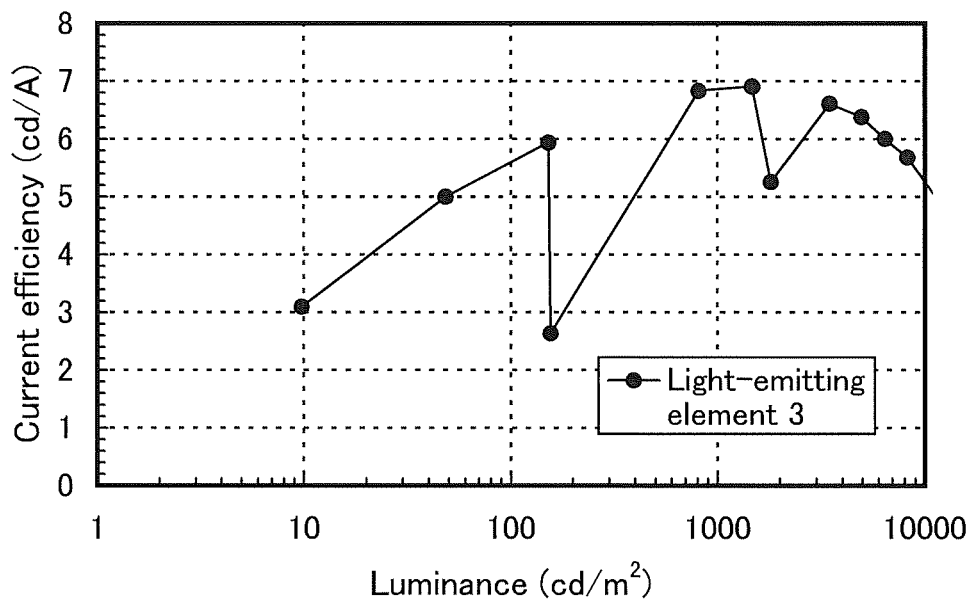
FIG. 27 shows luminance vs. current efficiency characteristics of Light-emitting Element 3.
Figure 28:
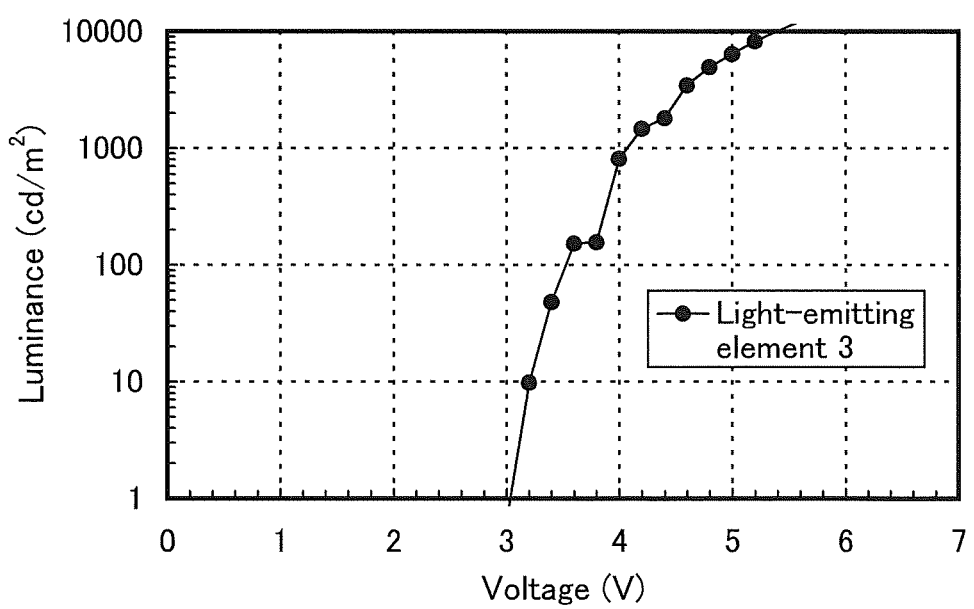
FIG. 28 shows voltage vs. luminance characteristics of Light-emitting Element 3.
Figure 29:
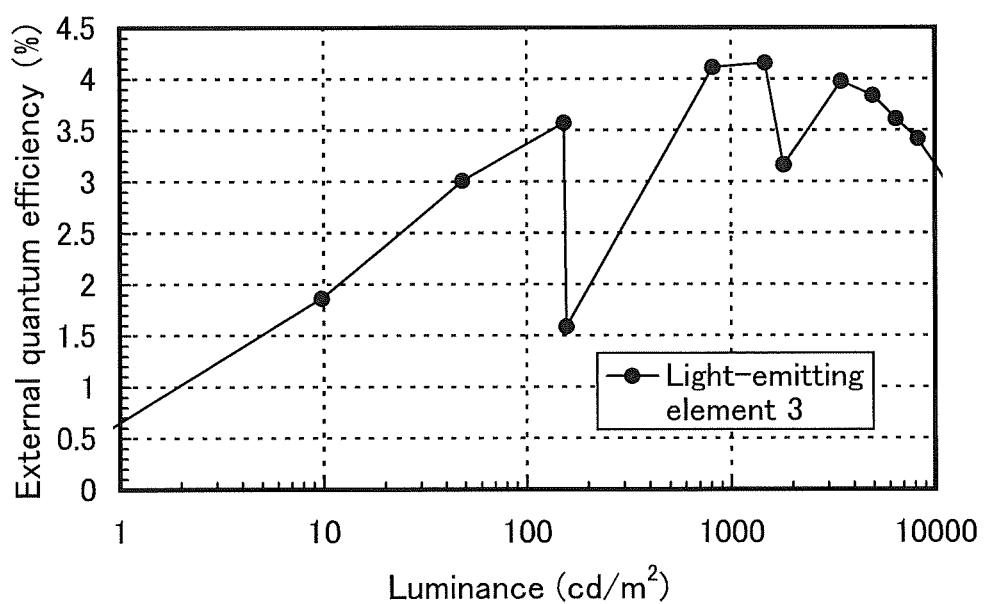
FIG. 29 shows luminance vs. external quantum efficiency characteristics of Light-emitting Element 3.
Figure 30:
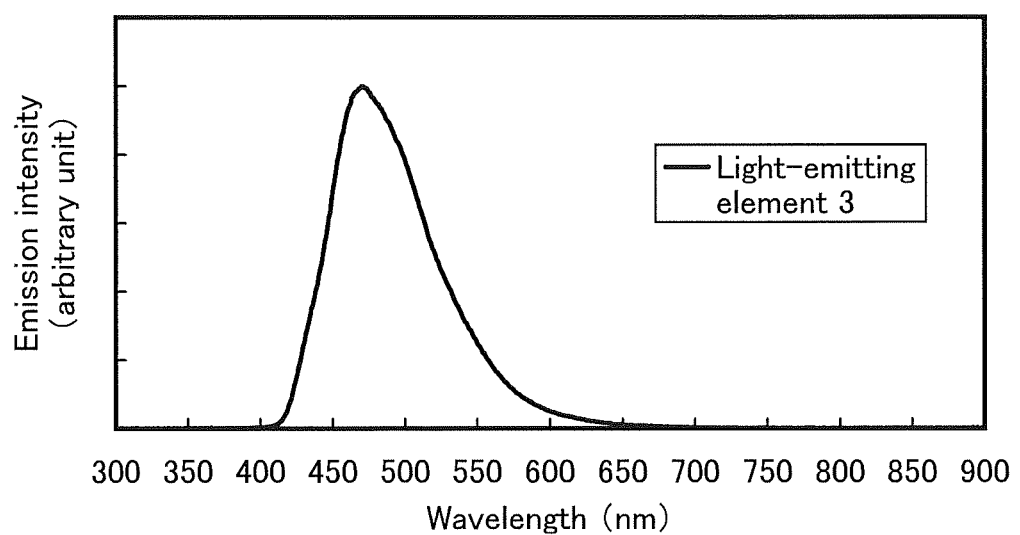
FIG. 30 shows an emission spectrum of Light-emitting Element 3.

FIG. 27 shows luminance vs. current density characteristics of Light-emitting Element 3. In FIG. 27, the horizontal axis represents luminance (cd/m$^2$) and the vertical axis represents current efficiency (cd/A). FIG. 28 shows the voltage vs. luminance characteristics. In FIG. 28, the horizontal axis represents applied voltage (V) and the vertical axis represents luminance (cd/m$^2$). FIG. 29 shows the luminance vs. external quantum efficiency characteristics. In FIG. 29, the horizontal axis represents luminance (cd/m$^2$) and the vertical axis represents external quantum efficiency (%). FIG. 30 shows the emission spectra with a current supply of 1 mA. In FIG. 30, the horizontal axis represents wavelength (nm) and the vertical axis represents intensity (arbitrary unit). Further, Table 6 shows the voltage (V), current density (mA/cm$^2$), CIE chromaticity coordinates (x, y), current efficiency (cd/A), and external quantum efficiency (%) of the light-emitting element at a luminance of around 810 cd/m$^2$.

TABLE 6

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting Element 3 | 4.0 | 12 | 0.17 | 0.24 | 810 | 6.8 | 4.1 |

As seen from FIG. 30 and the CIE chromaticity coordinates in Table 6, blue light emission is shown by Light-emitting Element 3, which was formed. FIG. 27, FIG. 28, FIG. 29, and Table 6 reveal that Light-emitting Element 3 exhibits good chromaticity, high current efficiency, and high external quantum efficiency.

As described above, 2mDBTPPA-II produced in Example 2 was used as the host material of the light-emitting layer, whereby the light-emitting element achieved high emission efficiency.

Figure 31:
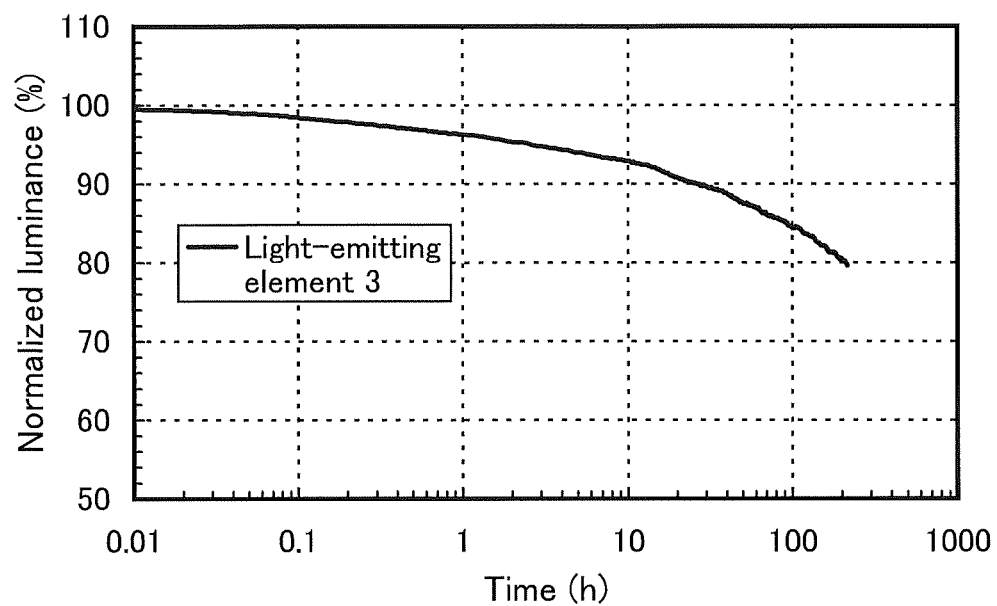
FIG. 31 shows results of reliability tests of Light-emitting Element 3.

Next, Light-emitting Element 3 was subjected to reliability tests. Results of the reliability tests are shown in FIG. 31. In FIG. 31, the vertical axis represents normalized luminance (%) with an initial luminance of 100%, and the horizontal axis represents driving time (h) of the elements. In the reliability tests, Light-emitting Element 3 of this example was driven under the conditions where the current density was constant and the initial luminance was 1000 cd/m$^2$. FIG. 31 shows that Light-emitting Element 3 kept 80% of the initial luminance after the driving for 220 hours. Thus, Light-emitting Element 3 shows high reliability. Furthermore, the results of the reliability tests demonstrate that the light-emitting element to which one embodiment of the present invention is applied is effective in realizing a light-emitting element having a long lifetime.

EXAMPLE 6

In this example, a light-emitting element of one embodiment of the present invention will be described referring to FIG. 37B.

A method of fabricating Light-emitting Element 4 of this example will now be described. Materials used in the present example are the same as those used in Example 5, and their chemical formulae are omitted here.
(Light-Emitting Element 4)

First, ITSO was deposited over the glass substrate 1100 by a sputtering method, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about 10$^{-4}$ Pa. Then, by an evaporation method using resistance heating, CzPA which is a substance having a high hole-transport property and molybdenum(VI) oxide which is an acceptor substance were co-evaporated to form the hole-injection layer 1111 over the first electrode 1101. The thickness of the hole-injection layer 1111 was 50 nm, and the weight ratio of CzPA to molybdenum(VI) oxide was controlled to be 4:2 CzPA:molybdenum(VI) oxide). Note that the co-evaporation method refers to an evaporation method in which evaporation is carried out from a plurality of evaporation sources at the same time in one treatment chamber.

Next, BPAFLP was deposited to a thickness of 10 nm over the hole-injection layer 1111, whereby the hole-transport layer 1112 was formed.

Further, PCBAPA was deposited to a thickness of 25 nm over the hole-transport layer 1112, whereby the first light-emitting layer 1113a was formed. Then, 2mDBTPPA-II synthesized in Example 2 and PCBAPA were co-evaporated to form the second light-emitting layer 1113b over the first light-emitting layer 1113a. The weight ratio of 2mDBTPPA-II to PCBAPA was adjusted to 1:0.1 (=2mDBTPPA-II:PCBAPA). The thickness of the second light-emitting layer 1113b was set to 30 nm.

Then, on the second light-emitting layer 1113b, a 10 nm thick layer of Alq and, a 15 nm thick layer of BPhen were deposited on the Alq layer, whereby the electron-transport layer 1114 including Alq and BPhen was obtained.

Further, a 1 nm thick film of LiF was formed over the electron-transport layer 1114 by evaporation, whereby the electron-injection layer 1115 was formed.

Lastly, a 200 nm thick film of aluminum was formed by evaporation to form a second electrode 1103 functioning as a cathode. Thus, Light-emitting Element 4 of this example was fabricated.

Note that, in the above evaporation process, evaporation was all performed by a resistance heating method.

Table 7 shows element structures of Light-emitting Element 4 formed as described above.

TABLE 7

| | First electrode | Hole-injection layer | Hole-transport layer | First light-emitting layer | Second light-emitting layer | Electron-transport layer | Electron-injection layer | Second electrode |
|---|---|---|---|---|---|---|---|---|
| Light-emitting Element 4 | ITSO 110 nm | CzPA:MoOx (=4:2) 50 nm | BPAFLP 10 nm | PCBAPA 25 nm | 2mDBTPPA-II:PCBAPA (=1:0.1) 30 nm | Alq 10 nm | BPhen 15 nm | LiF 1 nm | Al 200 nm |

Light-emitting Element 4 was sealed in a glove box containing a nitrogen atmosphere so as not to be exposed to air. Then, operation characteristics of the element were measured. Note that the measurement was carried out at room temperature (in the atmosphere kept at 25° C.).

Figure 32:
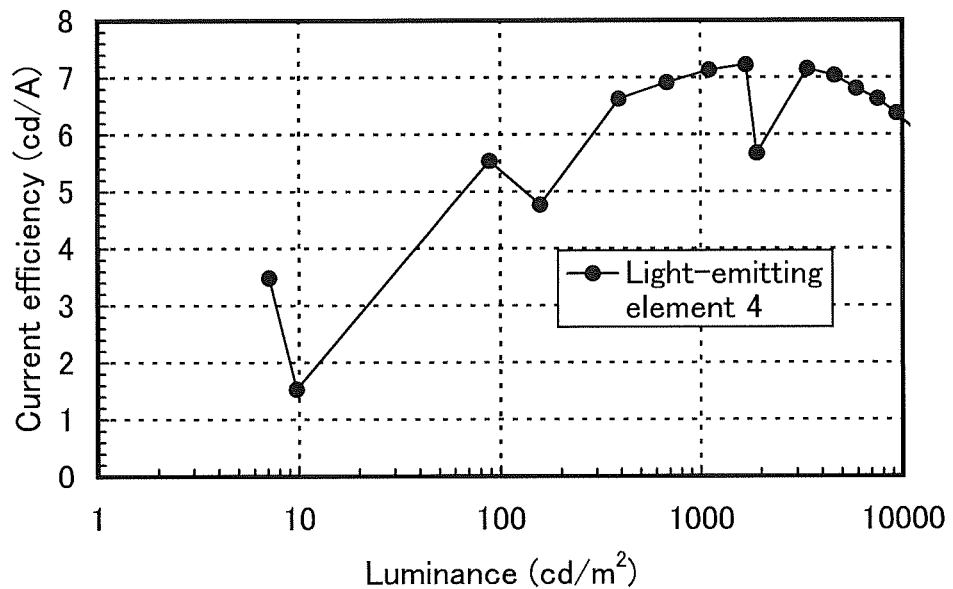
FIG. 32 shows luminance vs. current efficiency characteristics of Light-emitting Element 4.
Figure 33:
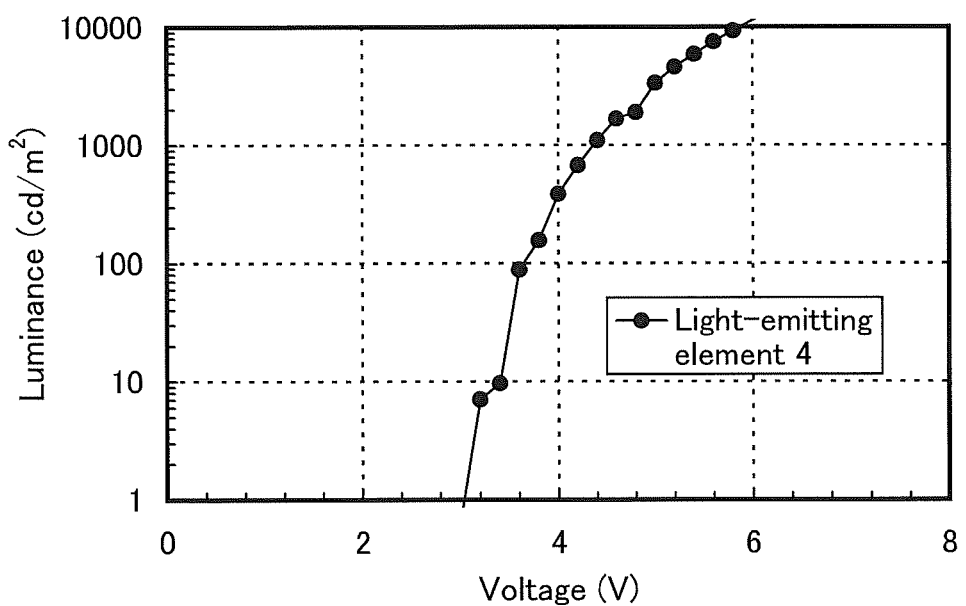
FIG. 33 shows voltage vs. luminance characteristics of Light-emitting Element 4.
Figure 34:
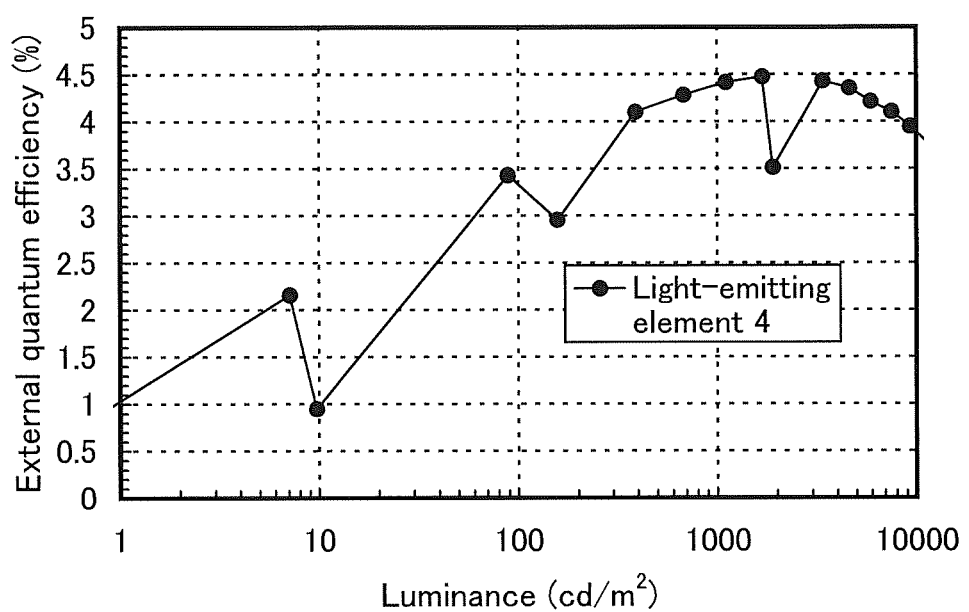
FIG. 34 shows luminance vs. external quantum efficiency characteristics of Light-emitting Element 4.
Figure 35:
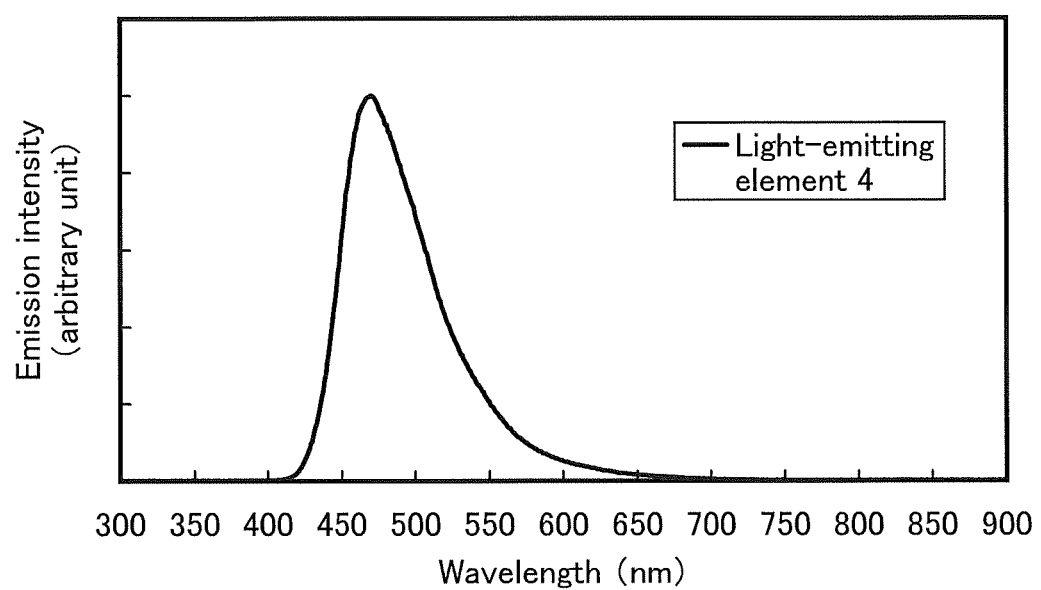
FIG. 35 shows an emission spectrum of Light-emitting Element 4.

FIG. 32 shows luminance vs. current density characteristics of Light-emitting Element 4. In FIG. 32, the horizontal axis represents luminance (cd/m$^2$) and the vertical axis represents current efficiency (cd/A). FIG. 33 shows the voltage vs. luminance characteristics. In FIG. 33, the horizontal axis represents applied voltage (V) and the vertical axis represents luminance (cd/m$^2$). FIG. 34 shows the luminance vs. external quantum efficiency characteristics. In FIG. 34, the horizontal axis represents luminance (cd/m$^2$) and the vertical axis represents external quantum efficiency (%). FIG. 35 shows the emission spectra with a current supply of 1 mA. In FIG. 35, the horizontal axis represents wavelength (nm) and the vertical axis represents intensity (arbitrary unit). Further, Table 8 shows the voltage (V), current density (mA/cm$^2$), CIE chromaticity coordinates (x, y), current efficiency (cd/A), and external quantum efficiency (%) of the Light-emitting Element 4 at a luminance of around 1100 cd/m$^2$.

TABLE 8

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting Element 4 | 4.4 | 16 | 0.16 | 0.23 | 1100 | 7.1 | 4.4 |

As seen from in FIG. 35 and the CIE chromaticity coordinates in Table 8, blue light emission is shown by Light-emitting Element 4, which was formed. FIG. 32, FIG. 33, FIG. 34, and Table 8 reveal that Light-emitting Element 4 exhibits good chromaticity, high current efficiency, and high external quantum efficiency.

As described above, 2mDBTPPA-II produced in Example 2 was used as the host material of the light-emitting layer, whereby the light-emitting element achieved high emission efficiency when the light-emitting layer had a two-layer structure as well.

Figure 36:
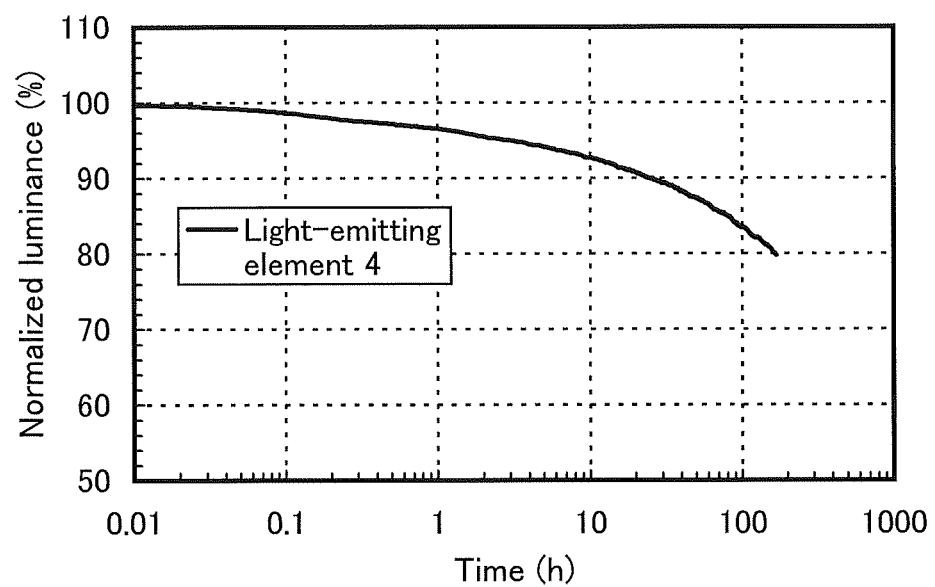
FIG. 36 shows results of reliability tests of Light-emitting Element 4.

Next, Light-emitting Element 4 was subjected to reliability tests. Results of the reliability tests are shown in FIG. 36. In FIG. 36, the vertical axis represents normalized luminance (%) with an initial luminance of 100%, and the horizontal axis represents driving time (h) of the elements. In the reliability tests, Light-emitting Element 4 of this example was driven under the conditions where the current density was constant and the initial luminance was 1000 cd/m$^2$. FIG. 36 shows that Light-emitting Element 4 kept 80% of the initial luminance after the driving for 170 hours. Thus, Light-emitting Element 4 shows high reliability. Furthermore, the results of the reliability tests demonstrate that the light-emitting element to which one embodiment of the present invention is applied is effective in realizing a light-emitting element having a long lifetime.

EXAMPLE 7

Synthesis Example 3

This example will show a method of synthesizing 4-[3-(9,10-diphenyl-2-anthryl)phenyl]-2,8-diphenyldibenzofuran (abbreviation: 2mDBFPPA-III) represented by Structural formula (147) described in Embodiment 1.

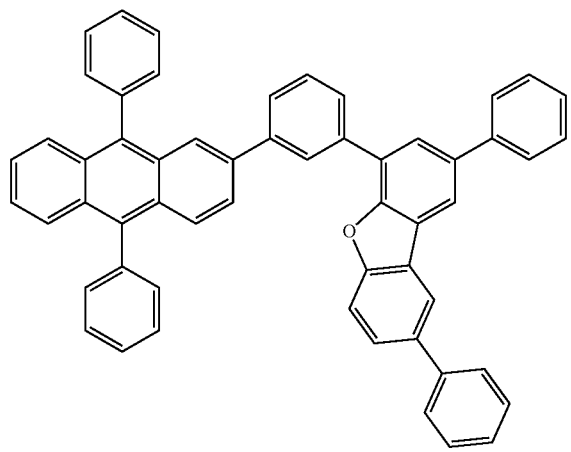

2mDBTPPA-III

Step 1: Synthesis of 2,8-dibromodibenzofuran

The synthesis scheme of Step 1 is shown in (E-1).

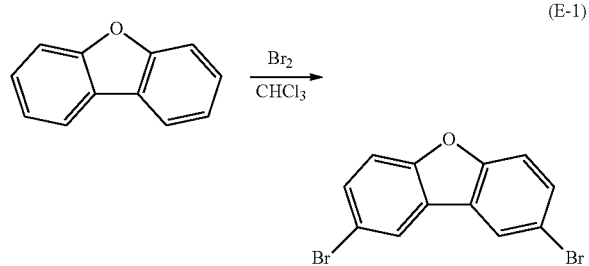

In a 500 mL three-neck flask were put 8.4 g (50 mmol) of dibenzofuran and 100 mL of carbon tetrachloride. A solution prepared by dissolving 17 g (110 mmol) of bromine in 50 mL of chloroform was dripped through a dropping funnel into the three-neck flask over about 20 minutes. Then, this solution was stirred at room temperature for 7 days. After that, this solution was washed with a saturated solution of sodium hydrogen carbonate, an aqueous solution of sodium thiosulfate and saturated brine. The organic layer was dried with magnesium sulfate, and this mixture was gravity filtered. The resulting filtrate was concentrated, and the obtained solid was recrystallized from chloroform. Accordingly, 6.4 g of a white powder was obtained in 40% yield, which was the substance to be produced.

Step 2: Synthesis of 2,8-diphenylbenzofuran

The synthesis scheme of Step 2 is shown in (E-2).

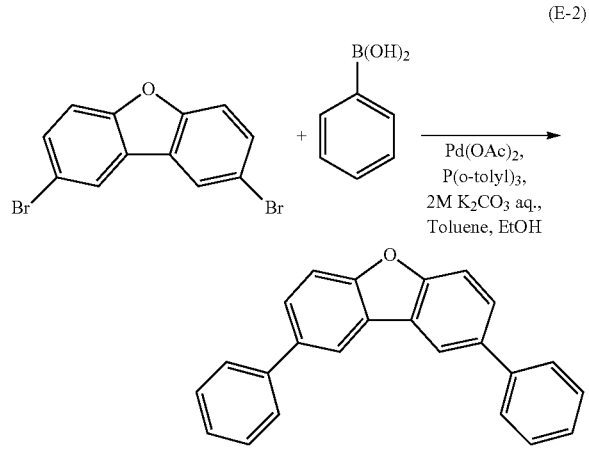

In a 300 mL three-neck flask were put 4.0 g (12 mmol) of 2,8-dibromodibenzofuran, 3.0 g (24 mmol) of phenylboronic acid, and 0.55 g (1.8 mmol) of tri(ortho-tolyl)phosphine. The air in the flask was replaced with nitrogen. To this mixture were added 45 mL of toluene, 15 mL of ethanol, and 15 mL of an aqueous solution of potassium carbonate (2.0 mol/L). While the pressure was reduced, this mixture was stirred to be degassed. Then, 81 mg (0.36 mmol) of palladium(II) acetate was added to this mixture, and the mixture was stirred under a nitrogen stream at 80° C. for 6 hours. After that, the aqueous layer of this mixture was extracted with toluene, and the toluene solution and the organic layer were combined and washed with saturated brine. The organic layer was dried with magnesium sulfate. Then, this mixture was gravity filtered. The resulting filtrate was concentrated to give an oily substance, and the oily substance was dissolved in about 20 mL of toluene. This solution was suction-filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The resulting filtrate was concentrated to give an oily substance, and a mixed solvent of toluene and hexane was added to the oily substance. The mixture was irradiated with ultrasonic waves, whereby a solid was precipitated. This solid was collected by suction filtration to give 2.4 g of a white powder in 63% yield, which was the substance to be produced.

Step 3: Synthesis of 2,8-diphenyldibenzofuran-4-boronic acid

The synthesis scheme of Step 3 is shown in (E-3).

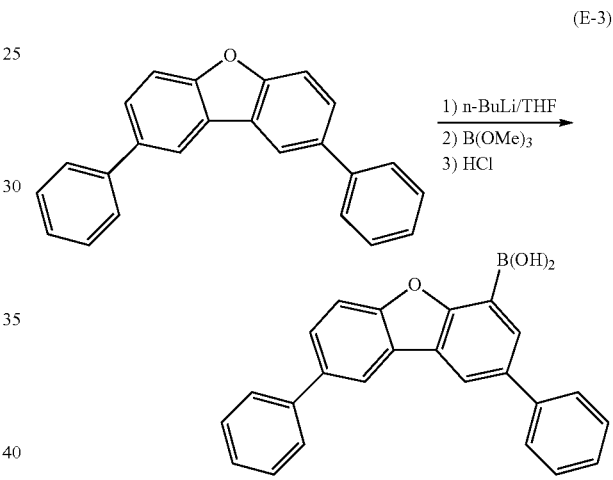

In a 200 mL three-neck flask was put 2.4 g (7.5 mmol) of 2,8-diphenyldibenzofuran. The air in the flask was replaced with nitrogen. To this mixture was added 40 mL of tetrahydrofuran (THF), and this solution was cooled to −80° C. Then, 5.6 mL (9.0 mmol) of n-butyllithium (a 1.6 mol/L hexane solution) was dripped into this solution with a syringe. After that, this solution was stirred for 2 hours while its temperature was returned to room temperature. Then, this solution was again cooled to −80° C., and 1.7 mL (15 mmol) of trimethyl borate was added to this solution. This solution was stirred for 3 days while its temperature was returned to room temperature. After that, about 30 mL of diluted hydrochloric acid (1.0 mol/L) was added to this solution, followed by stirring for 1 hour. Then, the aqueous layer of this mixture was extracted with ethyl acetate, and the ethyl acetate solution and the organic layer were combined and washed with saturated brine. The organic layer was dried with magnesium sulfate. Then, this mixture was gravity filtered. The resulting filtrate was concentrated to give an oily substance, and a mixed solvent of ethyl acetate and hexane was added to the oily substance. The mixture was irradiated with ultrasonic waves, whereby a solid was precipitated. This solid was collected by suction filtration to give 2.2 g of a white powder in 82% ☐ yield, which was the substance to be produced.

Step 4: Synthesis of 4-(3-bromophenyl)-2,8-diphenyldibenzofuran

The synthesis scheme of Step 4 is shown in (E-4).

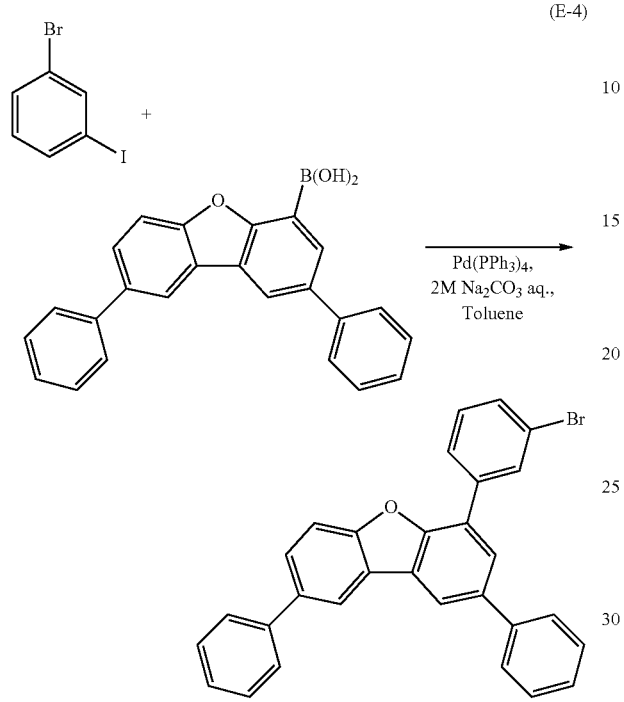

In a 100 mL three-neck flask were put 1.7 g (6.0 mmol) of 3-bromoiodobenzene and 2.2 g (6.0 mmol) of 2,8-diphenyldibenzofuran-4-boronic acid. The air in the flask was replaced with nitrogen. To this mixture were added 30 mL of toluene and 6.0 mL of an aqueous solution of sodium carbonate (2.0 mol/L). While the pressure was reduced, this mixture was stirred to be degassed. To this mixture was added 0.35 g (0.30 mmol) of tetrakis(triphenylphosphine)palladium(0), and the mixture was refluxed at 110° C. for 4 hours. After reaction, the aqueous layer was extracted with ethyl acetate, and the ethyl acetate solution and the organic layer were combined and washed with saturated brine. The organic layer was dried with magnesium sulfate. Then, this mixture was gravity filtered. The resulting filtrate was concentrated to give an oily substance, and the oily substance was dissolved in about 10 mL of toluene. This solution was suction-filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The resulting filtrate was concentrated to give an oily substance, and hexane was added to the oily substance. The mixture was irradiated with ultrasonic waves, whereby a solid was precipitated. This solid was collected by suction filtration to give 1.2 g of a white powder in 44% yield, which was the substance to be produced.

Step 5: Synthesis of 3-(2,8-diphenyldibenzofuran-4-yl)phenylboronic acid

The synthesis scheme of Step 5 is shown in (E-5).

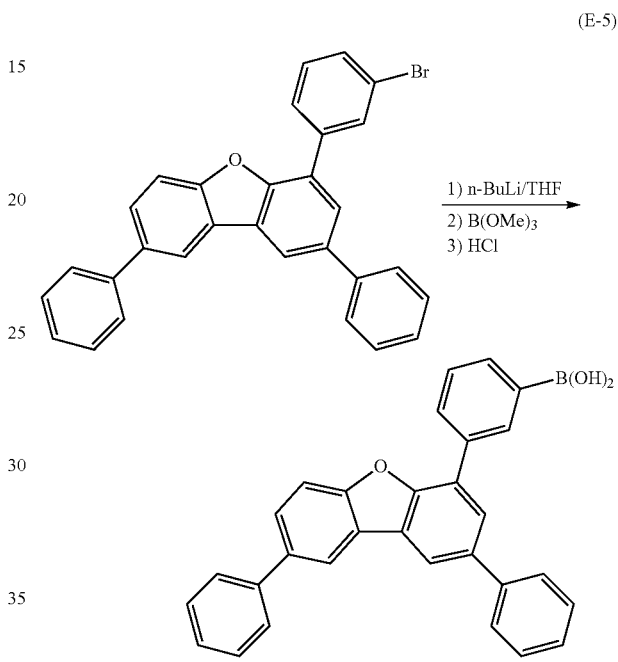

In a 50 mL three-neck flask was put 1.2 g (2.5 mmol) of 4-(3-bromophenyl)-2,8-diphenyldibenzofuran. The air in the flask was replaced with nitrogen. To this mixture was added 15 mL of tetrahydrofuran (THF), and this solution was cooled to −80° C. Then, 1.9 mL (3.0 mmol) of n-butyllithium (a 1.6 mol/L hexane solution) was dripped into this solution with a syringe. After that, this solution was stirred at the same temperature for 1 hour. Then, 0.56 L (5.0 mmol) of trimethyl borate was added to this solution, and the mixture was stirred for 18 hours while its temperature was returned to room temperature. After that, about 10 mL of diluted hydrochloric acid (1.0 mol/L) was added to this solution, followed by stirring for 1 hour. Then, the aqueous layer of this mixture was extracted with ethyl acetate, and the ethyl acetate solution and the organic layer were combined and washed with saturated brine. The organic layer was dried with magnesium sulfate. Then, this mixture was gravity filtered. The resulting filtrate was concentrated to give a solid, and a mixed solvent of chloroform and hexane was added to the solid. The mixture was irradiated with ultrasonic waves, whereby a solid was precipitated. This solid was collected by suction filtration to give 0.62 g of a light-brown powder in 58% □ yield, which was the substance to be produced.

Step 6: Synthesis of 4-[3-(9,10-diphenyl-2-anthryl)phenyl]-2,8-diphenyldibenzofuran (2mDBFPPA-III)

The synthesis scheme of Step 6 is shown in (E-6).

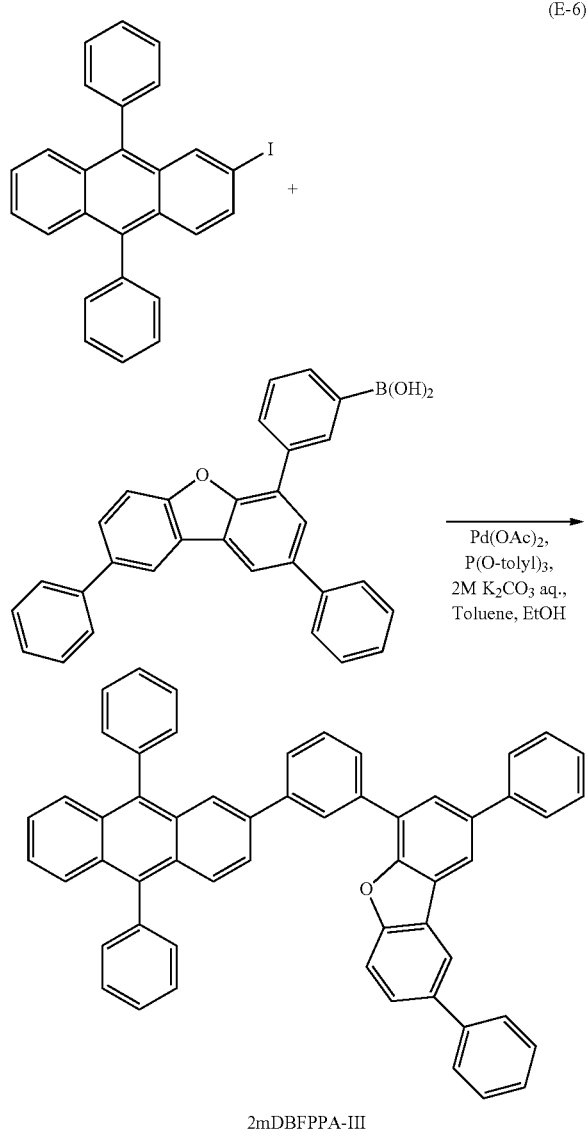

In a 50 mL three-neck flask were put 0.62 g (1.3 mmol) of 2-iode-9,10-diphenylanthracene, 0.60 g (1.3 mmol) of 3-(2,8-diphenyldibenzofuran-4-yl)phenylboronic acid, and 99 mg (0.33 mmol) of tri(ortho-tolyl)phosphine. The air in the flask was replaced with nitrogen. To this mixture were added 10 mL of toluene, 3.0 mL of ethanol, and 2.0 mL of an aqueous solution of potassium carbonate (2.0 mol/L). While the pressure was reduced, this mixture was stirred to be degassed. To this mixture was added 15 mg (0.065 mmol) of palladium(II) acetate, and the mixture was stirred at 80° C. for 4 hours. Then, the aqueous layer of the obtained mixture was extracted with toluene, and the toluene solution and the organic layer were combined and washed with saturated brine. The organic layer was dried with magnesium sulfate. Then, this mixture was gravity filtered. The resulting filtrate was concentrated to given an oily substance, and the obtained oily substance was purified by silica gel column chromatography to give a yellow oily substance. The chromatography was carried out using a mixed solvent having a 3:1 ratio of hexane to toluene as a developing solvent. Recrystallization of the oily substance from a mixed solvent of toluene and hexane gave 0.55 g of a yellow powder in 58% yield, which was the substance to be produced.

By a train sublimation method, 0.55 g of the obtained yellow powdered solid was purified. In the purification, the yellow powdered solid was heated at 320° C. under a pressure of 3.0 Pa with a flow rate of argon gas of 4.0 mL/min. After the purification, 0.50 g of a yellow solid was obtained in a yield of 90%, which was the substance to be produced.

A nuclear magnetic resonance (NMR) method identified this compound as 4-[3-(9,10-diphenyl-2-anthryl)phenyl]-2,8-diphenyldibenzofuran (abbreviation: 2mDBFPPA-III), which was the substance to be produced.

$^1$H NMR data of the obtained compound are: $^1$H NMR (CDCl$_3$, 300 MHz): δ=7.31-7.65 (m, 21H), 7.69-7.74 (m, 8H), 7.81-7.84 (m, 2H), 7.95 (dt, $J_1$=1.8 Hz, $J_2$=7.5 Hz, 1H), 8.03 (sd, $J_1$=1.5 Hz, 1H), 8.10 (s, 1H), 8.03 (dd, $J_1$=1.5 Hz, $J_2$=12.3 Hz, 2H).

Figure 38A:
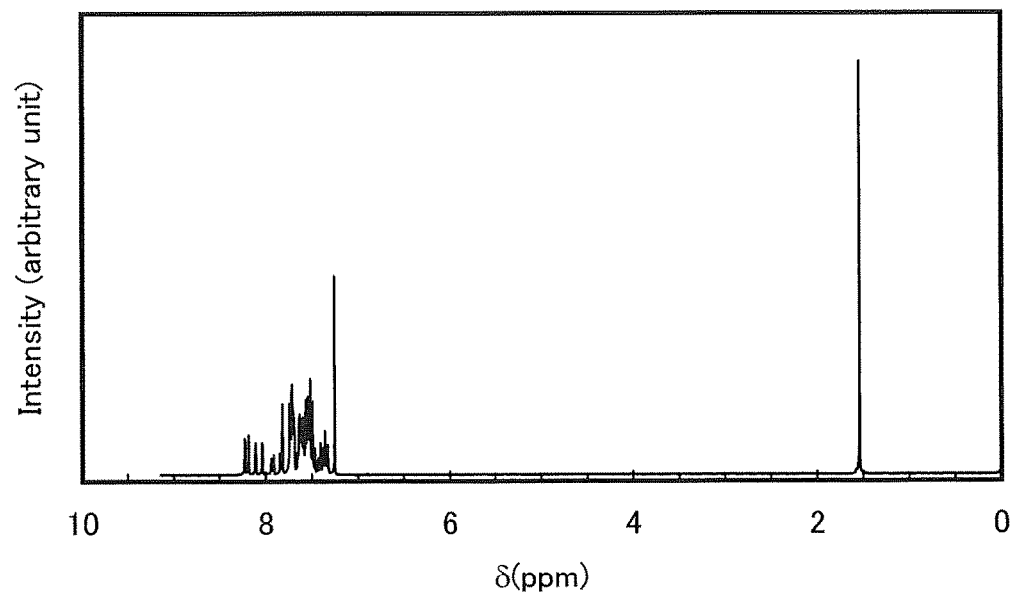
FIGS. 38A and 38B show $^1$H NMR charts of 4-[3-(9,10-diphenyl-2-anthryl)phenyl]-2,8-diphenyldibenzofuran.
Figure 38B:
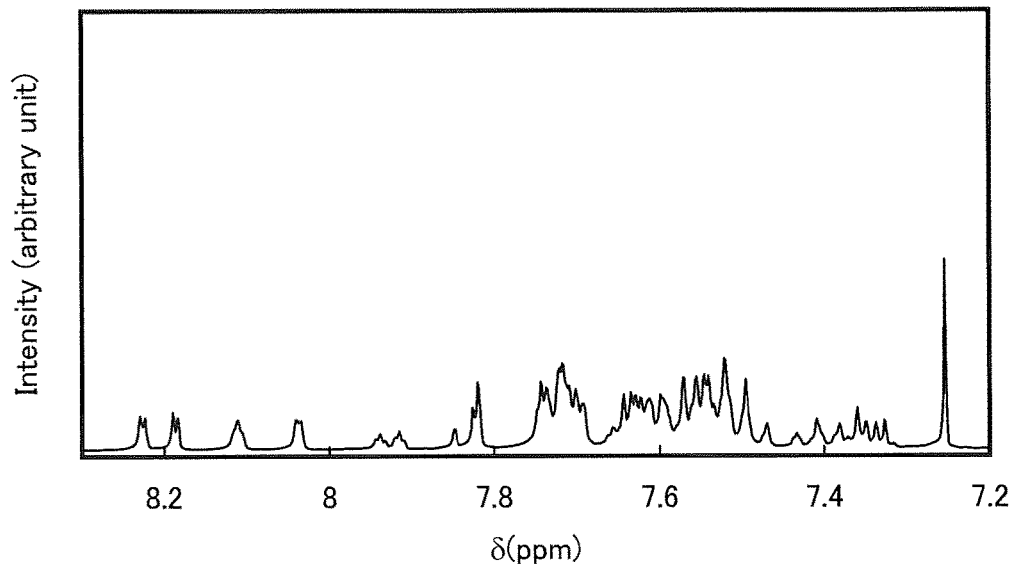

FIGS. 38A and 38B show the $^1$H NMR charts. Note that FIG. 38B is a chart showing an enlarged part of FIG. 38A in the range of 7.2 to 8.3 ppm.

Thermogravimetry-differential thermal analysis (TG-DTA) of 2mDBFPPA-III, which was obtained, was performed. A high vacuum differential type differential thermal balance (manufactured by Bruker AXS K. K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) demonstrates that the temperature at which the weight at the start of the measurement is reduced by 5% (5% weight loss temperature) is 448° C., which is indicative of high heat resistance.

Figure 39A:
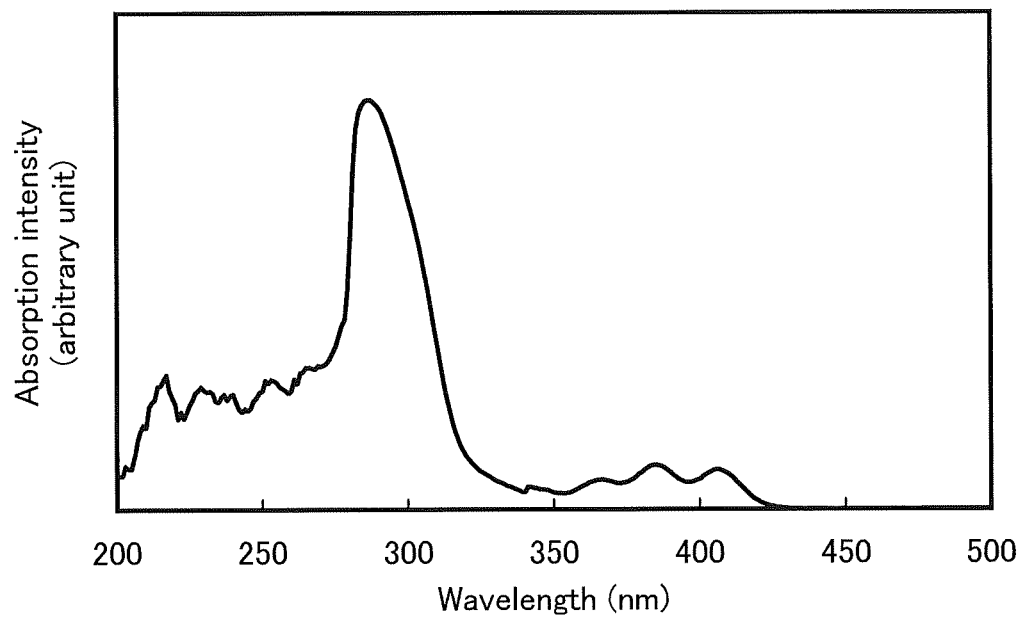
FIGS. 39A and 39B show an absorption spectrum and an emission spectrum of a toluene solution of 4-[3-(9,10-diphenyl-2-anthryl)phenyl]-2,8-diphenyldibenzofuran.
Figure 39B:
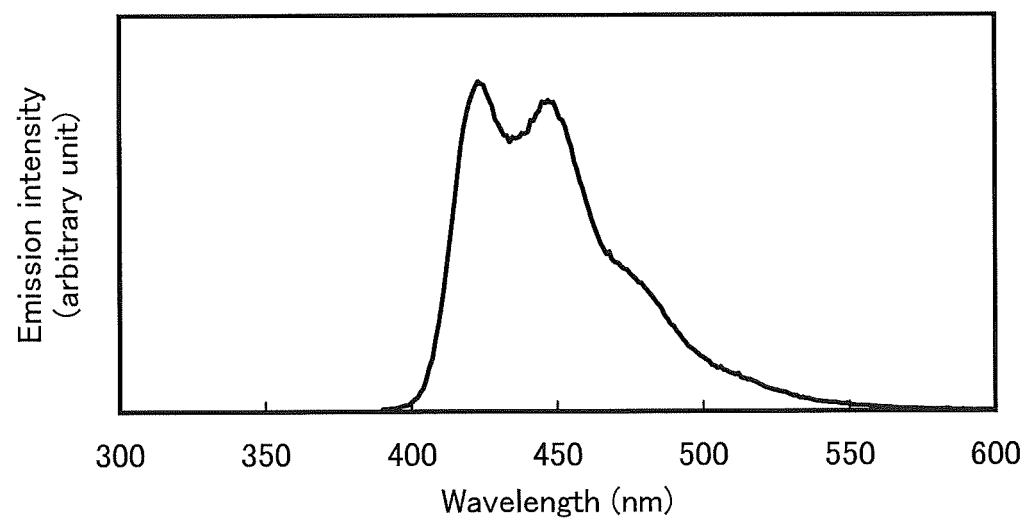
Figure 40A:
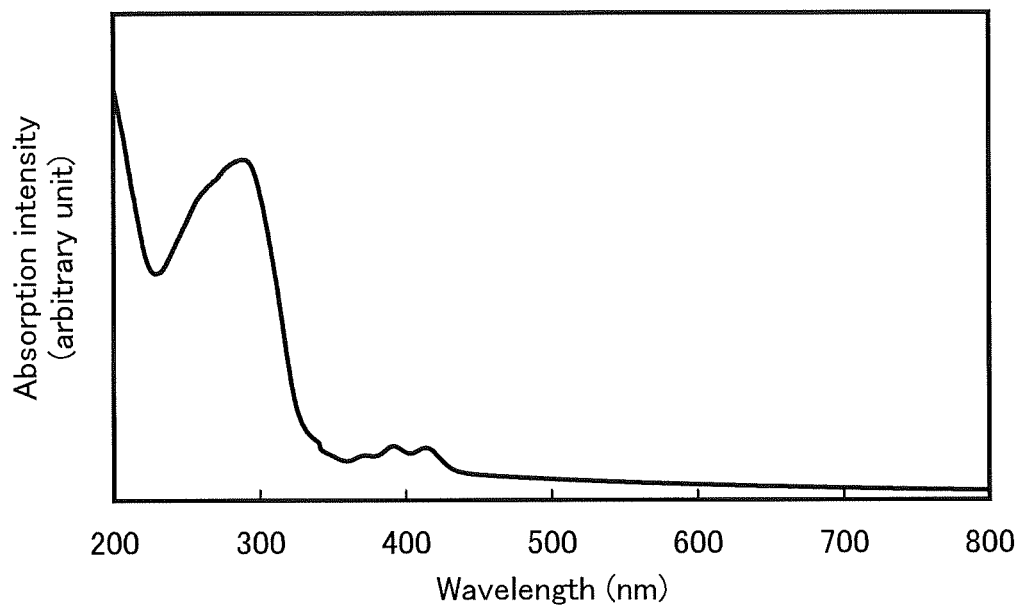
FIGS. 40A and 40B show an absorption spectrum and an emission spectrum of a thin film of 4-[3-(9,10-diphenyl-2-anthryl)phenyl]-2,8-diphenyldibenzofuran.
Figure 40B:
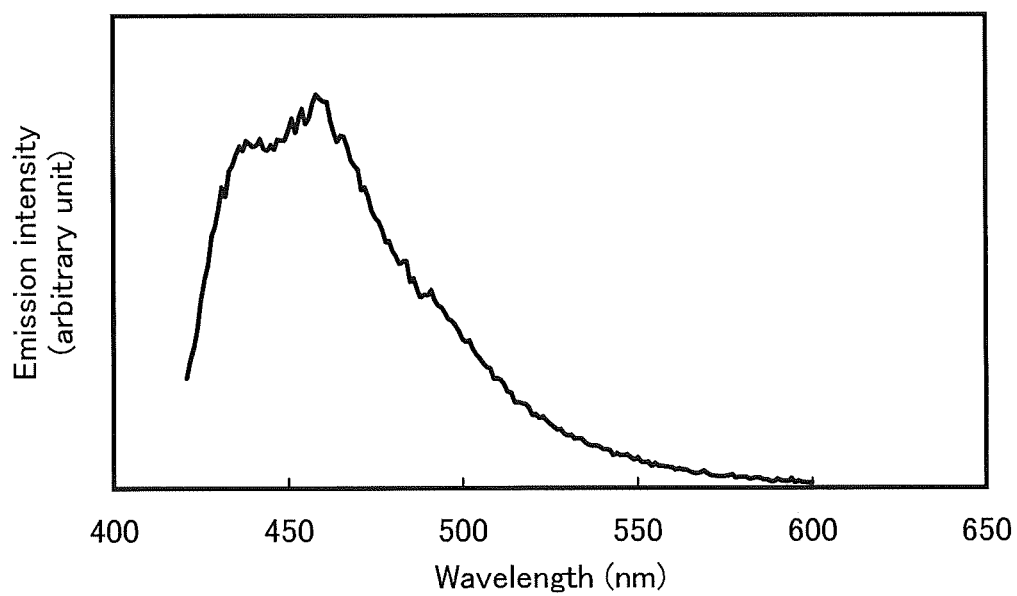

Further, FIG. 39A shows an absorption spectrum of a toluene solution of 2mDBFPPA-III, and FIG. 39B shows an emission spectrum thereof. FIG. 40A shows an absorption spectrum of a thin film of 2mDBFPPA-III, and FIG. 40B shows an emission spectrum thereof The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 39A and 39B and FIGS. 40A and 40B, the horizontal axis represents wavelength (nm) and the vertical axis represents intensity (arbitrary unit). In the case of the toluene solution, absorption was observed at around 365 nm, 385 nm and 406 nm and the emission wavelengths were 423 nm and 447 nm (excitation wavelength: 385 nm). In the case of the thin film, absorption was observed at around 288 nm, 371 nm, 391 nm and 414 nm, and the emission wavelengths were 439 nm and 459 nm (excitation wavelength: 413 nm).

The HOMO level and the LUMO level of the thin film of 2mDBFPPA-III were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, which was obtained from Tauc plot with an assumption of direct transition using data on the absorption spectrum of the thin film of 2mDBFPPA-III which is shown in FIG. 40A, was regarded as an optical energy gap and added to the value of the HOMO level. As a result, the HOMO level and LUMO level of 2mDBFPPA-III were found to be −5.77 eV and −2.92 eV, respectively.

The oxidation characteristic and reduction characteristic of 2mDBFPPA-III were measured. In the measurements of the oxidation and reduction characteristics, cyclic voltammetry (CV) measurement was employed, and an electrochemical analyzer (ALS model 600A, manufactured by BAS Inc.) was used.

As a solution used in the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 reference electrode for nonaqueous solvent) was used as a reference electrode. Note that the measurement was conducted at room temperature. In addition, the scan rate at the CV measurement was set to 0.1 V/s in all the measurement.

The reduction characteristic of 2mDBFPPA-III was examined by 100 measurement cycles in which the potential of the working electrode with respect to the reference electrode was scanned from −1.59 V to −2.25 V and then from −2.25 V to −1.59 V in each cycle. Similarly, the oxidation characteristic of 2mDBFPPA-III was evaluated by 100 measurement cycles in which the potential of the working electrode with respect to the reference electrode was scanned from 0.25 V to 1.00 V and then from 1.00 V to 0.25 V in each cycle.

Figure 41A:
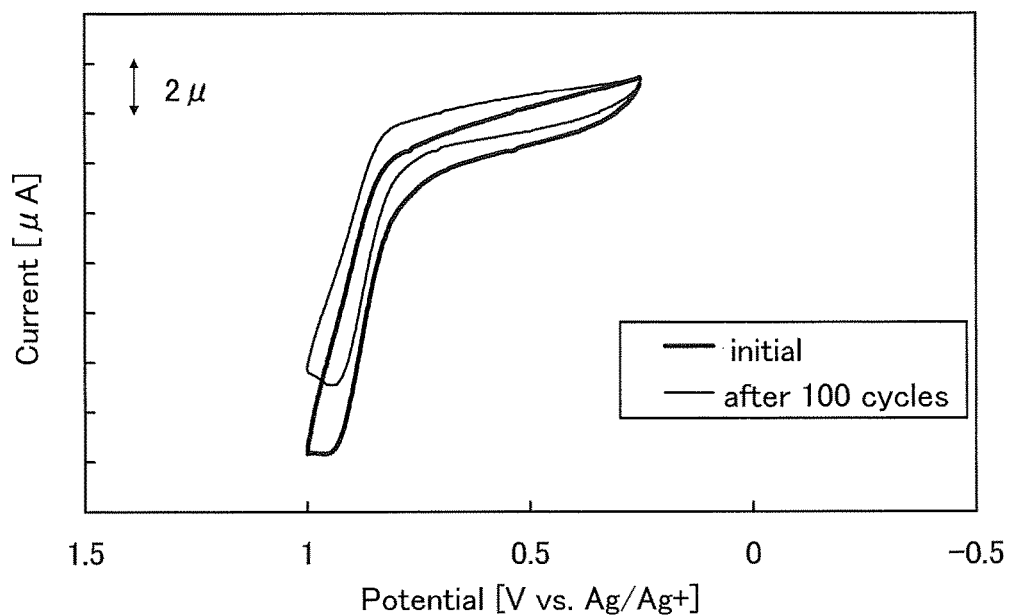
FIGS. 41A and 41B show CV measurement results of 4-[3-(9,10-diphenyl-2-anthryl)phenyl]-2,8-diphenyldibenzofuran.
Figure 41B:
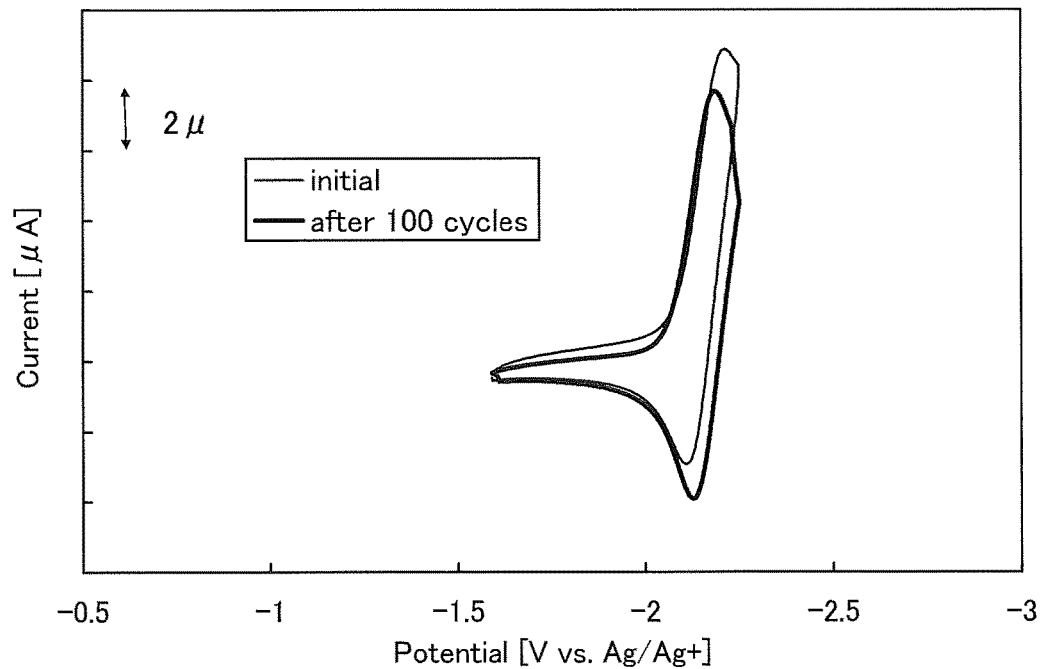

According to the measurement results, a peak current corresponding to oxidation at around 0.88 V (vs. Ag/Ag$^+$) and a peak current corresponding to reduction at around −2.16 V (vs. Ag/Ag$^+$) were observed. FIG. 41 shows a graph of the results.

Even after as many as 100 scan cycles, 2mDBFPPA-III showed no significant change in the peak position of the CV curves representing oxidation and reduction and kept the peak intensity at 81% of the initial intensity on the oxidation side and at 87% on the reduction side. Thus, it is understood that 2mDBFPPA-III is relatively stable, when subjected to repetitions of oxidation from a neutral state to an oxidized state and reduction from the oxidized state to the neutral state or repetitions of reduction from a neutral state to a reduced state and oxidation from the reduced state to the neutral state.

EXAMPLE 8

In this example, a light-emitting element of one embodiment of the present invention will be described referring to FIG. 37A. Chemical formulae of materials used in this example are shown below.

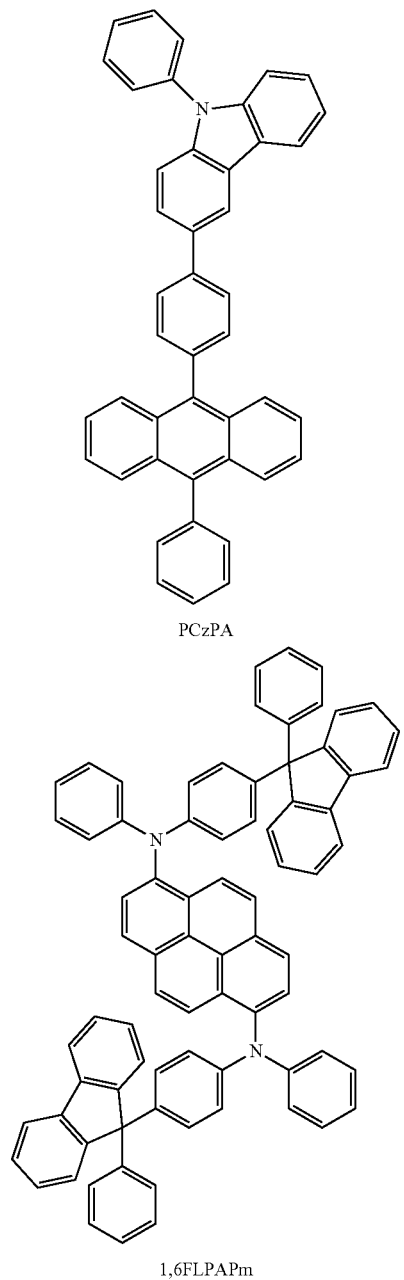

PCzPA 1,6FLPAPm

-continued

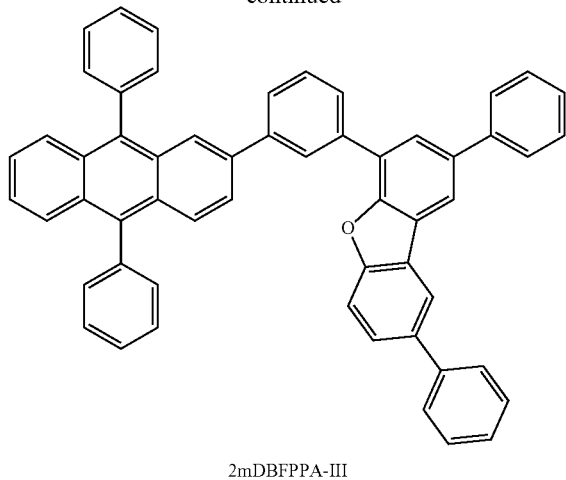

2mDBFPPA-III

A method of fabricating Light-emitting Element 5 of this example will now be described.

(Light-Emitting Element 5)

First, ITSO was deposited over the glass substrate 1100 by a sputtering method, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, 9-phenyl-3-[4-(10-phenyl-9-anthryl)phenyl]-9H-carbazole (abbreviation: PCzPA) which is a substance having a high hole-transport property and molybdenum(VI) oxide which is an acceptor substance were co-evaporated to form the hole-injection layer 1111 over the first electrode 1101. The thickness of the hole-injection layer 1111 was 50 nm, and the weight ratio of PCzPA to molybdenum(VI) oxide was controlled to be 4:2 (=PCzPA:molybdenum(VI) oxide). Note that the co-evaporation method refers to an evaporation method in which evaporation is carried out from a plurality of evaporation sources at the same time in one treatment chamber.

Next, PCzPA was deposited to a thickness of 10 nm over the hole-injection layer 1111, whereby the hole-transport layer 1112 was formed.

Furthermore, 4-[3-(9,10-diphenyl-2-anthryl)phenyl]-2,8-diphenyldibenzofuran (abbreviation: 2mDBFPPA-III) synthesized in Example 7 and N,N'-bis[4-(9-phenyl-9H-fluoren-9-yl)phenyl]-N,N'-diphenyl-pyrene-1,6-diamine (abbreviation: 1,6FLPAPrn) were co-evaporated to form the light-emitting layer 1113 over the hole-transport layer. The weight ratio of 2mDBFPPA-III to 1,6FLPAPrn was adjusted to 1:0.05 (=2mDBFPPA-III:1,6FLPAPm). The thickness of the light-emitting layer 1113 was set to 30 nm.

Then, over the light-emitting layer 1113, a 10 nm thick layer of Alq and, a 15 nm thick layer of BPhen were deposited on the Alq layer, whereby the electron-transport layer 1114 including Alq and BPhen was obtained.

Further, a 1 nm thick film of LiF was formed over the electron-transport layer 1114 by evaporation, whereby the electron-injection layer 1115 was formed.

Lastly, a 200 nm thick film of aluminum was formed by evaporation to form a second electrode 1103 functioning as a cathode. Thus, Light-emitting Element 5 of this example was fabricated.

Note that, in the above evaporation process, evaporation was all performed by a resistance heating method.

Table 9 shows element structures of Light-emitting Element 5 formed as described above.

TABLE 9

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 5 | ITSO 110 nm | PCzPA:MoOx (=4:2) 50 nm | PCzPA 10 nm | 2mDBFPPA-III:1, 6FLPAPrn (=1:0.05) 30 nm | Alq 10 nm | BPhen 15 nm | LiF 1 nm | Al 200 nm |

Light-emitting Element 5 was sealed in a glove box containing a nitrogen atmosphere so as not to be exposed to air. Then, operation characteristics of the Light-emitting Element 5 were measured. Note that the measurement was carried out at room temperature (in the atmosphere kept at 25° C.).

Figure 42:
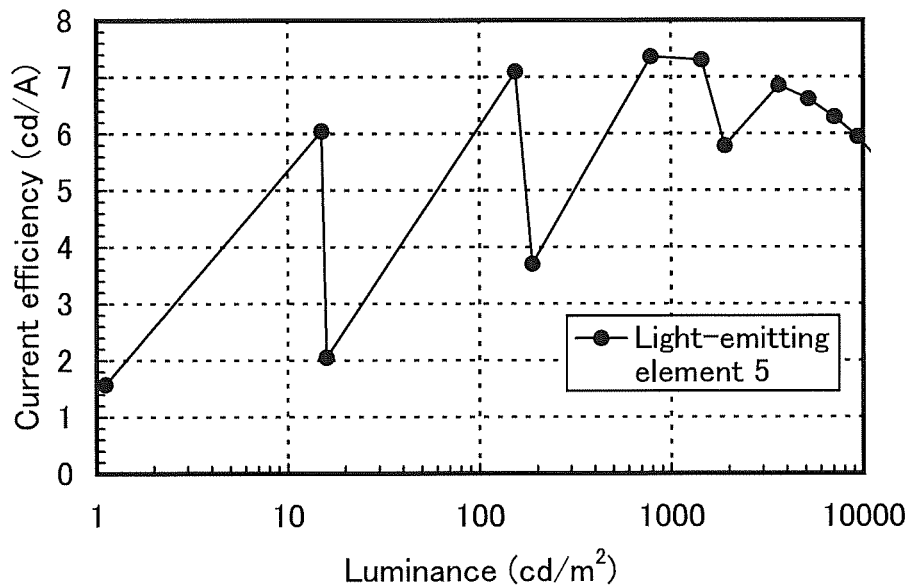
FIG. 42 shows luminance vs. current efficiency characteristics of Light-emitting Element 5.
Figure 43:
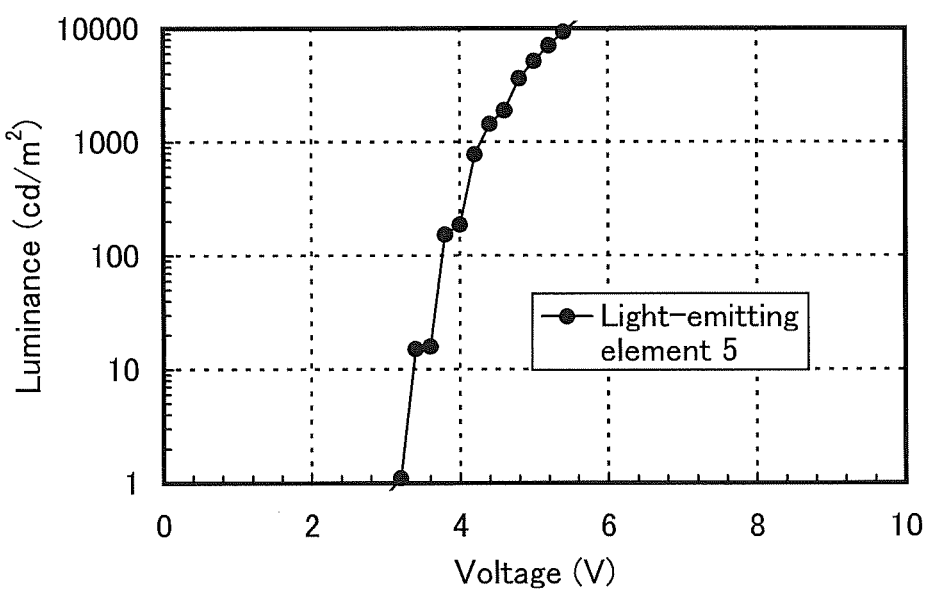
FIG. 43 shows voltage vs. luminance characteristics of Light-emitting Element 5.
Figure 44:
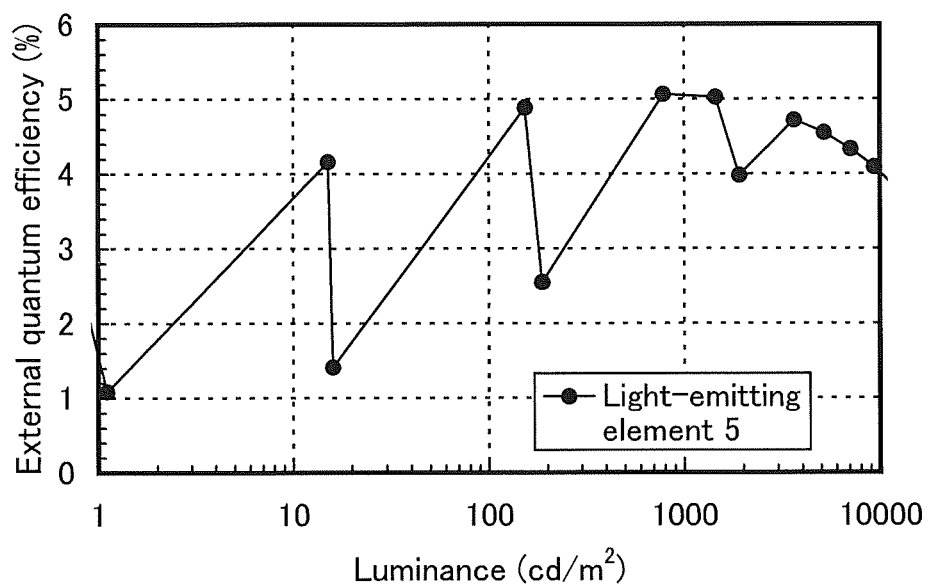
FIG. 44 shows luminance vs. external quantum efficiency characteristics of Light-emitting Element 5.
Figure 45:
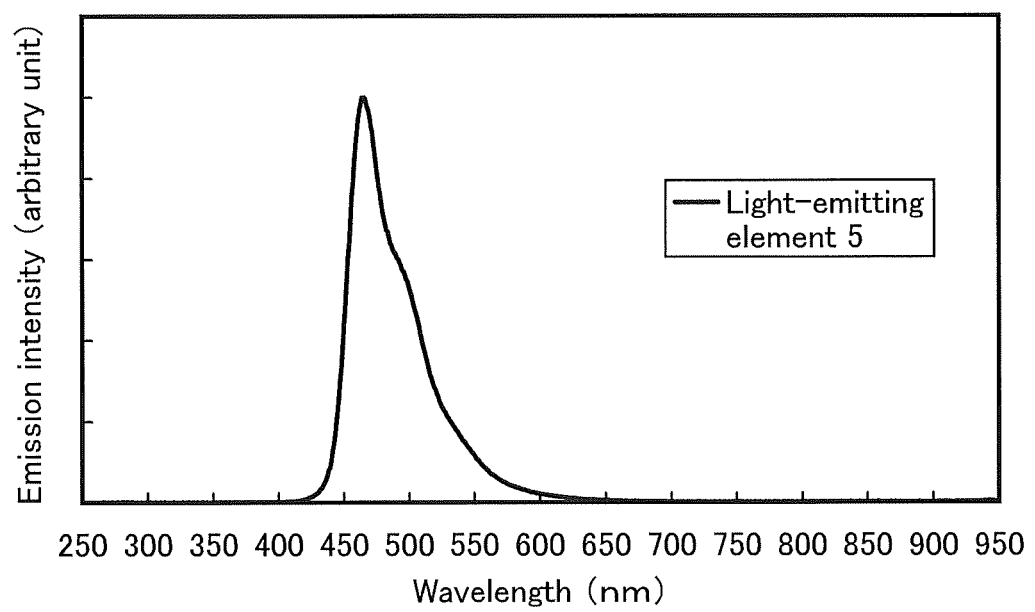
FIG. 45 shows an emission spectrum of Light-emitting Element 5.

FIG. 42 shows luminance vs. current density characteristics of Light-emitting Element 5. In FIG. 42, the horizontal axis represents luminance (cd/m$^2$) and the vertical axis represents current efficiency (cd/A). FIG. 43 shows the voltage vs. luminance characteristics. In FIG. 43, the horizontal axis represents applied voltage (V) and the vertical axis represents luminance (cd/m$^2$). FIG. 44 shows the luminance vs. external quantum efficiency characteristics. In FIG. 44, the horizontal axis represents luminance (cd/m$^2$) and the vertical axis represents external quantum efficiency (%). FIG. 45 shows the emission spectra with a current supply of 1 mA. In FIG. 45, the horizontal axis represents wavelength (nm) and the vertical axis represents intensity (arbitrary unit). Further, Table 10 shows the voltage (V), current density (mA/cm$^2$), CIE chromaticity coordinates (x, y), current efficiency (cd/A), and external quantum efficiency (%) of the light-emitting element at a luminance of around 780 cd/m$^2$.

TABLE 10

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 5 | 4.2 | 11 | 0.15 | 0.21 | 780 | 7.4 | 5.1 |

As seen from FIG. 45 and the CIE chromaticity coordinates in Table 10, blue light emission is shown by Light-emitting Element 5, which was formed. FIG. 42, FIG. 43, FIG. 44, and Table 10 reveal that Light-emitting Element 5 exhibits good chromaticity, high current efficiency, and high external quantum efficiency.

As described above, 2mDBFPPA-III produced in Example 7 was used as the host material of the light-emitting layer, whereby the light-emitting element achieved good chromaticity and high emission efficiency.

Figure 46:
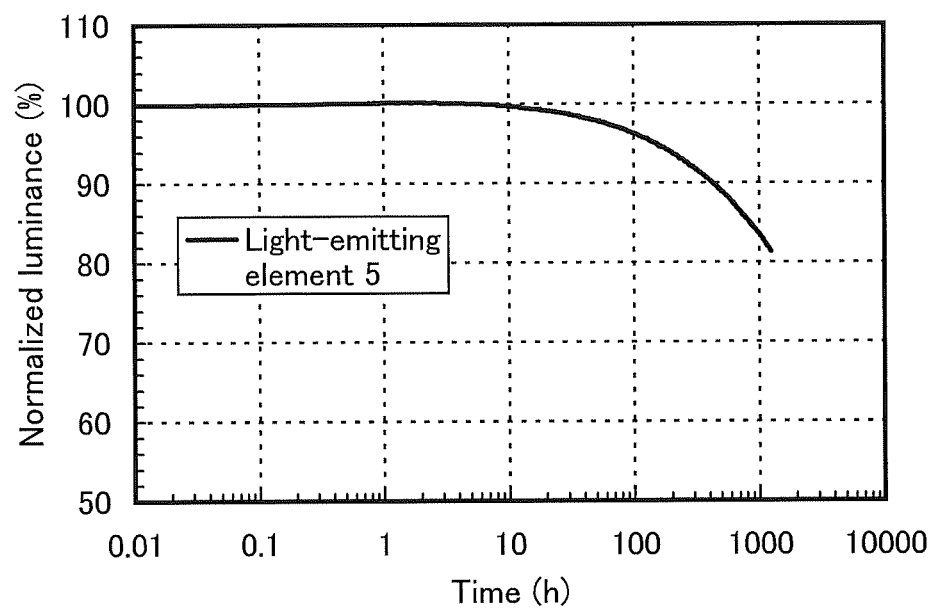
FIG. 46 shows results of reliability tests of Light-emitting Element 5.

Next, Light-emitting Element 5 was subjected to reliability tests. Results of the reliability tests are shown in FIG. 46. In FIG. 46, the vertical axis represents normalized luminance (%) with an initial luminance of 100%, and the horizontal axis represents driving time (h) of the element. In the reliability tests, Light-emitting Element 5 of this example was driven under the conditions where the current density was constant and the initial luminance was 1000 cd/m$^2$. FIG. 46 shows that Light-emitting Element 5 kept 81% of the initial luminance after the driving for 1300 hours. Thus, Light-emitting Element 5 shows high reliability. Furthermore, the results of the reliability tests demonstrate that the light-emitting element to which one embodiment of the present invention is applied is effective in realizing a light-emitting element having a long lifetime.

EXAMPLE 9

Synthesis Example 4

This example will show a method of synthesizing 2-[3-(9,10-diphenyl-2-anthryl)phenyl]dibenzofuran (abbreviation: 2mDBFPPA)) represented by Structural formula (158) described in Embodiment 1.

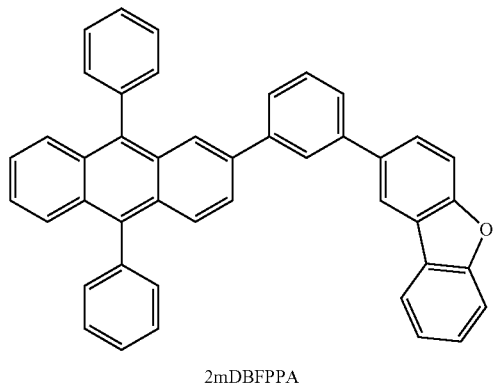 [SMILES: c1ccc(-c2c3ccccc3c(-c3ccccc3)c3cc(-c4cccc(-c5ccc6oc7ccccc7c6c5)c4)ccc23)cc1]

2mDBFPPA

Step 1: Synthesis of Dibenzofuran-2-boronic acid

The synthesis scheme of Step 1 is shown in (F-1).

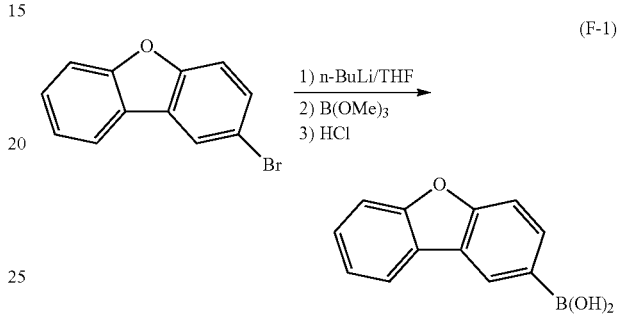

(F-1)

In a 300 mL three-neck flask was put 3.6 g (14 mmol) of 3-bromodibenzofuran. The air in the flask was replaced with nitrogen. To this mixture was added 70 mL of THF, and this solution was cooled to −80° C. Then, 10 mL (16 mmol) of n-butyllithium (a 1.6 mol/L hexane solution) was dripped into this solution with a syringe. After that, this solution was stirred at the same temperature for 2 hours. Then, 3.4 mL (30 mmol) of trimethyl borate was added to this solution, and the mixture was stirred for 4 days while its temperature was returned to room temperature. After that, about 30 mL of diluted hydrochloric acid (1.0 mol/L) was added to this solution, followed by stirring for 1 hour. Then, the aqueous layer of this mixture was extracted with ethyl acetate, and the ethyl acetate solution and the organic layer were combined and washed with saturated brine. The organic layer was dried with magnesium sulfate. Then, this mixture was gravity filtered. The resulting filtrate was concentrated to give a solid. The solid was washed with hexane, whereby 0.70 g of a white powder was obtained in 27% yield, which was the substance to be produced.

Step 2: Synthesis of 2-[3-(9,10-diphenyl-2-anthryl)phenyl]dibenzofuran (abbreviation: 2mDBFPPA)

The synthesis scheme of Step 2 is shown in (F-2).

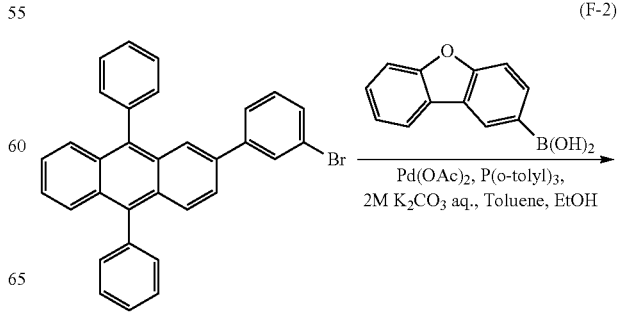

(F-2)

-continued

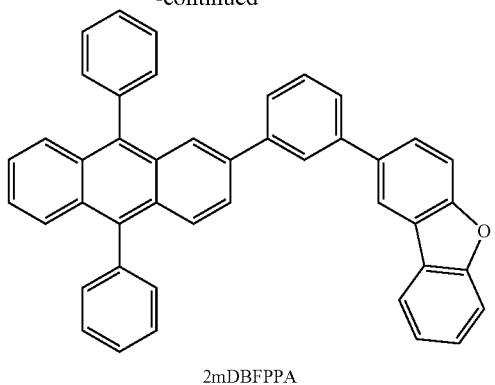

2mDBFPPA

In a 50 mL three-neck flask were put 1.2 g (2.4 mmol) of 2-(3-bromophenyl)-9,10-diphenylanthracene, 0.52 g (2.4 mmol) of dibenzofuran-2-boronic acid, and 0.18 g (0.60 mmol) of tri(ortho-tolyl)phosphine. The air in the flask was replaced with nitrogen. To this mixture were added 10 mL of toluene, 3.0 mL of ethanol, and 3.0 mL of an aqueous solution of sodium carbonate (2.0 mol/L). While the pressure was reduced, this mixture was stirred to be degassed. To this mixture was added 27 mg (0.12 mmol) of palladium(II) acetate, and the mixture was stirred at 80° C. for 3 hours. Then, the aqueous layer of the obtained mixture was extracted with toluene, and the toluene solution and the organic layer were combined and washed with saturated brine. The organic layer was dried with magnesium sulfate. Then, this mixture was gravity filtered. The resulting filtrate was concentrated, and the obtained oily substance was purified by silica gel column chromatography to give a yellow oily substance. The chromatography was carried out using a mixed solvent having a 5:1 ratio of hexane to toluene as a developing solvent, whereby an oily substance was obtained. Recrystallization of the oily substance from a mixed solvent of toluene and hexane gave 0.40 g of a yellow powder in 29% yield, which was the substance to be produced.

By a train sublimation method, 0.40 g of the obtained yellow powdered solid was purified. In the purification, the yellow powdered solid was heated at 270° C. under a pressure of 2.6 Pa with a flow rate of argon gas of 5.0 mL/min. After the purification, 0.35 g of a yellow solid was obtained in a yield of 87%, which was the substance to be produced.

A nuclear magnetic resonance (NMR) method identified this compound as 2- [3-(9,10-diphenyl-2-anthryl)phenyl] dibenzofuran (abbreviation: 2mDBFPPA), which was the substance to be produced.

$^1$H NMR data of the obtained compound are: $^1$H NMR (CDCl$_3$, 300 MHz): δ 6=7.32-7.38 (m, 3H), 7.43-7.74 (m, 20H), 7.81-7.83 (m, 2H), 7.98-8.01 (m, 2H), 8.13 (sd, J$_1$=1.8 Hz, 1H).

Figure 47A:
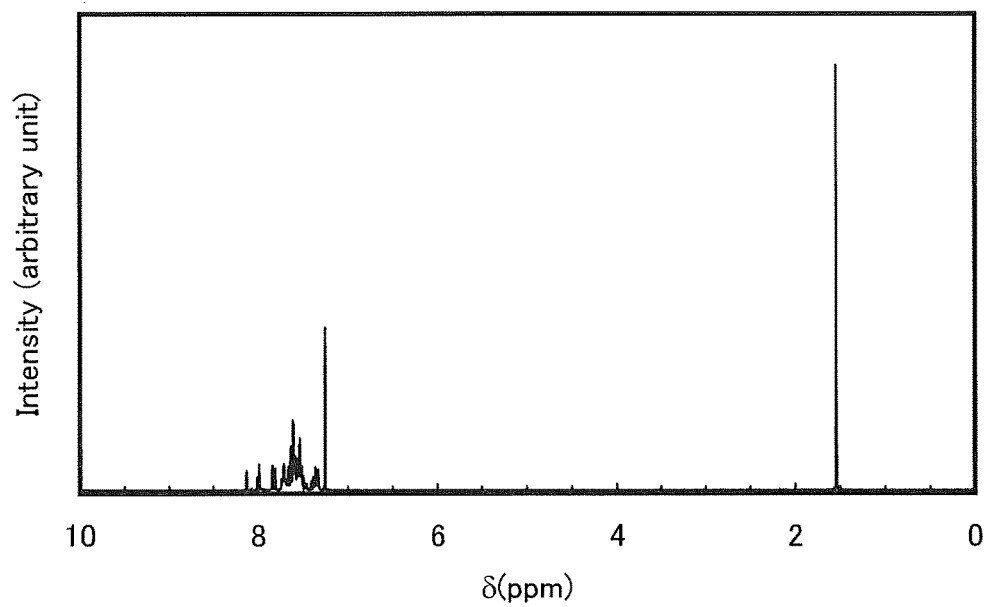
FIGS. 47A and 47B show $^1$H NMR charts of 2-[3-(9,10-diphenyl-2-anthryl)phenyl]dibenzofuran.
Figure 47B:
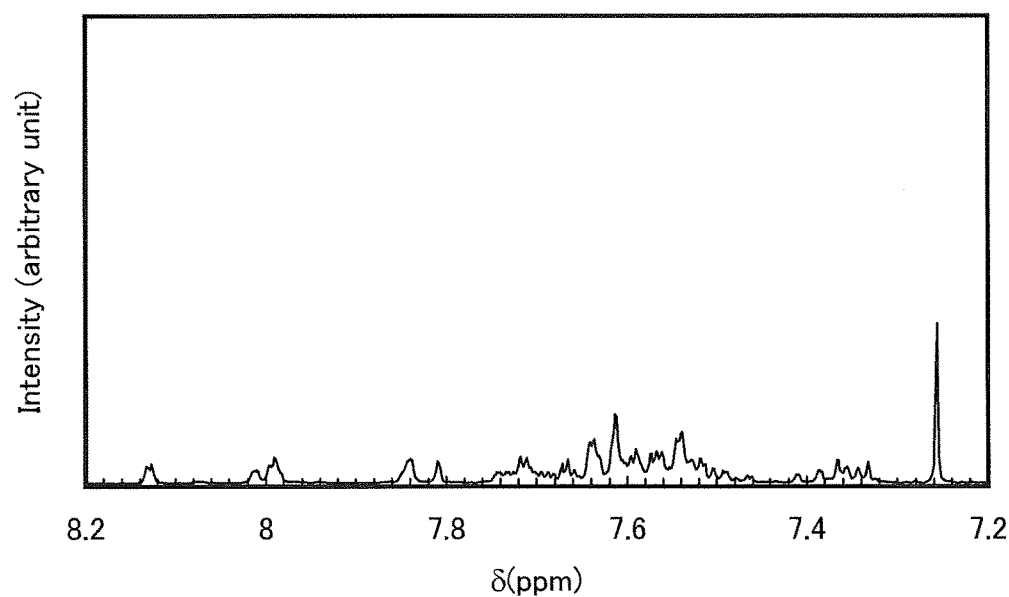

FIGS. 47A and 47B show the $^1$H NMR charts. Note that FIG. 47B is a chart showing an enlarged part of FIG. 47A in the range of 7.2 to 8.2 ppm.

Thermogravimetry-differential thermal analysis (TG-DTA) of 2mDBFPPA, which was obtained, was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) demonstrates that the temperature at which the weight at the start of the measurement is reduced by 5% (5% weight loss temperature) is 415° C., which is indicative of high heat resistance.

Figure 48A:
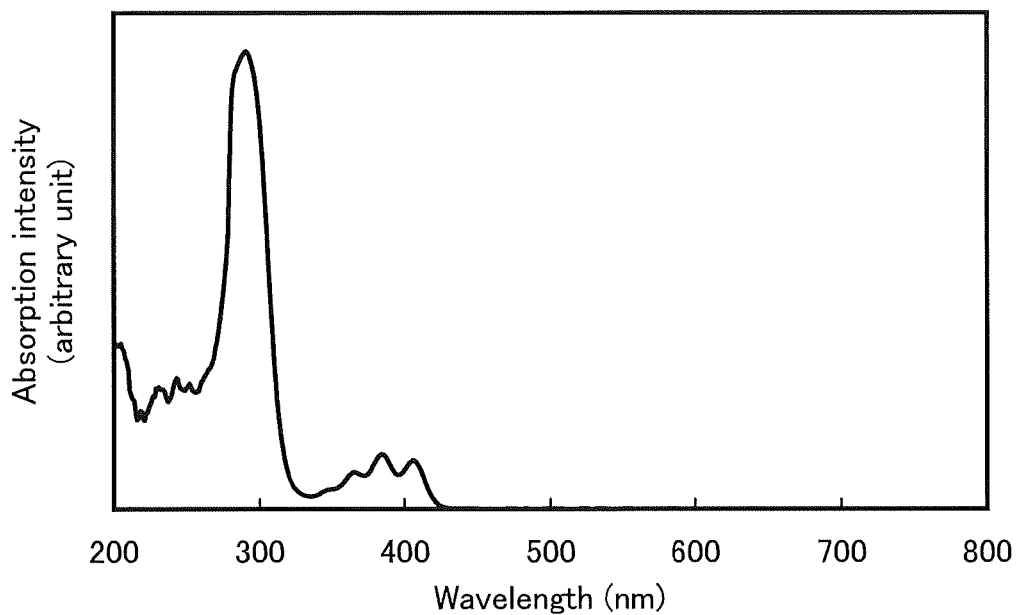
FIGS. 48A and 48B show an absorption spectrum and an emission spectrum of a toluene solution of 2-[3-(9,10-diphenyl-2-anthryl)phenyl]dibenzofuran.
Figure 48B:
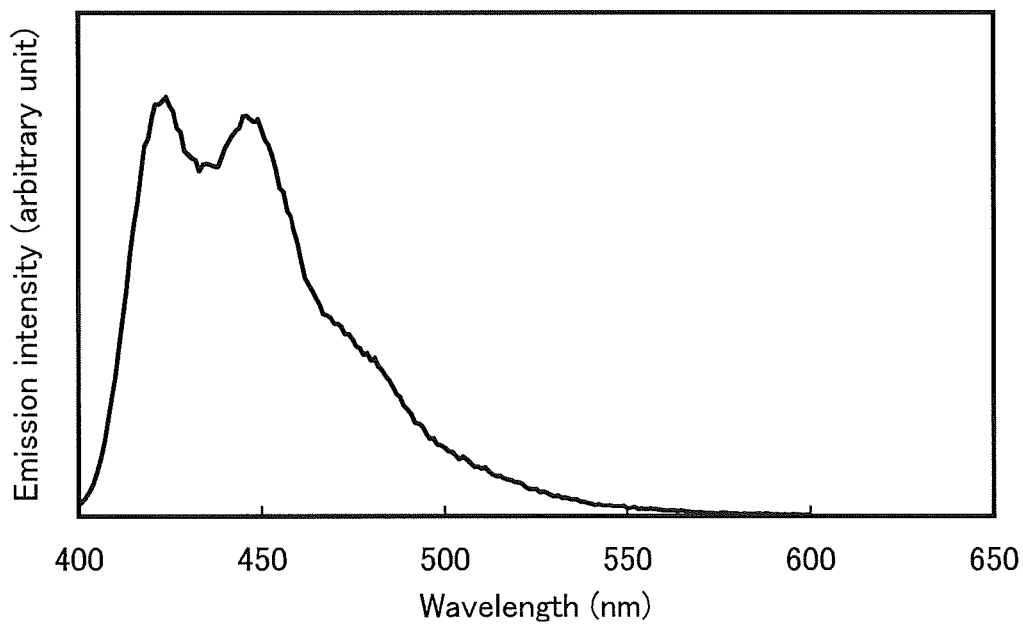
Figure 49A:
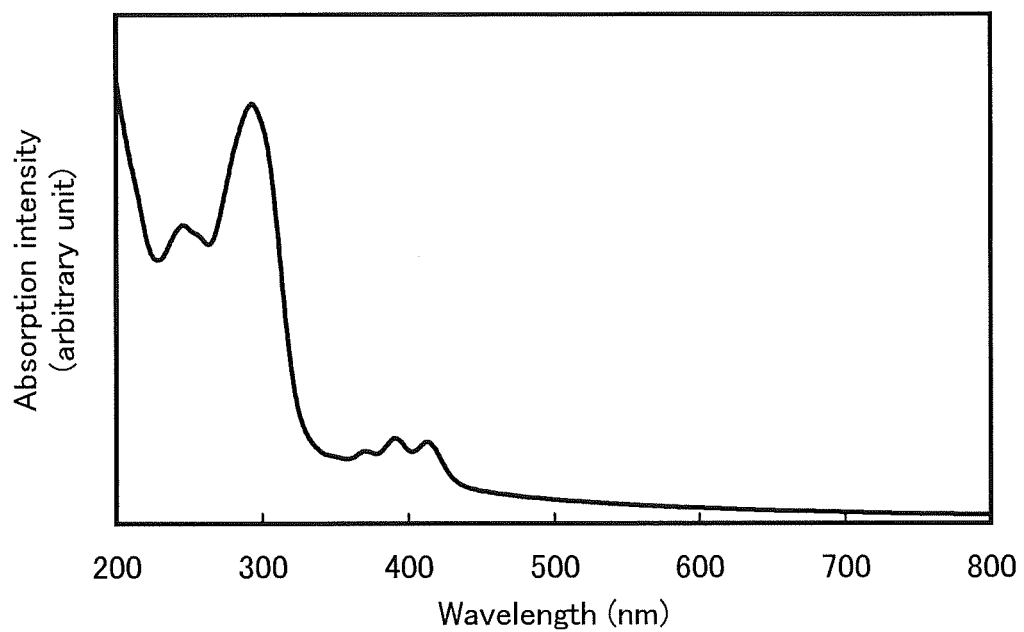
FIGS. 49A and 49B show an absorption spectrum and an emission spectrum of a thin film of 2-[3-(9,10-diphenyl-2-anthryl)phenyl]dibenzofuran.
Figure 49B:
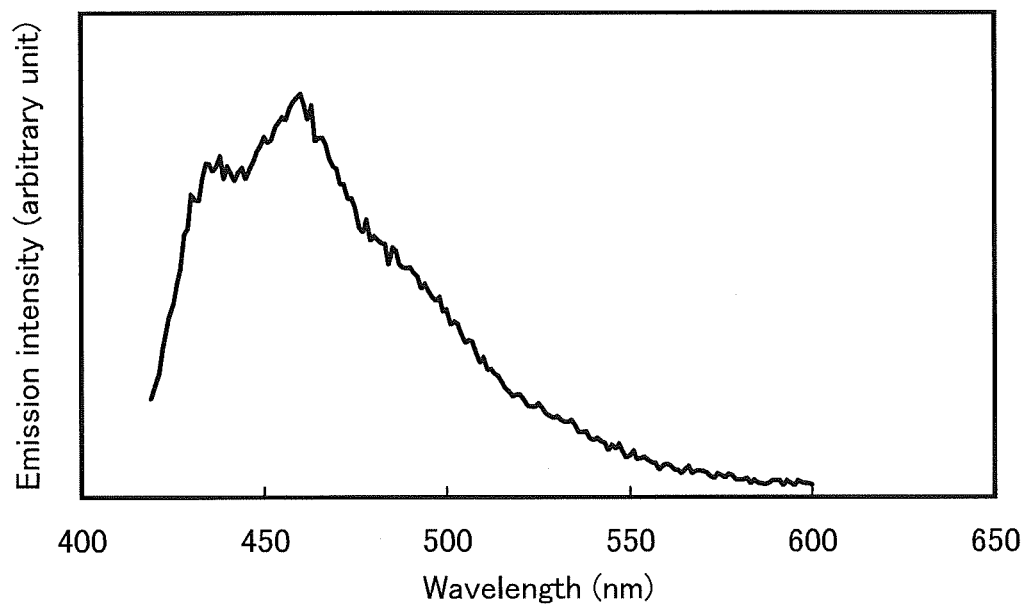

Further, FIG. 48A shows an absorption spectrum of a toluene solution of 2mDBFPPA, and FIG. 48B shows an emission spectrum thereof. FIG. 49A shows an absorption spectrum of a thin film of 2mDBFPPA, and FIG. 49B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 48A and 48B and FIGS. 49A and 49B, the horizontal axis represents wavelength (nm) and the vertical axis represents intensity (arbitrary unit). In the case of the toluene solution, absorption was observed at around 291 nm, 366 nm, 384 nm, and 406 nm and the emission wavelengths were 423 nm and 446 nm (excitation wavelength: 385 nm). In the case of the thin film, absorption was observed at around 246 nm, 293 nm, 371 nm and 413 nm, and the emission wavelengths were 437 nm and 459 nm (excitation wavelength: 413 nm).

The HOMO level and the LUMO level of the thin film of 2mDBFPPA were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, which was obtained from Tauc plot with an assumption of direct transition using data on the absorption spectrum of the thin film of 2mDBFPPA which is shown in FIG. 49A, was regarded as an optical energy gap and added to the value of the HOMO level. As a result, the HOMO level and LUMO level of 2mDBFPPA were found to be −5.71 eV and −2.85 eV, respectively.

The oxidation characteristic and reduction characteristic of 2mDBFPPA were measured. In the measurements of the oxidation and reduction characteristics, cyclic voltammetry (CV) measurement was employed, and an electrochemical analyzer (ALS model 600A, manufactured by BAS Inc.) was used.

As a solution used in the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 reference electrode for nonaqueous solvent) was used as a reference electrode. Note that the measurement was conducted at room temperature. In addition, the scan rate at the CV measurement was set to 0.1 V/s in all the measurement.

The reduction characteristic of 2mDBFPPA was examined by 100 measurement cycles in which the potential of the working electrode with respect to the reference electrode was scanned from −1.56 V to −2.27 V and then from −2.27 V to −1.56 V in each cycle. Similarly, the oxidation characteristic of 2mDBFPPA was evaluated by 100 measurement cycles in which the potential of the working electrode with respect to the reference electrode was scanned from 0.20 V to 1.05 V and then from 1.05 V to 0.20 V in each cycle.

Figure 50A:
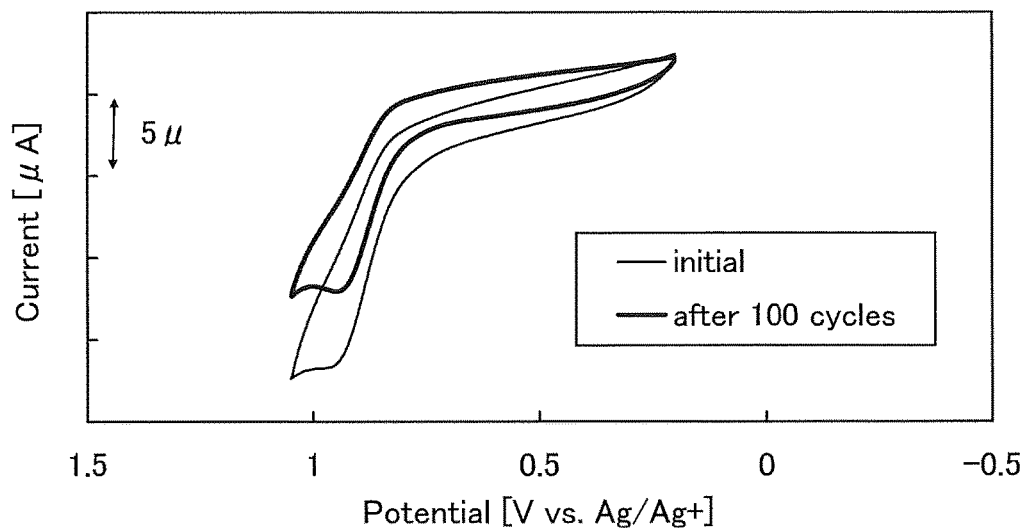
FIGS. 50A and 50B show CV measurement results of 2-[3-(9,10-diphenyl-2-anthryl)phenyl]dibenzofuran.
Figure 50B:
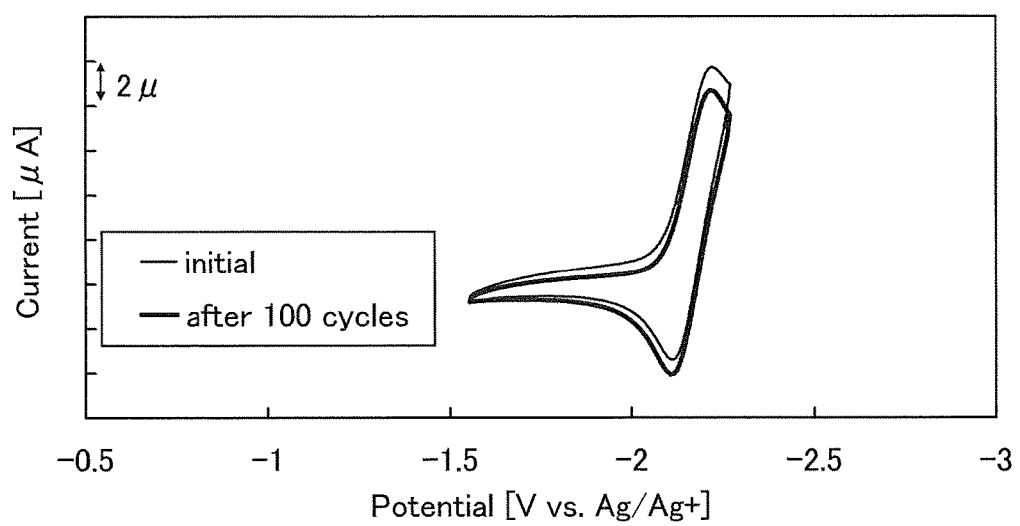

According to the measurement results, a peak current corresponding to oxidation at around 0.95 V (vs. Ag/Ag$^+$) and a peak current corresponding to reduction at around −2.22 V (vs. Ag/Ag$^+$) were observed. FIG. 50 shows a graph of the results.

Even after as many as 100 scan cycles, 2mDBFPPA showed no significant change in the peak position of the CV curves representing oxidation and reduction and kept the peak intensity at 73% of the initial intensity on the oxidation side and at 89% on the reduction side. Thus, it is understood that 2mDBFPPA is relatively stable, when subjected to repetitions of oxidation from a neutral state to an oxidized state and reduction from the oxidized state to the neutral state or repetitions of reduction from a neutral state to a reduced state and oxidation from the reduced state to the neutral state.

EXAMPLE 10

In this example, a light-emitting element of one embodiment of the present invention will be described referring to FIG. 37A. Chemical formulae of materials used in this example are shown below.

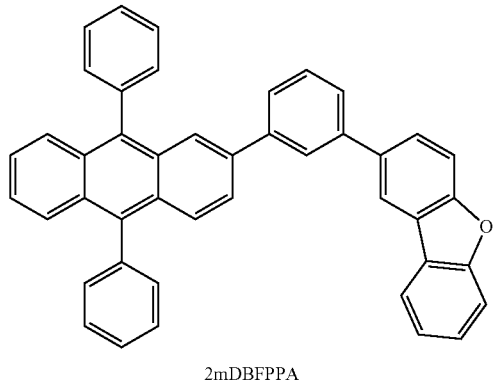 [SMILES: c1ccc(-c2c3ccccc3c(-c3ccccc3)c3cc(-c4cccc(-c5ccc6oc7ccccc7c6c5)c4)ccc23)cc1]

2mDBFPPA

A method of fabricating Light-emitting Element 6 of this example will now be described.

(Light-Emitting Element 6)

First, ITSO was deposited over the glass substrate 1100 by a sputtering method, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, PCzPA which is a substance having a high hole-transport property and molybdenum(VI) oxide which is an acceptor substance were co-evaporated to form the hole-injection layer 1111 over the first electrode 1101. The thickness of the hole-injection layer 1111 was 50 nm, and the weight ratio of PCzPA to molybdenum(VI) oxide was controlled to be 4:2 (=PCzPA:molybdenum(VI) oxide). Note that the co-evaporation method refers to an evaporation method in which evaporation is carried out from a plurality of evaporation sources at the same time in one treatment chamber.

Next, PCzPA was deposited to a thickness of 10 nm over the hole-injection layer 1111, whereby the hole-transport layer 1112 was formed.

Furthermore, 2-[3-(9,10-diphenyl-2-anthryl)phenyl]dibenzofuran (abbreviation: 2mDBFPPA) synthesized in Example 9 and 1,6FLPAPrn were co-evaporated to form the light-emitting layer 1113 over the hole-transport layer. The weight ratio of 2mDBFPPA to 1,6FLPAPrn was adjusted to 1:0.05 (=2mDBFPPA:1,6FLPAPrn). The thickness of the light-emitting layer 1113 was set to 30 nm.

Then, over the light-emitting layer 1113, a 10 nm thick layer of Alq and, a 15 nm thick layer of BPhen were deposited on the Alq layer, whereby the electron-transport layer 1114 including Alq and BPhen was obtained.

Further, a 1 nm thick film of LiF was formed over the electron-transport layer 1114 by evaporation, whereby the electron-injection layer 1115 was formed.

Lastly, a 200 nm thick film of aluminum was formed by evaporation to form a second electrode 1103 functioning as a cathode. Thus, Light-emitting Element 6 of this example was fabricated.

Note that, in the above evaporation process, evaporation was all performed by a resistance heating method.

Table 11 shows element structures of Light-emitting Element 6 formed as described above.

TABLE 11

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Light-emitting element 6 | ITSO 110 nm | PCzPA:MoOx (=4:2) 50 nm | PCzPA 10 nm | 2mDBFPPA:1, 6FLPAPrn (=1:0.05) 30 nm | Alq 10 nm | BPhen 15 nm | LiF 1 nm | Al 200 nm |

Light-emitting Element 6 was sealed in a glove box containing a nitrogen atmosphere so as not to be exposed to air. Then, operation characteristics of the Light-emitting Element 6 were measured. Note that the measurement was carried out at room temperature (in the atmosphere kept at 25° C.).

Figure 51:
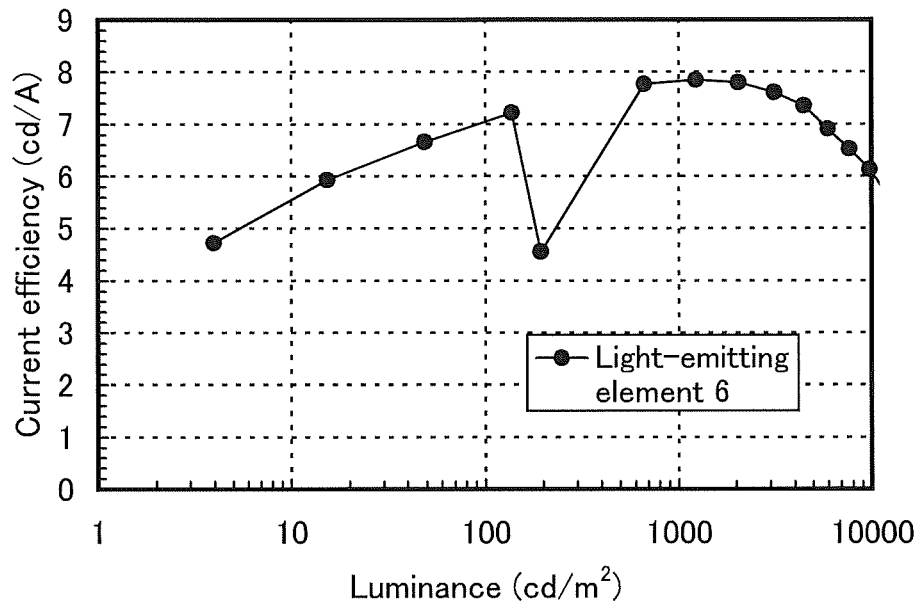
FIG. 51 shows luminance vs. current efficiency characteristics of Light-emitting Element 6.
Figure 52:
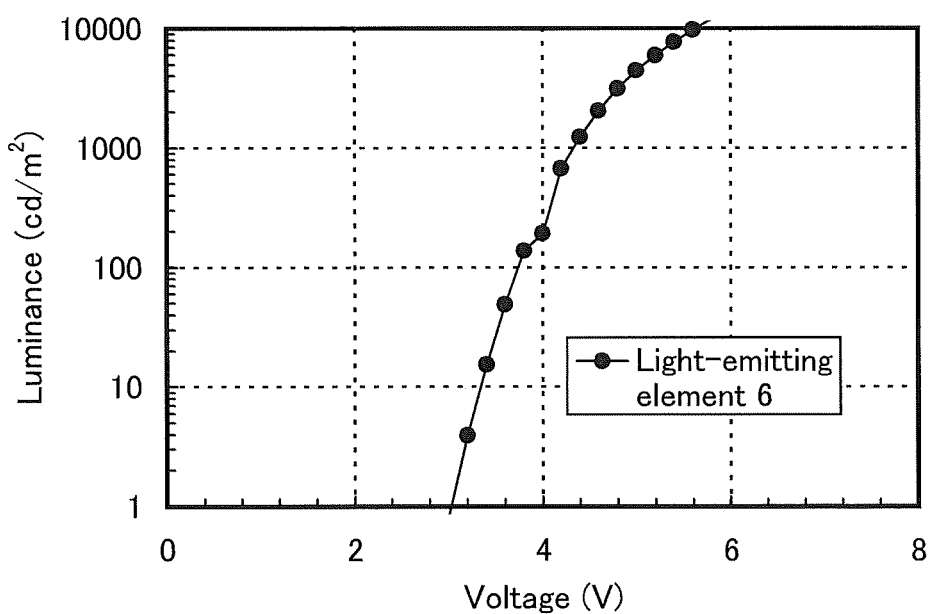
FIG. 52 shows voltage vs. luminance characteristics of Light-emitting Element 6.
Figure 53:
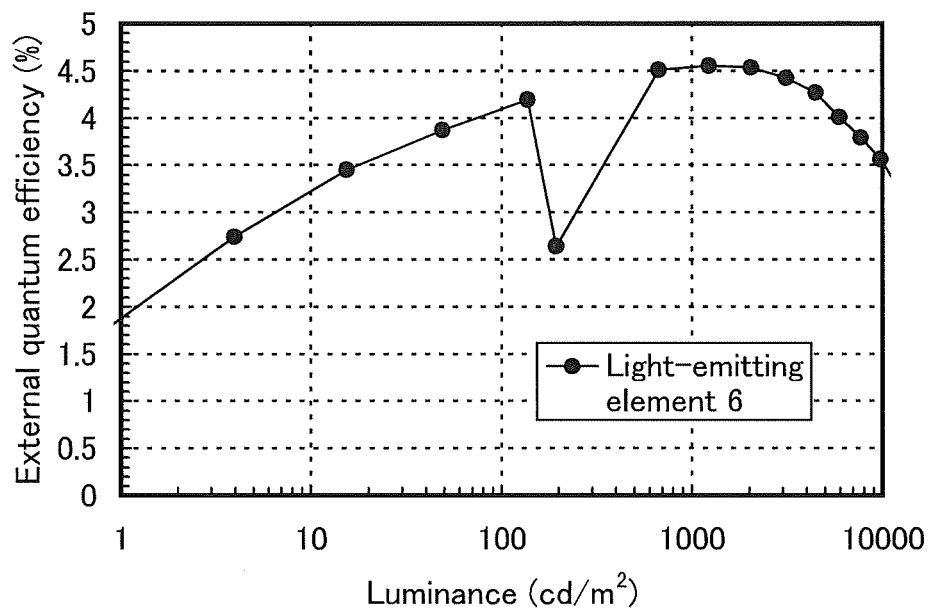
FIG. 53 shows luminance vs. external quantum efficiency characteristics of Light-emitting Element 6.
Figure 54:
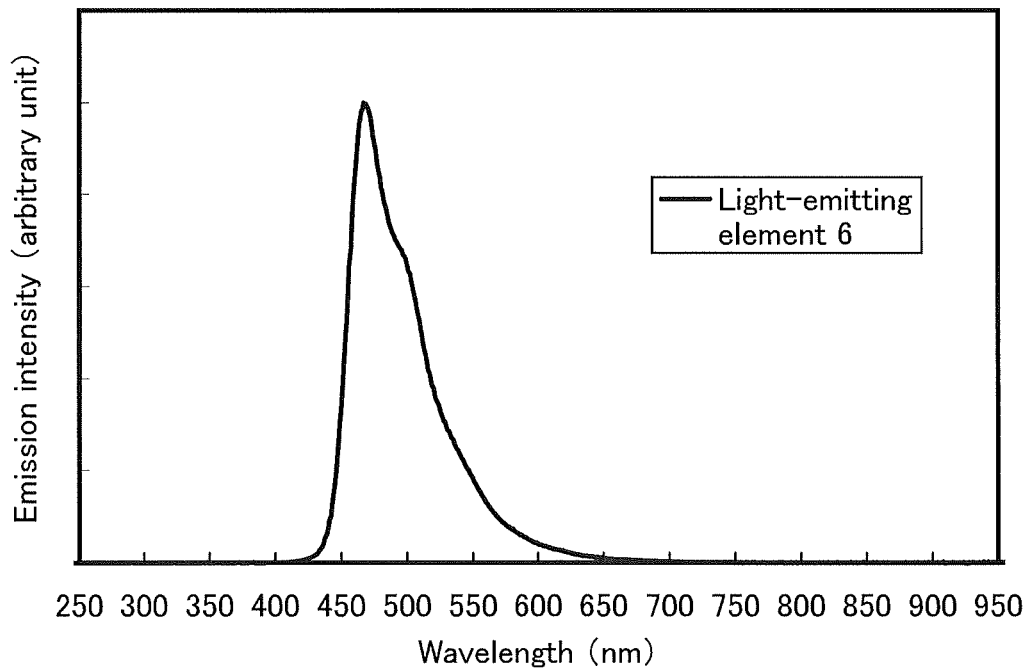
FIG. 54 shows an emission spectrum of Light-emitting Element 6.

FIG. 51 shows luminance vs. current density characteristics of Light-emitting Element 6. In FIG. 51, the horizontal axis represents luminance (cd/m$^2$) and the vertical axis represents current efficiency (cd/A). FIG. 52 shows the voltage vs. luminance characteristics. In FIG. 52, the horizontal axis represents applied voltage (V) and the vertical axis represents luminance (cd/m$^2$). FIG. 53 shows the luminance vs. external quantum efficiency characteristics. In FIG. 53, the horizontal axis represents luminance (cd/m$^2$) and the vertical axis represents external quantum efficiency (%). FIG. 54 shows the emission spectra with a current supply of 1 mA. In FIG. 54, the horizontal axis represents wavelength (nm) and the vertical axis represents intensity (arbitrary unit). Further, Table 12 shows the voltage (V), current density (mA/cm$^2$), CIE chromaticity coordinates (x, y), current efficiency (cd/A), and external quantum efficiency (%) of the Light-emitting Element 6 at a luminance of around 1200 cd/m$^2$.

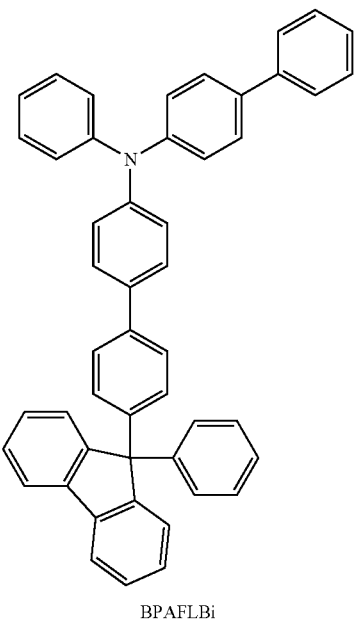 [SMILES: c1ccc(-c2ccc(N(c3ccccc3)c3ccc(-c4ccc(C5(c6ccccc6)c6ccccc6-c6ccccc65)cc4)cc3)cc2)cc1]

BPAFLBi

TABLE 12

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 6 | 4.4 | 16 | 0.16 | 0.26 | 1200 | 7.8 | 4.6 |

As seen from FIG. 54 and the CIE chromaticity coordinates in Table 12, blue light emission is shown by Light-emitting Element 6, which was formed. FIG. 51, FIG. 52, FIG. 53, and Table 12 reveal that Light-emitting Element 6 exhibits good chromaticity, high current efficiency, and high external quantum efficiency.

As described above, 2mDBFPPA produced in Example 9 was used as the host material of the light-emitting layer, whereby the light-emitting element achieved good chromaticity and high emission efficiency.

REFERENCE EXAMPLE 1

A method for synthesizing 4-phenyl-4'-[4-(9-phenylfluoren-9-yl)phenyl]triphenylamine (abbreviation: BPAFLBi) used in Examples 3 and 4 above will be specifically described. The structure of BPAFLBi is shown below.

Step 1: Synthesis Method of 9-(4'-bromo-4-biphenyl)-9-phenylfluorene

In a 500-mL three-neck flask was put 5.1 g (22 mmol) of 2-bromobiphenyl. The air in the flask was replaced with nitrogen. Then, 200 mL of tetrahydrofuran (abbreviation: THF) was added to the mixture, and the mixture was cooled to −78° C. Then, 14 mL (22 mmol) of an n-butyllithium hexane solution was dripped into this mixture solution, and the mixture was stirred for 2.5 hours. After that, 6.7 g (20 mmol) of 9-(4'-bromobiphenylyl)-9-phenylfluoren was added to this mixture, and the mixture was stirred at −78° C. for 2 hours and then at room temperature for 85 hours.

After reaction, 1N-diluted hydrochloric acid was added to this reaction solution until the mixed solution was made acid, and the mixture was stirred for 4 hours. The mixture was washed with water. After that, magnesium sulfate was added to the mixture so that moisture is removed. This suspension was filtered, and the filtrate was concentrated. The resulting substance was purified by silica gel column chromatography (the developing solvent was hexane). The obtained fractions were concentrated, followed by addition of methanol thereto. The resulting substance was irradiated with ultrasonic waves, and then recrystallized to give a white powder, which was the substance to be produced.

In a 200-mL recovery flask were put this white powder, 50 mL of glacial acetic acid, and 1.0 mL of hydrochloric acid. The mixture was heated, and stirred under a nitrogen atmosphere at 130° C. for 2.5 hours to be reacted.

After reaction, this reaction mixture solution was filtered. The resulting filtrate was dissolved in 100 mL of toluene, and the mixture was washed with water, aqueous sodium hydroxide, and water in this order. Magnesium sulfate was added to the mixture so that moisture is removed. This suspension was filtered, and the resulting filtrate was concentrated. Acetone and methanol were added to the resulting substance. The mixture was irradiated with ultrasonic waves and then recrystallized to give 6.3 g of a white powder in a yield of 67%, which was the substance to be produced. The reaction scheme is shown in the following (J-1).

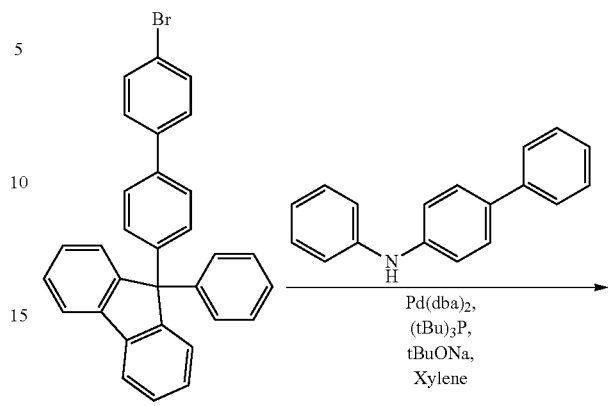

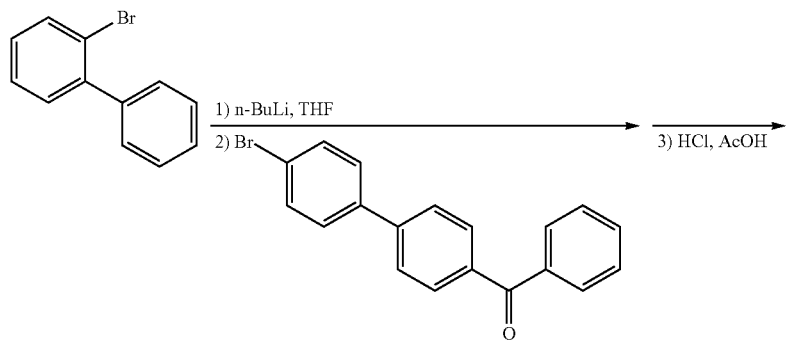

Step 2: Synthesis Method of 4-phenyl-4'-[4-(9-phenylfluoren-9-yl)phenyl]triphenylamine (abbreviation: BPAFLBi)

In a 100 mL three-neck flask were put 3.8 g (8.0 mmol) of 9-(4'-bromo-4-biphenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0). The air in the flask was replaced with nitrogen. Then, 20 mL of dehydrated xylene was added to this mixture. After the mixture was degassed while being stirred under reduced pressure, 0.2 mL (0.1 mmol) of tri(tert-butyl)phosphine (10 wt % hexane solution) was added to the mixture. This mixture was heated and stirred under a nitrogen atmosphere at 110° C. for 2 hours to be reacted.

After reaction, 200 mL of toluene was added to the reaction mixture solution, and the resulting suspension was filtered through Florisil (produced by Wako Pure Chemical Industries, Ltd., Catalog No. 540-00135) and Celite (produced by Wako Pure Chemical Industries, Ltd., Catalog No. 531-16855). The resulting filtrate was concentrated. The resulting substance was purified by silica gel column chromatography (the developing solvent has a 1:4 ratio of toluene to hexane). The obtained fractions were concentrated, and acetone and methanol were added to the mixture. The mixture was irradiated with ultrasonic waves and then recrystallized to give 4.4 g of a white powder in a yield of 86%, which was the substance to be produced. The reaction scheme of the above synthesis method is shown in the following (J-2).

-continued

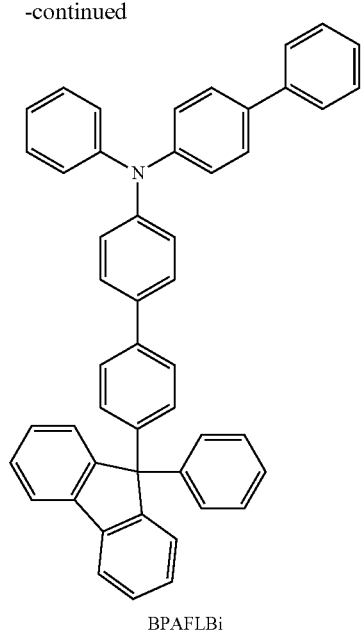

BPAFLBi

The Rf values of the produced substance, 9-(4'-bromo-4-biphenyl)-9-phenylfluorene, and 4-phenyl-diphenylamine were respectively 0.51, 0.56, and 0.28, which were found by silica gel thin layer chromatography (TLC) (the developing solvent has a 1:10 ratio of ethyl acetate to hexane).

The compound obtained through the above Step 2 was subjected to a nuclear magnetic resonance (NMR) method. The measurement data are shown below. The measurement results indicate that the obtained compound was BPAFLBi, which is a fluorene derivative.

$^1$H NMR (CDCl$_3$, 300 MHz): δ 6 (ppm)=7.04 (t, J=6.6, 1H), 7.12-7.49 (m, 30H), 7.55-7.58 (m, 2H), 7.77 (d, J=7.8, 2H).

REFERENCE EXAMPLE 2

A method for synthesizing 4-phenyl-4'-(9-phenylfluoren-9-yl)triphenylamine (abbreviation: BPAFLP) used in Examples 5 and 6 above will be specifically described. The structure of BPAFLP is shown below.

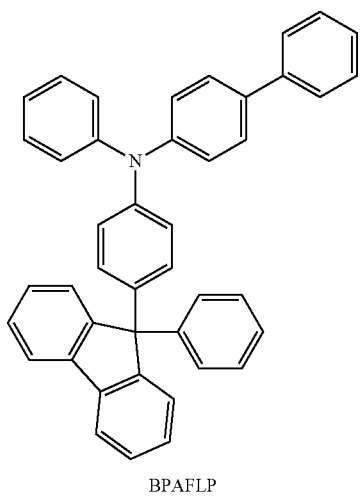 [SMILES: c1ccc(-c2ccc(N(c3ccccc3)c3ccc(C4(c5ccccc5)c5ccccc5-c5ccccc54)cc3)cc2)cc1]

BPAFLP

Step 1: Synthesis Method of 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was stirred and heated under reflux for 2.5 hours. Accordingly, a Grignard reagent was prepared.

In a 500-mL three-neck flask were put 10 g (40 mmol) of 4-bromobenzophenone and 100 mL of diethyl ether. After the Grignard reagent prepared as above was slowly dripped into this mixture, the mixture was heated and stirred under reflux for 9 hours.

After reaction, this mixture was filtered to give a residue. The residue was dissolved in 150 mL of ethyl acetate, and 1N-hydrochloric acid was added to the mixture, which was then stirred for 2 hours until it was made acid. The organic layer of the liquid was washed with water. Then, magnesium sulfate was added thereto so that moisture is removed. This suspension was filtered, and the resulting filtrate was concentrated to give a candy-like substance.

In a 500-mL recovery flask were put this candy-like substance, 50 mL of glacial acetic acid, and 1.0 mL of hydrochloric acid. The mixture was heated and stirred under a nitrogen atmosphere at 130° C. for 1.5 hours to be reacted.

After reaction, this reaction mixture solution was filtered to give a residue. The residue was washed with water, aqueous sodium hydroxide, water, and methanol in this order. Then, the mixture was dried to give 11 g of a white powder in 69% yield, which was the substance to be produced. The reaction scheme of the synthesis method is shown in the following (J-3).

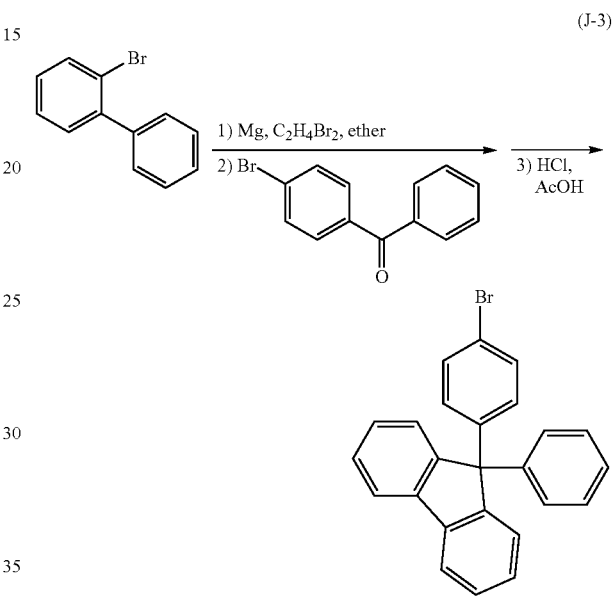

(J-3)

Step 2: Synthesis method of 4-phenyl-4'-(9-phenyl-fluoren-9-yl)triphenylamine (abbreviation: BPAFLP)

In a 100-mL three-neck flask were put 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide and 23 mg (0.04 mmol) of bis (dibenzylideneacetone)palladium(0). The air in the flask was replaced with nitrogen. Then, 20 mL of dehydrated xylene was added to this mixture. After the mixture was degassed while being stirred under reduced pressure, 0.2 mL (0.1 mmol) of tri(tert-butyl)phosphine (a 10 wt % hexane solution) was added to the mixture. This mixture was heated and stirred under a nitrogen atmosphere at 110 ° C. for 2 hours to be reacted.

After reaction, 200 mL of toluene was added to the reaction mixture solution, and the resulting suspension was filtered through Florisil (produced by Wako Pure Chemical Industries, Ltd., Catalog No. 540-00135) and Celite (produced by Wako Pure Chemical Industries, Ltd., Catalog No. 531-16855). The filtrate was concentrated, and the resulting substance was purified by silica gel column chromatography (the developing solvent has a 1:4 ratio of toluene to hexane). The obtained fractions were concentrated, and acetone and methanol were added to the mixture. The mixture was irradiated with ultrasonic waves and then recrystallized to give 4.1 g of a white powder in 92% yield, which was the substance to be produced. The reaction scheme of the above synthesis method is shown in the following (J-4).

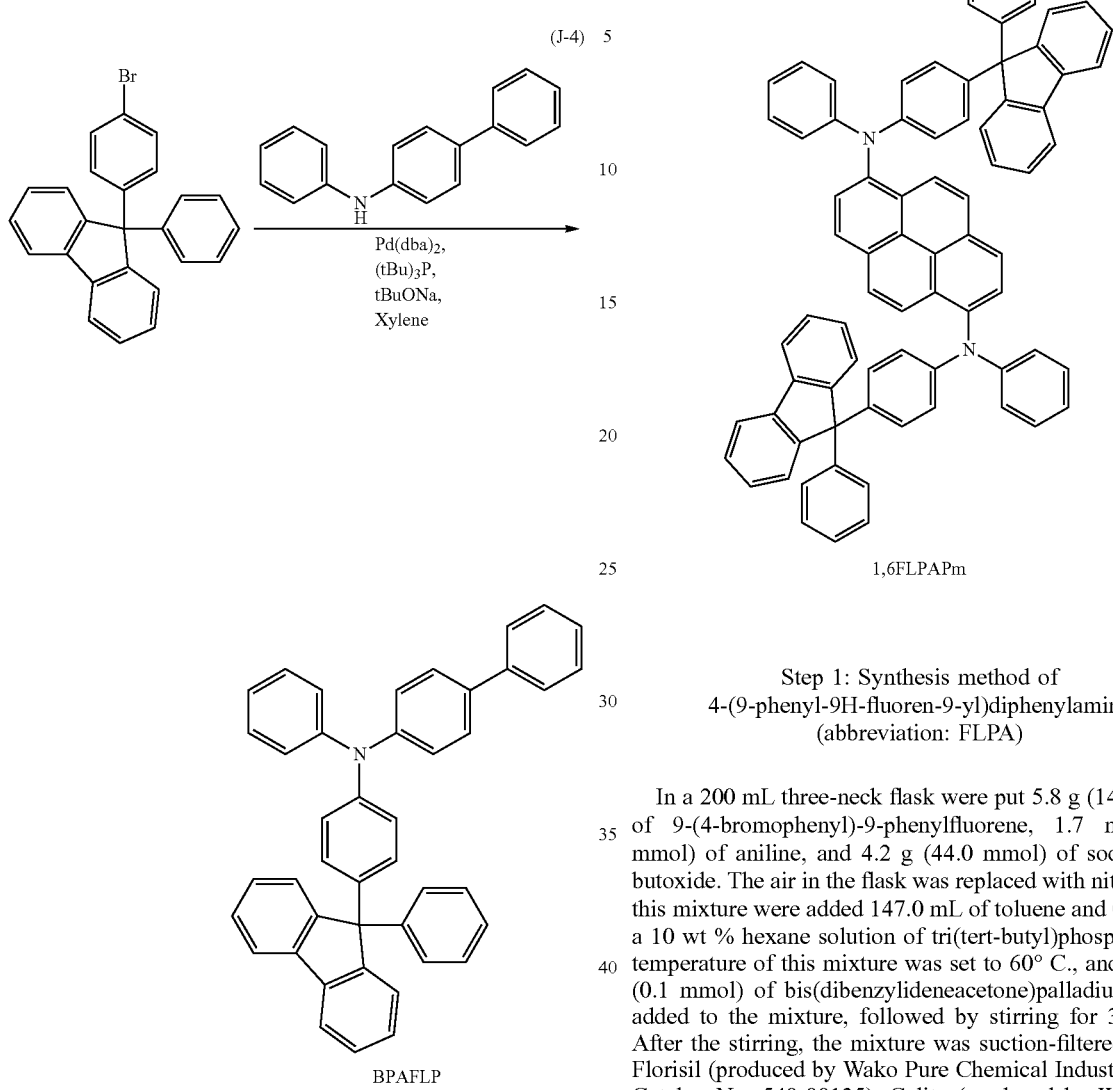

BPAFLP

The Rf values of the produced substance, 9-(4-bromophenyl)-9-phenylfluorene, and 4-phenyl-diphenylamine were respectively 0.41, 0.51, and 0.27, which were found by silica gel thin layer chromatography (TLC) (the developing solvent has a 1:10 ratio of ethyl acetate to hexane).

The compound obtained through the above Step 2 was subjected to a nuclear magnetic resonance (NMR) method. The measurement data are shown below. The measurement results indicate that the obtained compound was BPAFLP, which is a fluorene derivative.

$^1$H NMR (CDCl$_3$, 300 MHz): δ 6 (ppm)=6.63-7.02 (m, 3H), 7.06-7.11 (m, 6H), 7.19-7.45 (m, 18H), 7.53-7.55 (m, 2H), 7.75 (d, J =6.9, 2H).

REFERENCE EXAMPLE 3

In this example, N,N'-bis[4-(9-phenyl-9H-fluoren-9-yl) phenyl]-N,N'-diphenyl-pyrene-1,6-diamine (abbreviation: 1,6FLPAPrn) used in Examples 8 and 10 was produced.

Step 1: Synthesis method of 4-(9-phenyl-9H-fluoren-9-yl)diphenylamine (abbreviation: FLPA)

In a 200 mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide. The air in the flask was replaced with nitrogen. To this mixture were added 147.0 mL of toluene and 0.4 mL of a 10 wt % hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina. The resulting filtrate was concentrated to give a solid, which was then purified by silica gel column chromatography (the developing solvent has a 2:1 ratio of hexane to toluene). The obtained fractions were concentrated to give 6.0 g of a while solid in 99% yield, which was the substance to be produced. The synthesis scheme of Step 1 is shown in (E1-2) below.

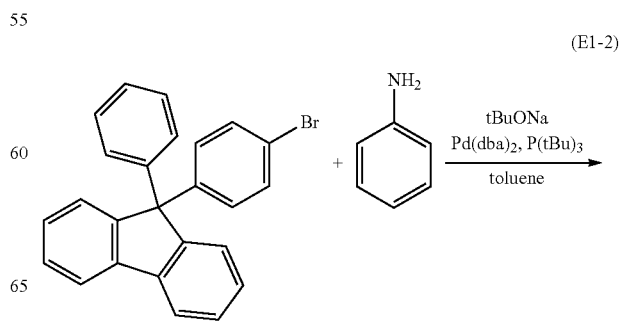

-continued

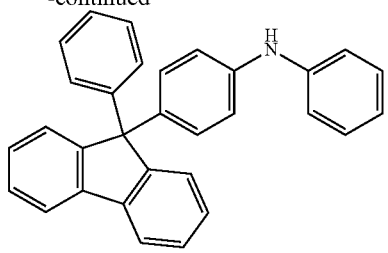

Step 2: Synthesis Method of 4-(10-phenyl-9-an-thryl)-4'-(9-phenyl-9H-fluoren-9-yl)triphenylamine (abbreviation: FLPAPA)

In a 50 mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviation: FLPA) and 0.3 g (3.6 mmol) of sodium tert-butoxide. The air in the flask was replaced with nitrogen. To this mixture were added 11.5 mL of toluene and 0.2 mL of a 10 wt % hexane solution of tri(tert-butyl)phosphine. The temperature of this mixture was set to 70° C., and 31.1 mg (0.05 mmol) of bis(dibenzylideneacetone)palladium(0) was added to the mixture, followed by stirring for 4.0 hours. After the stirring, the mixture was suction-filtered through Florisil, Celite, and alumina. The resulting filtrate was concentrated to give a solid, which was then purified by silica gel column chromatography (the developing solvent was chloroform). The obtained fractions were concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, whereby 0.8 g of a pale yellow powdered solid was obtained in 68% yield, which was the substance to be produced.

By a train sublimation method, 0.8 g of the obtained yellow solid was purified. Under a pressure of 2.7 Pa with a flow rate of argon at 5 mL/min, the sublimation purification was carried out at 360° C. After the purification, 0.4 g of the substance to be produced was obtained in a yield of 56%. The synthesis scheme of the above step is shown in the following (E2).

(E2)

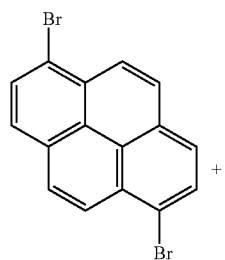

+

-continued

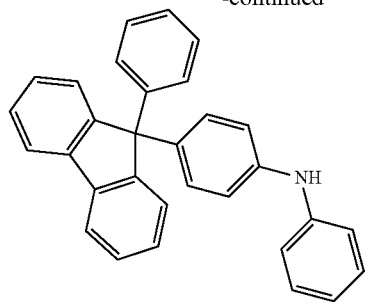

1,6FLPAPrn

A nuclear magnetic resonance (NMR) method and a mass spectrometry identified this compound as N,N'-bis[4-(9-phenyl-9H-fluoren-9-yl)phenyl]-N,N'-diphenyl-pyrene-1,6-diamine (abbreviation: 1,6FLPAPm), which was the substance to be produced.

$^1$H NMR data of the obtained compound are: $^1$H NMR (CDCl$_3$, 300 MHz): δ 6=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

This application is based on Japanese Patent Application serial no. 2009-260240 filed with the Japan Patent Office on Nov. 13, 2009, the entire contents of which are hereby incorporated by reference.

What is claimed is:
1. A compound having a structure represented by General Formula (G1),

(G1)

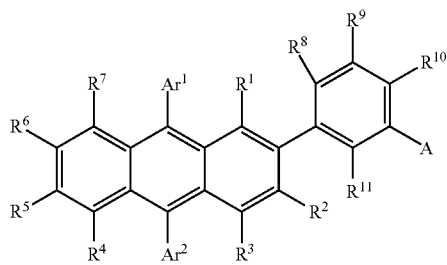

-continued (S1)
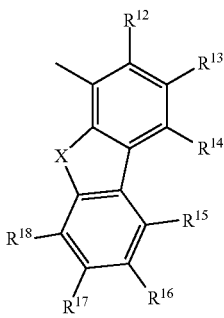

(S2)
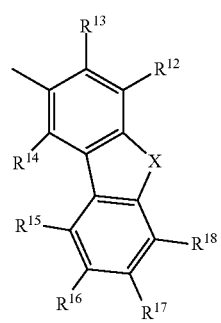

wherein:
Ar¹ and Ar² each independently represent a substituted or unsubstituted aryl group having 6 to 13 carbon atoms,
$R^1$ to $R^{11}$ each independently represent a hydrogen atom, an alkyl group having 1 to 4 carbon atoms, or a substituted or unsubstituted aryl group having 6 to 13 carbon atoms,
A represents a substituent represented by General Formula (S1) or General Formula (S2),
X represents oxygen or sulfur, and
$R^{12}$ to $R^{18}$ each independently represent a hydrogen atom, an alkyl group having 1 to 4 carbon atoms, or a substituted or unsubstituted aryl group having 6 to 13 carbon atoms.

2. The compound according to claim 1, wherein Ar¹ and Ar² each independently represents an unsubstituted aryl group having 6 to 13 carbon atoms.

3. The compound according to claim 1, wherein $R^1$ to $R^{11}$ each independently represent a hydrogen atom.

4. The compound according to claim 1, wherein $R^{12}$ to $R^{18}$ each independently represent a hydrogen atom.

5. The compound according to claim 1,
wherein the compound comprises a structure represented by General Formula (G2-1), (G2-1)
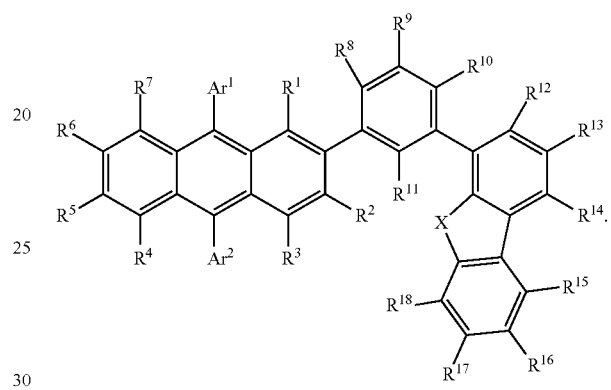

6. The compound according to claim 5, wherein Ar¹ and Ar² each independently represents an unsubstituted aryl group having 6 to 13 carbon atoms.

7. The compound according to claim 5, wherein $R^1$ to $R^{11}$ each independently represent a hydrogen atom.

8. The compound according to claim 5, wherein $R^{12}$ to $R^{18}$ each independently represent a hydrogen atom.

* * * * *